US011612890B2

(12) United States Patent
Kurz et al.

(10) Patent No.: US 11,612,890 B2
(45) Date of Patent: Mar. 28, 2023

(54) METHODS FOR ENCAPSULATING AND ASSAYING CELLS

(71) Applicant: Berkeley Lights, Inc., Emeryville, CA (US)

(72) Inventors: Volker L. S. Kurz, Oakland, CA (US); Jason M. McEwen, El Cerrito, CA (US); Kellen C. Mobilia, Dublin, CA (US); Alexander J. Mastroianni, Alameda, CA (US); Joshua J. Cardiel Rivera, Beaverton, OR (US)

(73) Assignee: Berkeley Lights, Inc., Emeryville, CA (US)

( * ) Notice: Subject to any disclaimer, the term of this patent is extended or adjusted under 35 U.S.C. 154(b) by 0 days.

(21) Appl. No.: 17/452,725

(22) Filed: Oct. 28, 2021

(65) Prior Publication Data

US 2022/0161255 A1 May 26, 2022

Related U.S. Application Data

(63) Continuation of application No. PCT/US2020/030846, filed on Apr. 30, 2020.

(60) Provisional application No. 62/850,557, filed on May 21, 2019, provisional application No. 62/841,229, filed on Apr. 30, 2019.

(51) Int. Cl.
*G01N 1/00* (2006.01)
*B01L 3/00* (2006.01)

(52) U.S. Cl.
CPC . *B01L 3/502715* (2013.01); *B01L 2200/0673* (2013.01); *B01L 2200/16* (2013.01); *B01L 2300/0636* (2013.01); *B01L 2300/087* (2013.01); *B01L 2300/0877* (2013.01)

(58) Field of Classification Search
CPC ....... B01L 3/502715; B01L 2200/0673; B01L 2200/16; B01L 2300/0636; B01L 2300/087; B01L 2300/0877
USPC .................................................. 422/502, 500
See application file for complete search history.

(56) References Cited

U.S. PATENT DOCUMENTS

| 6,294,063 | B1 | 9/2001 | Becker et al. |
| 6,379,929 | B1 | 4/2002 | Burns et al. |
| 6,408,878 | B2 | 6/2002 | Unger et al. |
| 6,942,776 | B2 | 9/2005 | Medora |

(Continued)

FOREIGN PATENT DOCUMENTS

| CN | 101275114 A | 10/2008 |
| CN | 102181361 A | 9/2011 |

(Continued)

OTHER PUBLICATIONS

Chen et al.; Thermally-actuated, phase change flow control for microfluidic systems; Lab on a Chip; 5(11); pp. 1277-1285; Aug. 2005.

(Continued)

*Primary Examiner* — Christine T Mui
(74) *Attorney, Agent, or Firm* — Shay Glenn LLP

(57) ABSTRACT

In biosciences and related fields, it can be useful to study cells in isolation so that cells having unique and desirable properties can be identified within a heterogenous mixture of cells. Processes and methods disclosed herein provide for encapsulating cells within a microfluidic device and assaying the encapsulated cells. Encapsulation can, among other benefits, facilitate analyses of cells that generate secretions of interest which would otherwise rapidly diffuse away or mix with the secretions of other cells.

32 Claims, 26 Drawing Sheets

(56) References Cited

U.S. PATENT DOCUMENTS

| | | |
|---|---|---|
| 6,958,132 B2 | 10/2005 | Chiou et al. |
| 7,090,759 B1 | 8/2006 | Seul |
| 7,699,969 B2 | 4/2010 | Manaresi et al. |
| 7,956,339 B2 | 6/2011 | Ohta et al. |
| 8,037,903 B2 | 10/2011 | Wang et al. |
| 8,581,167 B2 | 11/2013 | Lean et al. |
| 8,685,344 B2 | 4/2014 | Sudarsan et al. |
| 8,921,055 B2 | 12/2014 | Chapmen |
| 9,144,806 B2 | 9/2015 | Chen et al. |
| 9,403,172 B2 | 8/2016 | Short et al. |
| 10,058,865 B2 | 8/2018 | Breinlinger et al. |
| 10,690,628 B2 | 6/2020 | Chapman et al. |
| 10,723,988 B2 | 7/2020 | Lowe et al. |
| 10,799,865 B2 | 10/2020 | Lowe et al. |
| 11,007,520 B2 | 5/2021 | Lowe et al. |
| 2003/0008364 A1 | 1/2003 | Wang et al. |
| 2003/0175947 A1 | 9/2003 | Liu et al. |
| 2004/0032793 A1 | 2/2004 | Falcon |
| 2004/0072278 A1 | 4/2004 | Chou et al. |
| 2004/0086870 A1 | 5/2004 | Tyvoll et al. |
| 2004/0191789 A1 | 9/2004 | Manaresi et al. |
| 2004/0197905 A1 | 10/2004 | Hafeman |
| 2005/0112548 A1 | 5/2005 | Segawa et al. |
| 2005/0129581 A1 | 6/2005 | McBride et al. |
| 2005/0175981 A1 | 8/2005 | Voldman et al. |
| 2005/0274456 A1 | 12/2005 | Roitman et al. |
| 2006/0091015 A1 | 5/2006 | Lau |
| 2006/0154361 A1 | 7/2006 | Wikswo et al. |
| 2006/0177350 A1 | 8/2006 | Sano et al. |
| 2006/0263612 A1 | 11/2006 | Chen et al. |
| 2007/0095669 A1 | 5/2007 | Lau et al. |
| 2007/0183934 A1 | 8/2007 | Diercks et al. |
| 2007/0292312 A1 | 12/2007 | Bachman et al. |
| 2007/0292941 A1 | 12/2007 | Handique et al. |
| 2008/0003142 A1 | 1/2008 | Link et al. |
| 2008/0013092 A1 | 1/2008 | Maitezos et al. |
| 2008/0223721 A1 | 9/2008 | Cohen et al. |
| 2008/0302732 A1 | 12/2008 | Soh et al. |
| 2009/0021728 A1 | 1/2009 | Heinz et al. |
| 2009/0023608 A1 | 1/2009 | Hung et al. |
| 2009/0170186 A1 | 7/2009 | Wu et al. |
| 2009/0286300 A1 | 11/2009 | Le Vot et al. |
| 2010/0003666 A1 | 1/2010 | Lee et al. |
| 2010/0173393 A1 | 7/2010 | Handique et al. |
| 2010/0273681 A1 | 10/2010 | Cerrina et al. |
| 2011/0003325 A1 | 1/2011 | Durack |
| 2011/0030808 A1 | 2/2011 | Chiou et al. |
| 2011/0053151 A1 | 3/2011 | Hansen et al. |
| 2011/0117634 A1 | 5/2011 | Halamish et al. |
| 2011/0143964 A1 | 6/2011 | Zhou et al. |
| 2011/0262906 A1 | 10/2011 | Dimov et al. |
| 2011/0306108 A1 | 12/2011 | Douglas-Hamilton et al. |
| 2012/0009671 A1 | 1/2012 | Hansen et al. |
| 2012/0015347 A1 | 1/2012 | Singhal et al. |
| 2012/0024708 A1 | 2/2012 | Chiou et al. |
| 2012/0118740 A1 | 5/2012 | Garcia et al. |
| 2012/0156675 A1 | 6/2012 | Luerssen et al. |
| 2012/0208266 A1 | 8/2012 | Bookbinder et al. |
| 2012/0315203 A1 | 12/2012 | Baroud et al. |
| 2012/0325665 A1 | 12/2012 | Chiou et al. |
| 2013/0115606 A1 | 5/2013 | Hansen et al. |
| 2013/0118905 A1 | 5/2013 | Morimoto et al. |
| 2013/0130232 A1 | 5/2013 | Weibel et al. |
| 2013/0146459 A1 | 6/2013 | Bazant et al. |
| 2013/0171628 A1 | 7/2013 | Di Carlo et al. |
| 2013/0190212 A1 | 7/2013 | Handique et al. |
| 2013/0204076 A1 | 8/2013 | Han et al. |
| 2013/0261021 A1 | 10/2013 | Bocchi et al. |
| 2014/0045277 A1 | 2/2014 | Gordon et al. |
| 2014/0116881 A1 | 5/2014 | Chapman et al. |
| 2014/0154703 A1 | 6/2014 | Skelley et al. |
| 2014/0154791 A1 | 6/2014 | North et al. |
| 2015/0018226 A1 | 1/2015 | Hansen et al. |
| 2015/0064702 A1 | 3/2015 | Handique et al. |
| 2015/0151298 A1 | 6/2015 | White et al. |
| 2015/0151307 A1 | 6/2015 | Breinlinger et al. |
| 2015/0165436 A1 | 6/2015 | Chapman et al. |
| 2015/0167043 A1 | 6/2015 | Goluch et al. |
| 2015/0306598 A1 | 10/2015 | Khandros et al. |
| 2015/0306599 A1 | 10/2015 | Khandros et al. |
| 2016/0160259 A1 | 6/2016 | Du |
| 2016/0171686 A1 | 6/2016 | Du et al. |
| 2016/0184821 A1 | 6/2016 | Hobbs et al. |
| 2016/0199837 A1 | 7/2016 | Breinlinger et al. |
| 2016/0252495 A1 | 9/2016 | Ricicova et al. |
| 2016/0257918 A1 | 9/2016 | Chapman et al. |
| 2017/0021366 A1 | 1/2017 | Chapman et al. |
| 2017/0165667 A1 | 6/2017 | Beaumont et al. |
| 2017/0355595 A1 | 12/2017 | Breinlinger et al. |
| 2018/0015473 A1 | 1/2018 | Bharadwaj et al. |
| 2018/0298318 A1 | 10/2018 | Kurz et al. |
| 2019/0240665 A1 | 8/2019 | Lionberger et al. |

FOREIGN PATENT DOCUMENTS

| | | |
|---|---|---|
| CN | 107849505 A | 3/2018 |
| CN | 108603878 A | 9/2018 |
| CN | 109196094 A | 1/2019 |
| CN | 109311930 A | 2/2019 |
| CN | 109642869 A | 4/2019 |
| EP | 1065378 A2 | 1/2001 |
| JP | 2006090870 A | 4/2006 |
| JP | 2011000079 A | 1/2011 |
| JP | 2014219261 A | 11/2014 |
| KR | 20100008222 A | 1/2010 |
| WO | WO01/035071 A2 | 5/2001 |
| WO | WO02/088702 A2 | 11/2002 |
| WO | WO2005/100541 A2 | 10/2005 |
| WO | WO2008/119066 A1 | 10/2008 |
| WO | WO2010/115167 A2 | 10/2010 |
| WO | WO2010/147078 A1 | 12/2010 |
| WO | WO2010/147942 A1 | 12/2010 |
| WO | WO2012/037030 A2 | 3/2012 |
| WO | WO2012/072823 A1 | 6/2012 |
| WO | WO2013/019491 A1 | 2/2013 |
| WO | WO2015/061497 A1 | 4/2015 |
| WO | WO2015/164846 A1 | 10/2015 |
| WO | WO2015/164847 A1 | 10/2015 |
| WO | WO2016/172350 A1 | 10/2016 |
| WO | WO2016/172454 A1 | 10/2016 |
| WO | WO2017/048975 A1 | 3/2017 |
| WO | WO2017/095917 A1 | 6/2017 |
| WO | WO2017/181135 A2 | 10/2017 |
| WO | WO2017/205830 A1 | 11/2017 |
| WO | WO2018/064640 A1 | 4/2018 |
| WO | WO2018/067872 A1 | 4/2018 |
| WO | WO2018/071448 A1 | 4/2018 |
| WO | WO2018/102747 A1 | 6/2018 |
| WO | WO2018/102748 A1 | 6/2018 |
| WO | WO2019/018801 A1 | 1/2019 |
| WO | WO2019/075476 A2 | 4/2019 |
| WO | WO2019/079787 A1 | 4/2019 |
| WO | WO2020/168258 A1 | 8/2020 |
| WO | WO2020/223555 A1 | 11/2020 |

OTHER PUBLICATIONS

Chiou et al.; Massively Parallel Manipulation of Single Cells and Microparticles Using Optical Images; Nature; (436) pp. 370-372; Jul. 2005.

Chiou; Massively parallel optical manipulation of single cells, mirco- and nano-particles on optoelectronic devices; University of California at Berkeley; 147 pages (Dissertation); (year of pub. sufficiently earlier than effective US filing date and any foreign priority date) Fall 2005.

Chung et al., Imaging single-cell signaling dynamics with a deterministic high-density single-cell trap array; Anal.Chem.; 83(18); pp. 7044-7052; 14 pages (Author Manuscript); Aug. 23, 2011.

CN101275114A, Lou—Machine Translation, Oct. 1, 2008, 8 pages.

CN102181361A_Harbin Inst_Qu—Machine Translation, Sep. 14, 2011, 6 pages.

(56) References Cited

OTHER PUBLICATIONS

Communication pursuant to Article 94(3) EPC; EP Application 168826683-1101; dated Jan. 4, 2020; 6 pages.
Debra et al.; Fabrication and performance testing of a steady thermocapillary pump with no moving parts; Proceedings of the MEMS 2002 IEEE International Conference; Las Vegas, NV, USA; pp. 109-112; Jan. 20-24, 2002.
Hsu et al.; Sorting Of Differentiated Neurons Using Phototransistor-Based Optoelectronic Tweezers for Cell Replacement Therapy of Neurodegeneralive Diseases: Transducers 2009 Conf.; pp. 1598-1601; Jun. 2009.
Hua et al.; Microfluidic actuation using electrochemically generated bubbles; Analytical Chemistry; 74(24); pp. 6392-6396; Dec. 2002.
Hung et al.; Continuous Perfusion Microfluidic Cell Culture Array for High-Throughput Cell-Based Assays; Biotech and Bioengineering 89(1); pp. 1-8 ; Jan. 2005.
Iliescu et al.; Continuous field-flow separation of particle populations in a dielectrophoretic chip with three dimensional electrodes; Applied Physics Letters 90(23); pp. 234104, 4pages; Jun. 2007.
International Search Report and Written Opinion of PCT App. PCT/US2016/069249; dated Apr. 28, 2017; 14 pages.
JP2006090870A_Aicia Eng Ltd_Fujii—Machine Translation, Apr. 6, 2006, 12 pages.
JP2014219261A_Konica_Tsukagoshi—Machine Translation, Nov. 20, 2014, 13 pages.
KIPO computer-generated English language translation of KR 201000008222A_Kyun; 10 pages, 2010.
Leu et al.; Design and fabrication of thermocapillary micro bubble pump; Advanced Materials research; 528; pp. 23-26; 2012 (year of pub. sufficiently earlier than effective US filing date and any foreign priority date).
Liu et al.; Optofluidic control using photothermal nanoparticles; Nature Materials; 5(1); pp. 27-32; Jan. 2006.
Nevill et al.; Integrated Microfluidic Cell Culture and Lysis on a Chip; Lab Chip; (12) pp. 1689-1695; Oct. 2007.
Ohta et al.; Optically Controlled Cell Discrimination and Trapping Using Optoelectronic Tweezers; IEEE Journal of Selected Topics in Quantum Electronics, 13 (2); pp. 235-243; Apr. 23, 2007.
Ritchie et al.; Reconstitution of Membrane Proteins in Phospholipid Bilayer Nanodiscs; Methods Enzymol; 464; pp. 211-231; 23 pages; (Author Manuscript); Jan. 2009.
Somaweera et al.; "Generation of a Chemical Gradient Across an Array of 256 Cell Cultures in a Single Chip"; Analyst; 138(19); pp. 5566-5571; 14 pgs.; (Author Manuscript); Oct. 2013.
Valley et al.; A Unified Platform for Optoelectrowetting and Optoelectronic Tweezers; Lab Chip; 11(7); pp. 1292-1297; Jan. 2011.
Valley et al.; Optoelectronic Tweezers as a Tool for Parallel Single-Cell Manipulation and Stimulation; IEEE Trans Biomed Circuits Syst.; 3(6); pp. 424-431; Dec. 2009.
Vercruysse et al.; A high speed miniaturized cell sorter with lens-free imaging and thermal bubble based jet flow sorting; 18th International Conference on Miniaturized Systems for Chemistry and Life Science; pp. 382-384; Oct. 26-30, 2014.
WO2010147078, University of Tokyo, Machine Translation, Dec. 23, 2010; 12 pages.
Xie et al.; Exploring bubble oscillation and mass transfer enhancement In acoustic-assisted liquid-liquid extraction with a microfluidic device; Scientific Reports; 5(1); pp. 1-9; Jul. 2015.
Xu et al.; Recent Trends in Dielectrophoresis; Informacije MIDEM; 40(4) pp. 253-262; Dec. 2010.
Yi et al.; Microfluidics Technology for Manipulation and Analysis of Biological Cells; Anal Chim Acta; (560) pp. 1-23; Feb. 2006.
Zhang et al.; Laser-induced thermal bubbles for microfluidics applications; Lab on a Chip; 11(7); pp. 1389-1395; 2011 (year of pub. sufficiently earlier than effective US filing date and any foreign priority date).
Sackmann et al.; U.S. Appl. No. 17/401,783 entitled "Laser-assisted repositioning of a micro-object and culturing of an attachment-dependent cell in a microfiudic enviroment." filed Aug. 13, 2021.
Zhang et al.; "Click" Chemistry-Based Surface Modification of poly(dimethyisiloxane) for Protein Separation in a Microfluidic Chip; Electrophoresis; 31(18); p. 3129-3136; Sep. 20, 2010.
Zhang et al.;Azide Functional Monolayers Grafted to a Germanium Surface Model Substrates for ATR-IR Studies of interfacial Click Reactions; Langmuir ; 28(1); pp. 486-493; Dec. 8, 2011.

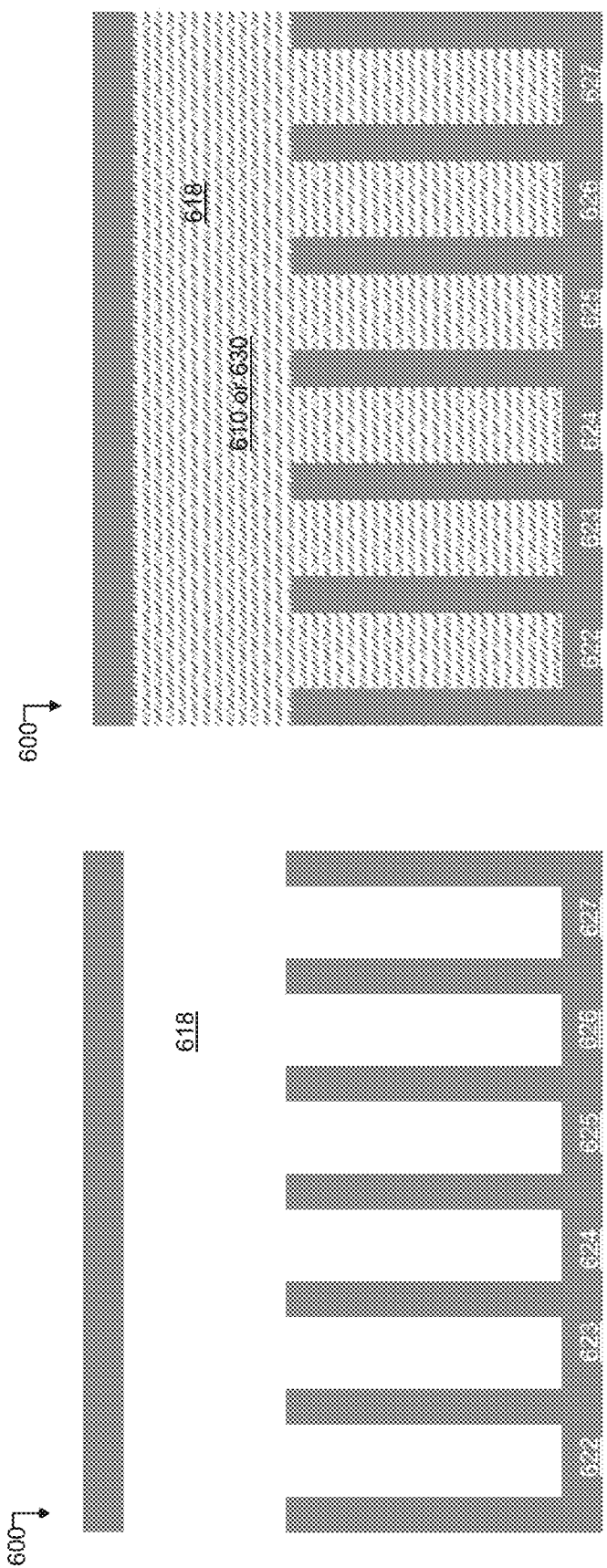

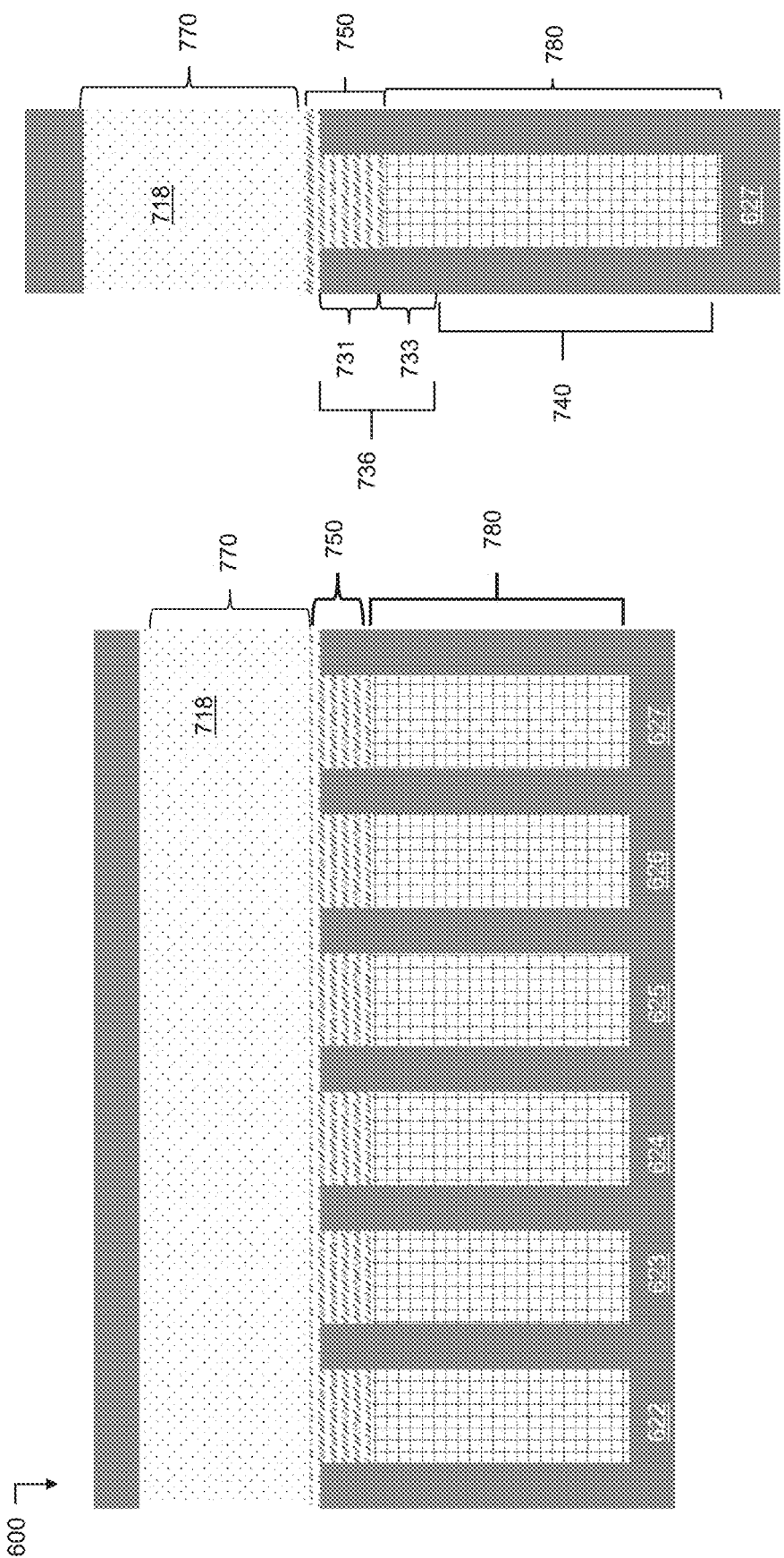

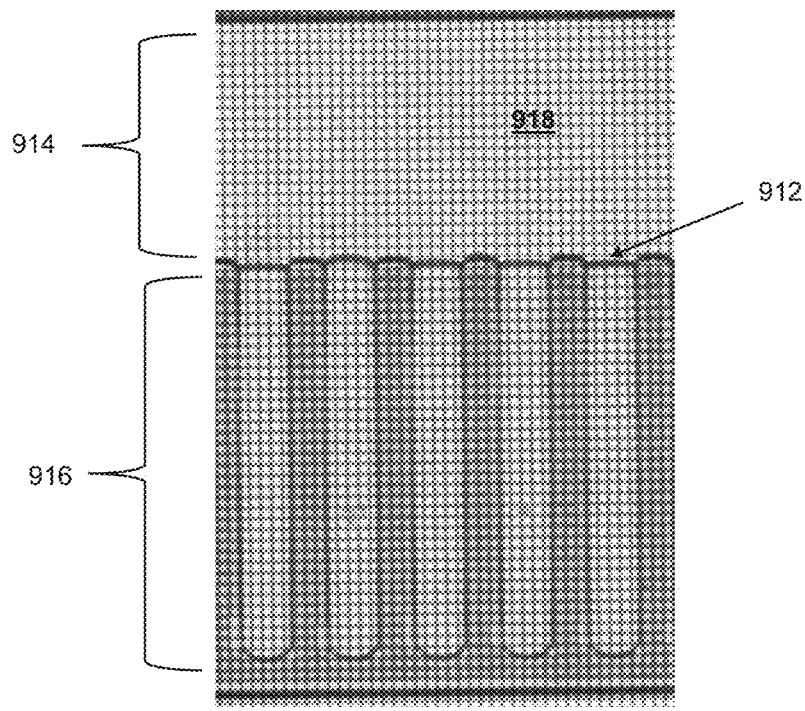
*FIG. 9A*
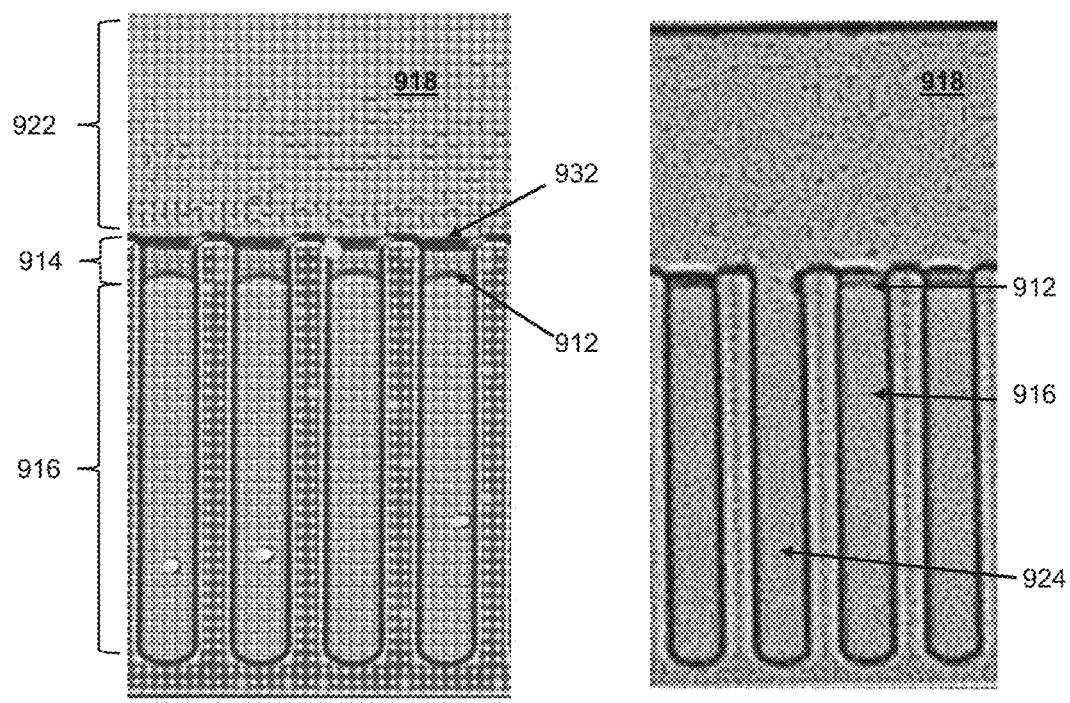
*FIG. 9B*  *FIG. 9C*

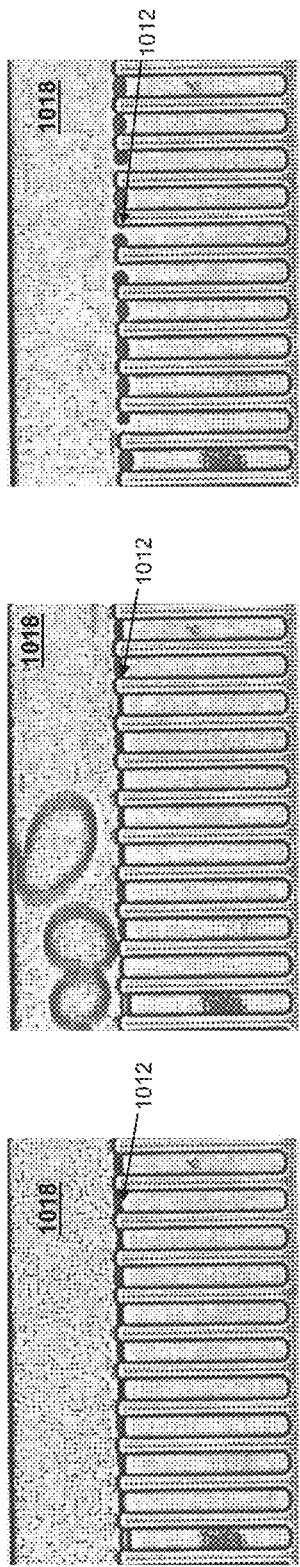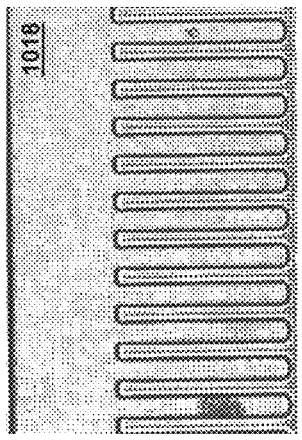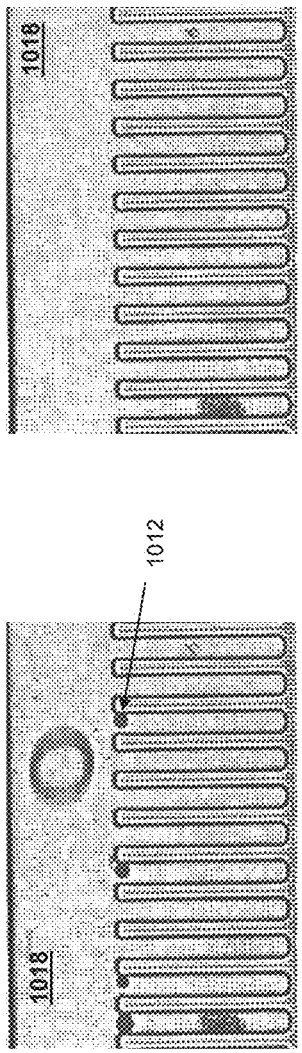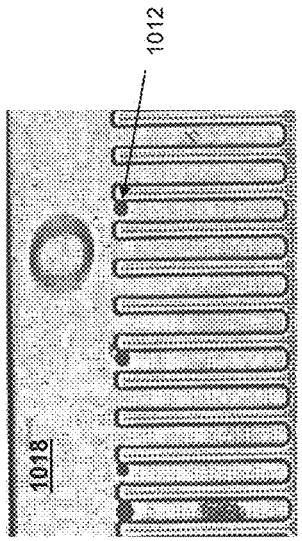
FIG. 10A  FIG. 10B  FIG. 10C  FIG. 10D  FIG. 10E

METHODS FOR ENCAPSULATING AND ASSAYING CELLS

CROSS REFERENCE TO RELATED APPLICATIONS

This application is a continuation of International Application No. PCT/US2020/030846, filed on Apr. 30, 2020, titled "METHODS FOR ENCAPSULATING AND ASSAYING CELLS", now International Publication No. WO 2020/223555, which claims the benefit of U.S. Provisional Application No. 62/841,229, filed on Apr. 30, 2019, titled "METHODS FOR ENCAPSULATING AND ASSAYING CELLS" and U.S. Provisional Application No. 62/850,557, filed on May 21, 2019, titled "METHODS FOR ENCAPSULATING AND ASSAYING CELLS", each of which is herein incorporated by reference in its entirety.

BACKGROUND

In biosciences and related fields, it can be useful to study cells in isolation so that cells having unique and desirable properties can be identified within a heterogenous mixture of cells. Some aspects and embodiments of the present disclosure include processes and methods for encapsulating cells within a microfluidic device and assaying the encapsulated cells. Encapsulation can, among other benefits, facilitate analyses of cells that generate secretions of interest which would otherwise rapidly diffuse away or mix with the secretions of other cells.

SUMMARY

In a first aspect, a process is provided for encapsulating cells in a microfluidic device having an enclosure including a channel and a plurality of chambers, each chamber of the plurality having an opening (e.g., a single opening) fluidically connecting the chamber to the channel, where at least a portion of surfaces forming the channel proximal to the opening to each chamber of the plurality may include a hydrophobic coating, said process including: filling the channel and the plurality of chambers in the enclosure of the microfluidic device with a first aqueous medium; disposing a first cell in a first chamber of the plurality of chambers; disposing a second cell in a second chamber of the plurality of chambers; and flowing a water immiscible fluidic medium into the channel, displacing substantially all of the first aqueous medium in the channel without substantially displacing the first aqueous medium in the chambers of the plurality of chambers, thereby reversibly encapsulating the first and second cells in their respective chambers.

In some embodiments, all of the channel surfaces proximal to and surrounding the opening to each chamber of the plurality of chambers may include the hydrophobic coating. In some other embodiments, all of the channel surfaces within 10 microns of the opening to each chamber of the plurality of chambers may include the hydrophobic coating.

In some variations, the hydrophobic coating may have a contact angle from about 45 degrees to about 100 degrees. In some embodiments, the hydrophobic coating may be covalently bonded to the at least a portion of the surfaces forming the channel proximal to the opening to each chamber of the plurality of chambers.

In some variations, the water immiscible fluidic medium may include an alkane, a fluoroalkane, an oil, a hydrophobic polymer, or any combination thereof.

In some variations, the process may further include aspirating the water immiscible fluidic medium out of the channel. In some embodiments, the rate of aspiration of the water immiscible fluidic medium out of the channel may be at or between 0.01 µl/sec and 1.0 µl/sec. In some embodiments, aspirating the water immiscible fluidic medium further may include subsequently aspirating a second aqueous medium into the channel. In some variations, the second aqueous medium may include a surfactant.

In some variations, at least a portion of the surfaces forming each chamber of the plurality may include a hydrophobic coating, and the at least a portion of the chamber surfaces having a hydrophobic coating may be located proximal to the opening to the channel, where the process may further include: generating an encapsulation layer of water immiscible fluidic media in each chamber of the plurality of chambers, where the encapsulation layer of each chamber of the plurality is located immediately adjacent to the channel and shares an interface with the first aqueous medium in the chamber so as to separate (e.g., isolate) the first aqueous medium in the chamber from a medium present in the channel (e.g., second aqueous medium, air, $CO_2$, another gas, or a different water immiscible fluidic medium). In some embodiments, all of the chamber surfaces proximal to and surrounding the opening of each chamber of the plurality of chambers may include the hydrophobic coating. In some other embodiments, all of the chamber surfaces within 10 microns of the opening of each chamber of the plurality of chambers may include the hydrophobic coating. In some variations, the hydrophobic coating of the channel surfaces may be the same as the hydrophobic coating of the chamber surfaces.

In some variations, the encapsulation layer of each chamber of the plurality of chambers may have an average thickness of about 5 µm to about 50 µm.

In some embodiments, the process may further include: selecting one (or more) of the first and second chambers having a cell disposed therein; and removing the encapsulation layer formed by the water immiscible fluidic medium at the opening to the channel of the selected chamber(s), thereby generating a de-encapsulated chamber. In some embodiments, selectively removing the encapsulation layer may include generating a bubble within the chamber (e.g., generating a bubble proximal to the encapsulation layer). In some variations, generating the bubble may include directing a laser at a location on an inner surface of a base of the chamber proximal to the interface between the first aqueous medium and the water immiscible fluid medium.

In some variations, the process may further include flowing a third aqueous medium into the channel. The third aqueous medium may include a reagent, such as an assay reagent or a lytic reagent (e.g., the third aqueous medium can be a lysis buffer), or an export buffer.

In some variations, the process may further include disposing a capture bead (e.g., a bead that binds biological material, such as a non-specific capture bead, an antigen-specific capture bead, an enzyme capture bead, or a nucleic acid capture bead) into one or both of the first and second chambers. In some variations, the process may further include unpenning the capture bead from the de-encapsulated chamber (e.g., and further analyzing material bound to the capture bead); and, optionally, exporting the capture bead from the microfluidic device (e.g., and further analyzing material bound to the capture bead).

In some variations, disposing the first and second cells in the first and second chambers may include: flowing in a cell-containing aqueous medium including a plurality of cells into the channel of the microfluidic device; and selecting the first and second cells from the plurality of cells in the cell-containing aqueous medium in the channel of the microfluidic device for disposition in each of the first and second chambers, respectively. In some embodiments, the selected first and second cells may be individually moved from the channel to the first and second chambers, respectively, using DEP force (e.g., light-actuated DEP force).

In some embodiments, each chamber of the plurality of chambers may be a sequestration pen having a single opening to the channel and may including an isolation region (e.g., having a single opening) and a connection region fluidically connecting the isolation region to the channel. In some variations, the connection region of each sequestration pen may include a proximal opening to the channel and a distal opening to the isolation region, the proximal opening of the connection region having a width $W_{con}$ ranging from about 20 microns to about 100 microns, and where a length $L_{con}$ of the connection region from the proximal opening to the distal opening may be as least 1.0 times the width $W_{con}$ of the proximal opening of the connection region. In some embodiments, the width $W_{con}$ at the proximal opening of each sequestration pen may be about 20 microns to about 60 microns or about 30 microns to about 90 microns. In some embodiments, the length $L_{con}$ of the connection region may be at least 1.5 times the width $W_{con}$. In some other embodiments, the length $L_{con}$ of the connection region may be at least 2.0 times the width $W_{con}$. In some embodiments, the length $L_{con}$ of the connection region may be between about 20 microns and about 500 microns.

In some variations, a ratio of a width $W_{ch}$ of the channel (e.g., a channel having a substantially uniform width) to a width $W_{op}$ of the opening of each chamber of the plurality of chambers (or a width $W_{con}$ of the proximal opening of the connection region of each sequestration pen) may be about 1.25 or greater (e.g., about 1.5 or greater, about 2.0 or greater, about 2.5 or greater, or about 3.0 or greater). In some variations, a width $W_{ch}$ of the channel (e.g., a channel having a substantially uniform width) at the opening of each chamber of the plurality (e.g., at a proximal opening to a connection region of a sequestration pen) may have a size between about 50 microns and about 500 microns. In some other variations, a width $W_{ch}$ of the channel (e.g., a channel having a substantially uniform width) at the opening of each chamber of the plurality (e.g., a proximal opening to a connection region of a sequestration pen) may have a size of about 70 microns to about 250 microns (e.g., about 80 microns to about 200 microns, about 90 microns to about 150 microns, or about 200 microns to about 250 microns).

In some variations, a height of the channel at the opening of each chamber of the plurality of chambers (or at the proximal opening of the connection region of each sequestration pen) may be between about 20 microns and about 100 microns (e.g., about 30 microns to about 50 microns, about 50 microns to about 70 microns, about 70 microns to about 90 microns, about 35 microns to about 45 microns, about 45 microns to about 55 microns, about 55 microns to about 65 microns, about 65 microns to about 75 microns, or about 75 microns to about 85 microns).

In some variations, a volume of each chamber of the plurality (or each sequestration pen) may range from about $2\times10^5$ to about $2\times10^6$ cubic microns.

In some variations, less than or equal to 50% of a total surface area of the surfaces forming the channel may include the hydrophobic coating. In some other variations, greater than or equal to 50% of a total surface area of the surfaces forming the channel may include the hydrophobic coating.

In some variations, each chamber of the plurality of chambers may include a plurality of surfaces forming the chamber, where at least one chamber surface of the plurality may include a hydrophilic coating. In some variations, the plurality of chambers may include a plurality of sequestration pens, each sequestration pen having a single opening to the channel and may include an isolation region (e.g., having a single opening) and a connection region fluidically connecting the isolation region to the channel, and where at least one surface (e.g., all surfaces) forming the isolation region of each sequestration pen may include the hydrophilic coating. In some variations, at least one surface (e.g., all surfaces) forming the connection region of each sequestration pen may include the hydrophilic coating. In some variations, each of the at least one surface (e.g., all surfaces) forming the connection region may include a portion proximal to the isolation region having the hydrophilic coating and a portion proximal to the channel having the hydrophobic coating, and, optionally, when all surfaces forming the connection region may include a portion proximal to the channel having the hydrophobic coating, providing a hydrophobic coating that encircles a portion of the connection region immediately adjacent to the channel.

In some variations, the hydrophobic coating may include a first covalently bound surface modification may including: a first linking group, and a first moiety, where the first moiety is nonpolar (e.g., an oleic acid moiety, alkynyl moiety, alkynyl-terminated PEG moiety, or fluorinated moiety). In some variations, the hydrophilic coating may include a plurality of second covalently bound surface modifications, each including a second linking group, and a second moiety, where the second moiety is polar (e.g., a methoxy terminated PEG moiety, a carboxylic acid, a carboxylic acid terminated PEG moiety, an alcohol moiety or an alcohol terminated PEG moiety).

In some variations, the hydrophobic coating may be formed by: contacting the at least a portion of surfaces forming the channel with a first modifying reagent; and reacting the first modifying reagent with a plurality of first reactive moieties on the at least a portion of surfaces forming the channel. In some variations, the hydrophilic coating may be formed by: contacting the at least one surface of the chamber (e.g., sequestration pen) with a hydrophilic modifying reagent; and reacting the second modifying reagent with a plurality of second reactive moieties on the at least one surface of the chamber.

In another aspect, a process is provided for assaying encapsulated cells in a microfluidic device having an enclosure including a channel and a plurality of chambers, each chamber of the plurality having an opening (e.g., a single opening) fluidically connecting the chamber to the channel, where at least a portion of surfaces forming the channel proximal to each chamber of the plurality includes a hydrophobic coating, where the process includes: filling the channel and the plurality of chambers in the enclosure of the microfluidic device with a first aqueous medium; disposing a first cell in a first chamber of the plurality of chambers; disposing a second cell in a second chamber of the plurality of chambers; flowing a water immiscible fluidic medium into the channel, displacing substantially all of the first aqueous medium in the channel without substantially displacing the first aqueous medium in any of the plurality of chambers, thereby reversibly encapsulating the first and second cells in their respective chambers; and monitoring an activity of the cell(s) encapsulated in the first and second chambers. In some variations, all of the channel surfaces proximal to and surrounding the opening to each chamber of the plurality of chambers may include the hydrophobic coating. In some variations, all of the channel surfaces within 10 microns of the opening to each chamber of the plurality of chambers may include the hydrophobic coating. In some variations, the hydrophobic coating may have a contact angle from about 45 degrees to about 100 degrees. In some variations, the hydrophobic coating may be covalently bonded to the portion of the surfaces forming the channel proximal to each chamber of the plurality of chambers.

In some variations, the water immiscible fluidic medium may include an alkane, a fluoroalkane, an oil, a hydrophobic polymer, or any combination thereof.

In some variations, the process may further include aspirating the water immiscible fluidic medium out of the channel. In some embodiments, the rate of aspiration of the water immiscible fluidic medium out of the channel may be at or between 0.01 µl/sec and 1.0 µl/sec. In some embodiments, aspirating the water immiscible fluidic medium further may include subsequently aspirating a second aqueous medium into the channel. In some embodiments, the second aqueous medium may include a surfactant.

In some variations, at least a portion of the surfaces forming each chamber of the plurality may include a hydrophobic coating, and the at least a portion of the chamber surfaces having a hydrophobic coating is located proximal to the opening to the channel, the process may further include: generating an encapsulation layer of water immiscible fluidic media in each chamber of the plurality of chamber, where the encapsulation layer of each chamber of the plurality may be located immediately adjacent to the channel and may share an interface with the first aqueous medium in the chamber so as to separate (e.g., isolate) the first aqueous medium in the chamber from a medium present in the channel (e.g., second aqueous medium, air, CO2, another gas, or a different water immiscible fluidic medium). In some variations, all of the chamber surfaces proximal to and surrounding the opening of each chamber of the plurality of chambers may include the hydrophobic coating. In some other variations, all of the chamber surfaces within 10 microns of the opening of each chamber of the plurality of chambers may include the hydrophobic coating. In some embodiments, the hydrophobic coating of the channel surfaces may be the same as the hydrophobic coating of the chamber surfaces.

In some variations, the encapsulation layer of each chamber of the plurality of chambers may have an average thickness of about 5 microns to about 50 microns.

In some variations, the process may further include: selecting one (or more) of the at least two chambers having a cell disposed therein; and removing the encapsulation layer formed by the immiscible fluidic medium at the opening to the channel of the selected chamber(s), thereby generating a de-encapsulated chamber. In some variations, selectively removing the encapsulation layer may include generating a bubble within the chamber (e.g., generating a bubble proximal to the encapsulation layer). In some variations, generating the bubble may include directing a laser at a location on an inner surface of a base of the chamber proximal to the interface between the first aqueous medium and the water immiscible fluidic medium.

In some variations, the process may further include flowing a third aqueous medium into the channel. The third aqueous medium may include a reagent, such as an assay reagent or a lytic reagent (e.g., the third aqueous medium can be a lysis buffer), or an export buffer.

In some variations, the process may further include disposing a capture bead (e.g., a bead that selectively binds biological material, such as an antigen capture bead, an enzyme capture bead, or a nucleic acid capture bead) into one or both of the first and second chambers.

In some variations, the process may further include unpenning the capture bead from the de-encapsulated chamber (e.g., further analyzing material bound to the capture bead); and, optionally, exporting the capture bead from the microfluidic device (e.g., and further analyzing material bound to the capture bead).

In some variations, disposing the first and second cells in the first and second chambers may include: flowing an aqueous medium including a plurality of cells into the channel of the microfluidic device; and selecting the first and second cells from the cell-containing aqueous medium in the channel of the microfluidic device for disposition in the first and second chambers, respectively. In some embodiments, the selected first and second cells may be individually moved from the channel to the first and second chambers, respectively, using DEP force (e.g., light-actuated DEP force).

In some variations, each chamber of the plurality of chambers may be a sequestration pen having a single opening to the channel and may include an isolation region (e.g., having a single opening) and a connection region fluidically connecting the isolation region to the channel. In some embodiments, the connection region of each sequestration pen may include a proximal opening to the channel and a distal opening to the isolation region, the proximal opening of the connection region having a width $W_{con}$ ranging from about 20 microns to about 100 microns, and where a length $L_{con}$ of the connection region from the proximal opening to the distal opening may be as least 1.0 times the width $W_{con}$ of the proximal opening of the connection region. In some embodiments, the width $W_{con}$ at the proximal opening of each sequestration pen may be about 20 microns to about 60 microns or about 30 microns to about 90 microns.

In some embodiments, the length $L_{con}$ of the connection region may be at least 1.5 times the width $W_{con}$. In some other embodiments, the length $L_{con}$ of the connection region may be at least 2.0 times the width $W_{con}$. In some embodiments, the length $L_{con}$ of the connection region may be between about 20 microns and about 500 microns.

In some variations, a ratio of a width $W_{ch}$ of the channel (e.g., a channel having substantially uniform width) to a width $W_{op}$ of the opening of each chamber of the plurality of chambers (or a width $W_{con}$ of the proximal opening of the connection region of each sequestration pen) to the channel may be about 1.25 or greater (e.g., about 1.5 or greater, about 2.0 or greater, about 2.5 or greater, or about 3.0 or greater). In some variations, a width $W_{ch}$ of the channel (e.g., a channel having substantially uniform width) at the opening of each chamber of the plurality of chambers (or at the proximal opening of the connection region of each sequestration pen) may be between about 50 microns and about 500 microns. In some variations, a width $W_{ch}$ of the channel (e.g., a channel having substantially uniform width) at the opening of each chamber of the plurality of chambers (or at the proximal opening of the connection region of each sequestration pen) may be about 70 microns to about 250 microns, about 80 microns to about 200 microns, or about 90 microns to about 150 microns.

In some variations, a height of the channel at the opening of each chamber of the plurality of chambers (or at the proximal opening of the connection region of each sequestration pen) may be between about 20 microns and about 100 microns (e.g., about 30 microns to about 50 microns, about 50 microns to about 70 microns, about 70 microns to about 90 microns, about 35 microns to about 45 microns, about 45 microns to about 55 microns, about 55 microns to about 65 microns, about 65 microns to about 75 microns, or about 75 microns to about 85 microns). In some variations, a volume of each chamber of the plurality of chambers (or each sequestration pen) may range from about $2 \times 10^5$ to about $2 \times 10^6$ cubic microns.

In some variations, less than or equal to 50% of a total surface area of the surfaces forming the channel may include the hydrophobic coating. In some other variations, greater than or equal to 50% of a total surface area of the surfaces forming the channel may include the hydrophobic coating.

In some variations, each chamber of the plurality of chambers may include a plurality of surfaces forming the chamber, where at least one chamber surface of the plurality may include a hydrophilic coating. In some variations, the plurality of chambers may include a plurality of sequestration pens, each sequestration pen having a single opening to the channel and may including an isolation region (e.g., having a single opening) and a connection region fluidically connecting the isolation region to the channel, and where at least one surface (e.g., all surfaces) forming the isolation region of each sequestration pen of the plurality may include the hydrophilic coating. In some variations, at least one surface (e.g., all surfaces) forming the connection region of each sequestration pen of the plurality may include the hydrophilic coating.

In some variations, each of the at least one surface (e.g., all surfaces) forming the connection region may include a portion proximal to the isolation region having the hydrophilic coating and a portion proximal to the channel having the hydrophobic coating, and, optionally when all surfaces forming the connection region may include a portion proximal to the channel having the hydrophobic coating, they provide a hydrophobic coating that encircles a portion of the connection region immediately adjacent to the channel.

In some variations, the hydrophobic coating may include a first covalently bound surface modification including: a first linking group, and a first moiety, where the first moiety is nonpolar (e.g., an oleic acid moiety, alkynyl moiety, alkynyl-terminated PEG moiety, or fluorinated moiety). In some variations, the hydrophilic coating may include a plurality of second covalently bound surface modifications, each including a second linking group, and a second moiety, where the second moiety may be polar (e.g., a methoxy terminated PEG moiety, a carboxylic acid, a carboxylic acid terminated PEG moiety, an alcohol moiety or an alcohol terminated PEG moiety).

In some variations, the process may further include incubating the first and second cells encapsulated in the first and second chambers for a first period of time before monitoring the activity of the first and second cells. In some variations, the process may further include incubating the first and second cells encapsulated in each of the first and second chambers for a first period of time and monitoring the activity of the first and second cells at a plurality of time points during the first period of time. In some variations, the process may further include monitoring the activity of the incubating first and second cells substantially continuously during the first period of time. In some variations, the first period of time may be at least 30 minutes. In some embodiments, the first period of time may be between 4 hours and 24 hours (e.g., between 8 hours and 12 hours, between 12 hours and 16 hours, between 16 hours and 20 hours).

In some variations, the process may further include incubating the cells at a temperature between 18° C. and 50° C. (e.g., between 25° C. and 37° C.).

In some variations, the first and second cells may express variable amounts of a molecule of interest or a reporter molecule. In some variations, the molecule of interest may be a small molecule. In some other variations, the molecule of interest may be a protein. In some further variations, the molecule of interest may be a nucleic acid. In some variations, the molecule of interest may be secreted.

In some variations, monitoring the activity of the first and second cells encapsulated in the first and second chambers, respectively, may include detecting the molecule of interest or reporter molecule present in each of the first and section chambers. In some variations, detecting the molecule of interest or reporter molecule may include detecting a fluorescent signal associated with or produced by the molecule of interest or reporter molecule. In some variations, detecting the molecule of interest or reporter molecule may include detecting binding of the molecule of interest or reporter molecule to a solid substrate, where the solid substrate (e.g., a bead) may include a receptor for the molecule of interest.

In some variations, monitoring the activity of the first and second cells may include imaging the first and second chambers, respectively. In some variations, the first and second cells may be imaged to monitor one or more phenotypic parameters of the cells. In some variations, monitoring the activity of the first and second cells may include monitoring cell growth.

In some variations, the water immiscible fluidic medium flowed/flowing through the channel may include soluble oxygen. The first aqueous medium may include a carbon/energy source and, optionally, other minerals and nutrients.

In some variations, the process may further include selecting cells of interest from the first and second cells for additional assays based upon a detected activity of the cell. e.g., based on predetermined criteria or relative to the detected activity of cells in other chambers of the microfluidic device). In some variations, the selection may be based upon an amount of expression of the molecule of interest, an amount of cell growth, or a combination thereof.

In some variations, the process may further include disposing a micro-object into each of the first and second chambers of the plurality of chambers, where the micro-object may include a molecule configured to affect or test a biological activity of the first and second cells disposed therein. In some variations, the molecule may be associated with the micro-object non-covalently. In some variations, disposing the micro-object into each of the first and second chambers may be performed prior to encapsulating the first and second cells within their respective chambers.

In some variations, the process may further include introducing a release reagent into each of the first and second chambers subsequent to introducing the micro-objects therein, where the release reagent is configured to trigger release of the molecule from the micro-objects. In some variations, introducing the release reagent into each of the first and second chambers may be performed prior to encapsulating the first and second cells within their respective chambers.

In some variations, the process may further include triggering release of the molecule from the micro-object. In some variations, triggering release of the molecule from the micro-objects may include increasing a temperature of each of the first and second chambers of the microfluidic device.

In some variations, triggering release may include directing laser illumination at the micro-object in each of the first and second chambers.

In some variations, the process may further include assessing whether the molecule may include by the micro-objects changes the expression of the molecule of interest (or the reporter molecule) by the first or second cells. In some variations, the process may further include quantifying the change in expression of the molecule of interest (or the reporter molecule) of the first and second cells (e.g., quantifying the change in the first cell relative to the second cell, or vice versa, or relative to one more cells disposed in chambers of the plurality of chambers other than the first and second chambers). In some variations, the micro-object may further include an identifier configured to permit tracking of the identity of the molecule.

In some variations, each chamber of the plurality of chambers opens laterally from the channel.

In some variations, the enclosure of the microfluidic device may further include: a base; a microfluidic circuit structure disposed on an inner surface of the base; and a cover disposed over the microfluidic circuit structure, where the base, the microfluidic circuit structure, and the cover together define the channel and the plurality of chambers. The inner surface of the base and/or an inner surface of the cover may include a metal, metal oxide, glass, polymer, or any combination thereof. In some variations, the cover or the base of the microfluidic device may include a DEP configuration. In some variations, the DEP configuration may be optically actuated.

In some variations, the first and second cells may be yeast cells.

In some variations, the first and second cells may be spores derived from filamentous fungus.

In some variations, the first and second cells may be mammalian cells. In some other variations, the first and second cells may be immune cells. In some further variations, the first and second cells may be T cells. In some variations, the first and second cells may be B cells. In some other variations, the first and second cells are bacterial cells. In some variations, the first and second cells may be plant cells. In some variations, the first and second cells may be fetal cells. In some variations, the first and second cells may be stem cells or progenitor cells.

In another aspect, a microfluidic device is provided, having an enclosure including a channel and a plurality of chambers, each chamber of the plurality of chambers having an opening (e.g., a single opening) fluidically connecting the chamber to the channel, where each chamber of the plurality of chambers is formed by a plurality of surfaces having a total surface area, with a first portion of the total surface of each chamber including a hydrophobic coating and a second portion of the total surface area of each chamber including a hydrophilic coating, and where the first portion of the total surface area of each chamber may be located proximal to a boundary between the chamber opening and the channel.

In some variations, the first portion of the total surface area of each chamber of the plurality of chambers is proximal to and surrounding the opening of the chamber to the channel (e.g., each surface forming the opening of the chamber may include the hydrophobic coating at a location proximal to the boundary between the chamber opening and the channel). In some variations, all of the total surface area of each chamber of the plurality of chambers located within about 10 microns (e.g., within about 20 microns, about 25 microns, about 30 microns, about 35 microns, about 40 microns, about 45 microns, about 50 microns, about 55 microns, about 60 microns, or more) of the boundary between the chamber opening and the channel may include the hydrophobic coating. In some variations, the channel may be formed by a plurality of surfaces having a total surface area, with one or more portions of the total surface area of the channel including a hydrophobic coating (e.g., the same hydrophobic coating as the plurality of chambers).

In some variations, each of the one or more portions of the total surface area of the channel including the hydrophobic coating may be located proximal to the boundary between the channel and a corresponding chamber of the plurality of chambers. In some variations, all of the total surface area of the channel located within about 10 microns (e.g., within about 20 microns, about 25 microns, about 30 microns, about 35 microns, about 40 microns, about 45 microns, about 50 microns, about 55 microns, about 60 microns, or more) of the boundaries between the channel and the openings of the plurality of chambers may include the hydrophobic coating.

In some variations, substantially all (e.g., at least 80%, 85%, 90%, 95%, 98%, 99%, or more) of the total surface area of the channel may include the hydrophobic coating. In some variations, the hydrophobic coating of the plurality of chambers may have a contact angle from about 45 degrees to about 100 degrees.

In some variations, each chamber of the plurality of chambers may be a sequestration pen including an isolation region and a connection region fluidically connecting the isolation region to the channel. In some variations, the hydrophobic coating of each sequestration pen may be present in the connection region and substantially absent from the isolation region (e.g., a total surface area of chamber surfaces forming the isolation region may include less than 5%, 4%, 3%, 2%, 1.5%, 1%, 0.5% of the hydrophobic coating).

In some variations, less than or equal to 50% of a total surface area of chamber surfaces forming the connection region of each sequestration pen may include the hydrophobic coating. In some other variations, greater than or equal to 50% of a total surface area of chamber surfaces forming the connection region of each sequestration pen may include the hydrophobic coating.

In some variations, chamber surfaces forming the connection region of each sequestration pen and including the hydrophobic coating may form a ring surrounding a proximal end of the connection region (e.g., starting at the boundary between the channel and the proximal opening of the connection region and extending into the connection region). In some variations, greater than or equal to 50% of a total surface area of chamber surfaces forming the isolation region of each sequestration pen may include the hydrophilic coating.

In some variations, substantially all of a total surface area of chamber surfaces forming the isolation region of each sequestration pen may include the hydrophilic coating (e.g., at least 80%, 85%, 90%, 95%, 98%, 99%, or more).

In some variations, the connection region of each sequestration pen may include a proximal opening to the channel and a distal opening to the isolation region, the proximal opening of the connection region having a width $W_{con}$ ranging from about 20 microns to about 100 microns (e.g., about 20 microns to about 60 microns, or about 30 microns to about 90 microns), and where a length $L_{con}$ of the connection region from the proximal opening to the distal opening is as least 1.0 times the width $W_{con}$ of the proximal opening of the connection region. In some variations, the length $L_{con}$ of the connection region may be at least 1.5 times the width $W_{con}$. In some other variations, the length $L_{con}$ of the connection region may be at least 2.0 times the width $W_{con}$. In some variations, the length $L_{con}$ of the connection region may be between about 20 microns and about 500 microns.

In some variations, a ratio of a width $W_{ch}$ of the channel (e.g., a channel having substantially uniform width) to a width $W_{op}$ of the opening of each chamber of the plurality of chambers (or a width $W_{con}$ of a proximal opening of the connection region of each sequestration pen) to the channel may be about 1.25 or greater (e.g., about 1.5 or greater, about 2.0 or greater, or about 3.0 or greater). In some variations, a width $W_{ch}$ of the channel (e.g., a channel having substantially uniform width) at the opening of each chamber of the plurality of chambers (or at a proximal opening of the connection region of each sequestration pen) may be between about 50 microns and about 500 microns.

In some variations, a width $W_{ch}$ of the channel (e.g., a channel having substantially uniform width) at the opening of each chamber of the plurality of chambers (or at a proximal opening of the connection region of each sequestration pen) may be about 70 microns to about 250 microns (e.g., about 80 microns to about 200 microns, or about 90 microns to about 150 microns). In some variations, a height of the channel at the opening of each chamber of the plurality of chambers (or at a proximal opening of the connection region of each sequestration pen) may be between about 20 microns and about 100 microns (e.g., about 30 microns to about 50 microns).

In some variations, a volume of each chamber of the plurality of chambers (or each sequestration pen) may range from about $2 \times 10^5$ to about $2 \times 10^6$ cubic microns.

In some variations, the enclosure of the microfluidic device may further include: a base; a microfluidic circuit structure disposed on an inner surface of the base; and a cover disposed over the microfluidic circuit structure, where the base, the microfluidic circuit structure, and the cover together define the channel and the plurality of chambers.

In some variations, the hydrophobic coating may include a first covalently bound surface modification may including: a first linking group, and a first moiety, where the first moiety is nonpolar (e.g., an oleic acid moiety, alkynyl moiety, PEG-linked alkynyl, or fluorinated moiety). In some variations, the hydrophilic coating may include a plurality of second covalently bound surface modifications, each including a second linking group, and a second moiety, where the second moiety is polar (e.g., a methoxy terminated PEG moiety, a carboxylic acid, a carboxylic acid terminated PEG moiety, an alcohol moiety or an alcohol terminated PEG moiety).

In another aspect a kit is provided for encapsulating cells, including: a microfluidic device having an enclosure including a channel and a plurality of chambers, each chamber of the plurality having an opening (e.g., a single opening) fluidically connecting the chamber to the channel, where at least a portion of inner surfaces forming the channel and each chamber may include a plurality of reactive moieties; a first surface modifying reagent may including a first linking group configured to covalently bind with the reactive moieties, and a first surface contact moiety, where the first surface contact moiety may be nonpolar (e.g., an oleic acid moiety, alkynyl moiety, PEG-linked alkynyl, or fluorinated moiety); and a second surface modifying reagent including a second linking group configured to covalently bind with the reactive moieties, and a second surface contact moiety, where the second surface contact moiety is polar (e.g., a methoxy terminated PEG moiety, a carboxylic acid, a carboxylic acid terminated PEG moiety, an alcohol moiety or an alcohol terminated PEG moiety), where the kit can be used to generate the microfluidic device as described herein and having any combination of features.

In some variations, the plurality of reactive moieties may include azido moieties or alkynyl moieties.

In some variations, the kit may further include a plurality of capture beads (e.g., beads that bind biological material, such as non-specific capture beads, antigen-specific capture beads, enzyme capture beads, or nucleic acid capture beads).

In some variations, the kit may further include one or more of an aqueous medium, a water immiscible fluidic medium (e.g., an alkane, a fluoroalkane, an oil, a hydrophobic polymer, or any combination thereof), an assay reagent (e.g., a lytic reagent, such as a lysis buffer), or an export buffer.

Additional aspects and embodiments of the methods and processes disclosed herein will become evident from the detailed description, examples, embodiments, and claims which follow hereafter.

BRIEF DESCRIPTION OF THE DRAWINGS

FIGS. 6A to 6L illustrate regioselectively introduced modified surfaces within a microfluidic devices according to some embodiments of the disclosure.

FIGS. 7C to 7D illustrates regioselectively introduced modified surfaces within a microfluidic device according to some embodiments of the disclosure.

FIGS. 9A to 9C illustrate an exemplary method for generating and removing a thin film encapsulation layer (or seal).

FIGS. 10A to 10E illustrates an exemplary method for bulk removal of the encapsulation layer.

FIGS. 13A and 13B show corresponding bright field and fluorescent images, respectively, 30 minutes after the start of the assay. FIGS. 13C and 13D show corresponding bright field and fluorescent images, respectively, of the same sequestration pens 16 hours after the start of the assay.

DETAILED DESCRIPTION

Figure 1A:
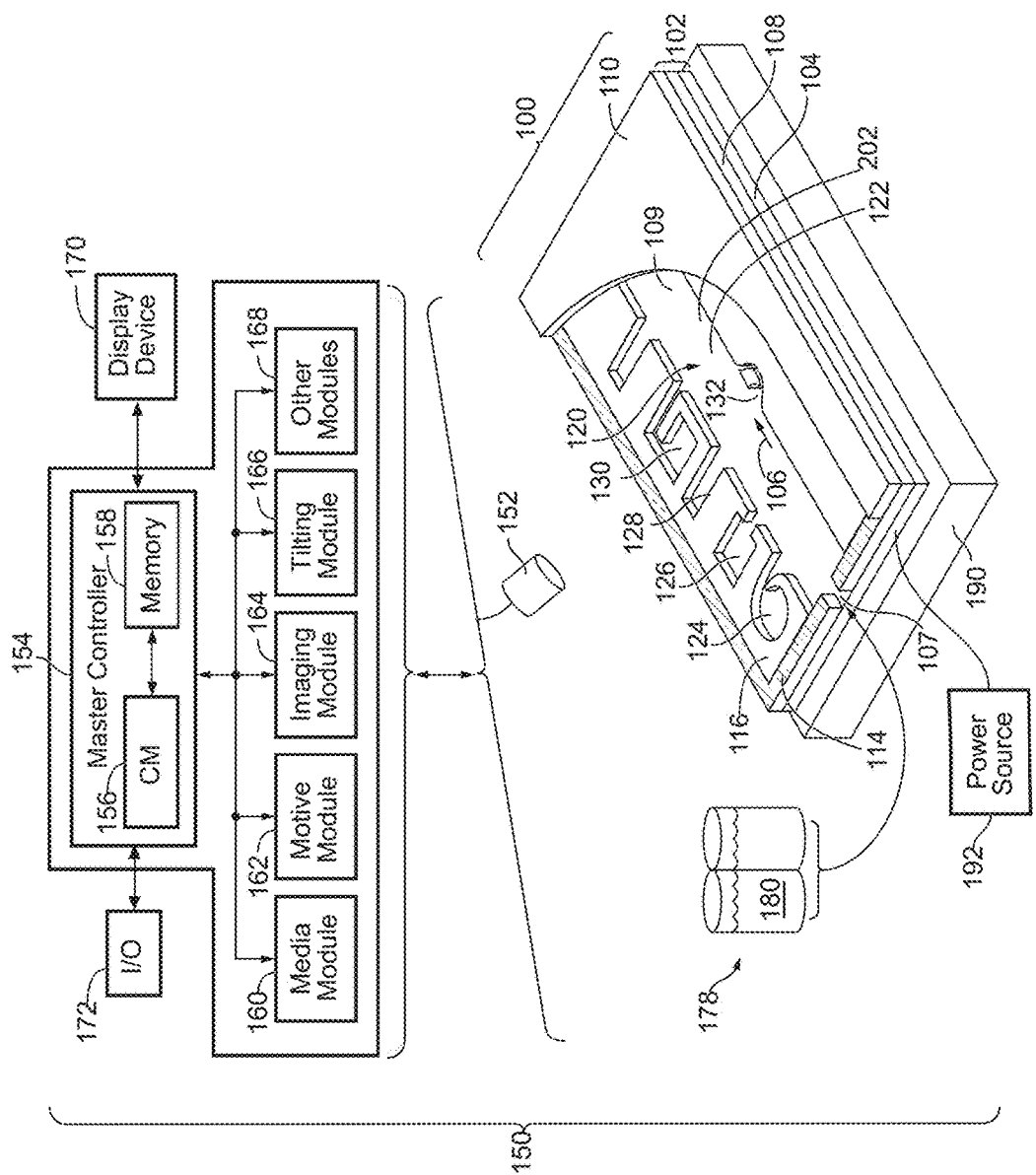
FIG. 1A illustrates a microfluidic device and a system with associated control equipment according to some embodiments of the disclosure.

This specification describes exemplary embodiments and applications of the disclosure. The disclosure, however, is not limited to these exemplary embodiments and applications or to the manner in which the exemplary embodiments and applications operate or are described herein. Moreover, the figures may show simplified or partial views, and the dimensions of elements in the figures may be exaggerated or otherwise not in proportion. In addition, as the terms "on," "attached to," "connected to," "coupled to," or similar words are used herein, one element (e.g., a material, a layer, a substrate, etc.) can be "on," "attached to," "connected to," or "coupled to" another element regardless of whether the one element is directly on, attached to, connected to, or coupled to the other element or there are one or more intervening elements between the one element and the other element. Also, unless the context dictates otherwise, directions (e.g., above, below, top, bottom, side, up, down, under, over, upper, lower, horizontal, vertical, "x," "y," "z," etc.), if provided, are relative and provided solely by way of example and for ease of illustration and discussion and not by way of limitation. In addition, where reference is made to a list of elements (e.g., elements a, b, c), such reference is intended to include any one of the listed elements by itself, any combination of less than all of the listed elements, and/or a combination of all of the listed elements. Section divisions in the specification are for ease of review only and do not limit any combination of elements discussed.

Where dimensions of microfluidic features are described as having a width or an area, the dimension typically is described relative to an x-axial and/or y-axial dimension, both of which lie within a plane that is parallel to the substrate and/or cover of the microfluidic device. The height of a microfluidic feature may be described relative to a z-axial direction, which is perpendicular to a plane that is parallel to the substrate and/or cover of the microfluidic device. In some instances, a cross sectional area of a microfluidic feature, such as a channel or a passageway, may be in reference to a x-axial/z-axial, a y-axial/z-axial, or an x-axial/y-axial area.

As used herein, "substantially" means sufficient to work for the intended purpose. The term "substantially" thus allows for minor, insignificant variations from an absolute or perfect state, dimension, measurement, result, or the like such as would be expected by a person of ordinary skill in the field but that do not appreciably affect overall performance. When used with respect to numerical values or parameters or characteristics that can be expressed as numerical values, "substantially" means within ten percent.

The term "ones" means more than one. As used herein, the term "plurality" can be 2, 3, 4, 5, 6, 7, 8, 9, 10, or more.

As used herein: μm means micrometer, $μm^3$ means cubic micrometer, pL means picoliter, nL means nanoliter, and μL (or uL) means microliter.

As used herein, "alkyl" refers to a straight or branched hydrocarbon chain radical consisting solely of carbon and hydrogen atoms, containing no unsaturation, having from one to six carbon atoms (e.g., $C_1$-$C_6$ alkyl). Whenever it appears herein, a numerical range such as "1 to 6" refers to each integer in the given range; e.g., "1 to 6 carbon atoms" means that the alkyl group may consist of 1 carbon atom, 2 carbon atoms, 3 carbon atoms, etc., up to and including 6 carbon atoms, although the present definition also covers the occurrence of the term "alkyl" where no numerical range is designated. In some embodiments, it is a $C_1$-$C_3$ alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, and the like. The alkyl is attached to the rest of the molecule by a single bond, for example, methyl (Me), ethyl (Et), n-propyl, 1-methylethyl (isopropyl), n-butyl, n-pentyl, 1,1-dimethylethyl (t-butyl), hexyl, and the like.

Unless stated otherwise specifically in the specification, an alkyl group may be optionally substituted by one or more substituents which independently are: aryl, arylalkyl, heteroaryl, heteroarylalkyl, hydroxy, halo, cyano, trifluoromethyl, trifluoromethoxy, nitro, trimethylsilanyl, —OR', —SR', —OC(O)—R', —N(R')$_2$, —C(O)R', C(O)OR', —OC(O)N(R')$_2$, —C(O)N(R')$_2$, —N(R')C(O)OR', —N(R')C(O)R', —N(R')C(O)N(R')$_2$, N(R')C(NR')N(R')$_2$, —N(R')S(O)$_t$R' (where t is 1 or 2), S(O)$_t$OR' (where t is 1 or 2), —S(O)$_t$N(R')$_2$ (where t is 1 or 2), or PO$_3$(R')$_2$ where each R' is independently hydrogen, alkyl, fluoroalkyl, aryl, aralkyl, heterocycloalkyl, or heteroaryl.

As referred to herein, a fluorinated alkyl moiety is an alkyl moiety having one or more hydrogens of the alkyl moiety replaced by a fluoro substituent. A perfluorinated alkyl moiety has all hydrogens attached to the alkyl moiety replaced by fluoro substituents.

As referred to herein, a "halo" moiety is a bromo, chloro, or fluoro moiety.

As referred to herein, an "olefinic" compound is an organic molecule which contains an "alkene" moiety. An alkene moiety refers to a group consisting of at least two carbon atoms and at least one carbon-carbon double bond. The non-alkene portion of the molecule may be any class of organic molecule, and in some embodiments, may include alkyl or fluorinated (including but not limited to perfluorinated) alkyl moieties, any of which may be further substituted.

As used herein, "air" refers to the composition of gases predominating in the atmosphere of the earth. The four most plentiful gases are nitrogen (typically present at a concentration of about 78% by volume, e.g., in a range from about 70-80%), oxygen (typically present at about 20.95% by volume at sea level, e.g. in a range from about 10% to about 25%), argon (typically present at about 1.0% by volume, e.g. in a range from about 0.1% to about 3%), and carbon dioxide (typically present at about 0.04%, e.g., in a range from about 0.01% to about 0.07%). Air may have other trace gases such as methane, nitrous oxide or ozone, trace pollutants and organic materials such as pollen, diesel particulates and the like. Air may include water vapor (typically present at about 0.25%, or may be present in a range from about 10 ppm to about 5% by volume). Air may be provided for use in culturing experiments as a filtered, controlled composition and may be conditioned as described herein.

As used herein, the term "disposed" encompasses within its meaning "located."

As used herein, a "microfluidic device" or "microfluidic apparatus" is a device that includes one or more discrete microfluidic circuits configured to hold a fluid, each microfluidic circuit comprised of fluidically interconnected circuit elements, including but not limited to region(s), flow path(s), channel(s), chamber(s), and/or pen(s), and at least one port configured to allow the fluid (and, optionally, micro-objects suspended in the fluid) to flow into and/or out of the microfluidic device. Typically, a microfluidic circuit of a microfluidic device will include a flow region, which may include a microfluidic channel, and at least one chamber, and will hold a volume of fluid of less than about 1 mL, e.g., less than about 750, 500, 250, 200, 150, 100, 75, 50, 25, 20, 15, 10, 9, 8, 7, 6, 5, 4, 3, or 2 µL. In certain embodiments, the microfluidic circuit holds about 1-2, 1-3, 1-4, 1-5, 2-5, 2-8, 2-10, 2-12, 2-15, 2-20, 5-20, 5-30, 5-40, 5-50, 10-50, 10-75, 10-100, 20-100, 20-150, 20-200, 50-200, 50-250, or 50-300 µL. The microfluidic circuit may be configured to have a first end fluidically connected with a first port (e.g., an inlet) in the microfluidic device and a second end fluidically connected with a second port (e.g., an outlet) in the microfluidic device.

As used herein, a "nanofluidic device" or "nanofluidic apparatus" is a type of microfluidic device having a microfluidic circuit that contains at least one circuit element configured to hold a volume of fluid of less than about 1 µL, e.g., less than about 750, 500, 250, 200, 150, 100, 75, 50, 25, 20, 15, 10, 9, 8, 7, 6, 5, 4, 3, 2, 1 nL or less. A nanofluidic device may comprise a plurality of circuit elements (e.g., at least 2, 3, 4, 5, 6, 7, 8, 9, 10, 15, 20, 25, 50, 75, 100, 150, 200, 250, 300, 400, 500, 600, 700, 800, 900, 1000, 1500, 2000, 2500, 3000, 3500, 4000, 4500, 5000, 6000, 7000, 8000, 9000, 10,000, or more). In certain embodiments, one or more (e.g., all) of the at least one circuit elements is configured to hold a volume of fluid of about 100 pL to 1 nL, 100 pL to 2 nL, 100 pL to 5 nL, 250 pL to 2 nL, 250 pL to 5 nL, 250 pL to 10 nL, 500 pL to 5 nL, 500 pL to 10 nL, 500 pL to 15 nL, 750 pL to 10 nL, 750 pL to 15 nL, 750 pL to 20 nL, 1 to 10 nL, 1 to 15 nL, 1 to 20 nL, 1 to 25 nL, or 1 to 50 nL. In other embodiments, one or more (e.g., all) of the at least one circuit elements are configured to hold a volume of fluid of about 20 nL to 200 nL, 100 to 200 nL, 100 to 300 nL, 100 to 400 nL, 100 to 500 nL, 200 to 300 nL, 200 to 400 nL, 200 to 500 nL, 200 to 600 nL, 200 to 700 nL, 250 to 400 nL, 250 to 500 nL, 250 to 600 nL, or 250 to 750 nL.

A microfluidic device or a nanofluidic device may be referred to herein as a "microfluidic chip" or a "chip"; or "nanofluidic chip" or "chip".

A "microfluidic channel" or "flow channel" as used herein refers to flow region of a microfluidic device having a length that is significantly longer than both the horizontal and vertical dimensions. For example, the flow channel can be at least 5 times the length of either the horizontal or vertical dimension, e.g., at least 10 times the length, at least 25 times the length, at least 100 times the length, at least 200 times the length, at least 500 times the length, at least 1,000 times the length, at least 5,000 times the length, or longer. In some embodiments, the length of a flow channel is about 100,000 microns to about 500,000 microns, including any value therebetween. In some embodiments, the horizontal dimension is about 100 microns to about 1000 microns (e.g., about 150 to about 500 microns) and the vertical dimension is about 25 microns to about 200 microns, (e.g., from about 40 to about 150 microns). It is noted that a flow channel may have a variety of different spatial configurations in a microfluidic device, and thus is not restricted to a perfectly linear element. For example, a flow channel may be, or include one or more sections having, the following configurations: curve, bend, spiral, incline, decline, fork (e.g., multiple different flow paths), and any combination thereof. In addition, a flow channel may have different cross-sectional areas along its path, widening and constricting to provide a desired fluid flow therein. The flow channel may include valves, and the valves may be of any type known in the art of microfluidics. Examples of microfluidic channels that include valves are disclosed in U.S. Pat. Nos. 6,408,878 and 9,227,200, each of which is herein incorporated by reference in its entirety.

As used herein, the term "obstruction" refers generally to a bump or similar type of structure that is sufficiently large so as to partially (but not completely) impede movement of target micro-objects between two different regions or circuit elements in a microfluidic device. The two different regions/circuit elements can be, for example, a microfluidic sequestration pen and a microfluidic channel, or a connection region and an isolation region of a microfluidic sequestration pen.

As used herein, the term "constriction" refers generally to a narrowing of a width of a circuit element (or an interface between two circuit elements) in a microfluidic device. The constriction can be located, for example, at the interface between a microfluidic sequestration pen and a microfluidic channel, or at the interface between an isolation region and a connection region of a microfluidic sequestration pen.

As used herein, the term "transparent" refers to a material which allows visible light to pass through without substantially altering the light as is passes through.

As used herein, "brightfield" illumination and/or image refers to white light illumination of the microfluidic field of view from a broad-spectrum light source, where contrast is formed by absorbance of light by objects in the field of view.

As used herein, "structured light" is projected light that is modulated to provide one or more illumination effects. A first illumination effect may be projected light illuminating a portion of a surface of a device without illuminating (or at least minimizing illumination of) an adjacent portion of the surface, e.g., a projected light pattern, as described more fully below, used to activate DEP forces within a DEP substrate. When using structured light patterns to activate DEP forces, the intensity, e.g., variation in duty cycle of a structured light modulator such as a DMD, may be used to change the optical power applied to the light activated DEP actuators, and thus change DEP force without changing the nominal voltage or frequency. Another illumination effect that may be produced by structured light includes projected light that may be corrected for surface irregularities and for irregularities associated with the light projection itself, e.g., fall-off at the edge of an illuminated field. Structured light is typically generated by a structured light modulator, such as a digital mirror device (DMD), a microshutter array system (MSA), a liquid crystal display (LCD), or the like. Illumination of a small area of the surface, e.g., a selected area of interest, with structured light improves the signal-to-noise-ratio (SNR), as illumination of only the selected area of interest reduces stray/scattered light, thereby lowering the dark level of the image. An important aspect of structured light is that it may be changed quickly over time. A light pattern from the structured light modulator, e.g., DMD, may be used to autofocus on difficult targets such as clean mirrors or surfaces that are far out of focus. Using a clean mirror, a number of self-test features may be replicated such as measurement of modulation transfer function and field curvature/tilt, without requiring a more expensive Shack-Hartmann sensor. In another use of structured light patterns, spatial power distribution may be measured at the sample surface with a simple power meter, in place of a camera. Structured light patterns may also be used as a reference feature for optical module/system component alignment as well used as a manual readout for manual focus. Another illumination effect made possible by use of structured light patterns is selective curing, e.g., solidification of hydrogels within the microfluidic device.

As used herein, the term "micro-object" refers generally to any microscopic object that may be isolated and/or manipulated in accordance with the present disclosure. Non-limiting examples of micro-objects include: inanimate micro-objects such as microparticles; microbeads (e.g., polystyrene beads, glass beads, amorphous solid substrates, Luminex™ beads, or the like); magnetic beads; microrods; microwires; quantum dots, and the like; biological micro-objects such as cells; biological organelles; vesicles, or complexes; synthetic vesicles; liposomes (e.g., synthetic or derived from membrane preparations); lipid nanorafts, and the like; or a combination of inanimate micro-objects and biological micro-objects (e.g., microbeads attached to cells, liposome-coated microbeads, liposome-coated magnetic beads, or the like). Beads may include moieties/molecules covalently or non-covalently attached, such as fluorescent labels, proteins (including receptor molecules), carbohydrates, antigens, small molecule signaling moieties, or other chemical/biological species capable of use in an assay. In some variations, beads/solid substrates including moieties/molecules may be capture beads, e.g., configured to bind molecules including small molecules, peptides, proteins or nucleic acids present in proximity either selectively or nonselectively. In one nonlimiting example, a capture bead may include a nucleic acid sequence configured to bind nucleic acids having a specific nucleic acid sequence or the nucleic acid sequence of the capture bead may be configured to bind a set of nucleic acids having related nucleic acid sequences. Either type of binding may be understood to be selective. Capture beads containing moieties/molecules may bind nonselectively when binding of structurally different but physico-chemically similar molecules is performed, for example, size exclusion beads or zeolites configured to capture molecules of selected size or charge. Lipid nanorafts have been described, for example, in Ritchie et al. (2009) "Reconstitution of Membrane Proteins in Phospholipid Bilayer Nanodiscs," Methods Enzymol., 464:211-231.

As used herein, the term "cell" is used interchangeably with the term "biological cell." Non-limiting examples of biological cells include eukaryotic cells, plant cells, animal cells, such as mammalian cells, reptilian cells, avian cells, fish cells, or the like, prokaryotic cells, bacterial cells, fungal cells, protozoan cells, or the like, cells dissociated from a tissue, such as muscle, cartilage, fat, skin, liver, lung, neural tissue, and the like, immunological cells, such as T cells, B cells, natural killer cells, macrophages, and the like, embryos (e.g., zygotes), oocytes, ova, sperm cells, hybridomas, cultured cells, cells from a cell line, cancer cells, infected cells, transfected and/or transformed cells, reporter cells, and the like. A mammalian cell can be, for example, from a human, a mouse, a rat, a horse, a goat, a sheep, a cow, a primate, or the like.

A colony of biological cells is "clonal" if all of the living cells in the colony that are capable of reproducing are daughter cells derived from a single parent cell. In certain embodiments, all the daughter cells in a clonal colony are derived from the single parent cell by no more than 10 divisions. In other embodiments, all the daughter cells in a clonal colony are derived from the single parent cell by no more than 14 divisions. In other embodiments, all the daughter cells in a clonal colony are derived from the single parent cell by no more than 17 divisions. In other embodiments, all the daughter cells in a clonal colony are derived from the single parent cell by no more than 20 divisions. The term "clonal cells" refers to cells of the same clonal colony.

As used herein, a "colony" of biological cells refers to 2 or more cells (e.g. about 2 to about 20, about 4 to about 40, about 6 to about 60, about 8 to about 80, about 10 to about 100, about 20 to about 200, about 40 to about 400, about 60 to about 600, about 80 to about 800, about 100 to about 1000, or greater than 1000 cells).

As used herein, the term "maintaining (a) cell(s)" refers to providing an environment comprising both fluidic and gaseous components and, optionally a surface, that provides the conditions necessary to keep the cells viable and/or expanding.

As used herein, the term "expanding" when referring to cells, refers to increasing in cell number.

As referred to herein, "gas permeable" means that the material or structure is permeable to at least one of oxygen, carbon dioxide, or nitrogen. In some embodiments, the gas permeable material or structure is permeable to more than one of oxygen, carbon dioxide and nitrogen and may further be permeable to all three of these gases.

A "component" of a fluidic medium is any chemical or biochemical molecule present in the medium, including solvent molecules, ions, small molecules, antibiotics, nucleotides and nucleosides, nucleic acids, amino acids, peptides, proteins, sugars, carbohydrates, lipids, fatty acids, cholesterol, metabolites, or the like.

As used herein in reference to a fluidic medium, "diffuse" and "diffusion" refer to thermodynamic movement of a component of the fluidic medium down a concentration gradient.

The phrase "flow of a medium" means bulk movement of a fluidic medium primarily due to any mechanism other than diffusion, and may encompass perfusion. For example, flow of a medium can involve movement of the fluidic medium from one point to another point due to a pressure differential between the points. Such flow can include a continuous, pulsed, periodic, random, intermittent, or reciprocating flow of the liquid, or any combination thereof. When one fluidic medium flows into another fluidic medium, turbulence and mixing of the media can result. Flowing can comprise pulling solution through and out of the microfluidic channel (e.g., aspirating) or pushing fluid into and through a microfluidic channel (e.g. perfusing).

The phrase "substantially no flow" refers to a rate of flow of a fluidic medium that, when averaged over time, is less than the rate of diffusion of components of a material (e.g., an analyte of interest) into or within the fluidic medium. The rate of diffusion of components of such a material can depend on, for example, temperature, the size of the components, and the strength of interactions between the components and the fluidic medium.

As used herein in reference to different regions within a microfluidic device, the phrase "fluidically connected" means that, when the different regions are substantially filled with fluid, such as fluidic media, the fluid in each of the regions is connected so as to form a single body of fluid. This does not mean that the fluids (or fluidic media) in the different regions are necessarily identical in composition. Rather, the fluids in different fluidically connected regions of a microfluidic device can have different compositions (e.g., different concentrations of solutes, such as proteins, carbohydrates, ions, or other molecules) which are in flux as solutes move down their respective concentration gradients and/or fluids flow through the device.

As used herein, a "flow path" refers to one or more fluidically connected circuit elements (e.g. channel(s), region(s), chamber(s) and the like) that define, and are subject to, the trajectory of a flow of medium. A flow path is thus an example of a swept region of a microfluidic device. Other circuit elements (e.g., unswept regions) may be fluidically connected with the circuit elements that comprise the flow path without being subject to the flow of medium in the flow path.

As used herein, "isolating a micro-object" confines a micro-object to a defined area within the microfluidic device.

A microfluidic (or nanofluidic) device can comprise "swept" regions and "unswept" regions. As used herein, a "swept" region is comprised of one or more fluidically interconnected circuit elements of a microfluidic circuit, each of which experiences a flow of medium when fluid is flowing through the microfluidic circuit. The circuit elements of a swept region can include, for example, regions, channels, and all or parts of chambers. As used herein, an "unswept" region is comprised of one or more fluidically interconnected circuit element of a microfluidic circuit, each of which experiences substantially no flux of fluid when fluid is flowing through the microfluidic circuit. An unswept region can be fluidically connected to a swept region, provided the fluidic connections are structured to enable diffusion but substantially no flow of media between the swept region and the unswept region. The microfluidic device can thus be structured to substantially isolate an unswept region from a flow of medium in a swept region, while enabling substantially only diffusive fluidic communication between the swept region and the unswept region. For example, a flow channel of a micro-fluidic device is an example of a swept region while an isolation region (described in further detail below) of a microfluidic device is an example of an unswept region.

As used herein, a "non-sweeping" rate of fluidic medium flow means a rate of flow sufficient to permit components of a second fluidic medium in an isolation region of the sequestration pen to diffuse into the first fluidic medium in the flow region and/or components of the first fluidic medium to diffuse into the second fluidic medium in the isolation region; and further wherein the first medium does not substantially flow into the isolation region.

Methods of Encapsulating Cells and Assaying Encapsulated Cells

As will be readily apparent to persons skilled in the art, the following descriptions of various aspects of the methods of encapsulating cells and assaying encapsulated cells can be combined as needed to achieve complex workflows. Thus, for example, the individual subheading (and the teachings provided under each such subheading) are intended to highlight aspects of the methods which can be combined, as appropriate, with aspects disclosed under any of the other subheadings (and elsewhere herein).

Microfluidic culturing and assay apparatuses provide highly multiplexed environments for maintaining, expanding and studying biological micro-objects including cells. However, in some experiments, it can be desirable to prevent secretion(s) produced or emitted from a particular micro-object from diffusing out of or otherwise moving away from the specific chamber of the microfluidic apparatus containing the micro-object of interest. To that end, it has been discovered that chambers (which in some variations may be sequestration pens) in a microfluidic device can be sealed from one another by flowing a water immiscible fluidic medium through a channel from which the chambers/sequestration pens open, thereby encapsulating each chamber/sequestration pen. The water immiscible fluid medium may fill the channel entirely. Alternatively, an aqueous medium may be subsequently introduced to displace all but a thin layer of the water immiscible fluid medium encapsulating or sealing the chambers/sequestration pens. The features of the microfluidic device as described herein (e.g., the positioning of the sequestration pen/chamber and the channel on a shared horizontal plane, the structural features of the channel, and the features of the sequestration pen including the connection region and isolation region features and dimensions) may be configured to assist in preventing the water immiscible medium in the channel from entering the sequestration pen, while also permitting the aqueous fluidic medium to be retained within the pen, and further, modified surfaces may be introduced in selected sub-regions which also assist with encapsulation and de-encapsulation.

Whether sealing is accomplished by filling the channel entirely with the water immiscible fluid medium or by forming a thin encapsulation layer, encapsulation can provide chamber-to-chamber isolation (e.g., isolating a sequestration pen from any other) permitting highly selective further manipulation, assay, and export of micro-objects from any individual chamber. The encapsulation may be removed, either individually or in bulk, to permit introduction or export of reagents, assay capture objects, secreted products or biological cells, providing flexible and controllable tools for a wide variety of microfluidic workflows. Some of the variety of the workflows are described herein, but the disclosure is not so limited and any suitable experiment may use the methods of encapsulation as one of skill can determine upon reading this disclosure.

Sealing, e.g., encapsulation, may be facilitated when a surface of the channel (e.g., a surface surrounding the opening to the chambers/sequestration pens) and/or a surface of a chamber/sequestration pen includes a covalently bound modification comprising a moiety (e.g., a first surface contact moiety or a first reactive moiety) that is substantially nonpolar or hydrophobic. In some variations, all of the surface area of the surfaces of the channel may be modified, e.g., each of the side walls, the inner surface of the base and the inner surface of the cover defining the channel may be modified, while in other variations, less than all the surfaces fo the channel may be modified, and the extent of modification may be described as a percentage of the total surface area of the channel as calculated from the sum of surfaces areas forming the side walls, and the inner surfaces of the base and cover of the microfluidic device defining the channel. In some variations, less than all of the surface area of the surfaces forming each chamber/sequestration pen may be modified. For example, in some variations, only the surface area proximal to the opening of the chamber/sequestration pen to the channel can be modified. The configuration of the features of the microfluidic device described herein (e.g., the positioning of chambers/sequestration pens and channel on a shared horizontal plane, the structural features of the channel, and the features of sequestration pens, including the connection region and isolation region features and dimensions) may assist the selective modification of the surfaces within the channel and/or chambers/sequestration pens.

When less than all of the total surface area of the surfaces forming the channel are modified with a hydrophobic surface, the extent of modification may be introduced selectively and controllably to modify regions of the surfaces forming the channel proximal to the openings of chambers/sequestration pens opening thereto. For instance, a portion of the channel (e.g., less than the entire channel, less than about 95%, about 90%, about 85%, about 80%, about 75%, about 70%, about 60%, about 50%, about 40%, about 35%, about 30%, about 25%, about 20%, about 10% or less) can have a hydrophobic surface of, for example, less than 50% of the total surface area of the channel (e.g., the inner surface of the cover, inner surface of the base, and microfluidic circuit material surfaces forming side walls of the channel). In certain embodiments, 100% of the surface area of a side wall of the channel having openings to the chambers/sequestration pens may have a hydrophobic surface, while the side wall of the channel distal to the openings of the chambers/sequestration pens may not have a hydrophobic surface. In some variations, at least a portion of surfaces forming the channel proximal to the opening to each chamber (e.g., sequestration pen) may include the hydrophobic coating. For example, channel surfaces located within about 10 microns of the opening to each chamber/sequestration pen may include the hydrophobic coating. In some other variations, the portion of surfaces forming the channel proximal to the opening to each chamber/sequestration pen and having the hydrophobic coating may include all regions of the surfaces located within about 20 microns, about 30 microns, about 40 microns, about 50 microns, about 60 microns, about 70 microns, about 80 microns, about 90 microns, about 100 microns, or more) of the opening to each chamber/sequestration pen. In some embodiments, the inner surface of the cover and/or the inner surface of the base forming (e.g. defining) the channel may have a hydrophobic coating on 50% or less of the area of the inner surface of the cover and/or base, and in particular may have the hydrophobic coating on all of the surface areas of the respective cover and/or base proximal to the side wall containing the openings to the chambers/sequestration pens, while none of the surface area of the inner surfaces of the respective cover and/or base distal to the side wall of the channel containing the openings to the chamber/sequestration pens may have the hydrophobic coating (e.g., the half of the channel surface proximal to the chambers/sequestration pens may have the hydrophobic coating, while the other half of the channel surface lacks the hydrophobic coating). Typically, when a hydrophobic surface modification is introduced in the channel, most or all of the surface area of the side wall of the channel containing the openings to the chambers/sequestration pens may have the hydrophobic coating. As the amount of hydrophobic modification increases, increasing percentages of the surface area of the inner surface of the cover and/or base also increases, extending from the intersection of the inner surfaces of the cover and/or base from the side wall proximal to the openings of the chambers/sequestration pens towards the distal side wall. Therefore, a hydrophobic surface may be controllably introduced to 100% of the surface area of the surfaces forming the channel; about 50% of the surface area, less than 50% of the surface area, e.g., from about 1% to about 49%, or more than 50% of the surface area, e.g., from about 50.1% to about 100%, and may be introduced in any selected percentage therebetween as desired, as described below in greater detail.

Alternatively, or in addition to the channel surface having a hydrophobic coating, the surface of a portion of the chamber/sequestration pen (e.g., the surface of a connection region most proximal to the channel) comprises a covalently bound modification comprising a moiety (e.g., a surface contact moiety or a reactive moiety) that is substantially nonpolar or hydrophobic. In some variations, a portion of the surfaces of the connection region at the opening to the channel may have hydrophobic surfaces introduced, where each surface so modified may have a length $L_{hydrophobic}$ (731 as illustrated in FIG. 7D) which is a fraction of the $L_{con}$ (736) of the connection region. Length $L_{hydrophobic}$ 731 may be about 5%, about 10%, about 20% about 25%, about 40% about 50%, about 75%, or any percentage therebetween, of $L_{con}$ of the connection region as described herein, and may extend from the proximal opening of the connection region at the channel towards the distal end of the connection region, where the connection region opens to the isolation region of the sequestration pen. In some variations, all of the surfaces defining the connection region are so modified for length $L_{hydrophobic}$, therefore each of the side walls, inner surface of the base, and inner surface of the cover defining the sequestration pen have a portion modified proximal to the opening of the sequestration pen at the channel. For example, the surfaces of the connection region having the hydrophobic coating may form a ring at the proximal opening of the connection region to the channel. This region of hydrophobicity can assist in retaining the encapsulation layer and, in particular, may assist in defining the distance that the encapsulation layer extends from a layer of contact with the aqueous medium within the rest of the sequestration pen out to the opening of the sequestration pen to the channel, and optionally into the channel surrounding the opening of the sequestration pen. For example, the encapsulation layer may extend from about 5 microns to about 50 microns from the contact point with the aqueous medium within the sequestration pen and extend towards and/or into the microfluidic channel.

In some variations, where the portion of the surfaces of the connection region at the opening to the channel has hydrophobic surfaces introduced, the surfaces having a length $L_{hydrophobic}$, which is a fraction of the $L_{con}$ of the connection region, the remainder of the surfaces of the connection region may have a hydrophilic surface introduced. The portion of surfaces of the connection region 736 having a hydrophilic surface of FIG. 7D may have a length $L_{remainder}$ 733, which extends from the boundary of the hydrophobic portion of the connection region (end of $L_{hydrophobic}$ 731, distal to sequestration pen opening) to the boundary with the isolation region 740 of FIG. 7D. Thus the connection region may have two sub-regions, a hydrophobic portion near the opening of the sequestration pen having a length $L_{hydrophobic}$ which is a fraction of Lcon of the connection region, and a hydrophilic portion near the distal opening of the connection region to the isolation region, which has a length $L_{remainder}$ which is the remainder of the length of Lcon, e.g., $L_{con}$-$L_{hydrophobic}$. Length $L_{remainder}$ may be about 5%, about 10%, about 20% about 25%, about 40% about 50%, about 75%, or any percentage therebetween, of $L_{con}$ of the connection region as described herein.

The nonpolar/hydrophobic moiety can, for example, comprise, consist of, or consist essentially of an alkane (including fluoroalkanes and perfluoroalkanes), an alkene, an alkyne, an aromatic ring (which may be functionalized with nonpolar groups, such as alkanes and the like), a polymer (e.g., polypropylene), or the like, as may be selected by one of skill. Exemplary but nonlimiting nonpolar/hydrophobic moieties are described further herein.

Preparation of Regioselectively Modified Surfaces within a Microfluidic Device.

Figures 6C, 6D, 6E:
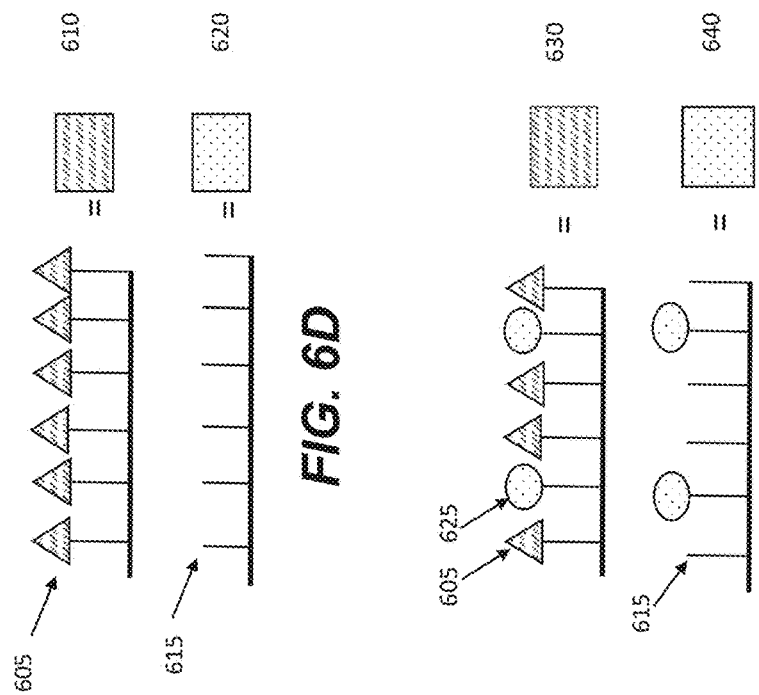
Figure 6G:
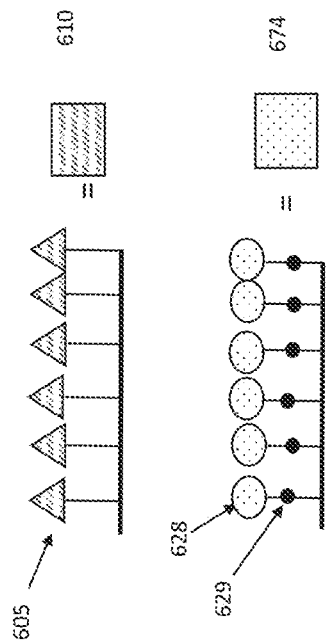

The regioselectively modified surfaces useful for encapsulating sequestration pens according to the methods of the disclosure may be introduced in a variety of ways. In some variations, the regioselectively modified surfaces may be introduced by regioselective photo-initiated photocleavage of hydrophobic surface ligands having photocleavable moieties incorporated therein, removing the hydrophobic moieties forming the hydrophobic surface. Such selective removal may be performed in regions of the microfluidic channels and/or chambers (e.g., sequestration pens) where hydrophobicity may not be desired. A microfluidic device presenting reactive moieties on surfaces of the channel and chambers (e.g., sequestration pens) such as microfluidic device 600 (FIG. 6A) may be reacted with a hydrophobic surface modifying reagent having a hydrophobic surface contact moiety, which may be any suitable hydrophobic surface contact moiety as is known (a non-limiting list of such hydrophobic surface contact moiety is described herein). The hydrophobic surface contact moiety may be linked via a photocleavable linker, to a reactive pair moiety which is configured to participate in Click chemistry reactions, such as an alkyne, including but not limited to a sterically hindered alkyne such as a dibenzocyclooctynyl (DBCO) reactive pair moiety. The photo-cleavable moiety included within the linker may include a nitro-substituted phenyl, nitro-substituted coumarinyl or any other suitable photo-cleavable moiety, as is known in the art. In some variations, the hydrophobic surface modifying reagent may be flowed into the microfluidic channel, displacing a carbon dioxide gaseous environment within the channel and sequestration pens, introducing hydrophobic modified surface 610, as shown in FIG. 6B, distributed throughout the inner surfaces of the channel and the sequestration pens. Photo-initiated photocleavage may be performed manually or in an automated fashion, e.g., using a programmable masking process. Laser illumination may be directed at selected portions of the microfluidic channel and/or sequestration pens to selectively cleave the hydrophobic moiety from the covalently bound surface modifying ligand, leaving a less hydrophobic (e.g., more hydrophilic) PEG "scar" ligand 615 (as shown in FIG. 6D) at the illuminated regions, thereby providing a less hydrophobic (or more hydrophilic) surface 620. Thus, a hydrophobic region may be selectively introduced (and retained) within the microfluidic channel that may be less than about 50% of the surface areas of the channel (or more than about 50% of the surface areas of the channel) disposed adjacent or proximal to the openings of the sequestration pens to the microfluidic channel, and nowhere else, as shown in FIG. 6C.

Similarly, a hydrophobic surface may be introduced and then removed by photo-initiated photocleavage from portions of the surface of each chamber/sequestration pen located distal to the opening of the chamber/sequestration pen to the channel. For example, the hydrophobic coating may be introduced onto all surfaces of the chamber/sequestration pen, the selectively removed from the surfaces of the isolation region of the sequestration pen and from a portion of the surfaces of the connection region of the sequestration pen, or even entirely from the surfaces of the sequestration pen. In some variations, a portion of the surfaces of the connection region at the opening to the channel may be retained as hydrophobic surfaces, each surface so modified may have a length $L_{hydrophobic}$, which is a fraction of the $L_{con}$ of the connection region. Length $L_{hydrophobic}$ may be about 5%, about 10%, about 20% about 25%, about 40% about 50%, about 75%, or any percentage therebetween, of $L_{con}$ of the connection region, and extends from the proximal opening of the connection region at the channel towards the distal end of the connection region meeting the isolation region of the sequestration pen. In some variations, all of the surfaces defining the connection region are so modified for length $L_{hydrophobic}$, therefore having a portion of each surface modified proximal to the opening of the sequestration pen at the channel. This region of hydrophobicity can assist in retaining the encapsulation layer and, in particular, may assist in defining the distance that the encapsulation layer extends from a contact with the aqueous medium within the rest of the sequestration pen out to the opening of the sequestration pen at the channel, and optionally into the channel surrounding the opening of the sequestration pen. For example, the encapsulation layer may extend from about 5 microns to about 50 microns from the contact point with the aqueous medium within the sequestration pen and extend towards and into the microfluidic channel.

An exemplary schematic representation of the ligands in each region of the microfluidic device is shown in FIG. 6D, where the hydrophobic ligands 605 form the modified surface 610 remaining near the openings of the sequestration pen and in the portion of the connection region near the opening to the channel. The cleaved ligands 615 remaining as the "scar" from the less hydrophobic (or more hydrophilic) surface 620 within the channel distal from the sequestration pen openings and within the connection region distal from the opening and within the isolation region of the sequestration pen. In some variations, photocleavage may be performed only within portions of the sequestration pen, and all of the surfaces of the channel may retain a hydrophobic surface having hydrophobic ligands 605.

In some other variations, the surface modifying reagent may be a mixture of two or more surface modifying reagents, only one of which includes a hydrophobic moiety and the photocleavable moiety, forming ligand 605. The second reagent contains a second, different surface coating moiety and a second linker, having no photocleavable moiety within its linker, and forms the second ligand 625. The second linker of the second reagent may be the same or different from the first linker of the first surface modifying reagents. In some variations, this second surface coating moiety may be a hydrophilic surface coating moiety. The surface 630 formed throughout the channel and sequestration pens of FIG. 6C has a mixed population of ligands 605 and 625 as shown schematically in FIG. 6E. When the regioselective photo-initiated cleavage is performed, a surface 640 having a combination of cleaved ligands 615 (including the remaining "scar" of the hydrophobic ligand 605) and the second ligand 625 may be formed, thus providing a surface that is more hydrophilic than the surface in the region that was not illuminated. In some embodiments, the hydrophobic region may extend from the region proximal to the openings of the chambers/sequestration pens to encompass all of the surfaces of the channel. In other embodiments, a portion of the channel may retain hydrophobic surfaces as described above. In this fashion, the degree of hydrophobicity of surface 640 compared to surface 630 may be fine-tuned by altering the composition of the ligands and the relative proportions of each ligand. In some embodiments, a ratio of hydrophobic photocleavable first ligands to nonphotocleavable second ligands, which may be a different hydrophobic second ligand, less hydrophobic second ligand, or hydrophilic second ligand, may be about 99:1; about 90:10; about 85:15; about 80:20: about 75:25; about 60:40; about 50:50; about 45:55; about 40:60; about 35:65; about 30:70; about 25:75; about 20:80 or any ratio therebetween. In some variations, a range of ratio of hydrophobic photocleavable ligands to non-photocleavable second ligands may be from about 99:1 to about 10:90; about 90:10 to about 50:50; about 90:10 to about 60:40; or about 90:10 to about 75:25.

In some other variations, a hydrophobic surface may be introduced regioselectively using temperature control of gaseous environments within regions of the microfluidic device. A microfluidic device presenting reactive moieties, such as azide or alkynyl moieties, on surfaces of the channel and chambers (e.g., sequestration pens) such as microfluidic device 600 (FIG. 6A) may be flushed with ambient air (e.g., not primed with 100% carbon dioxide gas) and cooled to a reduced temperature relative to ambient temperature. The reduced temperature may be about −40 degrees C.; about −35 degrees C.; about −25 degrees C.; about −20 degrees C.; about −10 degrees C.; about −5 degrees C.; about 0 degrees C.; about 5 degrees C.; about 10 degrees C.; about 15 degrees C.; about 20 degrees C. or about 25 degrees C.

A first (hydrophobic) surface modifying reagent, which may be any suitable hydrophobic surface modifying reagent as described herein, may be chilled to the same lowered temperature (5 degrees C.) as the microfluidic device. The reagent solution may be saturated with a selected percentage of carbon dioxide gas prior to use, which may be about 5%, about 10%, about 15%, about 20%, about 30%, about 50%, about 60%, about 70%, about 80%, about 90%, about 100%, or any percentage therebetween of carbon dioxide gas. A deionized water solution saturated with the same percentage of carbon dioxide is also prepared and chilled to 18 degrees C., or between about 15 degrees C. to about 20 degrees C. The carbon dioxide saturated deionized water solution may be introduced into the channel of the microfluidic device at slightly lower than atmospheric pressure. The channel fills with the deionized water solution, however, due to the low pressure of the fluidic introduction (i.e., via aspiration) and the unprimed nature of the surfaces within the microfluidic device, the deionized water solution may not enter the sequestration pens opening off of the microfluidic channel. The degree of entry into the sequestration pens also depends upon the percentage of carbon dioxide present (e.g., the partial pressure of carbon dioxide) within the deionized water solution. After introduction of the deionized water solution, the microfluidic device is warmed to a desired temperature, which may be about 30 degrees C.; about 35 degrees C., about 40 degrees C., about 45 degrees C., about 50 degrees C., about 55 degrees C., about 60 degrees C., about 70 degrees C., about 80 degrees C., about 90 degrees C. or any temperature therebetween. Upon warming, the trapped air in each sequestration pen may expand outward from the sequestration pen, forming a bubble extending into the microfluidic channel. The chilled hydrophobic surface modifying reagent may be slowly introduced (e.g., about 0.01 ul/s over a period of time of about 10 min to about 0.05 ul/sec over a period of time of about 20 sec, which range of aspiration rate/period of time avoids undesirable overextension of the bubbles within the sequestration pens) into the channel, flowing around the bubbles extending from the sequestration pens, and reacting only with surfaces in the channel where the bubbles do not extend. The hydrophobic surface modifying reagent may be permitted to contact the surfaces of the channel not excluded by the bubbles, for a period of time which may be about 15 min, about 30 min, about 45 min, about 60 min, or any number of minutes therebetween. Thus, a hydrophobic surface 650, presenting hydrophobic ligands 635 as shown in FIGS. 6H-I may be formed selectively. The extent of bubble extension out from the sequestration pen may be controlled by the temperature at which the microfluidic device is maintained at while the chilled first surface modifying reagent is slowly aspirated through the channel. In some variations, the bubble may extend beyond the opening of the sequestration pen to occupy about 60%, about 50%, about 40% about 30%, about 20%, about 10%, or about 5% of the area of the channel. Accordingly, the surface within the sequestration pens and within the region of the bubbles extending out into the channel is an unmodified surface 602 (e.g., azide moieties still present).

Figure 6F:
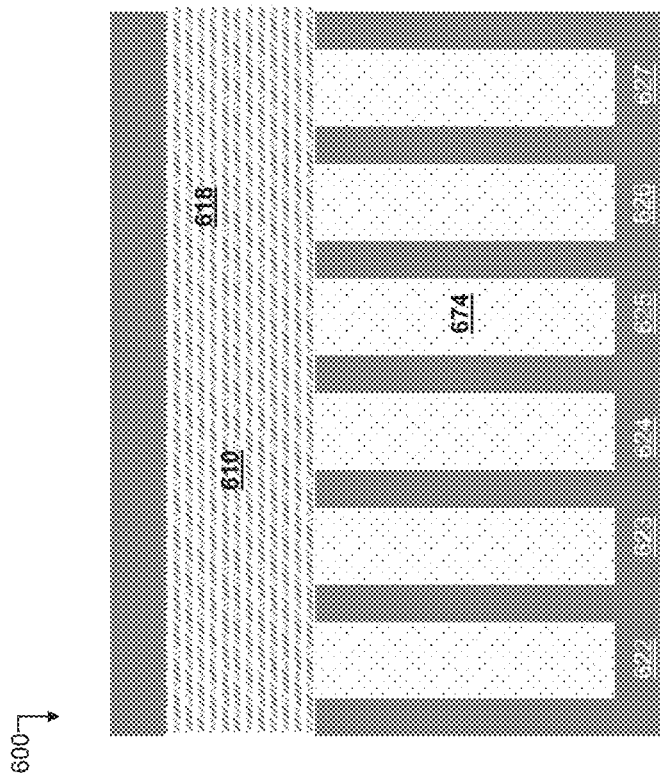
Figure 6I:
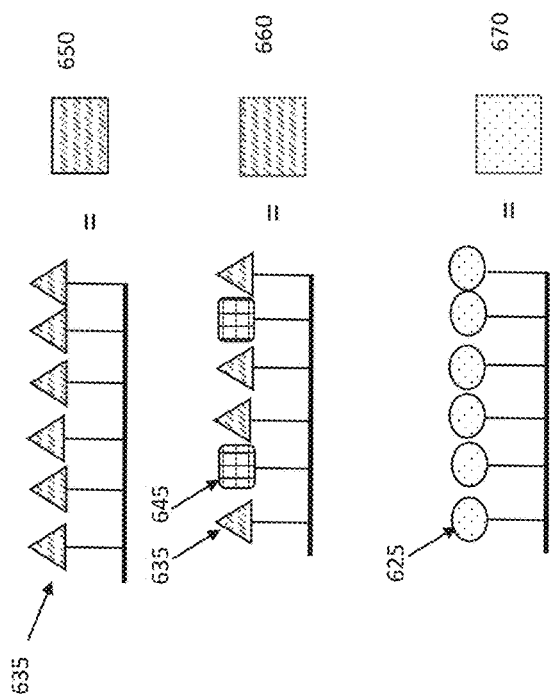
Figure 6H:
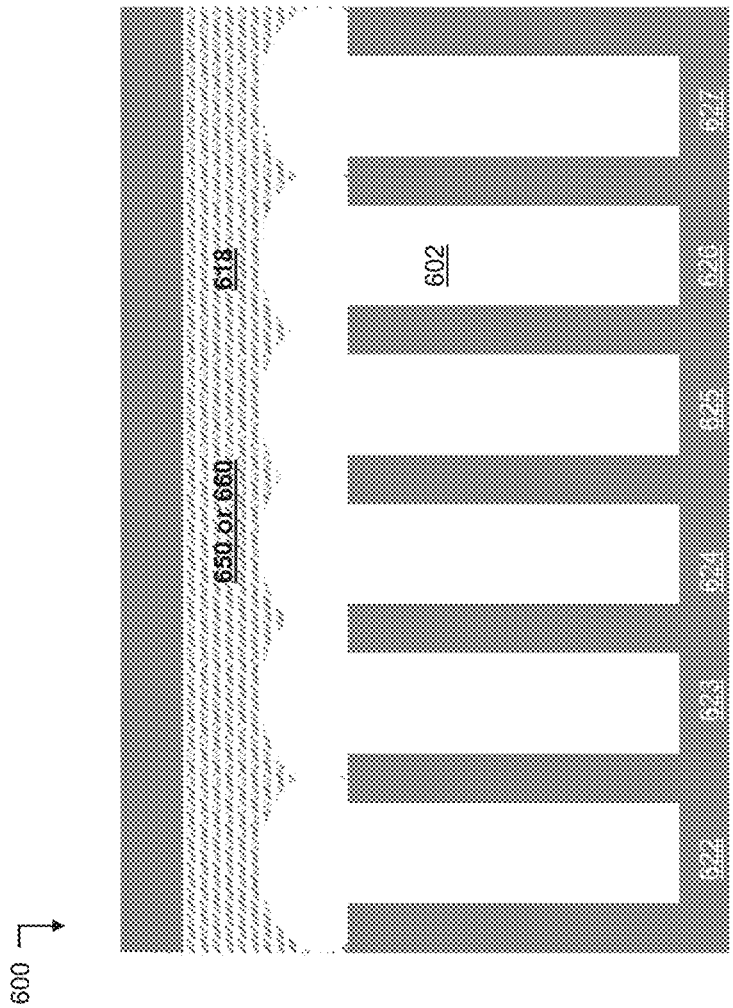

After completion of the reaction period, any remaining hydrophobic surface modifying reagent may be flushed from the channel and device. Additional flushing with water at 1 microliter/sec is continued for about 5 min. The microfluidic device having the hydrophobic surface modified microfluidic channel may then be dried by flushing with carbon dioxide gas while heating the microfluidic device to about 30 degrees C.; about 40° C.; about 40 degrees C.; about 45 degrees C.; about 50 degrees C., or more, thus priming the interior of the microfluidic device for regioselective surface modification with a second surface modification reagent in the remainder of the microfluidic channel and within the sequestration pens (e.g., where surface 602 as in FIG. 6H is present). The second surface modification may then be performed regioselectively by flowing a second surface modifying reagent through the microfluidic device. This second surface modifying reagent, which may be less hydrophobic than the first surface modifying reagent or may be a hydrophilic surface modifying reagent, may enter the sequestration pens and react with the remaining reactive moieties still present in the channel (where the bubbles had prevented previous modification) and in the sequestration pens, forming surface 670, composed of hydrophilic ligands 625 upon the modified surface, as shown in FIG. 6J. Thus, a hydrophobic surface 650 may be introduced to less than about 50%; about 45%; about 40%; about 35%; about 30%; about 25%; about 20%; about 15%; or less of the surface area of the channel and a hydrophilic surface 670 is introduced within the sequestration pen and in the proximity of the opening of the sequestration pen, extending into the channel.

The technique disclosed herein may also be used to regioselectively introduce any sort of combination of surface modifications to the channel, sequestration pens, and regions surrounding the opening of each sequestration pen to the channel, depending upon: the temperatures selected for the introduction of each surface modifying reagent, the percentage of carbon dioxide gas equilibrated in the microfluidic device environment, and/or the surface modifying reagents. In another variation, the hydrophobic surface 660 introduced in FIGS. 6H-6J, may include a combination of surface modifying ligands where a combination of two ligands 635 and 645 may be introduced as described where surface contact moiety 635 provides a hydrophobic surface contact moiety and surface contact moiety 645 may be: a different hydrophobic surface contact moiety, a hydrophilic surface contact moiety, or a surface contact moiety providing a different surface chemistry, which may be used in any ratio, thus fine tuning the hydrophobic surface 660 as needed for specific applications. In some embodiments, a ratio of hydrophobic ligand 635 to ligand 645 may be about 99:1; about 90:10; about 85:15; about 80:20; about 75:25; about 60:40; about 50:50; about 45:55; about 40:60; about 35:65;

about 30:70; about 25:75; about 20:80 or any ratio therebetween. In some variations, a range of ratio of hydrophobic ligand 635 to ligand 645 may be from about 99:1 to about 10:90; about 90:10 to about 50:50; about 90:10 to about 60:40; or about 90:10 to about 75:25.

In some other variations, the channel may have more than about 50%; about 55%; about 60%; about 65%; about 70%; about 75%; about 80%; about 85%; about 90%; or about 100% of a first hydrophobic coating 650 or 660, which may be any suitable hydrophobic coating as described herein, or known in the art, while the remaining portion of the channel (e.g., near the openings of the connection region of the sequestration pens) and the surfaces within the sequestration pens has a second, hydrophilic coating 670, which may be any suitable hydrophilic coating as described herein, or known in the art.

Figure 6K:
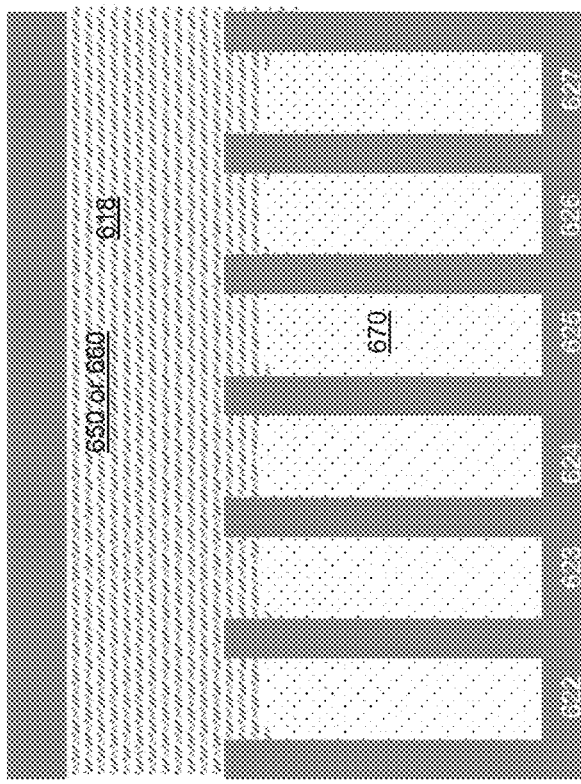
Figure 6J:
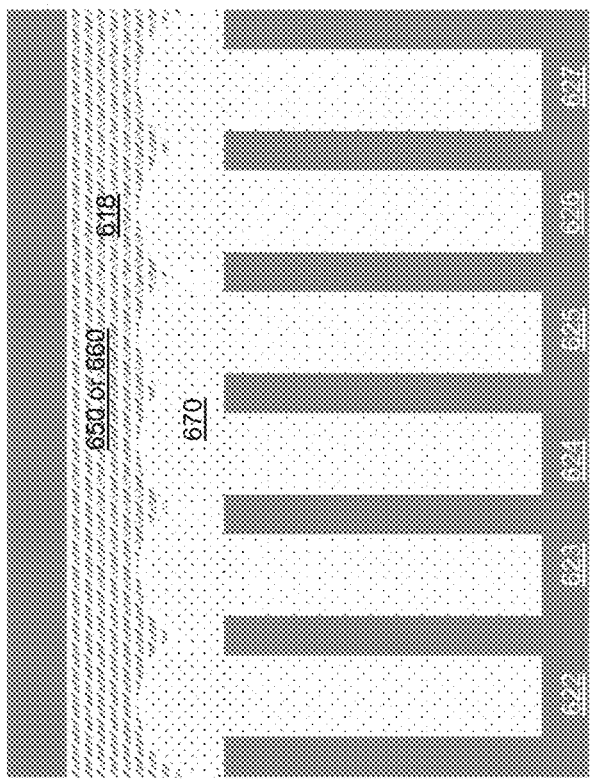

As shown in FIG. 6K, a microfluidic device 600 may have a hydrophobic surface 650 or 660, as described herein, throughout the entire channel, and may also extend into a portion of the chamber (or connection region of a sequestration pen), using temperature control and carbon dioxide content to controllably introduce the hydrophobic surface regioselectively. The portion of the connection region having the hydrophobic surface introduced thereto may be like the sub-region 731, as illustrated in FIG. 7D, and have a length $L_{hydrophobic}$ as described herein. The remainder of the connection region, which may be a portion of a connection region like sub-region 733 as illustrated in FIG. 7D, and have a length $L_{remainder}$. The surface introduced to the portion of the connection region having length $L_{remainder}$ and all of the isolation region of the sequestration pen may have a surface 670 introduced thereafter, which may be differently hydrophobic from that of the hydrophobic surface 650/670 or hydrophilic as desired.

In other variations, the channel may have less than 50% of a first hydrophobic coating, which may be any suitable hydrophobic coating as described herein, or known in the art, while the remaining portion of the channel (e.g., near the openings of the connection region of the sequestration pens) and the surfaces within the sequestration pens has a second hydrophobic coating, with the second hydrophobic coating different from the first hydrophobic coating and optionally any suitable hydrophobic coating as described herein, or known in the art.

In some other variations, the first surface modification reagent may include a mixture of surface modifying ligands, including a first hydrophobic ligand 635 and a second ligand 645, which may be differently hydrophobic, neutral or hydrophilic, and may be present within the first surface modification reagent in any ratio, thus providing a hydrophobic surface 660 as shown in FIGS. 6F-6L (methods used to provide the microfluidic device surfaces of FIG. 6F may also have such a combination surface 660 of ligands 635 and 645, although it is not shown in FIG. 6F). In some embodiments, a ratio of hydrophobic first ligands to second ligands of the first surface modification reagent, where the second ligand may be a different hydrophobic second ligand, less hydrophobic second ligand, or hydrophilic second ligand, and ratios may be about 99:1; about 90:10; about 85:15; about 80:20: about 75:25; about 60:40; about 50:50; about 45:55; about 40:60; about 35:65; about 30:70; about 25:75; about 20:80 or any ratio therebetween. In some variations, a range of ratios of hydrophobic first ligands to second ligands of the first surface modification reagent may be from about 99:1 to about 10:90; about 90:10 to about 50:50; about 90:10 to about 60:40; or about 90:10 to about 75:25.

Figure 6L:
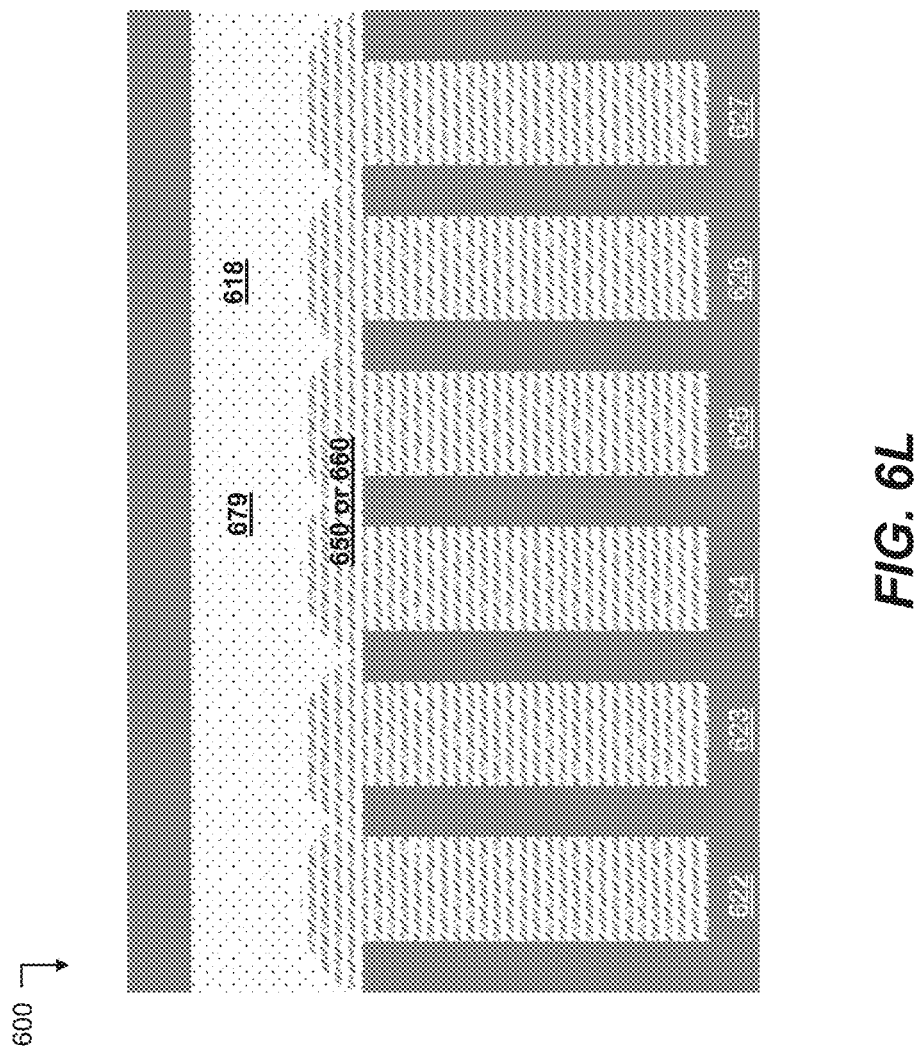

In some other variations, the first surface modification, introduced to more than 50%; less than 50% of the channel surface areas, or any proportion deemed suitable for a particular experiment, may be a hydrophilic surface modification (e.g., introduces ligands 625 into the portion of the channel distal to the openings of the sequestration pens to the channel, forming surface and the second surface modification, introduced to the surfaces of the channel near the openings of the sequestration pens and to the surface of the sequestration pens themselves may be a hydrophobic surface modification 650 (if only one type of hydrophobic ligand 635 is introduced) or 660 (when the second surface modification reagent introduces both hydrophobic first ligand 635 and second ligand 645), as shown in FIG. 6L.

In some other embodiments, one or both of the first and the second surface modification may be a mixture of surface modifying ligands, e.g., there may be a mixture of different chemical species in the first and/or the second surface modifying reagents. The proportions of the mixtures may be modified in any suitable ratio to provide specific physicochemical behavior by the surface modification introduced into each of the two differently modified regions of the microfluidic device.

Figure 7A:
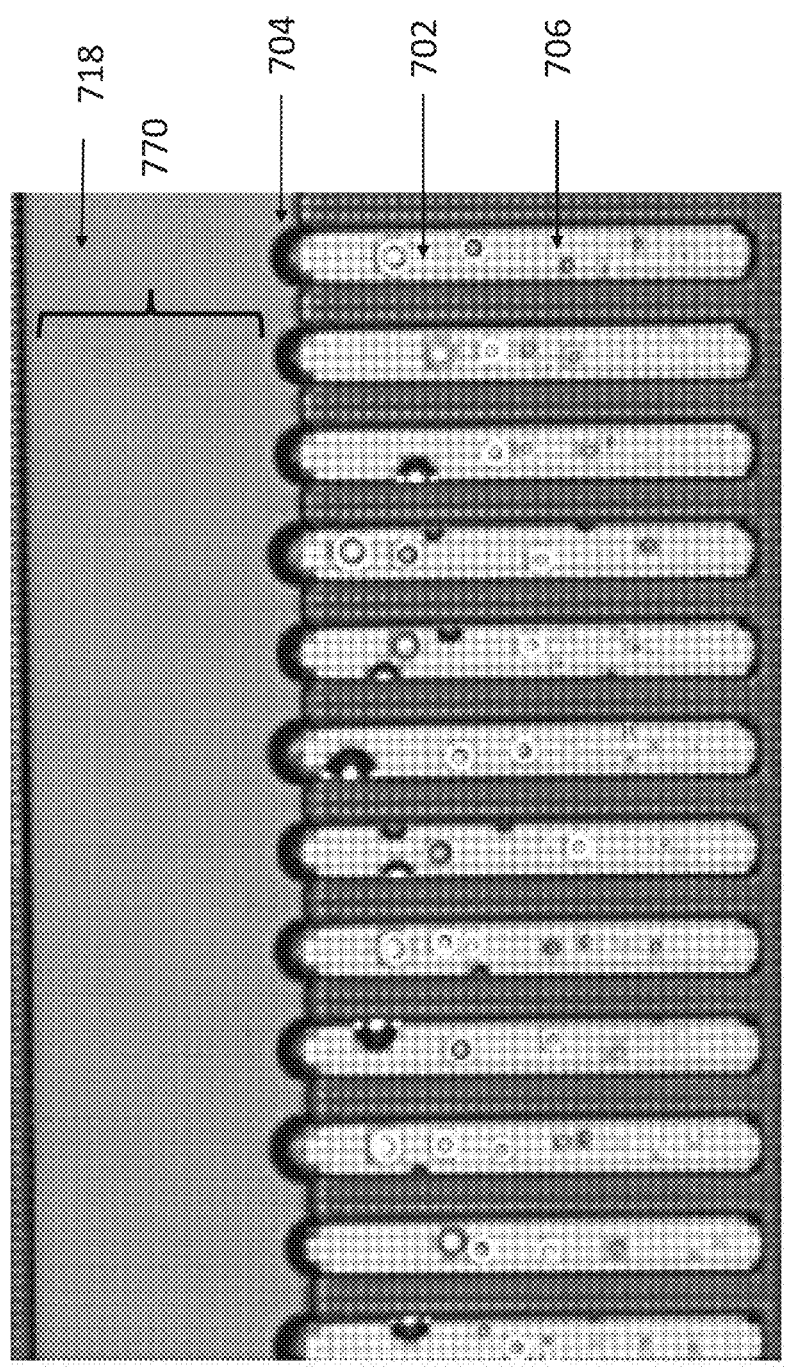
FIGS. 7A to 7B illustrates the preparation of regioselectively modified surfaces in individual chambers, which can support an encapsulation layer of defined thickness formed at the connection region of the chamber, according to some embodiments of the disclosure.
Figure 7B:
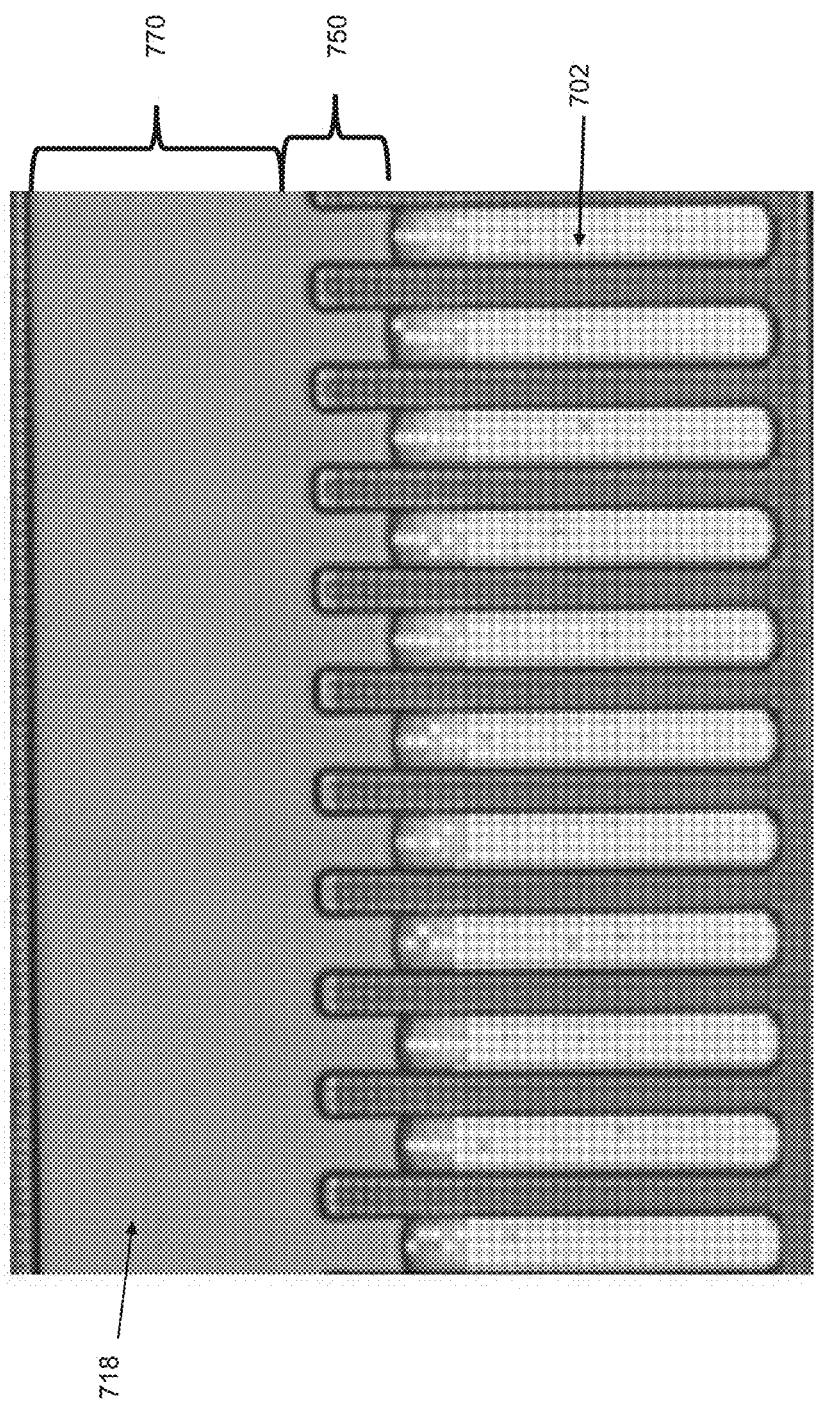

In another variation, more than two different surfaces may be introduced. For example, a microfluidic device may have a hydrophobic surface introduced to a limited region of the microfluidic channel, e.g., near the openings of the chambers (e.g., sequestration pens) to the channel as well as a portion of the surfaces of the chambers near the openings of the chambers to the channel, e.g., portions of the surfaces of the connection region of a sequestration pen, proximal to the opening to the channel, as shown in FIGS. 7A-7C. The remainder of the channel, e.g., distal to the openings of the chambers (sequestration pens) to the channel, may have a hydrophilic (or differently hydrophobic) surface. However, the interiors of the chambers (e.g., isolation region and the portion of the connection region proximal to the isolation region) may be left untreated for later surface modification, or may have a third, different surface modification introduced, as shown in FIG. 7C.

This may be accomplished, using a variation of the temperature and gas content controlled introduction described herein. The first surface modifying reagent solution, which is a hydrophilic or less hydrophobic surface modifying reagent may be introduced into the channel of the microfluidic device by aspirating the solution through the channel of the device at slightly lower than atmospheric pressure at a desired temperature, which may be around 30 degrees C. Due to the low pressure of the fluidic introduction and the unprimed nature of the surfaces within the microfluidic device, the first surface modifying reagent solution may not enter the sequestration pens opening off of the microfluidic channel 718. Warming the microfluidic device to a warmer temperature, such as, for example, around 36 degrees C., may permit air bubbles to expand from the pens, just slightly out into the channel, preventing the first surface modifying reagent from entering the sequestration pens, as shown in FIG. 7A, and the channel outside of the regions broached by the bubbles was modified with the hydrophilic first surface modifying reagent with surface 770, which may be similar to surfaces 670 of FIGS. 6F-6L. The surface 702 within the sequestration pens remained unreacted. The second surface modifying reagent, a hydrophobic reagent may then be flowed in at a colder temperature such as 18 degrees C. The bubbles from each sequestration pen may then shrink back into the sequestration pen, and permit entry of the hydrophobic reagent into a portion of the connection region of the sequestration pen, e.g., the portion of the connection region closest or proximal to the opening of the sequestration pen to the channel. A hydrophobic surface 750 may be formed just adjacent to the pen openings (where the bubbles extended in FIG. 7A) and into the portion of the connection region exposed by the shrinkage of the bubbles, as shown in FIG. 7B. The hydrophobic surface 750 may be like hydrophobic surface 650 of FIGS. 6F to 6L. In other variations, the hydrophobic surface 750 may have more than one type of ligand like mixed hydrophobic surface 660 of FIGS. 6F-6L.

The interior of the chambers, e.g., the isolation region and the portion of the connection region of the sequestration pens distal to the opening of the sequestration pen to the channel, may still retain an unmodified reactive moiety-containing surface, e.g., having azido or alkynyl moieties. A third surface modification may be carried out thereafter to introduce any desired surface modification into the sequestration pens, after priming with carbon dioxide. The surface modification may be any of the covalently bound surfaces as described in International Application Nos. PCT/US2016/028808, filed on Apr. 22, 2016, titled "Microfluidic Cell Culture"; PCT/US2017/034832, filed on May 26, 2017, titled "Covalently Modified Surfaces, Kits, and Methods of Preparation and Use"; and PCT/US2020/018388, filed on Feb. 14, 2020, titled "Laser Assisted Repositioning of a Micro-Object and Culturing of an Attachment-Dependent Cell in a Microfluidic Environment", each of which disclosures is herein incorporated by reference in its entirety. In some variations, the surface modifications (first surface modification and second surface modification) of the channel and the portion of the connection region of the sequestration pen may be introduced at a first time point, and the surface modification of the interior of the chamber (e.g., isolation region and portion of the connection region distal to the opening of the sequestration pen to the channel) may be performed at a later day or time. Thus, any desired combination of three surfaces may be introduced regioselectively into the microfluidic device. By changing the temperature of the microfluidic device during reaction, and the percentage of carbon dioxide present, the extent (e.g., "thickness") of the "band" of hydrophobic surface modification at the opening of the sequestration pen and penetrating into part of the connection region may be modified, e.g., the distance from the opening of the sequestration pen into the sequestration pen itself. For example, increasing the percentage of carbon dioxide introduced into the hydrophobic surface modification reagent, will permit greater penetration into the sequestration pen and produce a more extensive, e.g., "thicker", hydrophobic surface band supporting an encapsulating layer.

FIG. 7D shows the relationship between the different regions of a sequestration pen 627 and the different modified surfaces that may be introduced within the microfluidic device. Sequestration pen 627 is the same as sequestration pen 627 of FIG. 7C, having a hydrophilic surface 770 introduced to greater than 50% of the surfaces of the microfluidic channel 718, in particular, that the side wall of the channel distal to the opening of the sequestration pen 627 is modified with the hydrophilic surface. A hydrophobic surface 750 has been introduced to the portion of the channel 718 that is proximal to the openings of the sequestration pen. In this variation, the hydrophobic surface 750 extends into a portion of the connection region, as described herein. This portion is a sub-region 731 of the connection region, which is proximal to the opening of the connection region to the channel 718. The walls defining sub-region 731 have a length $L_{hydrophobic}$ as described herein, e.g., a fraction of $L_{con}$, which may be any fraction of $L_{con}$ as described herein. The other portion 733, e.g., sub-region, of the connection region has a modified surface 780, and extends from a boundary with sub-region 731 to the distal opening of the connection region to the isolation region 740 of sequestration pen 627. The modified surface in sub-region 733 is the same modified surface 780 as introduced within the isolation region 740, which may be any suitable modified surface for an isolation region as described herein. The surfaces of the walls, inner surfaces of the cover and base forming portion 733 has a length $L_{remainder}$ from the boundary with sub-region 731 to the distal opening which is the remainder of the length of $L_{con}$, e.g., $L_{con}$-$L_{hydrophobic}$, and may be resultingly be the fraction of $L_{con}$ as described above. While FIG. 7D specifically illustrates the surfaces introduced as described for FIGS. 7A-7C, the sub-regions described are not so limited. That is, sub-regions 731, 733 have the properties and dimensions shown regardless of whether the hydrophobic surface extends to any selected portion of the channel 718, e.g., may include all of the surfaces of the channel 718, and whether the surface 750 includes a single type of hydrophobic surface modifying ligand or includes a combination of a first hydrophobic ligand and another surface modifying ligands (or includes a mixture of more than two surface modifying ligands, where at least one of the surface modifying ligands is a hydrophobic surface modifying ligand).

In some aspects, a microfluidic device is provided, wherein the microfluidic device has an enclosure comprising a channel and a plurality of chambers, each chamber of the plurality of chambers having an opening (e.g., a single opening) fluidically connecting the chamber to the channel, wherein each chamber of the plurality of chambers is formed by a plurality of surfaces having a total surface area, with a first portion of the total surface of each chamber comprising a hydrophobic coating and a second portion of the total surface area of each chamber comprising a hydrophilic coating, and wherein the first portion of the total surface area of each chamber is located proximal to a boundary between the chamber opening and the channel.

The first portion of the total surface area of each chamber of the plurality of chambers may be proximal to and surrounding the opening of the chamber to the channel (e.g., each surface forming the opening of the chamber comprises the hydrophobic coating at a location proximal to the boundary between the chamber opening and the channel). In some variations, all of the total surface area of each chamber of the plurality of chambers located within about 10 microns (e.g., within about 20 microns, about 25 microns, about 30 microns, about 35 microns, about 40 microns, about 45 microns, about 50 microns, about 55 microns, about 60 microns, or more) of the boundary between the chamber opening and the channel may include the hydrophobic coating. The channel may be formed (e.g., defined) by a plurality of surfaces having a total surface area, with one or more portions of the total surface area of the channel having a hydrophobic coating (e.g., the same hydrophobic coating as the plurality of chambers). In some embodiments, each of the one or more portions of the total surface area of the channel having the hydrophobic coating may be located proximal to the boundary between the channel and a corresponding chamber of the plurality of chambers. In some embodiments, all of the total surface area of the channel located within about 10 microns (e.g., within about 20 microns, about 25 microns, about 30 microns, about 35 microns, about 40 microns, about 45 microns, about 50 microns, about 55 microns, about 60 microns, or more) of the boundaries between the channel and the openings of the plurality of chambers may have the hydrophobic coating. In some embodiments, substantially all (e.g., at least 80%, 85%, 90%, 95%, 98%, 99%, or more) of the total surface area of the channel may have the hydrophobic coating. In some variations, the hydrophobic coating of the plurality of chambers may have a contact angle from about 45 degrees to about 100 degrees.

In some variations, each chamber of the plurality of chambers may be a sequestration pen including an isolation region and a connection region fluidically connecting the isolation region to the channel. In some embodiments, the hydrophobic coating of each sequestration pen may be present in the connection region and substantially absent from the isolation region (e.g., a total surface area of chamber surfaces forming the isolation region comprises less than 5%, 4%, 3%, 2%, 1.5%, 1%, 0.5% of the hydrophobic coating). In some variations, less than or equal to 50% of a total surface area of chamber surfaces forming the connection region of each sequestration pen may have the hydrophobic coating. In some other variations, greater than or equal to 50% of a total surface area of chamber surfaces forming the connection region of each sequestration pen may have the hydrophobic coating. In some variations, chamber surfaces forming the connection region of each sequestration pen and comprising the hydrophobic coating may form a ring surrounding a proximal end of the connection region (e.g., starting at the boundary between the channel and the proximal opening of the connection region and extending into the connection region).

In some variations, greater than or equal to 50% of a total surface area of chamber surfaces forming the isolation region of each sequestration pen may include the hydrophilic coating. In some embodiments, substantially all of a total surface area of chamber surfaces forming the isolation region of each sequestration pen may include the hydrophilic coating (e.g., at least 80%, 85%, 90%, 95%, 98%, 99%, or more).

In some variations, the hydrophobic coating may include a first covalently bound surface modification comprising: a first linking group, and a first moiety, where the first moiety is nonpolar (e.g., an oleic acid moiety, alkynyl moiety, PEG-linked alkynyl, or fluorinated moiety). In some variations, the hydrophilic coating may include a plurality of second covalently bound surface modifications, each comprising a second linking group, and a second moiety, where the second moiety is polar (e.g., a methoxy terminated PEG moiety, a carboxylic acid, a carboxylic acid terminated PEG moiety, an alcohol moiety or an alcohol terminated PEG moiety).

In some variations, the connection region of each sequestration pen may include a proximal opening to the channel and a distal opening to the isolation region, where the proximal opening of the connection region may have a width $W_{con}$ ranging from about 20 microns to about 100 microns (e.g., about 20 microns to about 60 microns, or about 30 microns to about 90 microns), and wherein a length $L_{con}$ of the connection region from the proximal opening to the distal opening may be as least 1.0 times the width $W_{con}$ of the proximal opening of the connection region. In some embodiments, the length $L_{con}$ of the connection region may be at least 1.5 times the width $W_{con}$. In some other embodiments, the length $L_{con}$ of the connection region may be at least 2.0 times the width $W_{con}$. In some variations, the length $L_{con}$ of the connection region may be between about 20 microns and about 500 microns.

In some variations, a ratio of a width $W_{ch}$ of the channel (e.g., a channel having substantially uniform width) to a width $W_{op}$ of the opening of each chamber of the plurality of chambers (or a width $W_{con}$ of a proximal opening of the connection region of each sequestration pen) to the channel may be about 1.25 or greater (e.g., about 1.5 or greater, about 2.0 or greater, or about 3.0 or greater). In some embodiments, a width $W_{ch}$ of the channel (e.g., a channel having substantially uniform width) at the opening of each chamber of the plurality of chambers (or at a proximal opening of the connection region of each sequestration pen) may be between about 50 microns and about 500 microns. In some variations, a width $W_{ch}$ of the channel (e.g., a channel having substantially uniform width) at the opening of each chamber of the plurality of chambers (or at a proximal opening of the connection region of each sequestration pen) may be about 70 microns to about 250 microns (e.g., about 80 microns to about 200 microns, or about 90 microns to about 150 microns).

A height of the channel at the opening of each chamber of the plurality of chambers (or at a proximal opening of the connection region of each sequestration pen) may be between about 20 microns and about 100 microns (e.g., about 30 microns to about 50 microns, about 50 microns to about 70 microns, about 70 microns to about 90 microns, about 35 microns to about 45 microns, about 45 microns to about 55 microns, about 55 microns to about 65 microns, about 65 microns to about 75 microns, or about 75 microns to about 85 microns).

In some variations, a volume of each chamber of the plurality of chambers (or each sequestration pen) may range from about $2 \times 10^5$ to about $2 \times 10^6$ cubic microns.

In some variations, the enclosure of the microfluidic device may further include: a base; a microfluidic circuit structure disposed on an inner surface of the base; and a cover disposed over the microfluidic circuit structure, where the base, the microfluidic circuit structure, and the cover together define the channel and the plurality of chambers.

Generating and selectively removing encapsulation layers for biological cell analyses. Using microfluidic devices having modified surfaces introduced to the microfluidic channel and chambers (e.g., sequestration pens) as described herein, encapsulation layers may be generated and subsequently removed, in some variations, selectively, as shown in FIGS. 8A-8B and 9A-9C. Hydrophobic surfaces are present, at least in proximity to the openings of the chambers to the channel, or may be present in greater proportions throughout the channel and/or chambers of the microfluidic device. Hydrophobic surfaces may assist in supporting an encapsulation layer for each of the chambers. In some non-limiting embodiments, one or more surfaces of the channel may include a hydrophobic coating. In some variations, one or more surfaces of the channel may include a hydrophilic coating and/or one or more surfaces of each chamber or sequestration pen may include a hydrophilic coating. In some embodiments, one or more surfaces of the channel may include a hydrophobic coating and one or more surfaces of each chamber or sequestration pen may include a hydrophobic coating (e.g., a channel-proximal portion of each chamber can comprise a hydrophobic coating). In some variations, the hydrophobic coating may have a contact angle from about 45 degrees to about 100 degrees. In further embodiments, selective portions (e.g., greater than or equal to 1%, 5%, 10%, 15%, 20%, 25%, 30%, 40%, 50%, 60%, 70%, 80%, etc.) of the surface area of the surfaces of the channel and/or portions of the sequestration pen can be coated with a coating, as described herein. More specifically, in some embodiments, one or more surfaces or selective portions (e.g., greater than or equal to 1%, 5%, 10%, 15%, 20%, 25%, 30%, 40%, 50%, 60%, 70%, 80%, etc. of the surface area of the surfaces) of the channel may include a hydrophobic coating, and/or one or more surfaces or selective portions (e.g., greater than or equal to 1%, 5%, 10%, 15%, 20%, 25%, 30%, 40%, 50%, 60%, 70%, 80%, etc.) of each chamber or sequestration pen may include a hydrophilic coating. In some variations, at least a portion of surfaces forming the channel proximal to the opening to each chamber (e.g., sequestration pen) of the plurality may include the hydrophobic coating, e.g., channel surfaces located within about 10 microns of the opening to each chamber/sequestration pen may include the hydrophobic coating. In some other variations, the portion of surfaces forming the channel proximal to the opening to each chamber of a plurality of chambers may be surfaces located within about 20 microns, about 30 microns, about 40 microns, about 50 microns, about 60 microns, about 70 microns, about 80 microns, about 90 microns, about 100 microns, or more) of the opening to each chamber. In alternate embodiments, one or more surfaces or selective portions (e.g., greater than or equal to 1%, 5%, 10%, 15%, 20%, 25%, 30%, 40%, 50%, 60%, 70%, 80%, etc.) of the channel comprise a hydrophilic coating, and/or one or more surfaces or selective portions (e.g., greater than or equal to 1%, 5%, 10%, 15%, 20%, 25%, 30%, 40%, 50%, 60%, 70%, 80%, etc.) of the chambers or sequestration pens may include a hydrophilic coating. In yet other variations, one or more surfaces or selective portions (e.g., less than or equal to 5%, 10%, 15%, 20%, 25%, 30%, 40%, 50%) of the channel may comprise a hydrophobic coating. Optionally, one or more surfaces or selective portions (e.g., greater than or equal to 1%, 5%, 10%, 15%, 20%, 25%, 30%, 40%, 50%, 60%, 70%, 80%, etc.) of the chambers or sequestration pens may include a hydrophilic coating. The percentages of the surfaces having the surface coating as described may represent a surface area that may be calculated from the sum of the surfaces forming (e.g., defining) the channel or chamber, correspondingly (e.g., cover, base, and side walls formed by microfluidic circuit material). In some embodiments, each chamber of a plurality of chambers of the microfluidic device may include a surface comprising a hydrophilic coating. In some embodiments, wherein when a plurality of chambers of a microfluidic device is a plurality of sequestration pens, at least the isolation region of each sequestration pen may include a hydrophilic coating. In yet other embodiments, when the plurality of chambers comprises a plurality of sequestration pens comprising an isolation region and a connection region fluidically connecting the isolation region to the channel, a portion of the connection region proximal to the channel (e.g., a surface forming a ring at the proximal end of the connection region, which may be like region 731 of FIG. 7D having a length $L_{hydrophobic}$ as described herein) may include a hydrophobic coating.

In some variations, the hydrophobic coating may include a first covalently bound surface modification including a first linking group, and a first moiety, wherein the first moiety is nonpolar (e.g., an oleic acid moiety, alkynyl moiety, PEG-linked alkynyl, or fluorinated moiety). In some variations, the hydrophilic coating may include a plurality of second covalently bound surface modifications, each including a second linking group, and a second moiety, wherein the second moiety is polar (e.g., a methoxy terminated PEG moiety, a carboxylic acid, a carboxylic acid terminated PEG moiety, an alcohol moiety or an alcohol terminated PEG moiety).

In some embodiments, the connection region of each sequestration pen may include a proximal opening to the channel and a distal opening to the isolation region, the proximal opening of the connection region having a width $W_{con}$ ranging from about 2 microns to about 100 microns, about 20 microns to about 100 microns, about 2 microns to about 300 microns, or about 20 microns to about 300 microns; and where a length $L_{con}$ of the connection region from the proximal opening to the distal opening may be as least 1.0 times the width $W_{con}$ of the proximal opening of the connection region. A ratio of a width $W_{ch}$ of the channel (e.g., a channel having a substantially uniform width) to a width $W_{op}$ of the opening of each chamber of the plurality of chambers (or a width $W_{con}$ of the proximal opening of the connection region of each sequestration pen) may be at least 1.25 (e.g., at least 1.5, 2.0, 2.5, 3.0, or greater). In some embodiments, a width $W_{ch}$ of the channel (e.g., a channel having a substantially uniform width) at the opening of each chamber of the plurality (e.g., at a proximal opening to a connection region of a sequestration pen) may have a size between about 50 microns and about 500 microns. In this context, "substantially" uniform width means within +/−10% (e.g., 9%, 8%, 7%, 6%, 5%, 4%, 3%, 2%, or 1%) of the average width of the channel. A width $W_{ch}$ of the channel (e.g., a channel having a substantially uniform width) at the opening of each chamber of the plurality (e.g., a proximal opening to a connection region of a sequestration pen) may have a size of about 70 microns to about 250 microns (e.g., about 80 microns to about 200 microns, about 90 microns to about 150 microns, or about 200 microns to about 250 microns). The width of the channel and the number of channels in a single microfluidic chip can be related in that the aggregate width of all channels in the microfluidic chip (i.e., $W_{ch} \times N$, where $W_{ch}$ is the width of each channel and N is the number of channels) can be about 70 microns to about 250 microns×N, about 80 microns to about 200 microns×N, about 90 microns to about 150 microns×N, or about 200 microns to about 250 microns×N, where N is 1, 2, 3, 4, 5, 6, or more. A height of the channel at the opening of each chamber of the plurality of chambers (or at the proximal opening of the connection region of each sequestration pen) may be between about 20 microns and about 100 microns (e.g., about 30 microns to about 50 microns, about 50 microns to about 70 microns, about 70 microns to about 90 microns, about 35 microns to about 45 microns, about 45 microns to about 55 microns, about 55 microns to about 65 microns, about 65 microns to about 75 microns, or about 75 microns to about 85 microns). The volume of each chamber of the plurality (or each sequestration pen) may range from about $2 \times 10^5$ to about $2 \times 10^6$ cubic microns.

A number of parameters may contribute to the ability to seal a chamber, e.g., sequestration pen. Without being bound by theory, contact angle may be an important factor contributing to effectiveness of encapsulation by the encapsulating layer. The contact angle with the surfaces of the microfluidic device and the surface tension between the two immiscible media may contribute strongly to the burst pressure experienced by the encapsulating layer. Other parameters of note include the angle at the contraction/expansion, the width of the opening encapsulated, height and pressure of the medium in the channel/chamber.

The ability to encapsulate a chamber containing one or more micro-objects such as a biological cell, and subsequently selectively and controllably removing specific encapsulation layers, e.g., de-encapsulating a selected chamber, can provide advantages for analyses of various kinds.

Encapsulation can: inhibit (or prevent) secreted proteins, small molecules, and other biological products from exiting the chamber in which the molecules were produced (which can prevent cross-talk and additionally increase precision in analysis of rates of secretion); retain mobile biological cells within the chamber; retain nucleic acids after lysis of a biological cell; retain a capture bead, which may capture small molecules, proteins, or nucleic acids; and/or inhibit (or prevent) any buffers or reagents (e.g., assay reagents) introduced into the chamber from exiting that chamber and entering another chamber. Any of these properties may be usefully included in assays performed using encapsulated chambers.

One or more micro-objects, e.g., one or more cells and/or one or more capture beads, may be introduced into the chambers (e.g., sequestration pens), using DEP forces, gravity or any other motive force described herein. The cell or plurality of cells may be, but are not limited to: a mammalian cell; a bacterial cell; a plant cell; a yeast cell, or a spore derived from filamentous fungus. The cell or plurality of cells may be an immune cell, a fetal cell, a stem cell or a progenitor cell. The cell or plurality of cells may be a T cell or a B cell. The capture bead or plurality of capture beads may be, but are not limited to, any beads that bind biological material, such as non-specific capture beads, antigen capture beads, enzyme capture beads, nucleic acid capture beads, or any combination thereof.

In some embodiments, micro-objects may be flowed within an aqueous medium into the microfluidic channel, and some or all of the micro-objects may be selected from the micro-object-containing aqueous medium in the channel of the microfluidic device for disposition within one or more chambers. In some embodiments, only one cell may be disposed within a single chamber. Any other desired reagents/capture objects/feeder cells or other adjunct biological micro-object may also be introduced to the chamber. For example, one or more capture beads that non-specifically bind to biological material, such as peptides, proteins or small molecules, can be disposed in the chamber along with the cell(s); one or more antigen-specific capture beads or enzyme capture beads can be disposed in the chamber along with the cell(s); and/or one or more nucleic acid binding capture beads can be disposed in the chamber along with the cell(s). While the aqueous medium in the channel and chambers, e.g., a first aqueous medium, may initially have substantially the same composition, the aqueous medium in the chambers may become different over time, for example, as a result of cellular secretions into the first aqueous medium in chambers that contain biological cells; such secretions may bind to capture beads present in the chambers. The aqueous medium may include any kind of carbon/energy source, and in some variations, further include minerals and nutrients for supporting cell viability and growth. The chambers may be encapsulated with a layer of a water immiscible fluidic medium, which may separate, e.g., isolate, the first aqueous medium within each chamber from the medium in the channel. "Isolate" as used in this context may mean completely separate. Alternatively, separation/isolation may permit diffusion of certain types of molecules between the channel and the chamber, such as how steroids can diffuse through a plasma membrane or gas molecules, e.g., oxygen, may diffuse from a water immiscible fluid into an aqueous fluid. The encapsulation may optionally be reversible (e.g., selectively reversable for individual chambers/pens or globally reversable across the array of chambers/pens on the microfluidic device). The water immiscible fluidic medium may displace substantially all of the first aqueous medium in the channel, where "substantially all" in this context refers to at least about 95% (e.g., at least about 96%, about 97%, about 98%, about 99%, about 99.5%, about 99.8%, about 99.9% or more) of the aqueous medium in the channel. The layer of water immiscible fluidic medium may be introduced by flowing the water immiscible fluidic medium into the microfluidic channel or filling the channel with the water immiscible fluidic medium. The water immiscible fluidic medium can be any suitable water immiscible fluidic medium as described herein or as is known in the art. When the layer of water immiscible fluidic medium is introduced, it is introduced without substantially displacing the aqueous medium within the chamber, that is the aqueous medium within the chamber and cells and reagents contained therein, are not significantly displaced or dislodged. As used herein, "without substantially displacing" means about 20% or less (e.g., 18%, 15%, 12%, 10%, 9%, 8%, 7%, 6%, 5%, 4%, 3%, 2%, 1%, or less) of the medium in each chamber. In certain embodiments, the chamber comprises a connection region and an isolation region (as described elsewhere herein) and flowing a water immiscible fluidic medium into the channel displaces substantially all of the first aqueous medium in the channel without displacing any of the first aqueous medium in the isolation region of the chamber. In certain related embodiments, flowing a water immiscible fluidic medium into the channel displaces substantially all of the first aqueous medium in the channel while displacing 50% or less (e.g., 45%, 40%, 35%, 30%, 25%, 20%, or less) of the first aqueous medium in the connection region. The layer of water immiscible fluid may not significantly displace the aqueous medium within the chamber, in part due to the configuration and structure of the microfluidic device. For example, the features of the microfluidic device described herein (e.g., the positioning of the sequestration pen/chamber and the channel on a shared horizontal plane, the structural features of the channel, and the features of the sequestration pen including the connection region and isolation region features and dimensions) may be configured to prevent the water immiscible medium in the channel from entering the sequestration pen, while also permitting the aqueous fluidic medium to be retained within the pen.

In some embodiments, the immiscible fluidic medium is an oil. In some embodiments, the water immiscible fluidic medium can be oxygenated, or saturated with a gas or a mixture of gasses, for the purpose of providing a partial pressure gradient across the channel and the chamber. The water immiscible fluidic medium can be paired with the composition of the hydrophobic or hydrophilic coating such that the pairing is configured to facilitate thermodynamically favorable formation of an encapsulation layer in the connection region of the chamber or sequestration pen, e.g., at a portion (e.g., sub-region) of the connection region proximal to the microfluidic channel as described herein; thermodynamically favorable formation of an encapsulation layer can, for example, comprise the formation of hydrophobic interactions between the water immiscible fluidic medium and a hydrophobic coating.

Figure 8A:
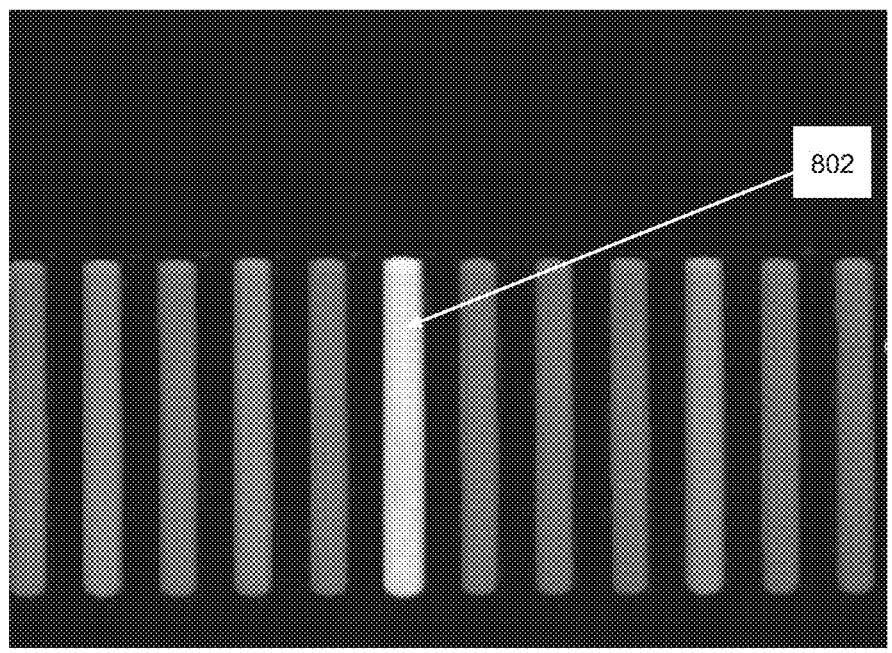
FIGS. 8A to 8B illustrates the encapsulation of individual cells in corresponding individual chambers, with an encapsulation layer of defined thickness formed at the connection region of the chamber.
Figure 8B:
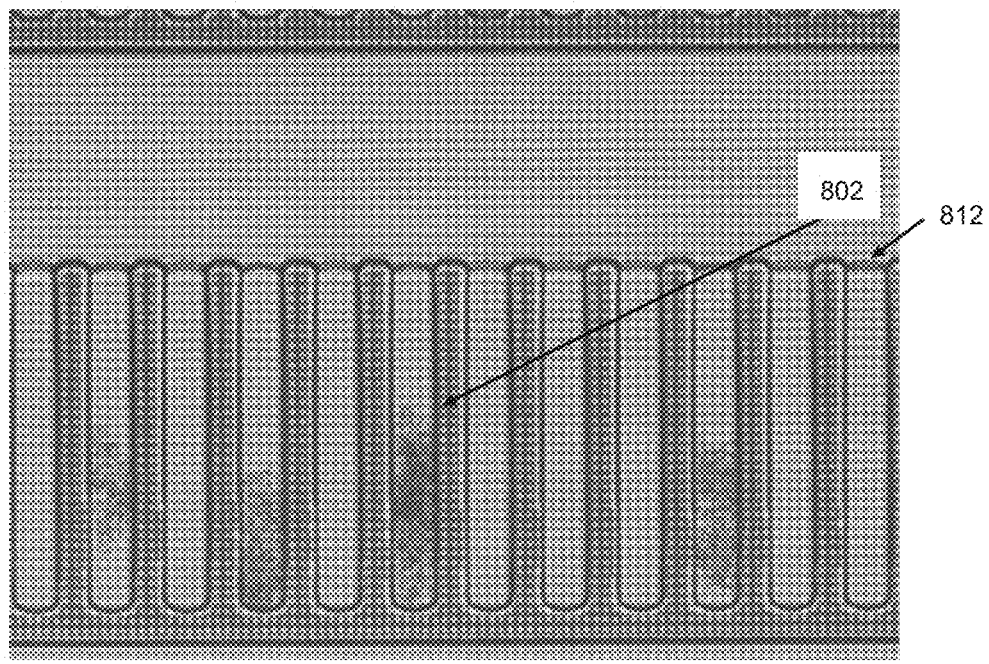

In some embodiments, as shown in FIG. 8B, a second aqueous medium can be introduced (e.g., aspirated or flowed) into the microfluidic channel, pulling more than about 40%, about 50%, about 60%, about 70%, about 80%, about 90%, or about 95% of the water immiscible fluidic medium out of the channel, leaving the remainder as an encapsulation layer 914. The second aqueous medium may be introduced subsequently to the introduction of the water immiscible fluidic medium, where "subsequently" as used in this context can mean directly after (e.g., following directly behind) the water immiscible fluidic medium, or after an intervening medium, such as air, 5% $CO_2$ in air, or another gas, or a different water immiscible fluidic medium has been aspirated into the channel. The second aqueous solution can be introduced at a rate that facilitates the formation of encapsulation layers, e.g., including at a rate that ranges from 0.01 ul/sec to 2.0 ul/sec. In some variations, the introduction of the second aqueous medium is made at less than or equal to about 1.0 ul/s, which minimizes gas bubble nucleation. The encapsulation layers generated in the disclosed methods can comprise a thickness within the range of about 1 micron to about 100 microns, depending on a number of variables, including but not limited to: the rate at which bulk of the water immiscible fluidic medium is removed (via aspiration of the second aqueous medium through the microfluidic channel or by flowing the second aqueous medium through the microfluidic channel) from the microfluidic channel, the composition of the water immiscible fluidic medium, the composition and distribution of the hydrophobic and/or hydrophilic coatings, and the length of the connection region $L_{con}$. In some variations, an encapsulation layer may be generated that extends from about 5 microns to about 50 microns from a contact surface with the aqueous medium in the chamber into the channel. In some variations, an encapsulation layer may have an average thickness of about 5 um to about 50 um (e.g., about 5 um to about 45 um, about 5 um to about 40 um, about 5 um to about 35 um, about 5 um to about 30 um, about 5 um to about 25 um, about 5 um to about 20 um, about 10 um to about 50 um, about 10 um to about 45 um, about 10 um to about 40 um, about 10 um to about 35 um, about 10 um to about 30 um, about 10 um to about 25 um, about 10 um to about 20 um, about 15 um to about 50 um, about 15 um to about 45 um, about 15 um to about 40 um, about 15 um to about 35 um, about 15 um to about 30 um, about 15 um to about 25 um, about 20 um to about 50 um, about 20 um to about 45 um, about 20 um to about 40 um, about 20 um to about 35 um, or about 20 um to about 30 um.

The cells so encapsulated within the chambers (e.g., sequestration pens) may be cultured (e.g., incubated) and/or assayed and/or monitored over time using brightfield and/or emission (e.g., fluorescence) microscopy for a period of time before removal of the encapsulation layer of a selected chamber or all chambers. For example, cells may be cultured for a period of time, including but not limited to: about 30 min; about 45 min; about 1 h; about 2 h; about 4 h; about 6 h; about 8 h; about 10 h; about 12 h; about 18 h; about 24 h; about 48 h; about 72 h; or more. In some embodiments, cells may be cultured for about 2 h to about 24 h, about 4 hours to about 24 hours (e.g., between about 8 h and about 12 h, between about 12 h and about 16 h, between about 16 h and about 20 h) or any length of time therebetween. The cells may be cultured for one period of time or may be cultured for repeated periods of time. The cells may be cultured at a temperature between about 18 degrees centigrade (C) and about 50 degrees C. (e.g., between about 25 degrees C. and about 37 degrees C.).

Monitoring may include monitoring an activity of the cells, which may form part of assaying the cells. Monitoring may be performed during a first period of culturing, and may be performed at a plurality of time points during the first period of culturing. Monitoring may be performed about every 5 min; about every 10 min; about every 15 min; about every 30 min; about every hour; or more. Alternatively, monitoring may be performed continuously or substantially continuously during a first period of culturing and/or additional periods of culturing. In yet other variations, monitoring may be performed after a first period of culturing or may be performed after each period of culturing.

Monitoring may include imaging the cells (and/or capture beads) encapsulated within the chambers, and may additionally include imaging the chambers, e.g., sequestration pens, in which the cell are disposed. Quantification can be performed on these images to determine the volume of cells, the density of cells, the amount of emission (e.g., fluorescence), the amount of secretions bound to capture beads (e.g., as determined by a fluorescent signal bound to a reporter molecule that binds to secreted molecules that are bound to the bead), the concentration of secreted small molecules, level of expression of a biomolecule and other metrics that may be relevant to the secretion of cells, cell health, and/or to distinguish one subpopulation of cells from another subpopulation of cells. Quantification can be performed at a single fixed time point or at discrete time points over a fixed period of time, and ratios, relationships, and/or other mathematical manipulations can be performed on the quantified information to make deductions about the cells in each of the chambers, over a population of similar cells encapsulated in discrete chambers across the micro-fluidic chip, or over populations of functionally different cells encapsulated in discrete chambers across the micro-fluidic chip.

The cells encapsulated within the chambers may express variable amounts of a molecule of interest or a reporter molecule (e.g., where the reporter molecule is indicative of an activity of the cell(s)). "Variable amounts" as used herein may encompass anything from no expression/secretion to extremely high levels of expression/secretion. The molecule of interest may be a small molecule, a carbohydrate, a peptide, a protein, a nucleic acid, or any other molecule capable of being produced by a biological cell. In some variations, the molecule of interest or reporter molecule (such as, but not limited to green fluorescent protein) may be secreted. In other variations, the molecule of interest or reporter molecule may be released from the cell via lysis. In yet other variations, the molecule of interest or reporter molecule may be monitored, detected and/or quantified while present intracellularly. As the encapsulation layer prevents secreted or released small molecules/carbohydrates/peptides/proteins/nucleic acids within the chamber from diffusing out of the chambers, the observed fluorescence/luminescence/optical density (e.g., detectable signal) in each of the chambers may be due only to the molecules produced by the cells or released from (e.g., content of the cell) of the cells resident in each chamber. There may be no contribution to the detectable signal in a selected chamber by molecules produced elsewhere within the device and correspondingly, the amount of detectable optical signal observed in a selected chamber may not be diminished by secreted small molecule, carbohydrate, peptide, protein, or nucleic acid diffusion out of that chamber. When encapsulated cells are monitored, the level of expression of a molecule of interest or reporter molecule may be more accurately be detected since the signal observed within the encapsulated sequestration pen is due only to the molecule of interest or reporter molecule due to the respective cell. Thresholds for selecting cells of interest for additional assay or further culturing may be pre-determined by the user, e.g. relative to a control or may be determined by relative levels of detected signal established over a plurality of sequestration pens within the microfluidic device.

Alternatively, or in addition, the cell(s) may be monitored to determine one or more phenotypic parameters of the cell, which include, but are not limited to cell surface markers (e.g., clusters of differentiation molecules (CD)); cell division rate, lifespan, morphological differences, and other inherent traits or characteristics that are observable or testable.

Alternatively, or in addition, the cell(s) may be monitored to determine cell growth, which can encompass the change in size of a cell or may include determining the expansion or the rate of expansion of a population of cells, e.g. a clonal population of cells.

In additional or alternative embodiments, encapsulation may be adapted to perform user specific objectives that rely on selectively or uniformly isolating a cell or population of cells into a chamber or pen for the purposes of performing an array of individual experiments, assays, or workflows on one or more genotypically or phenotypically distinct cells for the purpose of identifying or characterizing the genotypically or phenotypically distinct cells under varying or similar conditions. For example, in any one of the examples illustrated herein, the encapsulation layer can be configured to be relatively impermeable to diffusion of solutes in the aqueous solution disposed within the aqueous solution of the chamber, selectively impermeable to a class of soluble components in the aqueous solution of the chamber, and/or impermeable to the aqueous solution encapsulated in the pen. In some embodiments, encapsulation can be configured to perform any one of the following non-limiting utilities: to prevent cross-talk between pens or chambers, to restrict diffusion of small molecules between pens or chambers; to genetically characterize single cells; and/or to prevent migration of motile cells between pens or chambers.

Either during the course of culturing, assaying, manipulating the cells (e.g., lysing and capturing nucleic acids for nucleic acid sequencing and genetic characterization) or afterward, the encapsulation layer may be removed selectively or in bulk, thereby generating one or more de-encapsulated chambers (e.g., sequestration pen(s)). A single encapsulation layer or set of encapsulation layers can be removed either selectively or randomly.

Figure 11A:
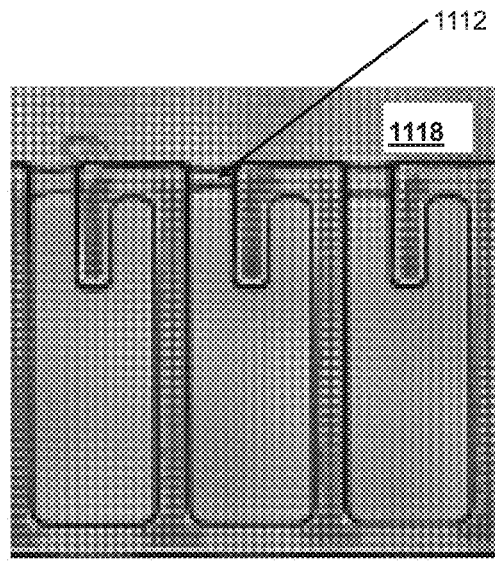
FIGS. 11A to 11D illustrate an exemplary method for selectively ablating the encapsulation layer.
Figure 11B:
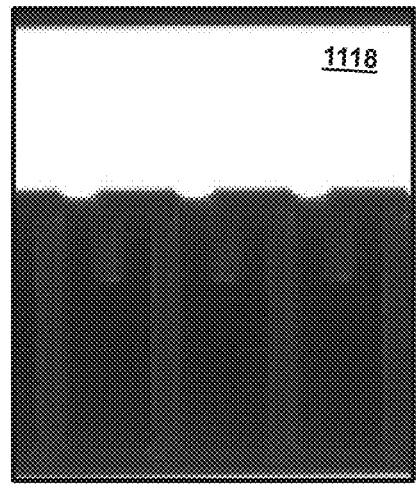
Figure 11C:
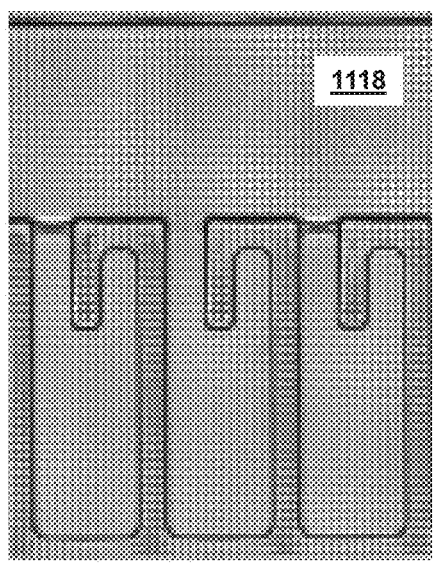

One or more encapsulation layers can be removed at defined time points during cell culture. In some embodiments, encapsulation can be used to selectively introduce different conditions to cells to assay the impact of the conditions on one or more cells or cell types. For example, in some embodiments, encapsulation layers can be removed in a specific order to support the selective perfusion of different types of medium into a single selected chamber or sequestration pen or selected sets of chambers or sequestration pens. In other non-limiting embodiments, encapsulation can be performed to isolate certain cells from harmful conditions (e.g., a lytic agent used for cell lysis), while de-encapsulation can be used to expose certain cells to such harmful conditions, e.g., lytic conditions. Additionally, or alternatively, encapsulation can be performed to selectively contain the components of a lysed cell in the chamber or pen for the purposes of retaining or restricting the diffusion of RNA/DNA outside of the chamber or pen. In further variations, de-encapsulation, whether in bulk or selective de-encapsulation may permit unpenning of micro-objects, e.g. cells or beads, either selectively or in bulk. Unpenning as used herein may refer to moving a micro-object out of a chamber/sequestration pen and distinguish from exporting a micro-object out of the chip after it has been unpenned. As shown in FIGS. 11A-11C, encapsulation and de-encapsulation can effectively segregate treatment from non-treatment chambers, as only the single chamber (e.g., sequestration pen) having the encapsulation layer selectively removed shows any fluorescence within the chamber. Encapsulation and/or de-encapsulation may be performed once, twice, three times, four times or any desired number of times during any workflow, as desired and designed for the particular workflow.

Methods for bulk removal of encapsulation layers can comprise flowing a medium comprising one or more surfactants through the channel. The types of surfactants and the rate of perfusion can be configured to remove encapsulation layers at a particular rate. The surfactant may be formulated in an aqueous solution of the surfactant, where the surfactant is present in about 0.1%; about 0.5%; about 1.0%; about 2%; about 3%; about 4%; about 5%; or any percentage therebetween. In some variations, the surfactant may be present at a concentration of about 0.1% or about 1.0%. The surfactant-containing aqueous medium may be flowed through the microfluidic channel at a rate of about 0.2 ul/s to about 1.0 ul/sec. In some other embodiments, the surfactant solution may be flowed through the microfluidic channel at about 2.0 ul/s; about 3.0 ul/s, about 4.0 ul/s or about 5 ul/s. As shown in FIGS. 10A to 10E, surfactant can be flowed within the channel to displace a water immiscible fluidic medium filling the channel or the flow of surfactant can displace a thin encapsulation layer of the water immiscible fluidic medium which caps the chamber (e.g., sequestration pen). The surfactant(s) may be any suitable surfactant as described herein or known in the art.

In some variations, when the encapsulation layer is a thin encapsulation layer, e.g., the entire channel is not filled with the water immiscible fluidic medium, as shown in at least FIGS. 9B-9C, 11A-11D; 12A-12C, the encapsulation layer may be removed by application of a targeted laser pulse to the aqueous medium within the chamber, proximal to the encapsulation layer. Proximal in this context means within about 100 um of the encapsulation layer (e.g., within about 90 um, about 80 um, about 70 um, about 60 um, or about 50 um). Laser illumination was selected to generate a bubble directed towards the thin encapsulation layer, pushing the water immiscible fluid of the encapsulation layer out into the microfluidic channel and away from the opening to the chamber. The power (the effective power exiting the optical system may be about 10-100 mW) and wavelength (which may be from about 450 nm to about 1000 nm, and may be about 800 nm) of the laser can be selected to nucleate bubbles in the medium that generate mechanical perturbations and shear forces sufficient to break the encapsulation layer. While laser illumination may require selection of a programmed ramp/delivery over a period of about 50 ms to deliver the threshold amount of energy to nucleate a bubble, the actual period of energy delivery required is much shorter, e.g. on the order of a few microseconds, e.g., about 3 ms, about 5 ms, about 6 ms, or the like. Once the bubble is nucleated, the bubble itself slows down further rate of increase of the size of the bubble, and longer illumination periods are not required, once the initiation/nucleation energy input has been exceeded. In some embodiments, selective removal (e.g., de-encapsulating) as illustrated in FIG. 11A-11D can be performed on the encapsulation layers of chamber or pens that comprise cells that have been encapsulated in the pens, allowing specific targeted cells to be exposed to new medium flowed through the channels. Methods for introducing additional aqueous medium of different composition (e.g., a second, third, fourth, fifth, etc.) can comprise one or more of the previous disclosed methods for generating the encapsulation layers, followed by the selective removal of one or more pens, and the flowing of a medium (e.g., a second, third, fourth, fifth, etc. type of medium) of different composition into the channel, at a rate and for a duration that facilitates medium exchange between the channel and the de-encapsulated chambers or sequestration pens. Once exchange is complete, a water immiscible fluidic medium can be flowed into the channel to reform the encapsulation layers.

In further embodiments, selective removal of a encapsulation layer on one or more chambers or pens can be configured as part of a method for performing a work flow or assay based on quantitative or qualitative features of a cell determined by imaging the cell or cells using microscopy (e.g., brightfield or emission (e.g., fluorescence) microscopy), imaging capture beads which have captured a molecule secreted by the cell or cells within the chambers or pens, or by exporting a capture bead(s) (e.g., after capturing a molecule secreted or released by a cell or cells) out of the microfluidic device, wherein the molecule and/or bead may be further analyzed by other methodologies.

In some variations, upon removal of the encapsulation layer on the one or more chambers or pens, one or more cells, one or more capture beads (e.g., a nucleic acid capture bead, a protein capture bead, small molecule capture bead, etc.), or any combination thereof, can be selectively or non-selectively moved from the chamber or pen in which it is (they are) located using methods including, but not limited to, a directly or indirectly generated force (e.g., forces generated by DEP, localized flow (e.g., generated by deformation of a deformable surface), gravity etc.). Following such movement to the channel, the cell(s), capture bead(s), or combination can be exported from the microfluidic device, e.g., by flowing an export buffer through the channel and out of the microfluidic device. Alternatively, or in addition, upon removal of the encapsulation layer of the one or more chambers or pens, one or more cells, one or more capture beads (e.g., a nucleic acid capture bead, a protein capture bead, small molecule capture bead, etc.), or any combination thereof, can be disposed within a chamber or pen using methods including, but not limited to, flowing one or more aqueous solutions comprising cells, capture bead(s) or any combination thereof and disposing the cells, capture beads, or combination into the chamber or sequestration pen using a directly or indirectly generated force (e.g., forces generated by DEP, localized flow (e.g., generated by deformation of a deformable surface), gravity etc.). These variations permit, for example, addition, subtraction, or replacement of capture beads, for monitoring secretions produced during different time periods (e.g., during first, second, third, etc. incubation/culture periods) and detecting changes in the secretions over time (e.g., by comparing the results obtained from the different incubation/culture periods), In addition, these variations permit addition, subtraction, or replacement of cells, for monitoring cell-cell interactions during different time periods (e.g., during first, second, third, etc. incubation/culture periods).

Following removal of the encapsulation layer on one or more chambers or pens, a water immiscible fluid medium can be flowed into the channel, thereby reencapsulating the one or more chambers or sequestration pens comprising the cells, capture beads, or combination thereof, the water immiscible fluid medium may substantially fill the channel.

In some variations, a fluid other than the immiscible fluid medium can then be flowed into the channel, driving out the immiscible fluid medium in a substantial portion of the channel, and thereby regenerating an encapsulation layer (e.g., an encapsulation layer with a defined thickness, as disclosed herein) configured to separate the other fluid in the channel from the medium in the one or more chambers or sequestration pens. The other fluid can be air or another gas (e.g., 5% $CO_2$ in air), or it can be an aqueous fluid, such as a buffer. The aqueous fluid can be a culture medium, a reagent buffer (e.g., lysis buffer, buffer comprising active or inducing agents, suspended small molecules, suspended biological agents, etc.), an export medium, or the like, as appropriate for subsequent steps in the workflow. Thus, in some variations, a second aqueous fluidic medium, which may be the same as a culturing medium, may be flowed into the channel to generate an encapsulation layer having a defined thickness, separating the second aqueous fluidic medium in the channel from the aqueous medium within the chamber/sequestration pen. The second aqueous fluidic medium may be introduced before, during or after a second, third, fourth, etc. time period of culturing. A targeted laser de-encapsulation, as illustrated in FIGS. 9B-9C, 11A-11D, can then be used to selectively remove the encapsulation layer of specific chambers or pens.

In some non-limiting embodiments, the selective removal of the encapsulation layer can be performed based on the automated or manual selection of specific chamber(s) or pen(s), wherein the selection is based on one or more quantitative or qualitative features of one or more sets of pixels of a single or stack of brightfield or emission (e.g., fluorescence) images taken of the chamber(s) or sequestration pens(s), wherein the features of the sets of pixels in the chamber(s) or sequestration pen(s) provide any combination of: an indication about physiological state of cell(s) in each individual chamber or sequestration pen, one or more features indicative of a genotypic or phenotypic characteristic of a cell(s) in each individual chamber or sequestration pen, the presence or absence of capture beads in the sequestration pen(s) or chamber(s), or a biologically significant occurrence in the chamber(s) or sequestration pen(s) that has been observed over a duration of time. In some variations, cell(s) of interest may be selected for additional assays based upon one of more of these selection criteria, which may be a predetermined criteria (e.g., a level of secreted molecule expression is detected). Alternatively, the cell(s) may be selected based on relative activity, e.g., the extent of cellular activity for that cell compared to detected activity of cells in other chambers of the microfluidic device. For instance, cells from a total of four chambers which express the highest level of fluorescent labelling for secreted molecule production may be selected for further assays, without requiring a particular threshold level of fluorescent labelling for the selected cells. The further assays may include labelling for different cell surface markers, detection of secretion of different molecules from the cell(s); detection of the effect of the secreted molecules upon a second different cell, or may include genetic analysis of one or more of the cell(s) within a chamber.

Methods for performing qualitative or quantitative analysis on images taken from a single or stack of brightfield or emission (e.g., fluorescence) images can be found, e.g., in PCT Publication No. WO 2018/102748, the entirety of which is herein incorporated by reference. In instances where a protocol is automated, a user may pre-load a reagent and select one or more qualitative or quantitative features or criterion, the removal of the encapsulation layer may then be automated such that selective removal of encapsulation layers is performed automatically based on the one or more qualitative or quantitative features previously identified by the user.

Removal of the encapsulation layers, whether selective or in bulk, exposes the cell(s) and/or capture bead(s)/solid substrates disposed in the unencapsulated chamber(s) or pen(s) to the reagent. The chamber(s) or sequestration pen(s)

can then be imaged to monitor for a specific response (e.g., changes in emission, fluorescence, etc.), the chamber(s) or sequestration pen(s) can be selectively resealed, other chamber(s) or sequestration pens(s) can be removed and exposed to the same or different reagents, and/or the cell(s) and/or micro-object(s) e.g., such as capture beads, can be exported for additional analysis off the microfluidic chip, including, but not limited to identification methods such as mass spectrometry, or quantification assays such as protease or other enzymatic assays capable of producing quantifiable assay results.

Figure 12A:
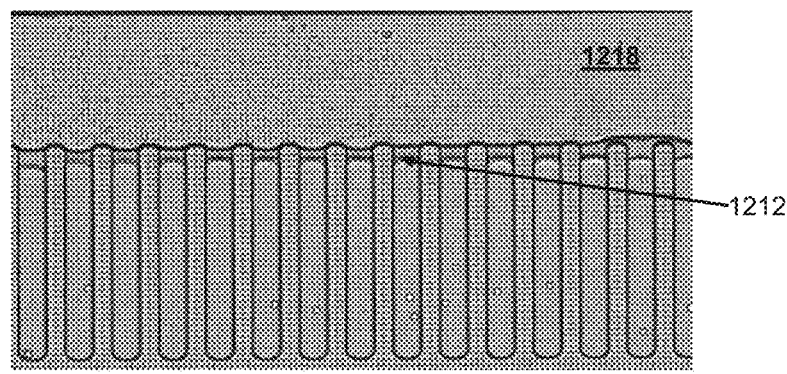
FIGS. 12A to 12C illustrate an exemplary method for culturing and selectively lysing cells.
Figure 12B:
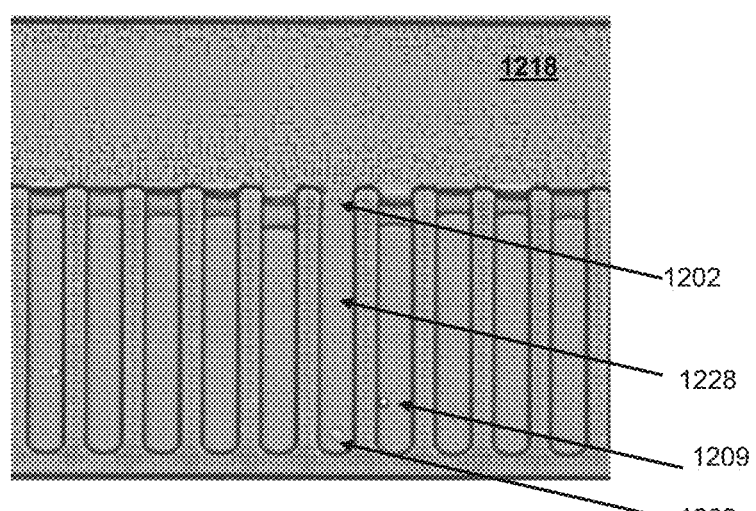
Figure 12C:
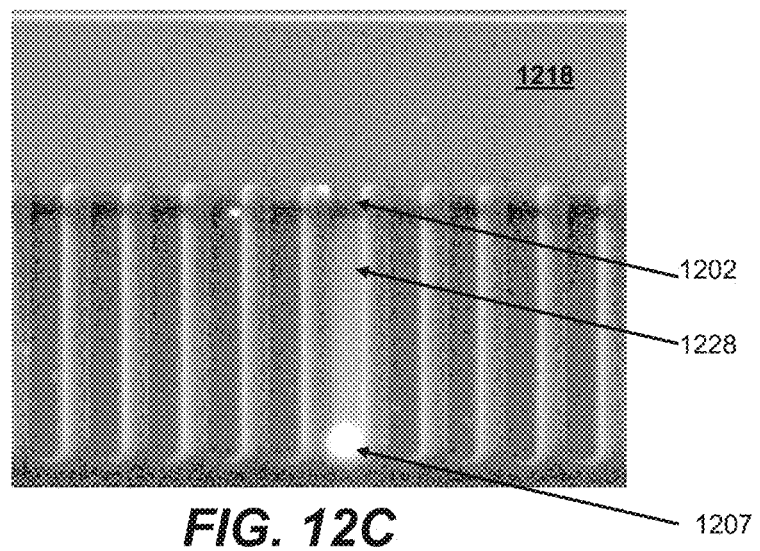

Some exemplary methods of biological cell analysis for which encapsulation and de-encapsulation are useful. As described above, encapsulating and de-encapsulating cells within chambers of a microfluidic device may permit selective and controllable culturing, assaying (including, but not limited to lysing a cell within a chamber), identification of optimized cells, and selective unpenning or export thereof. One exemplary, but non-limiting method is shown in FIGS. 12A-12C, and illustrate culturing and selectively lysing cells. Cells are encapsulated in chambers or sequestration pens with encapsulation layers using any combination of the methods disclosed herein. Once the cells are penned, a water immiscible fluid is flowed into the channel (e.g., an oil). An aqueous solution is then perfused into the channel, driving the water immiscible fluid out of the channel, as illustrated in FIG. 12A, such that cell(s) and culture media are disposed within the sequestration pens, and each sequestration pen is encapsulated by a thin film coating of water immiscible fluidic medium. External to the thin film or encapsulation layer in the channel, is the aqueous solution, which may be a buffer, such as cell lysis buffer; alternatively, the aqueous solution can be a culture medium or other type of buffer which is replaced (e.g., by flowing through the channel) a cell lysis buffer after a suitable amount of time. FIG. 12B is a brightfield image from the same field of view as FIGS. 12A and 12C, taken after the encapsulation layer of a single pen has been selectively removed (e.g., by laser-induced formation of a bubble). In FIG. 12B, the lysis buffer selectively diffuses from the channel into the sequestration pen. Lysing is confirmed in FIG. 12C, which is a fluorescent image of the same field of view as FIG. 12B after a Propidium Iodide stain has been perfused into the channel and diffused into the open pen where emission (e.g., fluorescence) is generated confirming that the cell is successfully lysed. In some non-limiting embodiments, a capture bead (e.g., nucleic acid capture bead) may be loaded into the channel. The capture bead (e.g., nucleic acid capture bead) can be loaded with the cell from a medium comprising cells and capture beads (e.g., nucleic acid capture beads), prior to loading the cell from a medium comprising only capture beads (e.g., nucleic acid capture bead), or after loading the cell for example with the lysis buffer (e.g., using optically actuated DEP force). The lysis buffer, nucleic acid capture bead, and cell may be encapsulated within a chamber allowing selective lysis of the cells and capture of the RNA/DNA from the lysed cell to the bead. In some variations, the bead may comprise primers for capturing nucleic acids and, optionally, a tag for sequencing. In further embodiments, the method can additionally include one or more of: applying a unique designator to a chamber or pen, identifying one or more capture beads (e.g., nucleic acid capture bead) in the channel or pen, observing one or more features of the capture bead (e.g., nucleic acid capture bead) in the pen, correlating the observed features of the micro-objects in the pen with a unique tag on the bead, sequencing a capture bead (e.g., nucleic acid capture bead), and correlating the features observed for the capture bead (e.g., nucleic acid capture bead) in the pen with the sequence information obtained from a tagged capture bead. Methods and devices for capturing nucleic acids on a micro-fluidic device are disclosed, for example, in PCT Application No. WO2015095623, the entire disclosure of which, except for any definitions, disclaimers, disavowals, and inconsistencies, is incorporated herein by reference. Additional methods and devices for capturing nucleic acids, along with methods and compositions for generating and utilizing DNA barcodes, are disclosed in PCT Application No. WO2018064640, the entire disclosure of which, except for any definitions, disclaimers, disavowals, and inconsistencies, is incorporated herein by reference.

Another exemplary method for biological cell analysis using encapsulation layers may include a method of assaying the effect of a molecule (which may be small molecule, e.g., a small organic molecule, having a molecular weight equal or less than 2000 Da, or a peptide) upon a biological cell disposed within a chamber, e.g., sequestration pen, of a microfluidic device, which has been encapsulated according to the methods described herein. The ability of molecules, especially small molecules, to diffuse quickly from chambers/sequestration pens of a microfluidic device makes the encapsulation of a chamber/sequestration pen an attractive method for controllably contacting cells with easily diffusible species.

The microfluidic device may have a hydrophobic coating on one or more surfaces within the microfluidic device, which may be any hydrophobic coating as described herein, the hydrophobic coating as disclosed herein may assist with the encapsulation of the chambers/sequestration pens. Biological cells may be flowed into the microfluidic device and are disposed within a chamber/sequestration pen.

The molecule, e.g., a small molecule, may be introduced into the chamber/sequestration pen incorporated onto/into or associated with a micro-object (e.g., bead or other solid substrate capable of being disposed into a chamber/sequestration pen of the microfluidic device). The molecule-bearing bead may be introduced into the chamber/sequestration pen before or after the biological cells have been introduced. The incorporation of the molecule may be physical impregnation into a dissolvable matrix or coating of the bead (e.g., non-covalently). Alternatively, the molecule may be associated with the bead by hydrostatic/hydrophobic/hydrophilic/ionic association (e.g., non-covalently) or may be associated with the bead by releasable attachment directly or indirectly to the bead (e.g., covalently or non-covalently). In any case, the amount of molecule loaded onto/in association with the bead may be known, and the concentration of the molecule released into the chamber/sequestration pen may be designed to deliver a known concentration of the small molecule. In some variations of the methods, the molecule-bearing beads may further include an identifier which permits tracking of the identity of the small molecule across the assay. The identifier may be any suitable identifier including RFID barcodes, chemical barcodes such as nucleic acid barcodes, physically detectable barcodes such as color-coded nanoparticles, such as quantum dots, or any identifier as is known in the art. Some non-limiting compositions for generating and utilizing DNA barcodes, are disclosed in PCT Application No. WO2018064640, incorporated by reference in its entirety.

The incorporation or releasable attachment of the molecule within/upon/with the bead may prevent molecule dissociation from the bead and/or be releasably detached controllably such that dissociation or detachment does not take place during introduction of the bead into the chamber/sequestration pen. This prevents cross-exposure of cells in different chambers/sequestration pens to the molecule, and delivers a known quantity of the molecule to the selected chamber/sequestration pen.

In some variations, a release reagent may be introduced to the chamber/sequestration pen after the molecule-bearing bead has already been disposed within the chamber. The release reagent may trigger the release of the molecule from its incorporation or association with the bead. The release reagent may include, but is not limited to temperature, enzymes, chemicals and light. For example, a release reagent that uses temperature differences may, for example, include introducing the molecule-bearing bead at a first, lower temperature, such as 15 degrees C. to about 25 degrees C., followed by an increase of temperature within the microfluidic device to about 27 degrees C. to about 37 degrees C. This may act to solubilize a gel matrix on a bead, which had immobilized the molecule. Alternatively, the increase of temperature may detach the molecule, for example, if the molecule was releasably attached to a bead by a hybridized oligonucleotide pair. The increased temperature may reach the melting temperature (Tm) for the hybridized oligonucleotide pair, "melting" it and releasing the molecule. In yet another alternative, a protease may be introduced to cleave peptide bonds which may specifically (in the case of a dissolvable bead containing the molecule) or specifically (in the case of a releasably attached molecule) release the molecule. In another alternative, the introduction of a reagent which alters the pH in the chamber/sequestration pen may trigger release of the molecule. In some other variations, a surfactant (such as, but not limited to, a non-ionic surfactant) may trigger release of the molecule from the bead. In yet other variations, a matrix or coating may be disrupted by a photo-initiated cleavage, or a molecule may be releasably detached by a photo-initiated cleavage, thereby triggering release of the molecule. In some variations, a release reagent may not be introduced and the molecule may dissociate or detach from the bead over a period of time, which may be pre-selected. For example, the molecule may be incorporated within a matrix or coating that is designed to dissolve within the aqueous medium of the chamber/sequestration pen over a specified period of time when contacted with water, e.g., a time-release or controlled release formulation. Other chemical release reagents may be used, as one of skill can devise.

Once the bead including the molecule is introduced into a chamber/sequestration pen containing one or more biological cells, and optionally, a release reagent has been introduced, an encapsulation layer may be introduced to seal the contents of the chamber/sequestration pen from the channel and/or other chambers/sequestration pens. The encapsulation layer, a water immiscible fluidic medium may fill the channel or it may form a thin encapsulating layer. In some variations, the encapsulation layer may extend into a portion of a connection region of the sequestration pen, as described herein, where the portion of the connection region may be a sub-region of the connection region proximal to the channel. The water immiscible fluidic medium may be any water immiscible fluidic medium described herein or known to one of skill to be suitable for the purpose.

The release reagent may then be triggered to release the molecule, and the known amount (concentration) of the molecule may be released to contact the biological cell in the chamber/sequestration pen for a period of time, which may be about 1 h, about 2 h, about 4 h, about 8 h, about 12 h, about 18 h, about 24 h, or more, while maintaining the biological cell. The encapsulation layer maintains the concentration of the molecule, and prevents cells in neighboring pens from being exposed to contaminating molecules from other pens. When the exposure time is complete, in some embodiments, the sequestration pens may be de-encapsulated and culture media may be flowed to wash out all test molecules from the microfluidic device. The de-encapsulation may be performed as described herein, and the encapsulating layer, whether it fills the entire channel or is present as a thin encapsulation layer, may be displaced in bulk, by flowing surfactant within the channel to displace the water immiscible fluidic medium. When the encapsulation layer is a thin encapsulation layer across the opening of the chamber/sequestration pen to the channel, selective de-encapsulation may be effected by directing a laser toward the boundary of the aqueous medium within the chamber/sequestration pen with the water immiscible fluidic medium, generating a bubble which breaks the encapsulating layer and permits aqueous media to diffuse in/out of the chamber/sequestration pen.

In some embodiments, an assay may be performed upon the cells to assess the effect of the molecules upon the biological cells, which may include adding assay media and/or assay reagents to the chambers/sequestration pens, and a detectable signal arising from the assay may be detected and optionally, quantified. In some variations, quantification may be relative to responses detected in some or all of the chambers/sequestration pens, e.g., relative to a control, normalized against a selected set of chambers/sequestration pens, or relative to an averaged response detected across the chambers/sequestration pens. Accordingly, quantification may be made relative to about 1, about 5, about 10, about 50, about 100, about 1000, about 5000, about 10,000 or all of the chambers/sequestration pens within the microfluidic device. Assaying and/or detection may be performed without re-encapsulating the chambers/sequestration pens or may include a step of re-encapsulating the chamber/sequestration pens by flowing a water immiscible fluidic medium within the channel to displace the aqueous medium containing the assay reagents. Further, in some embodiments, a thin encapsulation layer may be introduced by introducing a further aqueous medium into the channel and leaving a thin encapsulation layer.

One such version of this assay may be using cells containing a reporter gene construct with green fluorescent protein (GFP) under the control of a transcriptional promoter believed to be regulated by exposure to small molecules. The assay may permit determination of GFP expression timing, maximal signal and signal decay upon exposure of a plurality of cells, particularly a plurality of clonal cells, to a library of thousands of molecules. This may be used to identify an optimal ligand for pathway activation, and may use thousands of variants of the ligand in the experiment.

Ligand, e.g., molecule, concentration effects may be studied using this type of experiment, by using beads having the same ligand at different concentrations. Testing in parallel upon a plurality of cells, particularly a plurality of clonal cells may yield information about affinity and kinetics of regulation.

In another variation, the effect of the molecule upon a plurality of cells may be used to screen for an efficacious therapeutic molecule, where assay reagents, including a reagent providing a detectable signal, may be included within the encapsulated chamber/sequestration pen with the molecule-bearing bead and the biological cell. Performing this in parallel upon a plurality of cells, particularly a plurality of clonal cells, with a plurality of different molecules, which may optionally be present at different concentrations, may permit the elucidation of potency of these molecules such as IC50, EC50, LD50 or TD50.

In some other variations, qualitative or quantitative analysis of one or more products (e.g., molecules secreted by the cell(s)) produced in response to exposure to the bead-borne molecule as described above, may be studied, in addition to or in alternative to analysis of the direct effects on the cell(s) of the bead-borne molecule, as mentioned above. A capture bead(s) may be introduced into the chamber/sequestration pen containing the cell(s), bead-borne molecule and any other suitable reagents. Introduction of the capture bead may be made before/after/at the same time as introduction of cells and/or bead-borne molecule and/or other reagents, and may require one or more instances of encapsulating/de-encapsulating one or more chambers/sequestration pens. After release of the bead-borne molecule, culturing may be performed for a period of time, which may be about 30 min; about 45 min; about 1 h; about 2 h; about 4 h; about 6 h; about 8 h; about 10 h; about 12 h; about 18 h; about 24 h; about 48 h; about 72 h; or more. In some embodiments, cells may be cultured for about 2 h to about 24 h, about 4 hours to about 24 hours (e.g., between about 8 h and about 12 h, between about 12 h and about 16 h, between about 16 h and about 20 h) or any length of time therebetween. The cells and/or the chambers/pens may be imaged during or after the culturing period, which imaging results may be used to select one or more chambers/sequestration pens from which capture beads are to be retrieved. De-encapsulation, either in bulk or, in some embodiments, selective de-encapsulation as described herein, may be performed. Selected capture beads may be unpenned from the chambers/sequestration pens, and may be exported from the microfluidic device for further analysis (e.g., mass spectrometry, as described above and elsewhere herein.

In some variations, a process is provided for assaying encapsulated cells in a microfluidic device having an enclosure which includes a channel and a plurality of chambers, each chamber of the plurality having an opening (e.g., a single opening) fluidically connecting the chamber to the channel, wherein at least a portion of surfaces forming the channel proximal to each chamber of the plurality and/or at least a portion of surfaces of each chamber forming the opening and proximal to the channel comprises a hydrophobic coating, wherein the process comprises: filling the channel and the plurality of chambers in the enclosure of the microfluidic device with a first aqueous medium; disposing a first cell in a first chamber of the plurality of chambers; disposing a second cell in a second chamber of the plurality of chambers; disposing a micro-object into each of the first and second chambers of the plurality of chambers, where the micro-object includes a molecule (e.g., a test molecule); flowing a water immiscible fluidic medium into the channel, displacing the first aqueous medium in the channel without substantially displacing the first aqueous medium in any of the plurality of chambers, thereby reversibly encapsulating the cells in their respective chambers; and monitoring an activity of the cell(s) encapsulated in each of the first and the second chambers The cells may be any kind of cells as described herein.

In some variations, the molecule is configured to affect or text a biological activity of the cell disposed therein. The molecule may be a small molecule (e.g., a small organic molecule or a peptide). The molecule may be associated with the micro-object non-covalently or covalently. In some variations, the micro-object may further include an identifier configured to permit tracking of the identity of the molecule.

In some variations, disposing the micro-object into each of the first and the second chambers may be performed prior to encapsulating the cells within their respective chambers. In some variations, the process may further include introducing a release reagent into each of the first and second chambers subsequent to introducing the micro-object therein, where the release reagent is configured to trigger release of the molecule from the micro-object. Introducing the release reagent into each of the first and the second chambers may be performed prior to encapsulating the cells within their respective chambers.

In some variations, the process may further include triggering release of the molecule from the micro-object. In some embodiments, triggering release may include increasing a temperature of each of the first and the second chambers of the microfluidic device. In other embodiments, triggering release may include directing laser illumination at the micro-object in each of the first and the second chambers of the microfluidic device. In other embodiments, triggering release may include changing the pH of the first aqueous medium within each of the first and the second chambers. In other embodiments, triggering release may include enzymatic release by an enzymatic release reagent.

In some variations, the process may further include incubating the cell(s) encapsulated in each of the first and the second chambers for a first period of time before monitoring the activity of the cell(s); monitoring the activity of the cell(s) at a plurality of time points during the first period of time; or monitoring the activity of the incubating cell(s) substantially continuously during the first period of time. The first period of time during which cells may be incubated may be at least 30 minutes. In other embodiments, the first period of time may be between 4 hours and 24 hours (e.g., between 8 hours and 12 hours, between 12 hours and 16 hours, between 16 hours and 20 hours). In some embodiments, the water immiscible fluidic medium flowed/flowing through the channel may include soluble oxygen. In some embodiments, the first aqueous medium may include a carbon/energy source and, optionally, other minerals and nutrients.

In some variations, incubating the cells may be performed at a temperature between 18 degrees centigrade and 50° C. (e.g., between 25° C. and 37° C.).

In some variations, detecting the molecule of interest or reporter molecule may further include quantifying a detected signal. Quantifying the detected signal from the molecule or interest or reporter molecule may further include quantifying the detected signal in each of the first and the second chambers relative to each other or relative to one or more detected signals in other chambers of the microfluidic device.

In some variations, all of the channel surfaces proximal to and surrounding the opening to each chamber of the plurality of chambers may include the hydrophobic coating. In some other variations, all of the channel surfaces within 10 microns of the opening to each chamber of the plurality of chambers may include the hydrophobic coating. In some variations, the hydrophobic coating may have a contact angle from about 45 degrees to about 100 degrees. The hydrophobic coating may be covalently bonded to the portion of the surfaces forming the channel proximal to each chamber. In some variations, the hydrophobic coating may be covalently bonded to the portion of the surfaces forming the channel proximal to each chamber of the plurality of chambers.

In some variations, the water immiscible fluidic medium may include an alkane, a fluoroalkane, an oil, a hydrophobic polymer, or any combination thereof.

In some variations, the process may further include aspirating the water immiscible fluidic medium out of the channel. In some embodiments, the water immiscible fluidic medium may be aspirated at a rate at or between 0.01 ul/sec to 1.0 ul/sec. In some variations, aspirating the water immiscible fluidic medium may further include subsequently aspirating a second aqueous medium into the channel. In some embodiments, the second aqueous medium may include a surfactant.

In some variations, at least a portion of the surfaces forming each chamber of the plurality may include a hydrophobic coating, and the at least a portion of the chamber surfaces having a hydrophobic coating may be located proximal to the opening to the channel, and the process may further include generating an encapsulation layer of water immiscible fluidic media in each chamber of the plurality of chamber, wherein the encapsulation layer of each chamber of the plurality is located immediately adjacent to the channel and shares an interface with the first aqueous medium in the chamber so as to separate (e.g., isolate) the first aqueous medium in the chamber from a medium present in the channel (e.g., second aqueous medium, air, $CO_2$, another gas, or a different water immiscible fluidic medium). In some embodiments, all of the chamber surfaces proximal to and surrounding the opening of each chamber of the plurality of chambers may include the hydrophobic coating. In some embodiments, all of the chamber surfaces within 10 microns of the opening of each chamber of the plurality of chambers may include the hydrophobic coating. In some variations, the hydrophobic coating of the channel surfaces may be the same as the hydrophobic coating of the chamber surfaces.

In some variations, the process may further include generating an encapsulation layer of water immiscible fluidic media extending from about 5 microns to about 50 microns from a contact surface with the aqueous medium in the chamber into the channel.

In some variations, the process may further include selectively removing the encapsulation layer formed by the immiscible fluidic medium at an opening to the channel at one of the first and the second chambers, thereby generating a de-encapsulated chamber. In some variations, selective removal may include generating a bubble within the chamber (e.g., proximal to the encapsulation layer). Generating the bubble may include directing a laser at a location on an inner surface of a base of the chamber proximal to the interface between the first aqueous medium and the water immiscible fluidic medium. In some variations, the process may further include flowing in a third aqueous medium into the channel. In some embodiments, the third aqueous medium may include a lytic reagent (e.g., the third aqueous medium can be a lysis buffer).

In some variations, the process may further include disposing a capture bead (e.g., a bead that selectively binds biological material, such as a nucleic acid capture bead) into one or both chambers of the first and second chambers. In some embodiments, the process may include unpenning the capture bead from the de-encapsulated chamber. In some embodiments, the process may include exporting the capture bead from the microfluidic device and subjecting the capture bead to further analysis (e.g., mass spectrometry, ELISA, enzymatic assays, nucleic acid sequencing, or the like).

In some variations, disposing a cell in each of the first and the second chambers may include: flowing an aqueous medium including a plurality of cells into the channel of the microfluidic device; and selecting cells from the cell-containing aqueous medium in the channel of the microfluidic device for disposition in each of the first and the second chambers. Disposing the first and second cell may be individually moved from the channel into the first and second chambers, respectively, using DEP force (e.g., light-actuated DEP force).

In some variations, each chamber of the plurality of chambers may be a sequestration pen including an isolation region and a connection region fluidically connecting the isolation region to the channel. The sequestration pen may have a single opening to the channel. In some embodiments, the connection region of each sequestration pen may include a proximal opening to the channel and a distal opening to the isolation region, the proximal opening of the connection region having a width $W_{con}$ ranging from about 20 microns to about 100 microns, and where a length $L_{con}$ of the connection region from the proximal opening to the distal opening is as least 1.0 times the width $W_{con}$ of the proximal opening of the connection region. The chambers, sequestration pens, channels and the microfluidic device may have any combination of features as described herein.

In some variations, the hydrophobic coating may include less than or equal to 50% of a surface area calculated from the sum of the portion of surfaces forming the channel. In other variations, the hydrophobic coating may include greater than or equal to 50% of a surface area calculated from the sum of the surfaces forming the channel. In some variations, each chamber of the plurality of chambers may include a surface including a hydrophilic coating. In some embodiments, each chamber of the plurality of chambers (e.g., sequestration pen) may include a surface including a hydrophilic coating, and at least the isolation region of each sequestration pen includes the hydrophilic coating. In some embodiments, at least a portion of the connection region (e.g., a sub-region distal to the sequestration pen opening) of each sequestration pen proximal to the isolation region may include the hydrophilic coating. In some embodiments, a portion of the connection region of a sequestration pen proximal to the channel (e.g., a sub-region having a length $L_{hydrophobic}$, and which may be a surface forming a ring at the proximal end of the connection region) may include a hydrophobic coating.

In some embodiments, each of the at least one surface (e.g., all surfaces) forming the connection region may include a portion proximal to the isolation region having the hydrophilic coating and a portion proximal to the channel having the hydrophobic coating, and, optionally when all surfaces forming the connection region includes a portion proximal to the channel having the hydrophobic coating, they may provide a hydrophobic coating that encircles a portion of the connection region immediately adjacent to the channel.

In some variations, the hydrophobic coating may include a first covalently bound surface modification comprising: a first linking group, and a first moiety, wherein the first moiety is nonpolar (e.g., an oleic acid moiety, alkynyl moiety, PEG-linked alkynyl, or fluorinated moiety). In some variations, the hydrophilic coating may include a plurality of second covalently bound surface modifications, each comprising a second linking group, and a second moiety, wherein the second moiety is polar (e.g., a methoxy terminated PEG moiety, a carboxylic acid, a carboxylic acid terminated PEG moiety, an alcohol moiety or an alcohol terminated PEG moiety).

In some variations, the hydrophobic coating may include a first covalently bound surface modification having a first linking group, and a first moiety, where the first moiety is nonpolar. In some variations, the hydrophilic coating may include a plurality of second covalently bound surface modifications, each including a second linking group, and a second moiety, where the second moiety is polar.

In some variations, the cells may express variable amounts of a molecule of interest or a reporter molecule, which may be any molecule of interest or reporter molecule as described herein. In some variations, the method may further include incubating the first and second cells encapsulated in the first and second chambers for a first period of time before monitoring the activity of the first and second cells.

In some variations, monitoring the activity of the cell(s) encapsulated in each of the first and second chambers may include detecting the molecule of interest or reporter molecule. Detecting the molecule of interest or reporter molecule may include detecting a fluorescent signal associated with or produced by the molecule of interest. In some variations, detecting the molecule of interest may include detecting binding of the molecule of interest or reporter molecule to a solid substrate, where the solid substrate includes a receptor for the molecule of interest or reporter molecule. Monitoring the activity of the cell(s) may include imaging the chambers in which the cell(s) are disposed. In some other embodiments, the cell(s) may be imaged to monitor one or more phenotypic parameters of the cell. Monitoring the activity of the cell(s) may include monitoring cell growth.

In some variations, the process may further include selecting cell(s) of interest for additional assays based upon a detected activity of the cell(s) e.g., based on predetermined criteria or relative to the detected activity of cells in other chambers of the microfluidic device. In some embodiments, selection may be based upon the amount of expression of the molecule of interest, the amount of cell growth, or a combination thereof.

In some variations, the first and/or the second chamber may be de-encapsulated, and the respective capture beads may be unpenned. In some variations, the unpenned capture beads may be exported from the microfluidic device for further analysis. In some variations, the first and/or the second chamber may be de-encapsulated and cells of interests may be unpenned. In some embodiments, the unpenned cells of interest may be exported from the microfluidic device.

Lytic reagents. Lytic reagents suitable for use within the methods described herein may contain no detergent, as detergent will affect the encapsulating layer. Suitable reagents for lysing cell membranes including the outer cell membrane/wall and/or the nuclear membrane may include an enzymatic lysis agent such as a protease or may be lysozyme (e.g., for bacteria). The lytic reagent may be a lysis buffer, which may be hypotonic or isotonic. A hypotonic lysis buffer may including 10 nM HEPES, pH7.9; with magnesium chloride and potassium chloride. An isotonic lysis buffer may include 10 mM Tris HCl at pH 7.5, magnesium chloride, calcium chloride and 0.3M sucrose.

Surfactants. One useful surfactant for use is a non-ionic surfactant, CAPSTONE™ FS-30. However, surfactants for use in these methods for removing the encapsulation layers is not limited to CAPSTONE™ FS-30. Other non-ionic surfactants may be used, as is known by one of skill in the art. The concentration of non-ionic surfactants may be from about 0.1% to about 10%; about 0.1% to about 5%; about 0.1% to about 3%; about 0.1% to about 2%, or about 0.1% to about 1.0% v/v.

Water immiscible fluidic medium. The water immiscible fluidic medium used to seal the chambers/sequestration pens can be, for example, an alkane, a fluoro- or perfluoroalkane, or an oil, such as a silicone oil or a fluorinated oil. Specific examples of water immiscible fluidic media include isooctane (or heptamethyl nonane (HMN)), hexadecane, 2-(Trifluoromethyl)-3-ethoxydodecafluorohexane (HFE-7500, 3M™, Novec™), Fluorinert™ FC-40, (Aldrich Cat No. F9755), Fluorinert™ FC-70, (Aldrich Cat No. F9880), bis (2-ethylhexyl) carbonate (TEGOSOFT® DEC, (Evonik)), (Tridecafluoro-1,1,2,2,-tetrahydrooctyl) tetramethydisiloxane (Gelest Inc., Cat #SIB1816.0), silicone oil (5 centistoke viscosity, Gelest Inc. Cat. #DMS-T05), and the like.

Some of the above listed water immiscible fluidic media may be selected to solubilize oxygen gas, which may be transferred across the boundary with an aqueous medium, for example within a chamber or sequestration pen, and contribute to supporting the maintenance and expansion of biological cells during a period of time during which the chamber or sequestration pen may be encapsulated by the water immiscible fluidic medium. Some water immiscible fluidic media may have greater oxygen solubility than water itself, including but not limited to 5 cSt. Silicon oil, HFE-7500, or FC-40.

Hydrophobic moiety. Chambers, including sequestration pens, in a microfluidic device can be sealed from one another by flowing a water immiscible fluidic medium through a channel from which the chambers/sequestration pens open. Sealing is facilitated when a surface of the channel (e.g., a surface surrounding the opening to the chambers/sequestration pens) comprises a covalently bound modification comprising a moiety (e.g., a first surface contact moiety or a first hydrophobic reactive moiety e.g., alkynyl) that is substantially nonpolar or hydrophobic. Optionally, the surface of the chamber/sequestration pen (e.g., the surface of a connection region most proximal to the channel) also comprises a covalently bound modification comprising a moiety (e.g., a surface contact moiety or a reactive moiety) that is substantially nonpolar or hydrophobic. The nonpolar/hydrophobic moiety can, for example, comprise, consist of, or consist essentially of an alkane (including fluoroalkanes and perfluoroalkanes), an alkene, and alkyne, an aromatic ring (which may be functionalized with nonpolar groups, such as alkanes and the like), a polymer (e.g., polypropylene), or the like. In some variations, a hydrophobic surface may be introduced having one or more hydrophobic surface moiety having a contact angle of at least about 45 degrees. In some other variations, the hydrophobic surface may have a contact angle of less than about 100 degrees. In some embodiments, the hydrophobic surface may have a contact angle of about 45 degrees to about 100 degrees. In Table 1, some suitable surface modifying reagents, providing a hydrophobic surface are shown along with the respective contact angle of the hydrophobic surface, but the invention is not so limited. Other surface modifying reagents may be useful as well, including DBCO-maleimide (BROADPHARM® Cat. No. BP-22293); Sulfo DBCO-Maleimide (BROADPHARM® Cat. No. BP-22217); DBCO-PEG4-maleimide (BROADPHARM® Cat. No. BP-22294); Sulfo DBCO-PEG4-Maleimide (BROADPHARM® Cat. No. BP-22218) and/or DBCO-PEG4-DBCO (BROADPHARM® Cat. No. BP-23772).

TABLE 1

Exemplary hydrophobic surface modifying reagents and contact angle of the surface formed therefrom.

| Name | Contact Angle | Commercial Source |
| --- | --- | --- |
| 8-arm alkyne terminated PEG dendrimer, Mw = 6.9K | 44° | Sigma Cat. No. 760919 |
| DBCO-PEG4-alkyne | 52° | Conjuprobe Cat. No. CP-2039 |
| m-PEG4-DBCO | 54° | Broadpharm Cat. No. BP-24030 |
| 1,1,1-Trifluoroethyl-PEG3-Propargyl | 66° | Broadpharm Cat. No. BP-22938 |
| DBCO-PEG4-NH-Boc | 79° | Broadpharm Cat. No. BP-24105 |
| 7-azidoheptyltrimethoxy silane | 82° | |
| 11-azidoundecyltrimethoxy silane | 85° | |
| DBCO-oleic acid conjugate | 95° | Broadpharm Cat. No. BP-24249 |
| 2-(perfluorooctyl)ethyne | 101° | Fluoryx Cat. No. FC24-08-10 |

Hydrophilic moiety. Suitable hydrophilic moieties may include any hydrophilic contact moiety as described herein for surface modifying reagents. In some embodiments the hydrophilic surface contact moiety may be a polar moiety. The surface modifying reagents having a hydrophilic surface contact moiety can produced a covalently bonded coating surface that has a contact angle that is less than about 45 degrees. For example, a hydrophilic surface having methoxy-terminated PEG Mw-5k contact moieties may have a contact angle of about 32 degrees. Another non-limiting example of a hydrophilic surface may have surface contact moieties of sulfonic acid-terminated PEG4, which may have a contact angle of about 7 degrees.

In some embodiments, a hydrophobic coating may include an oleic acid moiety, alkynyl moiety, alkynyl terminated PEG moiety, or fluorinated surface contact moiety and a hydrophilic surface may include a methoxy terminated PEG moiety, a carboxylic acid, a carboxylic acid terminated PEG moiety, sulfonic acid, an alcohol moiety or an alcohol terminated PEG polar contact moieties. In some embodiments, the hydrophobic coating may include an oleic acid surface contact moiety and the hydrophilic coating may include a methoxy-terminated PEG surface contact moiety. In other embodiments, the hydrophobic coating may include an alkynyl surface contact moiety and the hydrophilic coating may include a methoxy-terminated PEG surface contact moiety. In yet other embodiments, the hydrophobic coating may include an alkynyl terminated PEG moiety and the hydrophilic coating may include a methoxy-terminated PEG surface contact moiety. In other embodiments, the hydrophobic coating may include a fluorinated surface contact moiety and the hydrophilic coating may include a methoxy-terminated PEG surface contact moiety. In yet other embodiments, the hydrophobic coating may include an oleic acid surface contact moiety and the hydrophilic coating may include a carboxylic acid or a carboxylic acid terminated PEG moiety. In other embodiments, the hydrophobic coating may include an alkynyl surface contact moiety and the hydrophilic coating may include a carboxylic acid or a carboxylic acid terminated PEG moiety. In further embodiments, the hydrophobic coating may include an alkynyl terminated PEG moiety and the hydrophilic coating may include a carboxylic acid or a carboxylic acid terminated PEG moiety. In yet other embodiments, the hydrophobic coating may include a fluorinated surface contact moiety and the hydrophilic coating may include a carboxylic acid or a carboxylic acid terminated PEG moiety.

Surface modifying reagent. The surface modifying reagent (Formula I) includes a surface contact moiety and a linking group, where the linking group may include a linker L and a reactive pair moiety RP which is the moiety that reacts with a reactive moiety present on the surface of a microfluidic device.

RP-L-surface contact moiety          Formula I

When the modified surface has been formed, the surface modifying ligand so formed has a structure like that of the surface modifying reagent but the linking group of the surface modifying ligand includes the coupling group CG formed by the reaction of the reaction pair moiety RP with the reactive moiety of the functionalized surface, and further includes the linker moiety connecting the reactive moiety to the surface of the microfluidic device.

Reaction pair moiety. The reaction pair moiety RP is a moiety that can react with the reactive moiety of the functionalized surface. For example, a reactive moiety $R_x$ may be alkyne and a corresponding reaction pair moiety RP may be an azide. Alternatively, $R_x$ may be azide and RP may be alkyne. Another reaction pair RP moiety may be a thiyl radical, derived from a disulfide, which may react with an alkynyl moiety present on the surface of the interior of the microfluidic device upon photoactivation. Other pairs of reactive moiety $R_x$: reaction pair moiety RP may include, but are not limited to cyano and azide; carboxylic acid and amine; olefin and nucleophile; amine and sulfonyl fluoride; trans cyclooctene and s-tetrazine, thiol and maleimide; halide and nucleophile; isocyanate and amines; epoxide and nucleophile; hydroxyamine and aldehyde or ester; and a masked hydroxyl such as acetate and nucleophile. A special case of Rx: RP pair may be biotin and streptavidin. This is not a covalent pairing but an extremely stable noncovalent binding pair that may be used as an $R_x$:RP pair.

When the functionalized surface has an azide or a alkynyl moiety as $R_x$, the surface modifying reagent has a reaction pair moiety RP which is an alkyne or azide respectively, which can react form a triazolylenyl moiety via a cyclization reaction ("Click reaction") as is known in the art. In some embodiments, the reactive moiety $R_x$ or the reaction pair RP moiety is an acyclic alkyne. In other embodiments, the reactive moiety $R_x$ or the reaction pair RP moiety is a cyclized alkyne, which may be part of a cyclooctyne. In some embodiments, the cyclooctyne may be strained. The cyclooctyne may have further cyclic rings fused to the cyclooctyne, such as benzo group, and may be a dibenzo-cyclooctyne. In other embodiments, the cyclooctyne may have fluoro substituents. When the alkyne of the surface modifying reagent is a cyclooctyne, the surface contact moiety of the reagent is attached to the cyclooctyne via the linker L, which may be attached to any suitable position on the cyclooctyne. When the alkyne of the functionalized surface is a cyclooctyne, the linking group attaching the cyclooctyne to the surface is attached to the cyclooctyne at any suitable position on the cyclooctyne.

Linker L may be a bond or may include 1 to 200 non-hydrogen atoms selected from any combination of silicon, carbon, nitrogen, oxygen, sulfur and phosphorus atoms, subject to chemical bonding limitations as is known in the art. In some embodiments, linker L may include 1 to 200 non-hydrogen atoms selected from any combination of silicon, carbon, nitrogen, oxygen, sulfur and phosphorus atoms, subject to chemical bonding limitations as is known in the art. Linker L or the surface contact moiety may include 0, 1, or 3 coupling groups CG.

Coupling Group CG. CG is a coupling group and may be any moiety such as but not limited to triazolylenyl, carboxamide, imide, ether, ester, keto, sulfonamide, sulfonate, cyclooctyl-fused diazine, alkene or aromatic moieties that may result from attaching the surface contact moiety to the remainder of the surface modifying reagent.

In some other embodiments, CG is the moiety resultant from reaction of the reactive moiety of the functionalized surface with a respective reaction pair moiety of a surface modifying reagent as described herein. For example, a functionalized surface having an azide reactive moiety may form a triazolylenyl CG moiety upon reacting with an alkynyl moiety in a Click reaction. Alternatively, a functionalized surface having an alkynyl reactive moiety may react with an azide reaction pair moiety of a surface modifying reagent to form a triazolylenyl moiety. In yet another alternative, the functionalized surface may present alkynyl moieties which may react with thiyl radicals to form a thio-olefin coupling group CG.

Coupling group CG may be a triazolylenyl moiety, which may be further substituted, and may have one or more additional ring systems fused with the triazolylenyl moiety. The additional fused ring system(s) may itself be further substituted with additional fused rings and may provide the attachment point to linker L-surface contact moiety. In some embodiments, the triazolylenyl moiety is fused with a cyclooctynyl ring system, which may be further substituted either with additional fused rings, including but not limited to dibenzocylcooctynyl, or other substitutions such as fluorine (difluorinated cyclooctyne (DIFO)).

CG may in some embodiments be a noncovalent binding pair. For example, the noncovalent binding of biotin with streptavidin provides a very stable binding pair and may be a CG. Further, since streptavidin has four binding sites, two portions of a surface modifying ligand, surface modifying reagent, or functionalized surface may be joined by the sequence of biotin/streptavidin/biotin. For example, a functionalized surface has a biotin reactive moiety, streptavidin is then introduced to bind to the biotin reactive moiety, and finally where a second biotinylated moiety (such as biotin-fibronectin) is introduced and bound to another of the binding sites on streptavidin. The product is a covalently bound surface modification having a surface contact moiety of fibronectin and the sequence of biotin/streptavidin/biotin is considered to be a single coupling group CG. The streptavidin is performing the role of linking two similarly functionalized portions together.

Surface contact moiety. The surface contact moiety of the surface modifying reagent or ligand may be any surface contact moiety as described herein and in other portions of the disclosure and may include non-polymeric or polymeric moieties. The surface contact moiety may include alkyl or fluoroalkyl (which includes perfluoroalkyl) moieties; alkenyl moieties, alkynyl moieties, mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acid; amino acids; or any combination thereof. The alkyl or perfluoroalkyl moieties may have a backbone chain length of greater than 10 carbons. In other embodiments, the surface contact moiety may include saccharide moieties, and may be dextran. In other embodiments, the surface contact moiety may include alkylene ether moieties. The alkylene ether moieties may be polyethylene glycol.

In other embodiments, a hydrophilic surface contact moiety may include but is not limited at least one alkylene oxide moiety. One useful class of alkylene ether containing polymers is polyethylene glycol (PEG $M_w$<100,000 Da). In some embodiments, a PEG may have an $M_w$ of about 100 Da, 300 Da, 500 Da, 1000 Da, or 5000 Da. In other embodiments, a hydrophilic surface contact moiety may include one or more saccharides. The covalently linked saccharides may be mono-, di-, or polysaccharides. Like charged moieties such as sulfonic acids or carboxylic acid contact moieties, the hydrophilic surface modifying ligand can form strong hydrogen bonds with water molecules such that the resulting water of hydration acts as a layer (or "shield") that separates the biological micro-objects from interactions with non-biological molecules (e.g., the silicon and/or silicon oxide of the substrate). In some variations, an alkylene oxide moiety may be considered to function as part of the linker L.

In various embodiments, the surface contact moiety may include non-polymeric moieties such as an alkyl moiety, a substituted alkyl moiety, such as a fluoroalkyl moiety (including but not limited to a perfluoroalkyl moiety), amino acid moiety, alcohol moiety, amino moiety, carboxylic acid moiety, phosphonic acid moiety, sulfonic acid moiety, sulfamic acid moiety, or saccharide moiety.

In some embodiments, the surface contact moiety may comprise carbon atoms forming a linear chain (e.g., a linear chain of at least 10 carbons, or at least 14, 16, 18, 20, 22, or more carbons) and may be an unbranched alkyl moiety. In some embodiments, the alkyl group may include a substituted alkyl group (e.g., some of the carbons in the alkyl group can be fluorinated or perfluorinated). In some embodiments, the alkyl group may include a first segment, which may include a perfluoroalkyl group, joined to a second segment, which may include a non-substituted alkyl group, where the first and second segments may be joined directly or indirectly (e.g., by means of an ether linkage). The first segment of the alkyl group may be located distal to the linking group, and the second segment of the alkyl group may be located proximal to the linking group.

Other surface contact moieties may include peptides or proteins for cell-specific interactions, including antigens, cell surface markers and the like.

Adherent motifs. Generally, a positively charged surface contact moiety such as poly-L-lysine, amine and the like may be used as surface contact moieties to provide anchoring attachments for attachment dependent cells. Another motif that may be used includes the tripeptide sequence RGD, which is available as a biotinylated reagent and is easily adaptable to the methods described herein. Other larger biomolecules that may be used include fibronectin, laminin or collagen, amongst others. A polyglutamic acid surface contact moiety may induce adherent cells to attach and grow viably. Another motif that may assist in providing an adherent site is an Elastin Like Peptide (ELP), which includes a repeat sequence of VPGXG, where X is a variable amino acid which can modulate the effects of the motif. Such adherent motifs may be introduced within the chambers or sequestration pens of the microfluidic device when cells requiring adhesive support are to be cultured within the chambers of the microfluidic device.

Cleavable moiety. The surface modifying reagent may further include a cleavable moiety, which may be located within the linker L or may be part of the surface contact moiety. The cleavable moiety may be configured to permit disruption of the covalently modified surface. In some embodiments, disruption may be useful to promote portability of the one or more biological cells after a period of culturing. The cleavable moiety may be a photocleavable moiety such as nitro-substituted benzyl esters (e.g., BROADPHARM® Catalog #BP-22675); a UV cleavable moiety such as a substituted 1,2-diphenyl ethyl ketoester moiety (e.g., a benzil derivative such as BROADPHARM® Catalog #BP 22689); or may be a moiety which can be cleaved under specific chemical conditions. For example, a disulfide linkage can be cleaved under conditions (e.g., reducing conditions such as dithiothreitol) that may not interfere with the growth or viability of the biological cells on the covalently modified surface. Other useful cleavable moieties that may be incorporated within surface modifying ligands or functionalized surfaces can include a vicinal diol moiety, which is cleavable by sodium periodate. The sodium periodate cleavage is another non-cytotoxic cleavage reagent. Diazo moieties, which are cleavable by dithionite, may also be a useful cleavable moiety. Additionally, a 5, 5, dimethyl-exo-cyclohexen-yl-1,3, dione moiety may be a useful cleavable moiety and may be cleaved by hydrazine solution.

Functionalized surface: A surface may be covalently modified by a functionalizing reagent, to introduce a functionalized surface modification to one or more surfaces of the microfluidic device, which presents a reactive moiety to the interior of the microfluidic device. The functionalized surface may be modified using surface modifying reagents as described to support culturing within the chambers and export ability from the chambers as well as support the encapsulating layer encapsulating the chambers.

Reactive moiety. The reactive moiety may be any of an alkyne moiety, azide moiety, amine moiety, carboxylic acid moiety, biotin moiety, streptavidin moiety, olefin moiety, trans cyclooctene moiety, s-tetrazine moiety, thiol moiety, maleimide moiety, halide moiety, cyano moiety, isocyanate moiety, epoxide moiety, hydroxyamine moiety, a masked hydroxyl such as acetate and the like, or sulfonyl fluoride moiety. This list of reactive moieties is not limiting and any suitable reactive moiety may be selected for use with an appropriate reaction pair moiety. While most reactive moieties react with a respective reaction pair moiety to form a covalently coupled CG, the high binding affinity between biotin and streptavidin permits its use as a reactive moiety/reaction pair moiety.

The functionalized surface formed by the reaction of a functionalizing reagent may have a structure of Formula II.

Formula II

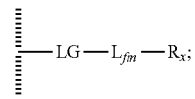

where LG is —W—Si(OZ)$_2$O— or —OP(O)$_2$O—; W is O, S, or N, Z is a bond to an adjacent silicon atom or is a bond to the surface, $L_{fm}$ is a linker comprising 1 to 200 non-hydrogen atoms selected from any combination of silicon, carbon, nitrogen, oxygen, sulfur and phosphorus atoms and further comprises 0, 1 or 2 coupling groups CG; and $R_x$ is a reactive moiety as defined above.

Copper catalysts. Copper catalysts may be used for some Click chemistry reactions. Any suitable copper (I) catalyst may be used. In some embodiments, copper(I) iodide, copper (I) chloride, copper (I) bromide or another copper (I) salt. In other embodiments, a copper (II) salt may be used in combination with a reducing agent such as ascorbate to generate a copper (I) species in situ. Copper sulfate or copper acetate are non-limiting examples of a suitable copper (II) salt. In other embodiments, a reducing agent such as ascorbate may be present in combination with a copper (I) salt to ensure sufficient copper(I) species during the course of the reaction. Copper metal may be used to provide Cu(I) species in a redox reaction also producing Cu(II) species. Coordination complexes of copper such as [CuBr(PPh$_3$)$_3$], silicotungstate complexes of copper, [Cu(CH$_3$CN)$_4$]PF$_6$, or (EtO)3P CuI may be used. In yet other embodiments, silica supported copper catalyst, copper nanoclusters or copper/cuprous oxide nanoparticles may be employed as the catalyst.

Other reaction enhancers. As described above, reducing agents such as sodium ascorbate may be used to permit copper(I) species to be maintained throughout the reaction, even if oxygen is not rigorously excluded from the reaction. Other auxiliary ligands may be included in the reaction mixture, to stabilize the copper(I) species. Triazolyl containing ligands can be used, including but not limited to tris(benzyl-1H-1,2,3-triazol-4-yl) methylamine (TBTA) or 3 [tris(3-hydroxypropyltriazolylmethyl)amine (THPTA). Another class of auxiliary ligand that can be used to facilitate reaction is a sulfonated bathophenanthroline, which is water soluble, as well, and can be used when oxygen can be excluded.

Other chemical couplings as is known in the art may be used to couple a surface modifying reagent to the functionalized surface as described for Reaction Pair moiety.

Solvents and reaction conditions. When an interior surface of a microfluidic device is the functionalized surface that reacts with a surface modifying reagent, the reaction may be performed by flowing a solution of the surface modifying reagent into and through the microfluidic device. In various embodiments, the surface modifying reagent solution may be an aqueous solution. Other useful solvents include aqueous dimethyl sulfoxide (DMSO), DMF, acetonitrile, or an alcohol may be used. The reaction may be performed at room temperature or at elevated temperatures. In some embodiments, the reaction is performed at a temperature in a range from about 15° C. to about 60° C.; about 15° C. to about 55° C.; about 15° C. to about 50° C.; about 20° C. to about 45° C. In some embodiments, the reaction to convert a functionalized surface of a microfluidic device to a covalently modified surface is performed at a temperature of about 15° C., 20° C., 25° C., 30° C., 35° C., 40° C., 45° C., 50° C., 55° C., or about 60° C.

Further details of suitable coating treatments and modifications, as well as methods of preparation, may be found at U.S. Patent Application Publication No. US2016/0312165 (Lowe, Jr., et al.), U.S. Patent Application Publication No US2017/0173580 (Lowe, Jr., et al), International Patent Application Publication WO2017/205830 (Lowe, Jr., et al.), and International Patent Application Publication WO2019/01880 (Beemiller et al.), each of which disclosures is herein incorporated by reference in its entirety.

Kits. A kit for encapsulating cells is provided comprising: a microfluidic device having an enclosure comprising a channel and a plurality of chambers, each chamber of the plurality having an opening (e.g., a single opening) fluidically connecting the chamber to the channel, wherein at least a portion of inner surfaces forming the channel and each chamber comprises a plurality of reactive moieties; a first surface modifying reagent comprising a first linking group configured to covalently bind with the reactive moieties, and a first surface contact moiety, wherein the first surface contact moiety is nonpolar (e.g., an oleic acid moiety, alkynyl moiety, PEG-linked alkynyl, or fluorinated moiety); and a second surface modifying reagent comprising a second linking group configured to covalently bind with the reactive moieties, and a second surface contact moiety, wherein the second surface contact moiety is polar (e.g., a methoxy terminated PEG moiety, a carboxylic acid, a carboxylic acid terminated PEG moiety, an alcohol moiety or an alcohol terminated PEG moiety). The first surface modifying reagent may have a chemical structure of Formula I, where RP, L, and surface contact moiety are as described herein. The first surface contact moiety of the first surface modification reagent may be any hydrophobic surface moiety as described herein, or known to one of skill in the art. The microfluidic device may be any microfluidic device having a plurality of reactive moieties as described herein and may have any combination of features. The second surface modifying reagent may have a chemical structure of Formula I, where RP, L, and surface contact moiety are as described herein. The second surface contact moiety of the second surface modification reagent may be any hydrophilic or polar surface moiety as described herein, or known to one of skill in the art. The plurality of reactive moieties of the microfluidic device may include azido moieties or alkynyl moieties. In some variations, the kit may include a plurality of capture beads (e.g., beads that bind biological material, such as non-specific capture beads, antigen-specific capture beads, enzyme capture beads, or nucleic acid capture beads).

The kit may further include other reagents to be used in producing a microfluidic device having at least one covalently modified surface. Suitable reaction media, buffers, or reaction accelerants may be provided in the kit. In some variations, the kit may include one or more of an aqueous medium, a water immiscible fluidic medium (e.g., an alkane, a fluoroalkane, an oil, a hydrophobic polymer, or any combination thereof), an assay reagent (e.g., a lytic reagent, such as a lysis buffer), or an export buffer. The auxiliary reagents and/or surface modifying reagent and/or secondary functionalizing reagent may be provided in separate containers.

The kit may further include a reagent suitable for sealing chambers (or sequestration pens) in a microfluidic device having at least one covalently modified surface. For example, the sealing reagent can be a water immiscible fluidic medium, such as an alkane, a fluoro- or perfluoroalkane, or an oil (e.g., a silicone oil or a fluorinated oil). Specific examples of water immiscible fluidic media include isooctane (or heptamethyl nonane (HMN)), 2-(Trifluoromethyl)-3-ethoxydodecafluorohexane (HFE-7500, 3M™, Novec™), bis(2-ethylhexyl) carbonate (TEGOSOFT® DEC, (Evonik Industries AG)), (Tridecafluoro-1,1,2,2,-tetrahydrooctyl) tetramethydisiloxane (Gelest Inc., Cat #SIB1816.0), silicone oil (5 centistoke viscosity, Gelest Inc., Cat. #DMS-T05), and the like. The sealing reagent may be provided in a separate container.

In other variations, a kit for or encapsulating cells is provided comprising a microfluidic device having an enclosure having a channel and a plurality of chambers, each chamber fluidically connected to the channel, wherein at least a portion of surfaces forming the channel proximal to each chamber includes a covalently bonded hydrophobic coating and a reagent suitable for sealing chambers (e.g., sequestration pens). In some variations, the hydrophobic coating may have a contact angle from about 45 degrees to about 100 degrees. In some variations, each chamber of the plurality of chambers may be sequestration pen having an isolation region and a connection region fluidically connecting the isolation region to the channel. The microfluidic device having at least a portion of surfaces having a covalently bonded hydrophobic coating may be any microfluidic device as described herein and may have any combination of features.

The sealing reagent can be a water immiscible fluidic medium, such as an alkane, a fluoro- or perfluoroalkane, or an oil (e.g., a silicone oil or a fluorinated oil). Specific examples of water immiscible fluidic media include isooctane (or heptamethyl nonane (HMN)), 2-(Trifluoromethyl)-3-ethoxydodecafluorohexane (HFE-7500, 3M™, Novec™), bis(2-ethylhexyl) carbonate (TEGOSOFT® DEC, (Evonik Industries AG)), (Tridecafluoro-1,1,2,2,-tetrahydrooctyl) tetramethydisiloxane (Gelest Inc., Cat #SIB1816.0), silicone oil (5 centistoke viscosity, Gelest Inc., Cat. #DMS-T05), and the like. The sealing reagent may be provided in a separate container.

Microfluidic device/system feature cross-applicability. It should be appreciated that various features of microfluidic devices, systems, and motive technologies described herein may be combinable or interchangeable. For example, features described herein with reference to the microfluidic device 100, 175, 200, 300, 320, 400, 450, 520 and system attributes as described in FIGS. 1A-5B may be combinable or interchangeable.

Microfluidic devices. FIG. 1A illustrates an example of a microfluidic device 100. A perspective view of the microfluidic device 100 is shown having a partial cut-away of its cover 110 to provide a partial view into the microfluidic device 100. The microfluidic device 100 generally comprises a microfluidic circuit 120 comprising a flow path 106 through which a fluidic medium 180 can flow, optionally carrying one or more micro-objects (not shown) into and/or through the microfluidic circuit 120.

As generally illustrated in FIG. 1A, the microfluidic circuit 120 is defined by an enclosure 102. Although the enclosure 102 can be physically structured in different configurations, in the example shown in FIG. 1A the enclosure 102 is depicted as comprising a support structure 104 (e.g., a base), a microfluidic circuit structure 108, and a cover 110. The support structure 104, microfluidic circuit structure 108, and cover 110 can be attached to each other. For example, the microfluidic circuit structure 108 can be disposed on an inner surface 109 of the support structure 104, and the cover 110 can be disposed over the microfluidic circuit structure 108. Together with the support structure 104 and cover 110, the microfluidic circuit structure 108 can define the elements of the microfluidic circuit 120, forming a three-layer structure.

The support structure 104 can be at the bottom and the cover 110 at the top of the microfluidic circuit 120 as illustrated in FIG. 1A. Alternatively, the support structure 104 and the cover 110 can be configured in other orientations. For example, the support structure 104 can be at the top and the cover 110 at the bottom of the microfluidic circuit 120. Regardless, there can be one or more ports 107 each comprising a passage into or out of the enclosure 102. Examples of a passage include a valve, a gate, a pass-through hole, or the like. As illustrated, port 107 is a pass-through hole created by a gap in the microfluidic circuit structure 108. However, the port 107 can be situated in other components of the enclosure 102, such as the cover 110.

Only one port 107 is illustrated in FIG. 1A but the microfluidic circuit 120 can have two or more ports 107. For example, there can be a first port 107 that functions as an inlet for fluid entering the microfluidic circuit 120, and there can be a second port 107 that functions as an outlet for fluid exiting the microfluidic circuit 120. Whether a port 107 function as an inlet or an outlet can depend upon the direction that fluid flows through flow path 106.

The support structure 104 can comprise one or more electrodes (not shown) and a substrate or a plurality of interconnected substrates. For example, the support structure 104 can comprise one or more semiconductor substrates, each of which is electrically connected to an electrode (e.g., all or a subset of the semiconductor substrates can be electrically connected to a single electrode). The support structure 104 can further comprise a printed circuit board assembly ("PCBA"). For example, the semiconductor substrate(s) can be mounted on a PCBA.

The microfluidic circuit structure 108 can define circuit elements of the microfluidic circuit 120. Such circuit elements can comprise spaces or regions that can be fluidly interconnected when microfluidic circuit 120 is filled with fluid, such as flow regions (which may include or be one or more flow channels), chambers (which class of circuit elements may also include sub-classes including sequestration pens), traps, and the like. Circuit elements can also include barriers, and the like. In the microfluidic circuit 120 illustrated in FIG. 1A, the microfluidic circuit structure 108 comprises a frame 114 and a microfluidic circuit material 116. The frame 114 can partially or completely enclose the microfluidic circuit material 116. The frame 114 can be, for example, a relatively rigid structure substantially surrounding the microfluidic circuit material 116. For example, the frame 114 can comprise a metal material. However, the microfluidic circuit structure need not include a frame 114. For example, the microfluidic circuit structure can consist of (or consist essentially of) the microfluidic circuit material 116.

The microfluidic circuit material 116 can be patterned with cavities or the like to define the circuit elements and interconnections of the microfluidic circuit 120, such as chambers, pens and microfluidic channels. The microfluidic circuit material 116 can comprise a flexible material, such as a flexible polymer (e.g. rubber, plastic, elastomer, silicone, polydimethylsiloxane ("PDMS"), or the like), which can be gas permeable. Other examples of materials that can form the microfluidic circuit material 116 include molded glass, an etchable material such as silicone (e.g. photo-patternable silicone or "PPS"), photo-resist (e.g., SU8), or the like. In some embodiments, such materials- and thus the microfluidic circuit material 116—can be rigid and/or substantially impermeable to gas. Regardless, microfluidic circuit material 116 can be disposed on the support structure 104 and inside the frame 114.

The microfluidic circuit 120 can include a flow region in which one or more chambers can be disposed and/or fluidically connected thereto. A chamber can have one or more openings fluidically connecting the chamber with one or more flow regions. In some embodiments, a flow region comprises or corresponds to a microfluidic channel 122. Although a single microfluidic circuit 120 is illustrated in FIG. 1A, suitable microfluidic devices can include a plurality (e.g., 2 or 3) of such microfluidic circuits. In some embodiments, the microfluidic device 100 can be configured to be a nanofluidic device. As illustrated in FIG. 1A, the microfluidic circuit 120 may include a plurality of microfluidic sequestration pens 124, 126, 128, and 130, where each sequestration pens may have one or more openings. In some embodiments of sequestration pens, a sequestration pen may have only a single opening in fluidic communication with the flow path 106. In some other embodiments, a sequestration pen may have more than one opening in fluidic communication with the flow path 106, e.g., n number of openings, but with n−1 openings that are valved, such that all but one opening is closable. When all the valved openings are closed, the sequestration pen limits exchange of materials from the flow region into the sequestration pen to occur only by diffusion. In some embodiments, the sequestration pens comprise various features and structures (e.g., isolation regions) that have been optimized for retaining micro-objects within the sequestration pen (and therefore within a microfluidic device such as microfluidic device 100) even when a medium 180 is flowing through the flow path 106.

The cover 110 can be an integral part of the frame 114 and/or the microfluidic circuit material 116. Alternatively, the cover 110 can be a structurally distinct element, as illustrated in FIG. 1A. The cover 110 can comprise the same or different materials than the frame 114 and/or the microfluidic circuit material 116. In some embodiments, the cover 110 can be an integral part of the microfluidic circuit material 116. Similarly, the support structure 104 can be a separate structure from the frame 114 or microfluidic circuit material 116 as illustrated, or an integral part of the frame 114 or microfluidic circuit material 116. Likewise, the frame 114 and microfluidic circuit material 116 can be separate structures as shown in FIG. 1A or integral portions of the same structure. Regardless of the various possible integrations, the microfluidic device can retain a three-layer structure that includes a base layer and a cover layer that sandwich a middle layer in which the microfluidic circuit 120 is located.

In some embodiments, the cover 110 can comprise a rigid material. The rigid material may be glass or a material with similar properties. In some embodiments, the cover 110 can comprise a deformable material. The deformable material can be a polymer, such as PDMS. In some embodiments, the cover 110 can comprise both rigid and deformable materials. For example, one or more portions of cover 110 (e.g., one or more portions positioned over sequestration pens 124, 126, 128, 130) can comprise a deformable material that interfaces with rigid materials of the cover 110. Microfluidic devices having covers that include both rigid and deformable materials have been described, for example, in U.S. Pat. No. 10,058,865 (Breinlinger et al.), the contents of which are incorporated herein by reference. In some embodiments, the cover 110 can further include one or more electrodes. The one or more electrodes can comprise a conductive oxide, such as indium-tin-oxide (ITO), which may be coated on glass or a similarly insulating material. Alternatively, the one or more electrodes can be flexible electrodes, such as single-walled nanotubes, multi-walled nanotubes, nanowires, clusters of electrically conductive nanoparticles, or combinations thereof, embedded in a deformable material, such as a polymer (e.g., PDMS). Flexible electrodes that can be used in microfluidic devices have been described, for example, in U.S. Pat. No. 9,227,200 (Chiou et al.), the contents of which are incorporated herein by reference. In some embodiments, the cover 110 and/or the support structure 104 can be transparent to light. The cover 110 may also include at least one material that is gas permeable (e.g., PDMS or PPS).

In the example shown in FIG. 1A, the microfluidic circuit 120 is illustrated as comprising a microfluidic channel 122 and sequestration pens 124, 126, 128, 130. Each pen comprises an opening to channel 122, but otherwise is enclosed such that the pens can substantially isolate micro-objects inside the pen from fluidic medium 180 and/or micro-objects in the flow path 106 of channel 122 or in other pens. The walls of the sequestration pen extend from the inner surface 109 of the base to the inside surface of the cover 110 to provide enclosure. The opening of the sequestration pen to the microfluidic channel 122 is oriented at an angle to the flow 106 of fluidic medium 180 such that flow 106 is not directed into the pens. The vector of bulk fluid flow in channel 122 may be tangential or parallel to the plane of the opening of the sequestration pen, and is not directed into the opening of the pen. In some instances, pens 124, 126, 128, 130 are configured to physically isolate one or more micro-objects within the microfluidic circuit 120. Sequestration pens in accordance with the present disclosure can comprise various shapes, surfaces and features that are optimized for use with DEP, OET, OEW, fluid flow, magnetic forces, centripetal, and/or gravitational forces, as will be discussed and shown in detail below.

The microfluidic circuit 120 may comprise any number of microfluidic sequestration pens. Although five sequestration pens are shown, microfluidic circuit 120 may have fewer or more sequestration pens. As shown, microfluidic sequestration pens 124, 126, 128, and 130 of microfluidic circuit 120 each comprise differing features and shapes which may provide one or more benefits useful for maintaining, isolating, assaying or culturing biological micro-objects. In some embodiments, the microfluidic circuit 120 comprises a plurality of identical microfluidic sequestration pens.

Figure 1B:
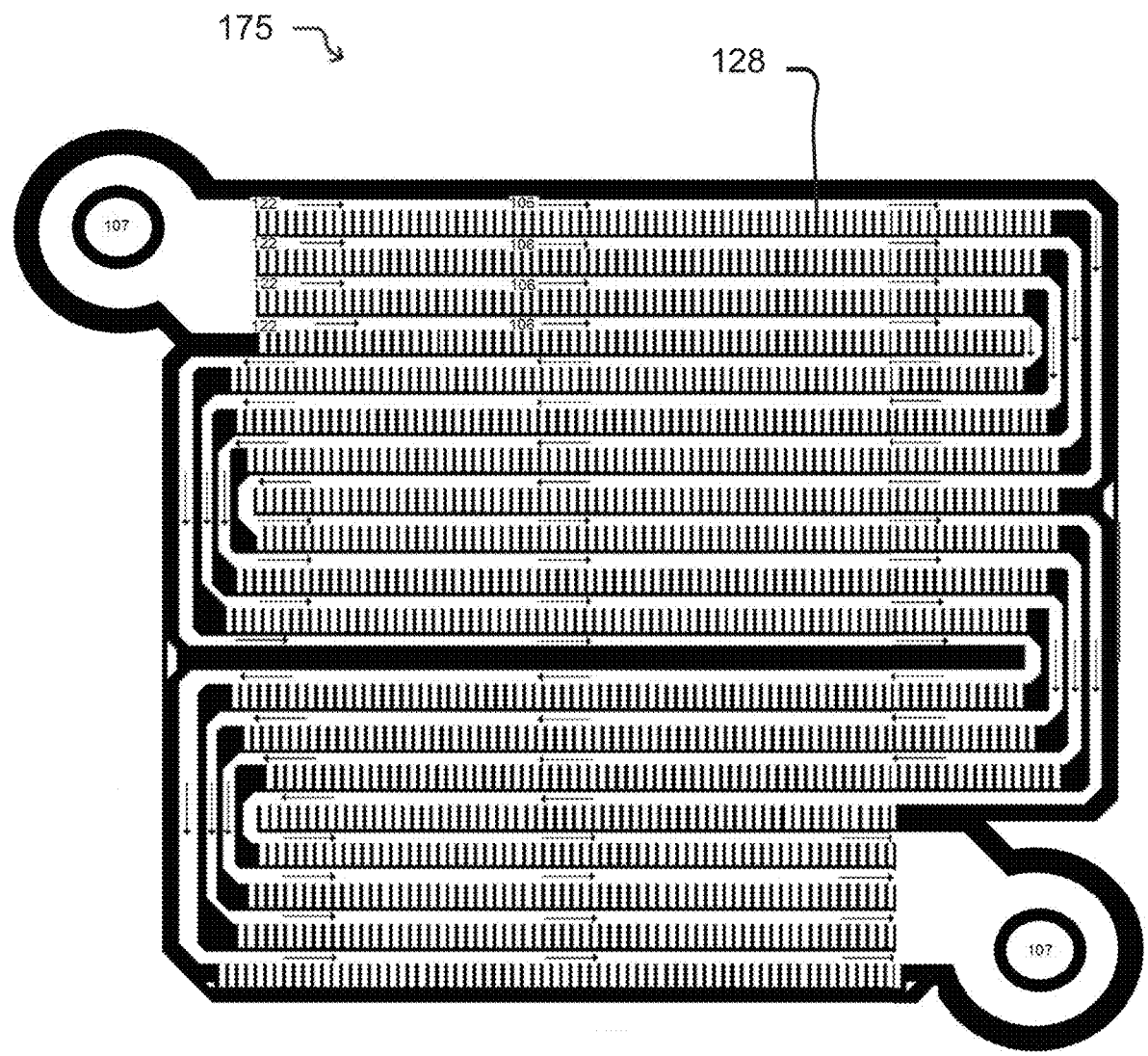
FIG. 1B illustrates a microfluidic device with sequestration pens according to an embodiment of the disclosure.

In the embodiment illustrated in FIG. 1A, a single flow path 106 containing a single channel 122 is shown. However, other embodiments may contain multiple channels 122 within a single flow path 106, as shown in FIG. 1B. The microfluidic circuit 120 further comprises an inlet valve or port 107 in fluid communication with the flow path 106, whereby fluidic medium 180 can access the flow path 106 (and channel 122). In some instances, the flow path 106 comprises a substantially straight path. In other instances, the flow path 106 is arranged in a non-linear or winding manner, such as a zigzag pattern, whereby the flow path 106 travels across the microfluidic device 100 two or more times, e.g., in alternating directions. The flow in the flow path 106 may proceed from inlet to outlet or may be reversed and proceed from outlet to inlet.

One example of a multi-channel device, microfluidic device 175, is shown in FIG. 1i, which may be like microfluidic device 100 in other respects. Microfluidic device 175 and its constituent circuit elements (e.g., channels 122 and sequestration pens 128) may have any of the dimensions discussed herein. The microfluidic circuit illustrated in FIG. 1B has two inlet/outlet ports 107 and a flow path 106 containing four distinct channels 122. The number of channels into which the microfluidic circuit is sub-divided may be chosen to reduce fluidic resistance. For example, the microfluidic circuit may include 1, 2, 3, 4, 5, 6, 7, 8, 9, 10, or more channels to provide a selected range of fluidic resistance. Microfluidic device 175 further comprises a plurality of sequestration pens opening off of each channel 122, where each of the sequestration pens is similar to sequestration pen 128 of FIG. 1A, and may have any of the dimensions or functions of any sequestration pen as described herein. However, the sequestration pens of microfluidic device 175 can have different shapes, such as any of the shapes of sequestration pens 124, 126, or 130 of FIG. 1A or as described anywhere else herein. Moreover, microfluidic device 175 can include sequestration pens having a mixture of different shapes. In some instances, a plurality of sequestration pens is configured (e.g., relative to a channel 122) such that the sequestration pens can be loaded with target micro-objects in parallel.

Returning to FIG. 1A, microfluidic circuit 120 further may include one or more optional micro-object traps 132. The optional traps 132 may be formed in a wall forming the boundary of a channel 122, and may be positioned opposite an opening of one or more of the microfluidic sequestration pens 124, 126, 128, 130. The optional traps 132 may be configured to receive or capture a single micro-object from the flow path 106, or may be configured to receive or capture a plurality of micro-objects from the flow path 106. In some instances, the optional traps 132 comprise a volume approximately equal to the volume of a single target micro-object.

Sequestration pens. The microfluidic devices described herein may include one or more sequestration pens, where each sequestration pen is suitable for holding one or more micro-objects (e.g., biological cells, or groups of cells that are associated together). The sequestration pens may be disposed within and open to a flow region, which in some embodiments is a microfluidic channel. Each of the sequestration pens can have one or more openings for fluidic communication to one or more microfluidic channels. In some embodiments, a sequestration pen may have only one opening to a microfluidic channel.

Figure 2A:
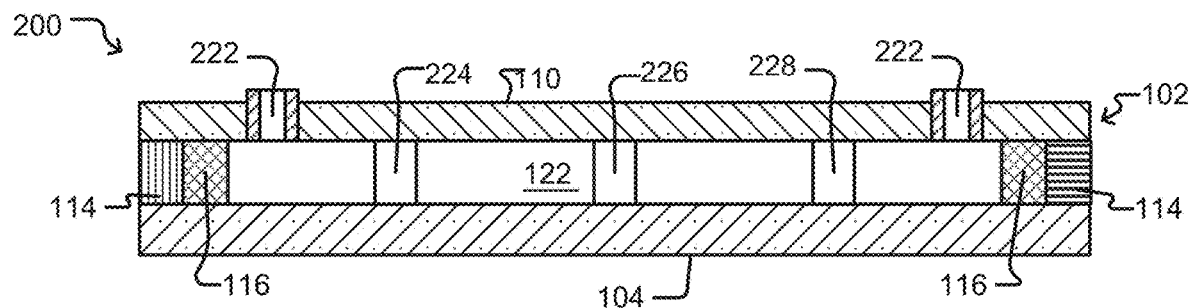
FIGS. 2A to 2B illustrate a microfluidic device having sequestration pens according to some embodiments of the disclosure.
Figure 2B:
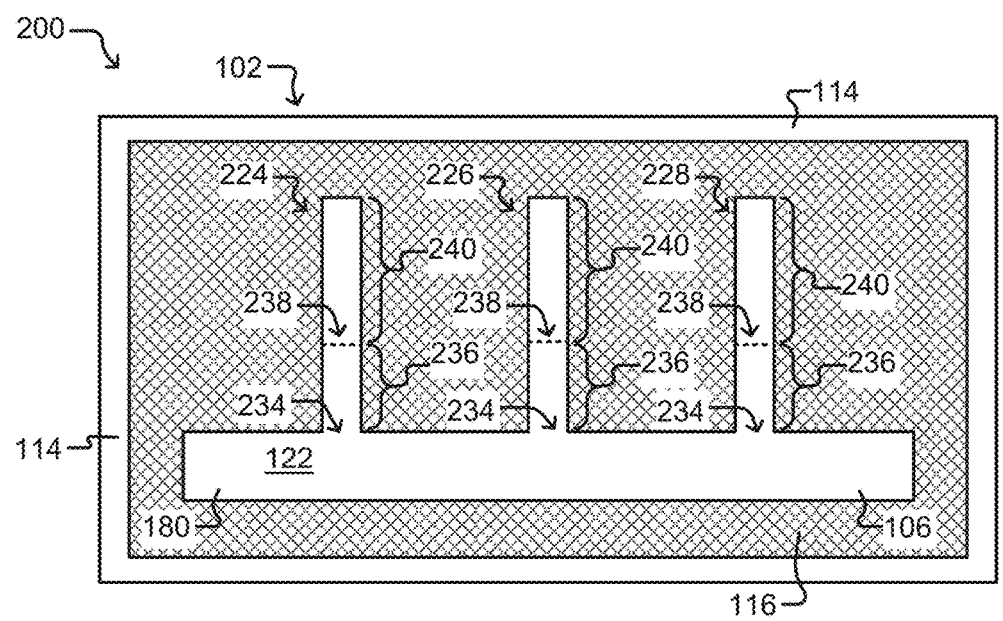
Figure 2C:
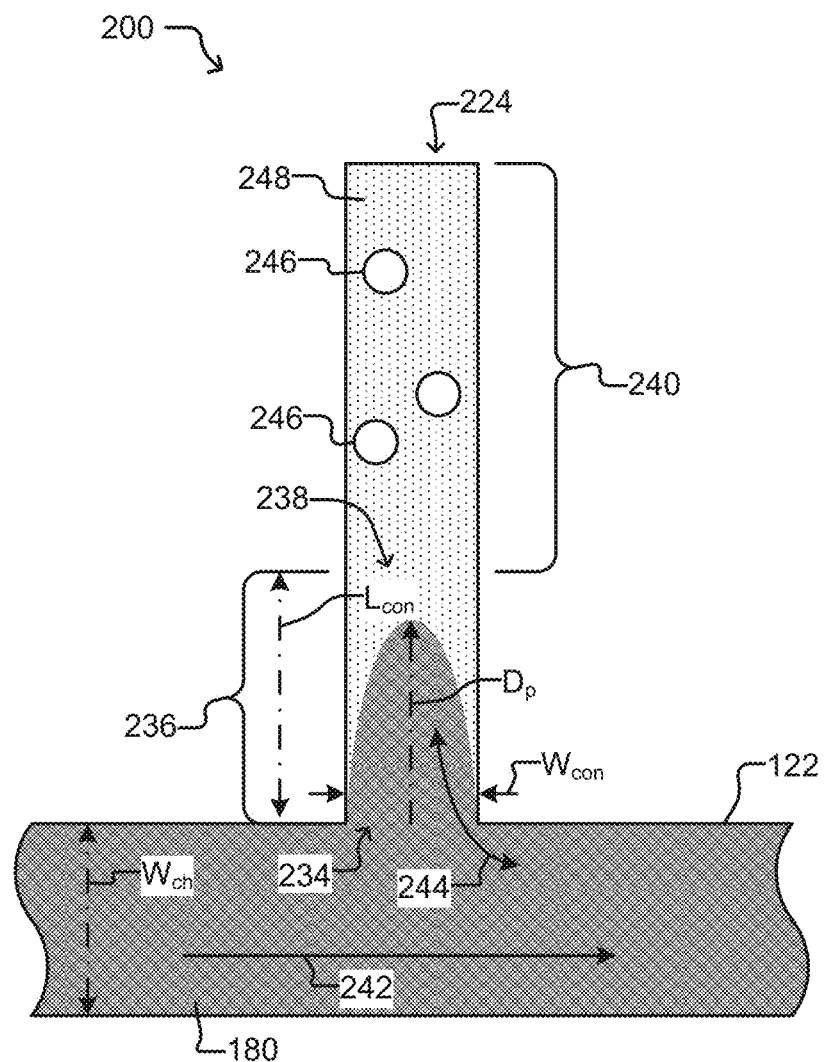
FIG. 2C illustrates a sequestration pen of a microfluidic device according to some embodiments of the disclosure.

FIGS. 2A-2C show sequestration pens 224, 226, and 228 of a microfluidic device 200, which may be like sequestration pen 128 of FIG. 1A. Each sequestration pen 224, 226, and 228 can comprise an isolation region 240 and a connection region 236 fluidically connecting the isolation region 240 to a flow region, which may, in some embodiments include a microfluidic channel, such as channel 122. The connection region 236 can comprise a proximal opening 234 to the flow region (e.g., microfluidic channel 122) and a distal opening 238 to the isolation region 240. The connection region 236 can be configured so that the maximum penetration depth of a flow of a fluidic medium (not shown) flowing in the microfluidic channel 122 past the sequestration pen 224, 226, and 228 does not extend into the isolation region 240, as discussed below for FIG. 2C. In some embodiments, streamlines from the flow in the microfluidic channel do not enter the isolation region. Thus, due to the connection region 236, a micro-object (not shown) or other material (not shown) disposed in the isolation region 240 of a sequestration pen 224, 226, and 228 can be isolated from, and not substantially affected by, a flow of fluidic medium 180 in the microfluidic channel 122.

The sequestration pens 224, 226, and 228 of FIGS. 2A-2C each have a single opening which opens directly to the microfluidic channel 122. The opening of the sequestration pen may open laterally from the microfluidic channel 122, as shown in FIG. 2A, which depicts a vertical cross-section of microfluidic device 200. FIG. 2B shows a horizontal cross-section of microfluidic device 200. An electrode activation substrate 206 can underlie both the microfluidic channel 122 and the sequestration pens 224, 226, and 228. The upper surface of the electrode activation substrate 206 within an enclosure of a sequestration pen, forming the floor of the sequestration pen, can be disposed at the same level or substantially the same level of the upper surface the of electrode activation substrate 206 within the microfluidic channel 122 (or flow region if a channel is not present), forming the floor of the flow channel (or flow region, respectively) of the microfluidic device. The electrode activation substrate 206 may be featureless or may have an irregular or patterned surface that varies from its highest elevation to its lowest depression by less than about 3 micrometers (microns), 2.5 microns, 2 microns, 1.5 microns, 1 micron, 0.9 microns, 0.5 microns, 0.4 microns, 0.2 microns, 0.1 microns or less. The variation of elevation in the upper surface of the substrate across both the microfluidic channel 122 (or flow region) and sequestration pens may be equal to or less than about 10%, 7%, 5%, 3%, 2%, 1%. 0.9%, 0.8%, 0.5%, 0.3% or 0.1% of the height of the walls of the sequestration pen. Alternatively, the variation of elevation in the upper surface of the substrate across both the microfluidic channel 122 (or flow region) and sequestration pens may be equal to or less than about 2%, 1%. 0.9%, 0.8%, 0.5%, 0.3%, 0.2%, or 0.1% of the height of the substrate. While described in detail for the microfluidic device 200, this may also apply to any of the microfluidic devices described herein.

The microfluidic channel 122 and connection region 236 can be examples of swept regions, and the isolation regions 240 of the sequestration pens 224, 226, and 228 can be examples of unswept regions. Sequestration pens like 224, 226, 228 have isolation regions wherein each isolation region has only one opening, which opens to the connection region of the sequestration pen. Fluidic media exchange in and out of the isolation region so configured can be limited to occurring substantially only by diffusion. As noted, the microfluidic channel 122 and sequestration pens 224, 226, and 228 can be configured to contain one or more fluidic media 180. In the example shown in FIGS. 2A-2B, ports 222 are connected to the microfluidic channel 122 and allow the fluidic medium 180 to be introduced into or removed from the microfluidic device 200. Prior to introduction of the fluidic medium 180, the microfluidic device may be primed with a gas such as carbon dioxide gas. Once the microfluidic device 200 contains the fluidic medium 180, the flow 242 (see FIG. 2C) of fluidic medium 180 in the microfluidic channel 122 can be selectively generated and stopped. For example, as shown, the ports 222 can be disposed at different locations (e.g., opposite ends) of the flow region (microfluidic channel 122), and a flow 242 of the fluidic medium can be created from one port 222 functioning as an inlet to another port 222 functioning as an outlet.

FIG. 2C illustrates a detailed view of an example of a sequestration pen 224, which may contain one or more micro-objects 246, according to some embodiments. The flow 242 of fluidic medium 180 in the microfluidic channel 122 past the proximal opening 234 of the connection region 236 of sequestration pen 224 can cause a secondary flow 244 of the fluidic medium 180 into and out of the sequestration pen 224. To sequester the micro-objects 246 in the isolation region 240 of the sequestration pen 224 from the secondary flow 244, the length $L_{con}$ of the connection region 236 of the sequestration pen 224 (i.e., from the proximal opening 234 to the distal opening 238) should be greater than the penetration depth $D_p$ of the secondary flow 244 into the connection region 236. The penetration depth $D_p$ depends upon a number of factors, including the shape of the microfluidic channel 122, which may be defined by a width $W_{con}$ of the connection region 236 at the proximal opening 234; a width $W_{ch}$ of the microfluidic channel 122 at the proximal opening 234; a height $H_{ch}$ of the channel 122 at the proximal opening 234; and the width of the distal opening 238 of the connection region 236. Of these factors, the width $W_{con}$ of the connection region 236 at the proximal opening 234 and the height $H_{ch}$ of the channel 122 at the proximal opening 234 tend to be the most significant. In addition, the penetration depth $D_p$ can be influenced by the velocity of the fluidic medium 180 in the channel 122 and the viscosity of fluidic medium 180. However, these factors (i.e., velocity and viscosity) can vary widely without dramatic changes in penetration depth $D_p$. For example, for a microfluidic chip 200 having a width $W_{con}$ of the connection region 236 at the proximal opening 234 of about 50 microns, a height $H_{ch}$ of the channel 122 at the proximal opening 122 of about 40 microns, and a width $W_{ch}$ of the microfluidic channel 122 at the proximal opening 122 of about 100 microns to about 150 microns, the penetration depth $D_p$ of the secondary flow 244 ranges from less than 1.0 times $W_{con}$ (i.e., less than 50 microns) at a flow rate of 0.1 microliters/sec to about 2.0 times $W_{con}$ (i.e., about 100 microns) at a flow rate of 20 microliters/sec, which represents an increase in $D_p$ of only about 2.5-fold over a 200-fold increase in the velocity of the fluidic medium 180.

In some embodiments, the walls of the microfluidic channel 122 and sequestration pen 224, 226, or 228 can be oriented as follows with respect to the vector of the flow 242 of fluidic medium 180 in the microfluidic channel 122: the microfluidic channel width $W_{ch}$ (or cross-sectional area of the microfluidic channel 122) can be substantially perpendicular to the flow 242 of medium 180; the width $W_{con}$ (or cross-sectional area) of the connection region 236 at opening 234 can be substantially parallel to the flow 242 of medium 180 in the microfluidic channel 122; and/or the length $L_{con}$ of the connection region can be substantially perpendicular to the flow 242 of medium 180 in the microfluidic channel 122. The foregoing are examples only, and the relative position of the microfluidic channel 122 and sequestration pens 224, 226 and 228 can be in other orientations with respect to each other.

In some embodiments, for a given microfluidic device, the configurations of the microfluidic channel 122 and the opening 234 may be fixed, whereas the rate of flow 242 of fluidic medium 180 in the microfluidic channel 122 may be variable. Accordingly, for each sequestration pen 224, a maximal velocity $V_{max}$ for the flow 242 of fluidic medium 180 in channel 122 may be identified that ensures that the penetration depth $D_p$ of the secondary flow 244 does not exceed the length $L_{con}$ of the connection region 236. When $V_{max}$ is not exceeded, the resulting secondary flow 244 can be wholly contained within the connection region 236 and does not enter the isolation region 240. Thus, the flow 242 of fluidic medium 180 in the microfluidic channel 122 (swept region) is prevented from drawing micro-objects 246 out of the isolation region 240, which is an unswept region of the microfluidic circuit, resulting in the micro-objects 246 being retained within the isolation region 240. Accordingly, selection of microfluidic circuit element dimensions and further selection of the operating parameters (e.g., velocity of fluidic medium 180) can prevent contamination of the isolation region 240 of sequestration pen 224 by materials from the microfluidic channel 122 or another sequestration pen 226 or 228. It should be noted, however, that for many microfluidic chip configurations, there is no need to worry about $V_{max}$ per se, because the chip will break from the pressure associated with flowing fluidic medium 180 at high velocity through the chip before $V_{max}$ can be achieved.

Components (not shown) in the first fluidic medium 180 in the microfluidic channel 122 can mix with the second fluidic medium 248 in the isolation region 240 substantially only by diffusion of components of the first medium 180 from the microfluidic channel 122 through the connection region 236 and into the second fluidic medium 248 in the isolation region 240. Similarly, components (not shown) of the second medium 248 in the isolation region 240 can mix with the first medium 180 in the microfluidic channel 122 substantially only by diffusion of components of the second medium 248 from the isolation region 240 through the connection region 236 and into the first medium 180 in the microfluidic channel 122. In some embodiments, the extent of fluidic medium exchange between the isolation region of a sequestration pen and the flow region by diffusion is greater than about 90%, 91%, 92%, 93%, 94% 95%, 96%, 97%, 98%, or greater than about 99% of fluidic exchange.

In some embodiments, the first medium 180 can be the same medium or a different medium than the second medium 248. In some embodiments, the first medium 180 and the second medium 248 can start out being the same, then become different (e.g., through conditioning of the second medium 248 by one or more cells in the isolation region 240, or by changing the medium 180 flowing through the microfluidic channel 122).

As illustrated in FIG. 2C, the width $W_{con}$ of the connection region 236 can be uniform from the proximal opening 234 to the distal opening 238. The width $W_{con}$ of the connection region 236 at the distal opening 238 can be any of the values identified herein for the width $W_{con}$ of the connection region 236 at the proximal opening 234. In some embodiments, the width of the isolation region 240 at the distal opening 238 can be substantially the same as the width $W_{con}$ of the connection region 236 at the proximal opening 234. Alternatively, the width $W_{con}$ of the connection region 236 at the distal opening 238 can be different (e.g., larger or smaller) than the width $W_{con}$ of the connection region 236 at the proximal opening 234. In some embodiments, the width $W_{con}$ of the connection region 236 may be narrowed or widened between the proximal opening 234 and distal opening 238. For example, the connection region 236 may be narrowed or widened between the proximal opening and the distal opening, using a variety of different geometries (e.g., chamfering the connection region, beveling the connection region). Further, any part or subpart of the connection region 236 may be narrowed or widened (e.g. a portion of the connection region adjacent to the proximal opening 234).

Figure 3:
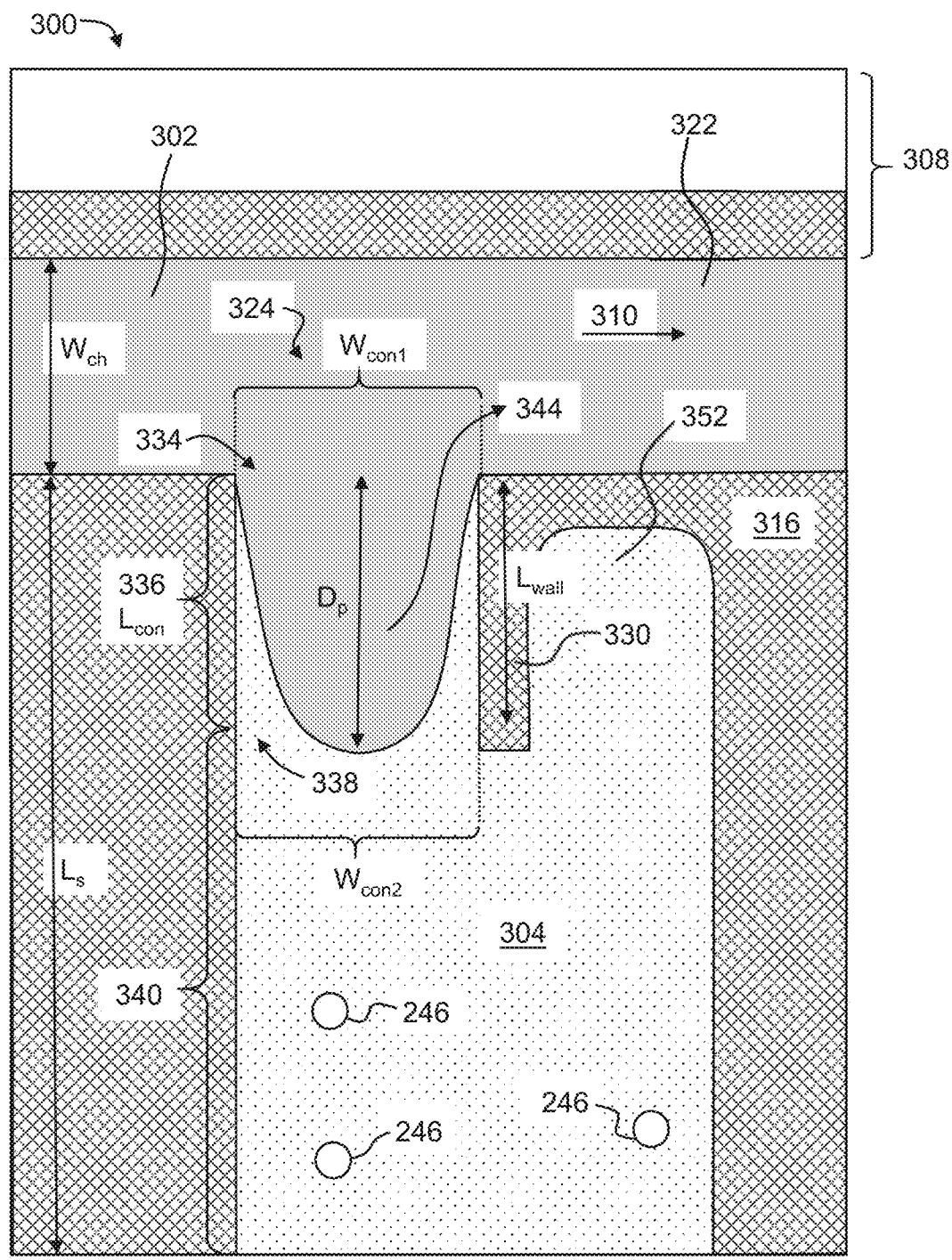
FIG. 3 illustrates a sequestration pen of a microfluidic device according to some embodiments of the disclosure.

FIG. 3 depicts another exemplary embodiment of a microfluidic device 300 containing microfluidic circuit structure 308, which includes a channel 322 and sequestration pen 324, which has features and properties like any of the sequestration pens described herein for microfluidic devices 100, 175, 200, 400, 520 and any other microfluidic devices described herein.

The exemplary microfluidic devices of FIG. 3 includes a microfluidic channel 322, having a width $W_{ch}$, as described herein, and containing a flow 310 of first fluidic medium 302 and one or more sequestration pens 324 (only one illustrated in FIG. 3). The sequestration pens 324 each have a length Ls, a connection region 336, and an isolation region 340, where the isolation region 340 contains a second fluidic medium 304. The connection region 336 has a proximal opening 334, having a width $W_{con1}$, which opens to the microfluidic channel 322, and a distal opening 338, having a width $W_{con2}$, which opens to the isolation region 340. The width $W_{con1}$ may or may not be the same as $W_{con2}$, as described herein. The walls of each sequestration pen 324 may be formed of microfluidic circuit material 316, which may further form the connection region walls 330. A connection region wall 330 can correspond to a structure that is laterally positioned with respect to the proximal opening 334 and at least partially extends into the enclosed portion of the sequestration pen 324. In some embodiments, the length $L_{con}$ of the connection region 336 is at least partially defined by length $L_{wall}$ of the connection region wall 330. The connection region wall 330 may have a length $L_{wall}$, selected to be more than the penetration depth $D_p$ of the secondary flow 344. Thus, the secondary flow 344 can be wholly contained within the connection region without extending into the isolation region 340.

The connection region wall 330 may define a hook region 352, which is a sub-region of the isolation region 340 of the sequestration pen 324. Since the connection region wall 330 extends into the inner cavity of the sequestration pen, the connection region wall 330 can act as a physical barrier to shield hook region 352 from secondary flow 344, with selection of the length of $L_{wall}$, contributing to the extent of the hook region. In some embodiments, the longer the length $L_{wall}$ of the connection region wall 330, the more sheltered the hook region 352.

In sequestration pens configured like those of FIGS. 2A-2C and 3, the isolation region may have a shape and size of any type, and may be selected to regulate diffusion of nutrients, reagents, and/or media into the sequestration pen to reach to a far wall of the sequestration pen, e.g., opposite the proximal opening of the connection region to the flow region (or microfluidic channel). The size and shape of the isolation region may further be selected to regulate diffusion of waste products and/or secreted products of a biological micro-object out from the isolation region to the flow region via the proximal opening of the connection region of the sequestration pen. In general, the shape of the isolation region is not critical to the ability of the sequestration pen to isolate micro-objects from direct flow in the flow region.

In some other embodiments of sequestration pens, the isolation region may have more than one opening fluidically connecting the isolation region with the flow region of the microfluidic device. However, for an isolation region having a number of n openings fluidically connecting the isolation region to the flow region (or two or more flow regions), n−1 openings can be valved. When the n−1 valved openings are closed, the isolation region has only one effective opening, and exchange of materials into/out of the isolation region occurs only by diffusion.

Examples of microfluidic devices having pens in which biological micro-objects can be placed, cultured, and/or monitored have been described, for example, in U.S. Pat. No. 9,857,333 (Chapman, et al.), U.S. Pat. No. 10,010,882 (White, et al.), and U.S. Pat. No. 9,889,445 (Chapman, et al.), each of which is incorporated herein by reference in its entirety.

Microfluidic circuit element dimensions. Various dimensions and/or features of the sequestration pens and the microfluidic channels to which the sequestration pens open, as described herein, may be selected to limit introduction of contaminants or unwanted micro-objects into the isolation region of a sequestration pen from the flow region/microfluidic channel; limit the exchange of components in the fluidic medium from the channel or from the isolation region to substantially only diffusive exchange; facilitate the transfer of micro-objects into and/or out of the sequestration pens; and/or facilitate growth or expansion of the biological cells. Microfluidic channels and sequestration pens, for any of the embodiments described herein, may have any suitable combination of dimensions, may be selected by one of skill from the teachings of this disclosure, as follows.

The proximal opening of the connection region of a sequestration pen may have a width (e.g., $W_{con}$ or $W_{con1}$) that is at least as large as the largest dimension of a micro-object (e.g., a biological cell, which may be a plant cell, such as a plant protoplast) for which the sequestration pen is intended. In some embodiments, the proximal opening has a width (e.g., $W_{con}$ or $W_{con1}$) of about 20 microns, about 40 microns, about 50 microns, about 60 microns, about 75 microns, about 100 microns, about 150 microns, about 200 microns, or about 300 microns. The foregoing are examples only, and the width (e.g., $W_{con}$ or $W_{con1}$) of a proximal opening can be selected to be a value between any of the values listed above (e.g., about 20-200 microns, about 20-150 microns, about 20-100 microns, about 20-75 microns, about 20-60 microns, about 50-300 microns, about 50-200 microns, about 50-150 microns, about 50-100 microns, about 50-75 microns, about 75-150 microns, about 75-100 microns, about 100-300 microns, about 100-200 microns, or about 200-300 microns).

In some embodiments, the connection region of the sequestration pen may have a length (e.g., $L_{con}$) from the proximal opening to the distal opening to the isolation region of the sequestration pen that is at least 0.5 times, at least 0.6 times, at least 0.7 times, at least 0.8 times, at least 0.9 times, at least 1.0 times, at least 1.1 times, at least 1.2 times, at least 1.3 times, at least 1.4 times, at least 1.5 times, at least 1.75 times, at least 2.0 times, at least 2.25 times, at least 2.5 times, at least 2.75 times, at least 3.0 times, at least 3.5 times, at least 4.0 times, at least 4.5 times, at least 5.0 times, at least 6.0 times, at least 7.0 times, at least 8.0 times, at least 9.0 times, or at least 10.0 times the width (e.g., $W_{con}$ or $W_{con1}$) of the proximal opening. Thus, for example, the proximal opening of the connection region of a sequestration pen may have a width (e.g., $W_{con}$ or $W_{con1}$) from about 20 microns to about 200 microns (e.g., about 50 microns to about 150 microns), and the connection region may have a length $L_{con}$ that is at least 1.0 times (e.g., at least 1.5 times, or at least 2.0 times) the width of the proximal opening. As another example, the proximal opening of the connection region of a sequestration pen may have a width (e.g., $W_{con}$ or $W_{con1}$) from about 20 microns to about 100 microns (e.g., about 20 microns to about 60 microns), and the connection region may have a length $L_{con}$ that is at least 1.0 times (e.g., at least 1.5 times, or at least 2.0 times) the width of the proximal opening.

The microfluidic channel of a microfluidic device to which a sequestration pen opens may have specified size (e.g., width or height). In some embodiments, the height (e.g., $H_{ch}$) of the microfluidic channel at a proximal opening to the connection region of a sequestration pen can be within any of the following ranges: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height (e.g., $H_{ch}$) of the microfluidic channel (e.g., 122) can be selected to be between any of the values listed above. Moreover, the height (e.g., $H_{ch}$) of the microfluidic channel 122 can be selected to be any of these heights in regions of the microfluidic channel other than at a proximal opening of a sequestration pen.

The width (e.g., $W_{ch}$) of the microfluidic channel at the proximal opening to the connection region of a sequestration pen can be within any of the following ranges: about 20-500 microns, 20-400 microns, 20-300 microns, 20-200 microns, 20-150 microns, 20-100 microns, 20-80 microns, 20-60 microns, 30-400 microns, 30-300 microns, 30-200 microns, 30-150 microns, 30-100 microns, 30-80 microns, 30-60 microns, 40-300 microns, 40-200 microns, 40-150 microns, 40-100 microns, 40-80 microns, 40-60 microns, 50-1000 microns, 50-500 microns, 50-400 microns, 50-300 microns, 50-250 microns, 50-200 microns, 50-150 microns, 50-100 microns, 50-80 microns, 60-300 microns, 60-200 microns, 60-150 microns, 60-100 microns, 60-80 microns, 70-500 microns, 70-400 microns, 70-300 microns, 70-250 microns, 70-200 microns, 70-150 microns, 70-100 microns, 80-100 microns, 90-400 microns, 90-300 microns, 90-250 microns, 90-200 microns, 90-150 microns, 100-300 microns, 100-250 microns, 100-200 microns, 100-150 microns, 100-120 microns, 200-800 microns, 200-700 microns, or 200-600 microns. The foregoing are examples only, and the width (e.g., $W_{ch}$) of the microfluidic channel can be a value selected to be between any of the values listed above. Moreover, the width (e.g., $W_{ch}$) of the microfluidic channel can be selected to be in any of these widths in regions of the microfluidic channel other than at a proximal opening of a sequestration pen. In some embodiments, the width $W_{ch}$ of the microfluidic channel at the proximal opening to the connection region of the sequestration pen (e.g., taken transverse to the direction of bulk flow of fluid through the channel) can be substantially perpendicular to a width (e.g., $W_{con}$ or $W_{con1}$) of the proximal opening.

A cross-sectional area of the microfluidic channel at a proximal opening to the connection region of a sequestration pen can be about 500-50,000 square microns, 500-40,000 square microns, 500-30,000 square microns, 500-25,000 square microns, 500-20,000 square microns, 500-15,000 square microns, 500-10,000 square microns, 500-7,500 square microns, 500-5,000 square microns, 1,000-25,000 square microns, 1,000-20,000 square microns, 1,000-15,000 square microns, 1,000-10,000 square microns, 1,000-7,500 square microns, 1,000-5,000 square microns, 2,000-20,000 square microns, 2,000-15,000 square microns, 2,000-10,000 square microns, 2,000-7,500 square microns, 2,000-6,000 square microns, 3,000-20,000 square microns, 3,000-15,000 square microns, 3,000-10,000 square microns, 3,000-7,500 square microns, or 3,000 to 6,000 square microns. The foregoing are examples only, and the cross-sectional area of the microfluidic channel at the proximal opening can be selected to be between any of the values listed above. In various embodiments, and the cross-sectional area of the microfluidic channel at regions of the microfluidic channel other than at the proximal opening can also be selected to be between any of the values listed above. In some embodiments, the cross-sectional area is selected to be a substantially uniform value for the entire length of the microfluidic channel.

In some embodiments, the microfluidic chip is configured such that the proximal opening (e.g., 234 or 334) of the connection region of a sequestration pen may have a width (e.g., $W_{con}$ or $W_{con1}$) from about 20 microns to about 200 microns (e.g., about 50 microns to about 150 microns), the connection region may have a length $L_{con}$ (e.g., 236 or 336) that is at least 1.0 times (e.g., at least 1.5 times, or at least 2.0 times) the width of the proximal opening, and the microfluidic channel may have a height (e.g., $H_{ch}$) at the proximal opening of about 30 microns to about 60 microns. As another example, the proximal opening (e.g., 234 or 334) of the connection region of a sequestration pen may have a width (e.g., $W_{con}$ or $W_{con1}$) from about 20 microns to about 100 microns (e.g., about 20 microns to about 60 microns), the connection region may have a length $L_{con}$ (e.g., 236 or 336) that is at least 1.0 times (e.g., at least 1.5 times, or at least 2.0 times) the width of the proximal opening, and the microfluidic channel may have a height (e.g., $H_{ch}$) at the proximal opening of about 30 microns to about 60 microns. The foregoing are examples only, and the width (e.g., $W_{con}$ or $W_{con1}$) of the proximal opening (e.g., 234 or 274), the length (e.g., $L_{con}$) of the connection region, and/or the width (e.g., $W_{ch}$) of the microfluidic channel (e.g., 122 or 322), can be a value selected to be between any of the values listed above.

In some embodiments, the size $W_C$ (e.g., cross-sectional width $W_{ch}$, diameter, area, or the like) of the channel 122, 322, 618, 718 can be about one and a quarter (1.25), about one and a half (1.5), about two, about two and a half (2.5), about three (3), or more times the size Wo (e.g., cross-sectional width $W_{con}$, diameter, area, or the like) of a chamber opening, e.g., sequestration pen opening 234, 334, and the like. This can reduce the extent of secondary flow and the rate of diffusion (or diffusion flux) through the opening 234, 334 for materials diffusing from a selected chamber (e.g., like sequestration pens 224, 226 of FIG. 2B) into channel 122, 322, 618, 718 and subsequently re-entering a downstream or adjacent chamber (e.g., like sequestration pen 228). The rate of diffusion of a molecule (e.g., an analyte of interest, such as an antibody) is dependent on a number of factors, including (without limitation) temperature, viscosity of the medium, and the coefficient of diffusion $D_0$ of the molecule. For example, the $D_0$ for an IgG antibody in aqueous solution at about 20° C. is about $4.4 \times 10^{-7}$ cm$^2$/sec, while the kinematic viscosity of cell culture medium is about $9 \times 10^{-4}$ m$^2$/sec. Thus, an antibody in cell culture medium at about 20° C. can have a rate of diffusion of about 0.5 microns/sec. Accordingly, in some embodiments, a time period for diffusion from a biological microobject located within a sequestration pen such as 224, 226, 228, 324 into the channel 122, 322, 618, 718 can be about 10 minutes or less (e.g., about 9, 8, 7, 6, 5 minutes, or less). The time period for diffusion can be manipulated by changing parameters that influence the rate of diffusion. For example, the temperature of the media can be increased (e.g., to a physiological temperature such as about 37° C.) or decreased (e.g., to about 15° C., 10° C., or 4° C.) thereby increasing or decreasing the rate of diffusion, respectively. Alternatively, or in addition, the concentrations of solutes in the medium can be increased or decreased as discussed herein to isolate a selected pen from solutes from other upstream pens.

Accordingly, in some variations, the width (e.g., $W_{ch}$) of the microfluidic channel at the proximal opening to the connection region of a sequestration pen may be about 50 to 500 microns, about 50 to 300 microns, about 50 to 200 microns, about 70 to 500 microns, about to 70-300 microns, about 70 to 250 microns, about 70 to 200 microns, about 70 to 150 microns, about 70 to 100 microns, about 80 to 500 microns, about 80 to 300 microns, about 80 to 250 microns, about 80 to 200 microns, about 80 to 150 microns, about 90 to 500 microns, about 90 to 300 microns, about 90 to 250 microns, about 90 to 200 microns, about 90 to 150 microns, about 100 to 500 microns, about 100 to 300 microns, about 100 to 250 microns, about 100 to 200 microns, or about 100 to 150 microns. In some embodiments, the width $W_{ch}$ of the microfluidic channel at the proximal opening to the connection region of a sequestration pen may be about 70 to 250 microns, about 80 to 200 microns, or about 90 to 150 microns. The width $W_{con}$ of the opening of the chamber (e.g., sequestration pen) may be about 20 to 100 microns; about 30 to 90 microns; or about 20 to 60 microns. In some embodiments, $W_{ch}$ is about 70-250 microns and $W_{con}$ is about 20 to 100 microns; $W_{ch}$ is about 80 to 200 microns and $W_{con}$ is about 30 to 90 microns; $W_{ch}$ is about 90 to 150 microns, and $W_{con}$ is about 20 to 60 microns; or any combination of the widths of $W_{ch}$ and $W_{con}$ thereof.

In some embodiments, the proximal opening (e.g., 234 or 334) of the connection region of a sequestration pen has a width (e.g., $W_{con}$ or $W_{con1}$) that is 2.0 times or less (e.g., 2.0, 1.9, 1.8, 1.5, 1.3, 1.0, 0.8, 0.5, or 0.1 times) the height (e.g., $H_{ch}$) of the flow region/microfluidic channel at the proximal opening, or has a value that lies within a range defined by any two of the foregoing values.

In some embodiments, the width $W_{con1}$ of a proximal opening (e.g., 234 or 334) of a connection region of a sequestration pen may be the same as a width $W_{con2}$ of the distal opening (e.g., 238 or 338) to the isolation region thereof. In some embodiments, the width $W_{con1}$ of the proximal opening may be different than a width $W_{con2}$ of the distal opening, and $W_{con1}$ and/or $W_{con2}$ may be selected from any of the values described for $W_{con}$ or $W_{con1}$. In some embodiments, the walls (including a connection region wall) that define the proximal opening and distal opening may be substantially parallel with respect to each other. In some embodiments, the walls that define the proximal opening and distal opening may be selected to not be parallel with respect to each other.

The length (e.g., $L_{con}$) of the connection region can be about 1-600 microns, 5-550 microns, 10-500 microns, 15-400 microns, 20-300 microns, 20-500 microns, 40-400 microns, 60-300 microns, 80-200 microns, about 100-150 microns, about 20-300 microns, about 20-250 microns, about 20-200 microns, about 20-150 microns, about 20-100 microns, about 30-250 microns, about 30-200 microns, about 30-150 microns, about 30-100 microns, about 30-80 microns, about 30-50 microns, about 45-250 microns, about 45-200 microns, about 45-100 microns, about 45-80 microns, about 45-60 microns, about 60-200 microns, about 60-150 microns, about 60-100 microns or about 60-80 microns. The foregoing are examples only, and length (e.g., $L_{con}$) of a connection region can be selected to be a value that is between any of the values listed above.

The connection region wall of a sequestration pen may have a length (e.g., $L_{wall}$) that is at least 0.5 times, at least 0.6 times, at least 0.7 times, at least 0.8 times, at least 0.9 times, at least 1.0 times, at least 1.1 times, at least 1.2 times, at least 1.3 times, at least 1.4 times, at least 1.5 times, at least 1.75 times, at least 2.0 times, at least 2.25 times, at least 2.5 times, at least 2.75 times, at least 3.0 times, or at least 3.5 times the width (e.g., $W_{con}$ or $W_{con1}$) of the proximal opening of the connection region of the sequestration pen. In some embodiments, the connection region wall may have a length $L_{wall}$ of about 20-200 microns, about 20-150 microns, about 20-100 microns, about 20-80 microns, or about 20-50 microns. The foregoing are examples only, and a connection region wall may have a length $L_{wall}$ selected to be between any of the values listed above.

A sequestration pen may have a length LS of about 40-600 microns, about 40-500 microns, about 40-400 microns, about 40-300 microns, about 40-200 microns, about 40-100 microns or about 40-80 microns. The foregoing are examples only, and a sequestration pen may have a length LS selected to be between any of the values listed above.

According to some embodiments, a sequestration pen may have a specified height (e.g., $H_s$). In some embodiments, a sequestration pen has a height $H_s$ of about 20 microns to about 200 microns (e.g., about 20 microns to about 150 microns, about 20 microns to about 100 microns, about 20 microns to about 60 microns, about 30 microns to about 150 microns, about 30 microns to about 100 microns, about 30 microns to about 60 microns, about 40 microns to about 100 microns, about 40 microns to about 150 microns, about 40 microns to about 100 microns, or about 40 microns to about 60 microns). The foregoing are examples only, and a sequestration pen can have a height $H_s$ selected to be between any of the values listed above.

The height $H_{con}$ of a connection region at a proximal opening of a sequestration pen can be a height within any of the following heights: 20-100 microns, 20-90 microns, 20-80 microns, 20-70 microns, 20-60 microns, 20-50 microns, 30-100 microns, 30-90 microns, 30-80 microns, 30-70 microns, 30-60 microns, 30-50 microns, 40-100 microns, 40-90 microns, 40-80 microns, 40-70 microns, 40-60 microns, or 40-50 microns. The foregoing are examples only, and the height $H_{con}$ of the connection region can be selected to be between any of the values listed above. Typically, the height $H_{con}$ of the connection region is selected to be the same as the height $H_{ch}$ of the microfluidic channel at the proximal opening of the connection region. Additionally, the height $H_s$ of the sequestration pen is typically selected to be the same as the height $H_{con}$ of a connection region and/or the height $H_{ch}$ of the microfluidic channel. In some embodiments, $H_s$, $H_{con}$, and $H_{ch}$ may be selected to be the same value of any of the values listed above for a selected microfluidic device.

The isolation region can be configured to contain only one, two, three, four, five, or a similar relatively small number of micro-objects. In other embodiments, the isolation region may contain more than 10, more than 50 or more than 100 micro-objects. Accordingly, the volume of an isolation region can be, for example, at least $1\times10^4$, $1\times10^5$, $5\times10^5$, $8\times10^5$, $1\times10^6$, $2\times10^6$, $4\times10^6$, $6\times10^6$, $1\times10^7$, $3\times10^7$, $5\times10^7$ $1\times10^8$, $5\times10^8$, or $8\times10^8$ cubic microns, or more. The foregoing are examples only, and the isolation region can be configured to contain numbers of micro-objects and volumes selected to be between any of the values listed above (e.g., a volume between $1\times10^5$ cubic microns and $5\times10^5$ cubic microns, between $5\times10^5$ cubic microns and $1\times10^6$ cubic microns, between $1\times10^6$ cubic microns and $2\times10^6$ cubic microns, or between $2\times10^6$ cubic microns and $1\times10^7$ cubic microns).

According to some embodiments, a sequestration pen of a microfluidic device may have a specified volume. The specified volume of the sequestration pen (or the isolation region of the sequestration pen) may be selected such that a single cell or a small number of cells (e.g., 2-10 or 2-5) can rapidly condition the medium and thereby attain favorable (or optimal) growth conditions. In some embodiments, the sequestration pen has a volume of about $5\times10^5$, $6\times10^5$, $8\times10^5$, $1\times10^6$, $2\times10^6$, $4\times10^6$, $8\times10^6$, $1\times10^7$, $3\times10^7$, $5\times10^7$, or about $8\times10^7$ cubic microns, or more. In some embodiments, the sequestration pen has a volume of about 1 nanoliter to about 50 nanoliters, 2 nanoliters to about 25 nanoliters, 2 nanoliters to about 20 nanoliters, about 2 nanoliters to about 15 nanoliters, or about 2 nanoliters to about 10 nanoliters. The foregoing are examples only, and a sequestration pen can have a volume selected to be any value that is between any of the values listed above.

According to some embodiments, the flow of fluidic medium within the microfluidic channel (e.g., 122 or 322) may have a specified maximum velocity (e.g., $V_{max}$). In some embodiments, the maximum velocity (e.g., $V_{max}$) may be set at around 0.2, 0.5, 0.7, 1.0, 1.3, 1.5, 2.0, 2.5, 3.0, 3.5, 4.0, 4.5, 5.0, 5.5, 6.0, 6.7, 7.0, 7.5, 8.0, 8.5, 9.0, 10, 11, 12, 13, 14, 15, 16, 17, 18, 19, or 20 microliters/sec. The foregoing are examples only, and the flow of fluidic medium within the microfluidic channel can have a maximum velocity (e.g., $V_{max}$) selected to be a value between any of the values listed above.

In various embodiment, the microfluidic device has sequestration pens configured as in any of the embodiments discussed herein where the microfluidic device has about 5 to about 10 sequestration pens, about 10 to about 50 sequestration pens, about 25 to about 200 sequestration pens, about 100 to about 500 sequestration pens, about 200 to about 1000 sequestration pens, about 500 to about 1500 sequestration pens, about 1000 to about 2500 sequestration pens, about 2000 to about 5000 sequestration pens, about 3500 to about 7000 sequestration pens, about 5000 to about 10,000 sequestration pens, about 7,500 to about 15,000 sequestration pens, about 12,500 to about 20,000 sequestration pens, about 15,000 to about 25,000 sequestration pens, about 20,000 to about 30,000 sequestration pens, about 25,000 to about 35,000 sequestration pens, about 30,000 to about 40,000 sequestration pens, about 35,000 to about 45,000 sequestration pens, or about 40,000 to about 50,000 sequestration pens. The sequestration pens need not all be the same size and may include a variety of configurations (e.g., different widths, different features within the sequestration pen).

Coating solutions and coating agents. In some embodiments, at least one inner surface of the microfluidic device includes a coating material that provides a layer of organic and/or hydrophilic molecules suitable for maintenance, expansion and/or movement of biological micro-object(s) (i.e., the biological micro-object exhibits increased viability, greater expansion and/or greater portability within the microfluidic device). The conditioned surface may reduce surface fouling, participate in providing a layer of hydration, and/or otherwise shield the biological micro-objects from contact with the non-organic materials of the microfluidic device interior.

In some embodiments, substantially all the inner surfaces of the microfluidic device include the coating material. The coated inner surface(s) may include the surface of a flow region (e.g., channel), chamber, or sequestration pen, or a combination thereof. In some embodiments, each of a plurality of sequestration pens has at least one inner surface coated with coating materials. In other embodiments, each of a plurality of flow regions or channels has at least one inner surface coated with coating materials. In some embodiments, at least one inner surface of each of a plurality of sequestration pens and each of a plurality of channels is coated with coating materials. The coating may be applied before or after introduction of biological micro-object(s), or may be introduced concurrently with the biological micro-object(s). In some embodiments, the biological micro-object(s) may be imported into the microfluidic device in a fluidic medium that includes one or more coating agents. In other embodiments, the inner surface(s) of the microfluidic device (e.g., a microfluidic device having an electrode activation substrate such as, but not limited to, a device including dielectrophoresis (DEP) electrodes) may be treated or "primed" with a coating solution comprising a coating agent prior to introduction of the biological micro-object(s) into the microfluidic device. Any convenient coating agent/coating solution can be used, including but not limited to: serum or serum factors, bovine serum albumin (BSA), polymers, detergents, enzymes, and any combination thereof.

Synthetic polymer-based coating materials. The at least one inner surface may include a coating material that comprises a polymer. The polymer may be non-covalently bound (e.g., it may be non-specifically adhered) to the at least one surface. The polymer may have a variety of structural motifs, such as found in block polymers (and copolymers), star polymers (star copolymers), and graft or comb polymers (graft copolymers), all of which may be suitable for the methods disclosed herein. A wide variety of alkylene ether containing polymers may be suitable for use in the microfluidic devices described herein, including but not limited to Pluronic® polymers such as Pluronic® L44, L64, P85, and F127 (including F127NF). Other examples of suitable coating materials are described in US2016/0312165, the contents of which are herein incorporated by reference in their entirety.

Covalently linked coating materials. In some embodiments, the at least one inner surface includes covalently linked molecules that provide a layer of organic and/or hydrophilic molecules suitable for maintenance/expansion of biological micro-object(s) within the microfluidic device, providing a conditioned surface for such cells. The covalently linked molecules include a linking group, wherein the linking group is covalently linked to one or more surfaces of the microfluidic device, as described below. The linking group is also covalently linked to a surface modifying moiety configured to provide a layer of organic and/or hydrophilic molecules suitable for maintenance/expansion/movement of biological micro-object(s).

In some embodiments, the covalently linked moiety configured to provide a layer of organic and/or hydrophilic molecules suitable for maintenance/expansion of biological micro-object(s) may include alkyl or fluoroalkyl (which includes perfluoroalkyl) moieties; mono- or polysaccharides (which may include but is not limited to dextran); alcohols (including but not limited to propargyl alcohol); polyalcohols, including but not limited to polyvinyl alcohol; alkylene ethers, including but not limited to polyethylene glycol; polyelectrolytes (including but not limited to polyacrylic acid or polyvinyl phosphonic acid); amino groups (including derivatives thereof, such as, but not limited to alkylated amines, hydroxyalkylated amino group, guanidinium, and heterocylic groups containing an unaromatized nitrogen ring atom, such as, but not limited to morpholinyl or piperazinyl); carboxylic acids including but not limited to propiolic acid (which may provide a carboxylate anionic surface); phosphonic acids, including but not limited to ethynyl phosphonic acid (which may provide a phosphonate anionic surface); sulfonate anions; carboxybetaines; sulfobetaines; sulfamic acids; or amino acids.

In various embodiments, the covalently linked moiety configured to provide a layer of organic and/or hydrophilic molecules suitable for maintenance/expansion of biological micro-object(s) in the microfluidic device may include non-polymeric moieties such as an alkyl moiety, amino acid moiety, alcohol moiety, amino moiety, carboxylic acid moiety, phosphonic acid moiety, sulfonic acid moiety, sulfamic acid moiety, or saccharide moiety. Alternatively, the covalently linked moiety may include polymeric moieties, which may include any of these moieties.

In some embodiments, a microfluidic device may have a hydrophobic layer upon the inner surface of the base which includes a covalently linked alkyl moiety. The covalently linked alkyl moiety may comprise carbon atoms forming a linear chain (e.g., a linear chain of at least 10 carbons, or at least 14, 16, 18, 20, 22, or more carbons) and may be an unbranched alkyl moiety. In some embodiments, the alkyl group may include a substituted alkyl group (e.g., some of the carbons in the alkyl group can be fluorinated or perfluorinated). In some embodiments, the alkyl group may include a first segment, which may include a perfluoroalkyl group, joined to a second segment, which may include a non-substituted alkyl group, where the first and second segments may be joined directly or indirectly (e.g., by means of an ether linkage). The first segment of the alkyl group may be located distal to the linking group, and the second segment of the alkyl group may be located proximal to the linking group.

In other embodiments, the covalently linked moiety may include at least one amino acid, which may include more than one type of amino acid. Thus, the covalently linked moiety may include a peptide or a protein. In some embodiments, the covalently linked moiety may include an amino acid which may provide a zwitterionic surface to support cell growth, viability, portability, or any combination thereof.

In other embodiments, the covalently linked moiety may further include a streptavidin or biotin moiety. In some embodiments, a modified biological moiety such as, for example, a biotinylated protein or peptide may be introduced to the inner surface of a microfluidic device bearing covalently linked streptavidin, and couple via the covalently linked streptavidin to the surface, thereby providing a modified surface presenting the protein or peptide.

In other embodiments, the covalently linked moiety may include at least one alkylene oxide moiety and may include any alkylene oxide polymer as described above. One useful class of alkylene ether containing polymers is polyethylene glycol (PEG $M_w$<100,000 Da) or alternatively polyethylene oxide (PEO, $M_w$>100,000). In some embodiments, a PEG may have an $M_w$ of about 1000 Da, 5000 Da, 10,000 Da or 20,000 Da. In some embodiments, the PEG polymer may further be substituted with a hydrophilic or charged moiety, such as but not limited to an alcohol functionality or a carboxylic acid moiety.

The covalently linked moiety may include one or more saccharides. The covalently linked saccharides may be mono-, di-, or polysaccharides. The covalently linked saccharides may be modified to introduce a reactive pairing moiety which permits coupling or elaboration for attachment to the surface. One exemplary covalently linked moiety may include a dextran polysaccharide, which may be coupled indirectly to a surface via an unbranched linker.

The coating material providing a conditioned surface may comprise only one kind of covalently linked moiety or may include more than one different kind of covalently linked moiety. For example, a polyethylene glycol conditioned surface may have covalently linked alkylene oxide moieties having a specified number of alkylene oxide units which are all the same, e.g., having the same linking group and covalent attachment to the surface, the same overall length, and the same number of alkylene oxide units. Alternatively, the coating material may have more than one kind of covalently linked moiety attached to the surface. For example, the coating material may include the molecules having covalently linked alkylene oxide moieties having a first specified number of alkylene oxide units and may further include a further set of molecules having bulky moieties such as a protein or peptide connected to a covalently attached alkylene oxide linking moiety having a greater number of alkylene oxide units. The different types of molecules may be varied in any suitable ratio to obtain the surface characteristics desired. For example, the conditioned surface having a mixture of first molecules having a chemical structure having a first specified number of alkylene oxide units and second molecules including peptide or protein moieties, which may be coupled via a biotin/streptavidin binding pair to the covalently attached alkylene linking moiety, may have a ratio of first molecules:second molecules of about 99:1; about 90:10; about 75:25; about 50:50; about 30:70; about 20:80; about 10:90; or any ratio selected to be between these values. In this instance, the first set of molecules having different, less sterically demanding termini and fewer backbone atoms can help to functionalize the entire substrate surface and thereby prevent undesired adhesion or contact with the silicon/silicon oxide, hafnium oxide or alumina making up the substrate itself. The selection of the ratio of mixture of first molecules to second molecules may also modulate the surface modification introduced by the second molecules bearing peptide or protein moieties.

Conditioned surface properties. Various factors can alter the physical thickness of the conditioned surface, such as the manner in which the conditioned surface is formed on the substrate (e.g. vapor deposition, liquid phase deposition, spin coating, flooding, and electrostatic coating). In some embodiments, the conditioned surface may have a thickness of about 1 nm to about 10 nm. In some embodiments, the covalently linked moieties of the conditioned surface may form a monolayer when covalently linked to the surface of the microfluidic device (which may include an electrode activation substrate having dielectrophoresis (DEP) or electrowetting (EW) electrodes) and may have a thickness of less than 10 nm (e.g., less than 5 nm, or about 1.5 to 3.0 nm). These values are in contrast to that of a surface prepared by spin coating, for example, which may typically have a thickness of about 30 nm. In some embodiments, the conditioned surface does not require a perfectly formed monolayer to be suitably functional for operation within a DEP-configured microfluidic device. In other embodiments, the conditioned surface formed by the covalently linked moieties may have a thickness of about 10 nm to about 50 nm.

Unitary or Multi-part conditioned surface. The covalently linked coating material may be formed by reaction of a molecule which already contains the moiety configured to provide a layer of organic and/or hydrophilic molecules suitable for maintenance/expansion of biological micro-object(s) in the microfluidic device, and may have a structure of Formula I, as shown below. Alternatively, the covalently linked coating material may be formed in a two-part sequence, having a structure of Formula II, by coupling the moiety configured to provide a layer of organic and/or hydrophilic molecules suitable for maintenance and/or expansion of biological micro-object(s) to a surface modifying ligand that itself has been covalently linked to the surface. In some embodiments, the surface may be formed in a two-part or three-part sequence, including a streptavidin/biotin binding pair, to introduce a protein, peptide, or mixed modified surface.

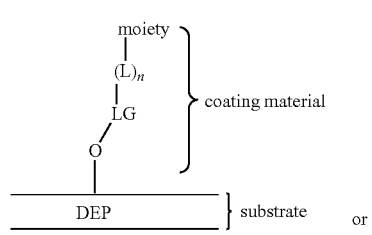

Formula I

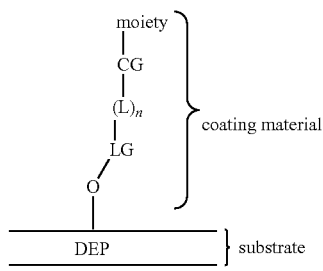

Formula II

The coating material may be linked covalently to oxides of the surface of a DEP-configured or EW-configured substrate. The coating material may be attached to the oxides via a linking group ("LG"), which may be a siloxy or phosphonate ester group formed from the reaction of a siloxane or phosphonic acid group with the oxides. The moiety configured to provide a layer of organic and/or hydrophilic molecules suitable for maintenance/expansion of biological micro-object(s) in the microfluidic device can be any of the moieties described herein. The linking group LG may be directly or indirectly connected to the moiety configured to provide a layer of organic and/or hydrophilic molecules suitable for maintenance/expansion of biological micro-object(s) in the microfluidic device. When the linking group LG is directly connected to the moiety, optional linker ("L") is not present and n is 0. When the linking group LG is indirectly connected to the moiety, linker L is present and n is 1. The linker L may have a linear portion where a backbone of the linear portion may include 1 to 200 non-hydrogen atoms selected from any combination of silicon, carbon, nitrogen, oxygen, sulfur and/or phosphorus atoms, subject to chemical bonding limitations as is known in the art. It may be interrupted with any combination of one or more moieties, which may be chosen from ether, amino, carbonyl, amido, and/or phosphonate groups, arylene, heteroarylene, or heterocyclic groups. In some embodiments, the coupling group CG represents the resultant group from reaction of a reactive moiety $R_x$ and a reactive pairing moiety $R_{px}$ (i.e., a moiety configured to react with the reactive moiety $R_x$). CG may be a carboxamidyl group, a triazolylene group, substituted triazolylene group, a carboxamidyl, thioamidyl, an oxime, a mercaptyl, a disulfide, an ether, or alkenyl group, or any other suitable group that may be formed upon reaction of a reactive moiety with its respective reactive pairing moiety. In some embodiments, CG may further represent a streptavidin/biotin binding pair.

Further details of suitable coating treatments and modifications, as well as methods of preparation, may be found at U.S. Patent Application Publication No. US2016/0312165 (Lowe, Jr., et al.), U.S. Patent Application Publication No US2017/0173580 (Lowe, Jr., et al), International Patent Application Publication WO2017/205830 (Lowe, Jr., et al.), and International Patent Application Publication WO2019/01880 (Beemiller et al.), each of which disclosures is herein incorporated by reference in its entirety.

Microfluidic device motive technologies. The microfluidic devices described herein can be used with any type of motive technology. As described herein, the control and monitoring equipment of the system can comprise a motive module for selecting and moving objects, such as micro-objects or droplets, in the microfluidic circuit of a microfluidic device. The motive technology(ies) may include, for example, dielectrophoresis (DEP), electrowetting (EW), and/or other motive technologies. The microfluidic device can have a variety of motive configurations, depending upon the type of object being moved and other considerations. Returning to FIG. 1A, for example, the support structure 104 and/or cover 110 of the microfluidic device 100 can comprise DEP electrode activation substrates for selectively inducing motive forces on micro-objects in the fluidic medium 180 in the microfluidic circuit 120 and thereby select, capture, and/or move individual micro-objects or groups of micro-objects.

In some embodiments, motive forces are applied across the fluidic medium 180 (e.g., in the flow path and/or in the sequestration pens) via one or more electrodes (not shown) to manipulate, transport, separate and sort micro-objects located therein. For example, in some embodiments, motive forces are applied to one or more portions of microfluidic circuit 120 in order to transfer a single micro-object from the flow path 106 into a desired microfluidic sequestration pen. In some embodiments, motive forces are used to prevent a micro-object within a sequestration pen from being displaced therefrom. Further, in some embodiments, motive forces are used to selectively remove a micro-object from a sequestration pen that was previously collected in accordance with the embodiments of the current disclosure.

In some embodiments, the microfluidic device is configured as an optically-actuated electrokinetic device, such as in optoelectronic tweezer (OET) and/or optoelectrowetting (OEW) configured device. Examples of suitable OET configured devices (e.g., containing optically actuated dielectrophoresis electrode activation substrates) can include those illustrated in U.S. Patent No. RE 44,711 (Wu, et al.) (originally issued as U.S. Pat. No. 7,612,355), U.S. Pat. No. 7,956,339 (Ohta, et al.), U.S. Pat. No. 9,908,115 (Hobbs et al.), and U.S. Pat. No. 9,403,172 (Short et al), each of which is incorporated herein by reference in its entirety. Examples of suitable OEW configured devices can include those illustrated in U.S. Pat. No. 6,958,132 (Chiou, et al.), and U.S. Pat. No. 9,533,306 (Chiou, et al.), each of which is incorporated herein by reference in its entirety. Examples of suitable optically-actuated electrokinetic devices that include combined OET/OEW configured devices can include those illustrated in U.S. Patent Application Publication No. 2015/0306598 (Khandros, et al.), U.S. Patent Application Publication No 2015/0306599 (Khandros, et al.), and U.S. Patent Application Publication No. 2017/0173580 (Lowe, et al.), each of which is incorporated herein by reference in its entirety.

It should be understood that, for purposes of simplicity, the various examples of FIGS. 1-5B may illustrate portions of microfluidic devices while not depicting other portions. Further, FIGS. 1-5B may be part of, and implemented as, one or more microfluidic systems. In one non-limiting example, FIGS. 4A and 4B show a side cross-sectional view and a top cross-sectional view, respectively, of a portion of an enclosure 102 of the microfluidic device 400 having a region/chamber 402, which may be part of a fluidic circuit element having a more detailed structure, such as a growth chamber, a sequestration pen (which may be like any sequestration pen described herein), a flow region, or a flow channel. For instance, microfluidic device 400 may be similar to microfluidic devices 100, 175, 200, 300, 520 or any other microfluidic device as described herein. Furthermore, the microfluidic device 400 may include other fluidic circuit elements and may be part of a system including control and monitoring equipment 152, described above, having one or more of the media module 160, motive module 162, imaging module 164, optional tilting module 166, and other modules 168. Microfluidic devices 175, 200, 300, 520 and any other microfluidic devices described herein may similarly have any of the features described in detail for FIGS. 1A-1B and 4A-4B.

Figure 4A:
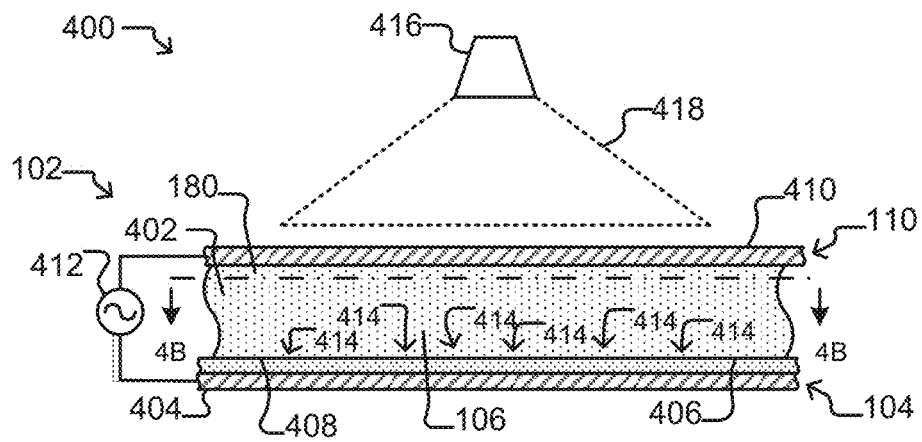
FIGS. 4A to 4B illustrate electrokinetic features of a microfluidic device according to some embodiments of the disclosure.

As shown in the example of FIG. 4A, the microfluidic device 400 includes a support structure 104 having a bottom electrode 404 and an electrode activation substrate 406 overlying the bottom electrode 404, and a cover 110 having a top electrode 410, with the top electrode 410 spaced apart from the bottom electrode 404. The top electrode 410 and the electrode activation substrate 406 define opposing surfaces of the region/chamber 402. A fluidic medium 180 contained in the region/chamber 402 thus provides a resistive connection between the top electrode 410 and the electrode activation substrate 406. A power source 412 configured to be connected to the bottom electrode 404 and the top electrode 410 and create a biasing voltage between the electrodes, as required for the generation of DEP forces in the region/chamber 402, is also shown. The power source 412 can be, for example, an alternating current (AC) power source.

Figure 4B:
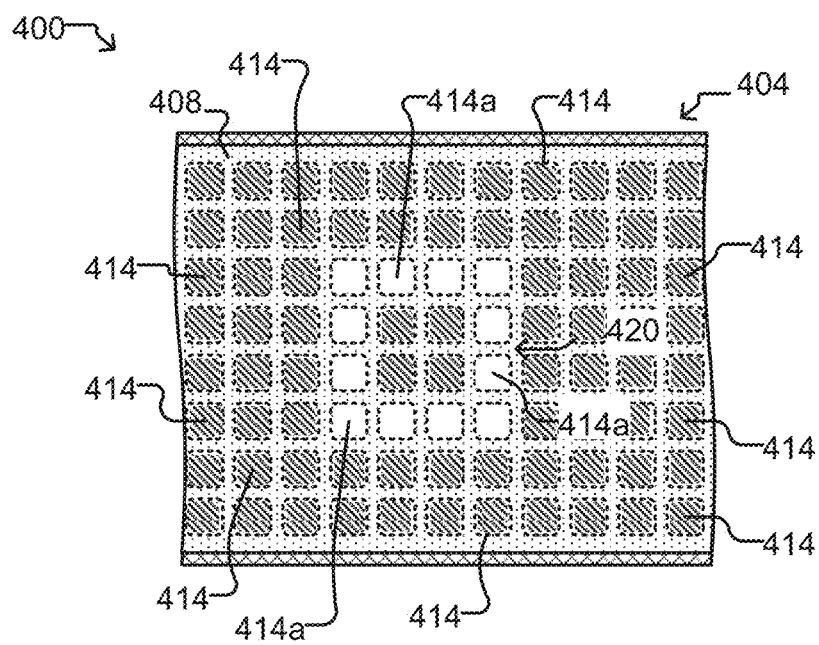

In certain embodiments, the microfluidic device 200 illustrated in FIGS. 4A and 4B can have an optically-actuated DEP electrode activation substrate. Accordingly, changing patterns of light 418 from the light source 416, which may be controlled by the motive module 162, can selectively activate and deactivate changing patterns of DEP electrodes at regions 414 of the inner surface 408 of the electrode activation substrate 406. (Hereinafter the regions 414 of a microfluidic device having a DEP electrode activation substrate are referred to as "DEP electrode regions.") As illustrated in FIG. 4B, a light pattern 418 directed onto the inner surface 408 of the electrode activation substrate 406 can illuminate select DEP electrode regions 414a (shown in white) in a pattern, such as a square. The non-illuminated DEP electrode regions 414 (cross-hatched) are hereinafter referred to as "dark" DEP electrode regions 414. The relative electrical impedance through the DEP electrode activation substrate 406 (i.e., from the bottom electrode 404 up to the inner surface 408 of the electrode activation substrate 406 which interfaces with the fluidic medium 180 in the flow region 106) is greater than the relative electrical impedance through the fluidic medium 180 in the region/chamber 402 (i.e., from the inner surface 408 of the electrode activation substrate 406 to the top electrode 410 of the cover 110) at each dark DEP electrode region 414. An illuminated DEP electrode region 414a, however, exhibits a reduced relative impedance through the electrode activation substrate 406 that is less than the relative impedance through the fluidic medium 180 in the region/chamber 402 at each illuminated DEP electrode region 414a.

With the power source 412 activated, the foregoing DEP configuration creates an electric field gradient in the fluidic medium 180 between illuminated DEP electrode regions 414a and adjacent dark DEP electrode regions 414, which in turn creates local DEP forces that attract or repel nearby micro-objects (not shown) in the fluidic medium 180. DEP electrodes that attract or repel micro-objects in the fluidic medium 180 can thus be selectively activated and deactivated at many different such DEP electrode regions 414 at the inner surface 408 of the region/chamber 402 by changing light patterns 418 projected from a light source 416 into the microfluidic device 400. Whether the DEP forces attract or repel nearby micro-objects can depend on such parameters as the frequency of the power source 412 and the dielectric properties of the fluidic medium 180 and/or micro-objects (not shown). Depending on the frequency of the power applied to the DEP configuration and selection of fluidic media (e.g., a highly conductive media such as PBS or other media appropriate for maintaining biological cells), negative DEP forces may be produced. Negative DEP forces may repel the micro-objects away from the location of the induced non-uniform electrical field. In some embodiments, a microfluidic device incorporating DEP technology may generate negative DEP forces.

The square pattern 420 of illuminated DEP electrode regions 414a illustrated in FIG. 4B is an example only. Any pattern of the DEP electrode regions 414 can be illuminated (and thereby activated) by the pattern of light 418 projected into the microfluidic device 400, and the pattern of illuminated/activated DEP electrode regions 414 can be repeatedly changed by changing or moving the light pattern 418.

In some embodiments, the electrode activation substrate 406 can comprise or consist of a photoconductive material. In such embodiments, the inner surface 408 of the electrode activation substrate 406 can be featureless. For example, the electrode activation substrate 406 can comprise or consist of a layer of hydrogenated amorphous silicon (a-Si:H). The a-Si:H can comprise, for example, about 8% to 40% hydrogen (calculated as 100*the number of hydrogen atoms/the total number of hydrogen and silicon atoms). The layer of a-Si:H can have a thickness of about 500 nm to about 2.0 µm. In such embodiments, the DEP electrode regions 414 can be created anywhere and in any pattern on the inner surface 408 of the electrode activation substrate 406, in accordance with the light pattern 418. The number and pattern of the DEP electrode regions 214 thus need not be fixed, but can correspond to the light pattern 418. Examples of microfluidic devices having a DEP configuration comprising a photoconductive layer such as discussed above have been described, for example, in U.S. Patent No. RE 44,711 (Wu, et al.) (originally issued as U.S. Pat. No. 7,612,355), each of which is incorporated herein by reference in its entirety.

In other embodiments, the electrode activation substrate 406 can comprise a substrate comprising a plurality of doped layers, electrically insulating layers (or regions), and electrically conductive layers that form semiconductor integrated circuits, such as is known in semiconductor fields. For example, the electrode activation substrate 406 can comprise a plurality of phototransistors, including, for example, lateral bipolar phototransistors, with each phototransistor corresponding to a DEP electrode region 414. Alternatively, the electrode activation substrate 406 can comprise electrodes (e.g., conductive metal electrodes) controlled by phototransistor switches, with each such electrode corresponding to a DEP electrode region 414. The electrode activation substrate 406 can include a pattern of such phototransistors or phototransistor-controlled electrodes. The pattern, for example, can be an array of substantially square phototransistors or phototransistor-controlled electrodes arranged in rows and columns. Alternatively, the pattern can be an array of substantially hexagonal phototransistors or phototransistor-controlled electrodes that form a hexagonal lattice. Regardless of the pattern, electric circuit elements can form electrical connections between the DEP electrode regions 414 at the inner surface 408 of the electrode activation substrate 406 and the bottom electrode 404, and those electrical connections (i.e., phototransistors or electrodes) can be selectively activated and deactivated by the light pattern 418, as described above.

Examples of microfluidic devices having electrode activation substrates that comprise phototransistors have been described, for example, in U.S. Pat. No. 7,956,339 (Ohta et al.) and U.S. Pat. No. 9,908,115 (Hobbs et al.), the entire contents of each of which are incorporated herein by reference. Examples of microfluidic devices having electrode activation substrates that comprise electrodes controlled by phototransistor switches have been described, for example, in U.S. Pat. No. 9,403,172 (Short et al.), which is incorporated herein by reference in its entirety.

In some embodiments of a DEP configured microfluidic device, the top electrode 410 is part of a first wall (or cover 110) of the enclosure 402, and the electrode activation substrate 406 and bottom electrode 404 are part of a second wall (or support structure 104) of the enclosure 102. The region/chamber 402 can be between the first wall and the second wall. In other embodiments, the electrode 410 is part of the second wall (or support structure 104) and one or both of the electrode activation substrate 406 and/or the electrode 410 are part of the first wall (or cover 110). Moreover, the light source 416 can alternatively be used to illuminate the enclosure 102 from below.

With the microfluidic device 400 of FIGS. 4A-4B having a DEP electrode activation substrate, the motive module 162 of control and monitoring equipment 152, as described for FIG. 1A herein, can select a micro-object (not shown) in the fluidic medium 180 in the region/chamber 402 by projecting a light pattern 418 into the microfluidic device 400 to activate a first set of one or more DEP electrodes at DEP electrode regions 414a of the inner surface 408 of the electrode activation substrate 406 in a pattern (e.g., square pattern 420) that surrounds and captures the micro-object. The motive module 162 can then move the in situ-generated captured micro-object by moving the light pattern 418 relative to the microfluidic device 400 to activate a second set of one or more DEP electrodes at DEP electrode regions 414. Alternatively, the microfluidic device 400 can be moved relative to the light pattern 418.

In other embodiments, the microfluidic device 400 may be a DEP configured device that does not rely upon light activation of DEP electrodes at the inner surface 408 of the electrode activation substrate 406. For example, the electrode activation substrate 406 can comprise selectively addressable and energizable electrodes positioned opposite to a surface including at least one electrode (e.g., cover 110). Switches (e.g., transistor switches in a semiconductor substrate) may be selectively opened and closed to activate or inactivate DEP electrodes at DEP electrode regions 414, thereby creating a net DEP force on a micro-object (not shown) in region/chamber 402 in the vicinity of the activated DEP electrodes. Depending on such characteristics as the frequency of the power source 412 and the dielectric properties of the medium (not shown) and/or micro-objects in the region/chamber 402, the DEP force can attract or repel a nearby micro-object. By selectively activating and deactivating a set of DEP electrodes (e.g., at a set of DEP electrodes regions 414 that forms a square pattern 420), one or more micro-objects in region/chamber 402 can be selected and moved within the region/chamber 402. The motive module 162 in FIG. 1A can control such switches and thus activate and deactivate individual ones of the DEP electrodes to select, and move particular micro-objects (not shown) around the region/chamber 402. Microfluidic devices having a DEP electrode activation substrates that includes selectively addressable and energizable electrodes are known in the art and have been described, for example, in U.S. Pat. No. 6,294,063 (Becker, et al.) and U.S. Pat. No. 6,942,776 (Medoro), each of which is incorporated herein by reference in its entirety.

Regardless of whether the microfluidic device 400 has a dielectrophoretic electrode activation substrate, an electrowetting electrode activation substrate or a combination of both a dielectrophoretic and an electrowetting activation substrate, a power source 412 can be used to provide a potential (e.g., an AC voltage potential) that powers the electrical circuits of the microfluidic device 400. The power source 412 can be the same as, or a component of, the power source 192 referenced in FIG. 1A. Power source 412 can be configured to provide an AC voltage and/or current to the top electrode 410 and the bottom electrode 404. For an AC voltage, the power source 412 can provide a frequency range and an average or peak power (e.g., voltage or current) range sufficient to generate net DEP forces (or electrowetting forces) strong enough to select and move individual micro-objects (not shown) in the region/chamber 402, as discussed above, and/or to change the wetting properties of the inner surface 408 of the support structure 104 in the region/chamber 202, as also discussed above. Such frequency ranges and average or peak power ranges are known in the art. See, e.g., U.S. Pat. No. 6,958,132 (Chiou, et al.), U.S. Pat. No. RE44,711 (Wu, et al.) (originally issued as U.S. Pat. No. 7,612,355), and U.S. Patent Application Publication Nos. 2014/0124370 (Short, et al.), 2015/0306598 (Khandros, et al.), 2015/0306599 (Khandros, et al.), and 2017/0173580 (Lowe, Jr. et al.), each of which disclosures are herein incorporated by reference in its entirety.

Other forces may be utilized within the microfluidic devices, alone or in combination, to move selected micro-objects. Bulk fluidic flow within the microfluidic channel may move micro-objects within the flow region. Localized fluidic flow, which may be operated within the microfluidic channel, within a sequestration pen, or within another kind of chamber (e.g., a reservoir) can be also be used to move selected micro-objects. Localized fluidic flow can be used to move selected micro-objects out of the flow region into a non-flow region such as a sequestration pen or the reverse, from a non-flow region into a flow region. The localized flow can be actuated by deforming a deformable wall of the microfluidic device, as described in U.S. Pat. No. 10,058,865 (Breinlinger, et al.), which is incorporated herein by reference in its entirety.

Gravity may be used to move micro-objects within the microfluidic channel, into a sequestration pen, and/or out of a sequestration pen or other chamber, as described in U.S. Pat. No. 9,744,533 (Breinlinger, et al.), which is incorporated herein by reference in its entirety. Use of gravity (e.g., by tilting the microfluidic device and/or the support to which the microfluidic device is attached) may be useful for bulk movement of cells into or out of the sequestration pens from/to the flow region. Magnetic forces may be employed to move micro-objects including paramagnetic materials, which can include magnetic micro-objects attached to or associated with a biological micro-object. Alternatively, or in additional, centripetal forces may be used to move micro-objects within the microfluidic channel, as well as into or out of sequestration pens or other chambers in the microfluidic device.

In another alternative mode of moving micro-objects, laser-generated dislodging forces may be used to export micro-objects or assist in exporting micro-objects from a sequestration pen or any other chamber in the microfluidic device, as described in International Patent Publication No. WO2017/117408 (Kurz, et al.), which is incorporated herein by reference in its entirety.

In some embodiments, DEP forces are combined with other forces, such as fluidic flow (e.g., bulk fluidic flow in a channel or localized fluidic flow actuated by deformation of a deformable surface of the microfluidic device, laser generated dislodging forces, and/or gravitational force), so as to manipulate, transport, separate and sort micro-objects and/or droplets within the microfluidic circuit 120. In some embodiments, the DEP forces can be applied prior to the other forces. In other embodiments, the DEP forces can be applied after the other forces. In still other instances, the DEP forces can be applied at the same time as the other forces or in an alternating manner with the other forces.

System. Returning to FIG. 1A, a system 150 for operating and controlling microfluidic devices is shown, such as for controlling the microfluidic device 100. The electrical power source 192 can provide electric power to the microfluidic device 100, providing biasing voltages or currents as needed. The electrical power source 192 can, for example, comprise one or more alternating current (AC) and/or direct current (DC) voltage or current sources.

System 150 can further include a media source 178. The media source 178 (e.g., a container, reservoir, or the like) can comprise multiple sections or containers, each for holding a different fluidic medium 180. Thus, the media source 178 can be a device that is outside of and separate from the microfluidic device 100, as illustrated in FIG. 1A. Alternatively, the media source 178 can be located in whole or in part inside the enclosure 102 of the microfluidic device 100. For example, the media source 178 can comprise reservoirs that are part of the microfluidic device 100.

FIG. 1A also illustrates simplified block diagram depictions of examples of control and monitoring equipment 152 that constitute part of system 150 and can be utilized in conjunction with a microfluidic device 100. As shown, examples of such control and monitoring equipment 152 can include a master controller 154 comprising a media module 160 for controlling the media source 178, a motive module 162 for controlling movement and/or selection of micro-objects (not shown) and/or medium (e.g., droplets of medium) in the microfluidic circuit 120, an imaging module 164 for controlling an imaging device (e.g., a camera, microscope, light source or any combination thereof) for capturing images (e.g., digital images), and an optional tilting module 166 for controlling the tilting of the microfluidic device 100. The control equipment 152 can also include other modules 168 for controlling, monitoring, or performing other functions with respect to the microfluidic device 100. As shown, the monitoring equipment 152 can further include a display device 170 and an input/output device 172.

The master controller 154 can comprise a control module 156 and a digital memory 158. The control module 156 can comprise, for example, a digital processor configured to operate in accordance with machine executable instructions (e.g., software, firmware, source code, or the like) stored as non-transitory data or signals in the memory 158. Alternatively, or in addition, the control module 156 can comprise hardwired digital circuitry and/or analog circuitry. The media module 160, motive module 162, imaging module 164, optional tilting module 166, and/or other modules 168 can be similarly configured. Thus, functions, processes acts, actions, or steps of a process discussed herein as being performed with respect to the microfluidic device 100 or any other microfluidic apparatus can be performed by any one or more of the master controller 154, media module 160, motive module 162, imaging module 164, optional tilting module 166, and/or other modules 168 configured as discussed above. Similarly, the master controller 154, media module 160, motive module 162, imaging module 164, optional tilting module 166, and/or other modules 168 may be communicatively coupled to transmit and receive data used in any function, process, act, action or step discussed herein.

The media module 160 controls the media source 178. For example, the media module 160 can control the media source 178 to input a selected fluidic medium 180 into the enclosure 102 (e.g., through an inlet port 107). The media module 160 can also control removal of media from the enclosure 102 (e.g., through an outlet port (not shown)). One or more media can thus be selectively input into and removed from the microfluidic circuit 120. The media module 160 can also control the flow of fluidic medium 180 in the flow path 106 inside the microfluidic circuit 120. The media module 160 may also provide conditioning gaseous conditions to the media source 178, for example, providing an environment containing 5% $CO_2$ (or higher). The media module 160 may also control the temperature of an enclosure of the media source, for example, to provide feeder cells in the media source with proper temperature control.

Motive module. The motive module 162 can be configured to control selection and movement of micro-objects (not shown) in the microfluidic circuit 120. The enclosure 102 of the microfluidic device 100 can comprise one or more electrokinetic mechanisms including a dielectrophoresis (DEP) electrode activation substrate, optoelectronic tweezers (OET) electrode activation substrate, electrowetting (EW) electrode activation substrate, and/or an opto-electrowetting (OEW) electrode activation substrate, where the motive module 162 can control the activation of electrodes and/or transistors (e.g., phototransistors) to select and move micro-objects and/or droplets in the flow path 106 and/or within sequestration pens 124, 126, 128, and 130. The electrokinetic mechanism(s) may be any suitable single or combined mechanism as described within the paragraphs describing motive technologies for use within the microfluidic device. A DEP configured device may include one or more electrodes that apply a non-uniform electric field in the microfluidic circuit 120 sufficient to exert a dielectrophoretic force on micro-objects in the microfluidic circuit 120. An OET configured device may include photo-activatable electrodes to provide selective control of movement of micro-objects in the microfluidic circuit 120 via light-induced dielectrophoresis.

The imaging module 164 can control the imaging device. For example, the imaging module 164 can receive and process image data from the imaging device. Image data from the imaging device can comprise any type of information captured by the imaging device (e.g., the presence or absence of micro-objects, droplets of medium, accumulation of label, such as fluorescent label, etc.). Using the information captured by the imaging device, the imaging module 164 can further calculate the position of objects (e.g., micro-objects, droplets of medium) and/or the rate of motion of such objects within the microfluidic device 100.

The imaging device (part of imaging module 164, discussed below) can comprise a device, such as a digital camera, for capturing images inside microfluidic circuit 120. In some instances, the imaging device further comprises a detector having a fast frame rate and/or high sensitivity (e.g. for low light applications). The imaging device can also include a mechanism for directing stimulating radiation and/or light beams into the microfluidic circuit 120 and collecting radiation and/or light beams reflected or emitted from the microfluidic circuit 120 (or micro-objects contained therein). The emitted light beams may be in the visible spectrum and may, e.g., include fluorescent emissions. The reflected light beams may include reflected emissions originating from an LED or a wide spectrum lamp, such as a mercury lamp (e.g. a high-pressure mercury lamp) or a Xenon arc lamp. The imaging device may further include a microscope (or an optical train), which may or may not include an eyepiece.

Support Structure. System 150 may further comprise a support structure 190 configured to support and/or hold the enclosure 102 comprising the microfluidic circuit 120. In some embodiments, the optional tilting module 166 can be configured to activate the support structure 190 to rotate the microfluidic device 100 about one or more axes of rotation. The optional tilting module 166 can be configured to support and/or hold the microfluidic device 100 in a level orientation (i.e. at 0° relative to x- and y-axes), a vertical orientation (i.e. at 90° relative to the x-axis and/or the y-axis), or any orientation therebetween. The orientation of the microfluidic device 100 (and the microfluidic circuit 120) relative to an axis is referred to herein as the "tilt" of the microfluidic device 100 (and the microfluidic circuit 120). For example, support structure 190 can optionally be used to tilt the microfluidic device 100 (e.g., as controlled by optional tilting module 166) to 0.1°, 0.2°, 0.3°, 0.4°, 0.5°, 0.6°, 0.7°, 0.8°, 0.9°, 1°, 2°, 3°, 4°, 5°, 10°, 15°, 20°, 25°, 30°, 35° 40°, 45° 50°, 55° 60°, 65°, 70°, 75°, 80°, 90° relative to the x-axis or any degree therebetween. When the microfluidic device is tilted at angles greater than about 15, tilting may be performed to create bulk movement of micro-objects into/out of sequestration pens from/into the flow region (e.g., microfluidic channel). In some embodiments, the support structure 190 can hold the microfluidic device 100 at a fixed angle of 0.1°, 0.2°, 0.3°, 0.4°, 0.5°, 0.6°, 0.7°, 0.8°, 0.9°, 1°, 2°, 3°, 4°, 5°, or 100 relative to the x-axis (horizontal), so long as DEP is an effective force to move micro-objects out of the sequestration pens into the microfluidic channel. Since the surface of the electrode activation substrate is substantially flat, DEP forces may be used even when the far end of the sequestration pen, opposite its opening to the microfluidic channel, is disposed at a position lower in a vertical direction than the microfluidic channel.

In some embodiments where the microfluidic device is tilted or held at a fixed angle relative to horizontal, the microfluidic device 100 may be disposed in an orientation such that the inner surface of the base of the flow path 106 is positioned at an angle above or below the inner surface of the base of the one or more sequestration pens opening laterally to the flow path. The term "above" as used herein denotes that the flow path 106 is positioned higher than the one or more sequestration pens on a vertical axis defined by the force of gravity (i.e. an object in a sequestration pen above a flow path 106 would have a higher gravitational potential energy than an object in the flow path), and inversely, for positioning of the flow path 106 below one or more sequestration pens. In some embodiments, the support structure 190 may be held at a fixed angle of less than about 5°, about 4°, about 3° or less than about 2° relative to the x-axis (horizontal), thereby placing the sequestration pens at a lower potential energy relative to the flow path. In some other embodiments, when long term culturing (e.g., for more than about 2, 3, 4, 5, 6, 7 or more days) is performed within the microfluidic device, the device may be supported on a culturing support and may be tilted at a greater angle of about 10°, 15°, 20°, 25°, 30°, or any angle therebetween to retain biological micro-objects within the sequestration pens during the long term culturing period. At the end of the culturing period, the microfluidic device containing the cultured biological micro-objects may be returned to the support 190 within system 150, where the angle of tilting is decreased to values as described above, affording the use of DEP to move the biological micro-objects out of the sequestration pens. Further examples of the use of gravitational forces induced by tilting are described in U.S. Pat. No. 9,744,533 (Breinlinger et al.), the contents of which are herein incorporated by reference in its entirety.

Figure 5A:
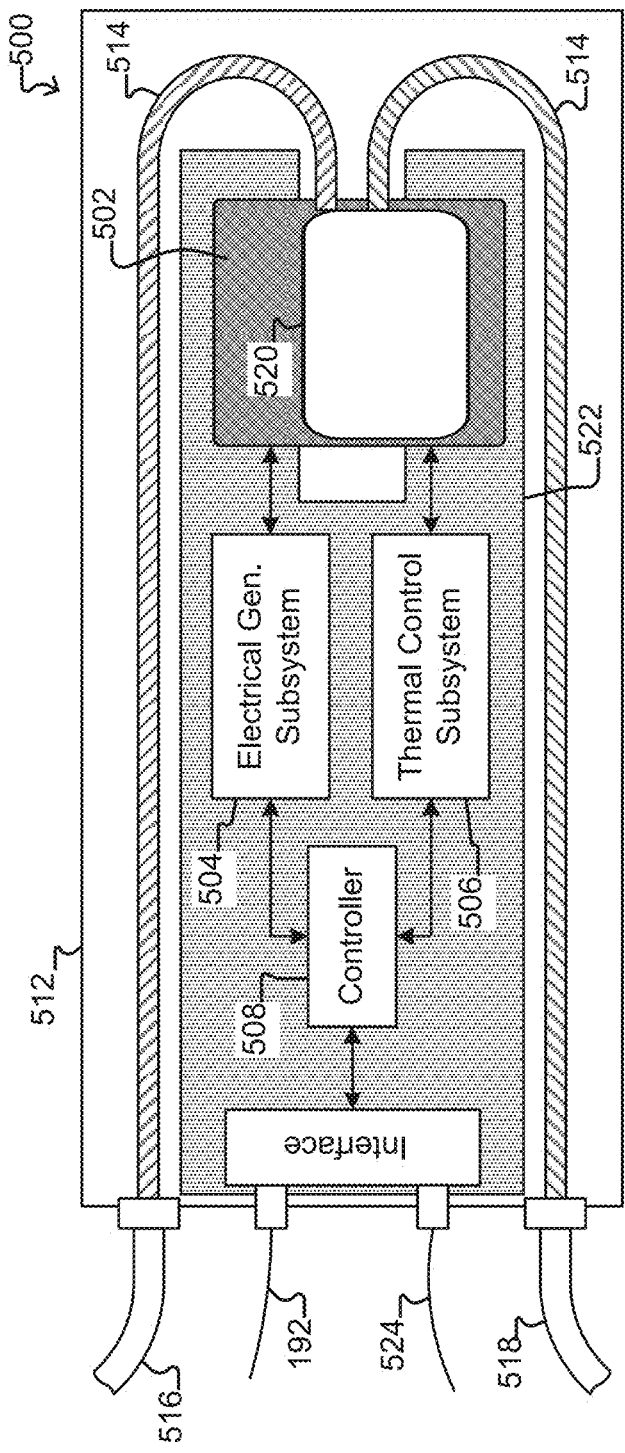
FIG. 5A illustrates a system for use with a microfluidic device and associated control equipment according to some embodiments of the disclosure.

Nest. Turning now to FIG. 5A, the system 150 can include a structure (also referred to as a "nest") 500 configured to hold a microfluidic device 520, which may be like microfluidic device 100, 200, or any other microfluidic device described herein. The nest 500 can include a socket 502 capable of interfacing with the microfluidic device 520 (e.g., an optically-actuated electrokinetic device 100, 200, etc.) and providing electrical connections from power source 192 to microfluidic device 520. The nest 500 can further include an integrated electrical signal generation subsystem 504. The electrical signal generation subsystem 504 can be configured to supply a biasing voltage to socket 502 such that the biasing voltage is applied across a pair of electrodes in the microfluidic device 520 when it is being held by socket 502. Thus, the electrical signal generation subsystem 504 can be part of power source 192. The ability to apply a biasing voltage to microfluidic device 520 does not mean that a biasing voltage will be applied at all times when the microfluidic device 520 is held by the socket 502. Rather, in most cases, the biasing voltage will be applied intermittently, e.g., only as needed to facilitate the generation of electrokinetic forces, such as dielectrophoresis or electrowetting, in the microfluidic device 520.

As illustrated in FIG. 5A, the nest 500 can include a printed circuit board assembly (PCBA) 522. The electrical signal generation subsystem 504 can be mounted on and electrically integrated into the PCBA 522. The exemplary support includes socket 502 mounted on PCBA 522, as well.

In some embodiments, the nest 500 can comprise an electrical signal generation subsystem 504 configured to measure the amplified voltage at the microfluidic device 520 and then adjust its own output voltage as needed such that the measured voltage at the microfluidic device 520 is the desired value. In some embodiments, the waveform amplification circuit can have a +6.5V to −6.5V power supply generated by a pair of DC-DC converters mounted on the PCBA 322, resulting in a signal of up to 13 Vpp at the microfluidic device 520.

In certain embodiments, the nest 500 further comprises a controller 508, such as a microprocessor used to sense and/or control the electrical signal generation subsystem 504. Examples of suitable microprocessors include the Arduino™ microprocessors, such as the Arduino Nano™ The controller 508 may be used to perform functions and analysis or may communicate with an external master controller 154 (shown in FIG. 1A) to perform functions and analysis. In the embodiment illustrated in FIG. 3A the controller 308 communicates with the master controller 154 (of FIG. 1A) through an interface (e.g., a plug or connector).

As illustrated in FIG. 5A, the support structure 500 (e.g., nest) can further include a thermal control subsystem 506. The thermal control subsystem 506 can be configured to regulate the temperature of microfluidic device 520 held by the support structure 500. For example, the thermal control subsystem 506 can include a Peltier thermoelectric device (not shown) and a cooling unit (not shown). In the embodiment illustrated in FIG. 5A, the support structure 500 comprises an inlet 516 and an outlet 518 to receive cooled fluid from an external reservoir (not shown) of the cooling unit, introduce the cooled fluid into the fluidic path 514 and through the cooling block, and then return the cooled fluid to the external reservoir. In some embodiments, the Peltier thermoelectric device, the cooling unit, and/or the fluidic path 514 can be mounted on a casing 512 of the support structure 500. In some embodiments, the thermal control subsystem 506 is configured to regulate the temperature of the Peltier thermoelectric device so as to achieve a target temperature for the microfluidic device 520. Temperature regulation of the Peltier thermoelectric device can be achieved, for example, by a thermoelectric power supply, such as a Pololu™ thermoelectric power supply (Pololu Robotics and Electronics Corp.). The thermal control subsystem 506 can include a feedback circuit, such as a temperature value provided by an analog circuit. Alternatively, the feedback circuit can be provided by a digital circuit.

The nest 500 can include a serial port 524 which allows the microprocessor of the controller 508 to communicate with an external master controller 154 via the interface. In addition, the microprocessor of the controller 508 can communicate (e.g., via a Plink tool (not shown)) with the electrical signal generation subsystem 504 and thermal control subsystem 506. Thus, via the combination of the controller 508, the interface, and the serial port 524, the electrical signal generation subsystem 504 and the thermal control subsystem 506 can communicate with the external master controller 154. In this manner, the master controller 154 can, among other things, assist the electrical signal generation subsystem 504 by performing scaling calculations for output voltage adjustments. A Graphical User Interface (GUI) (not shown) provided via a display device 170 coupled to the external master controller 154, can be configured to plot temperature and waveform data obtained from the thermal control subsystem 506 and the electrical signal generation subsystem 504, respectively. Alternatively, or in addition, the GUI can allow for updates to the controller 508, the thermal control subsystem 506, and the electrical signal generation subsystem 504.

Figure 5B:
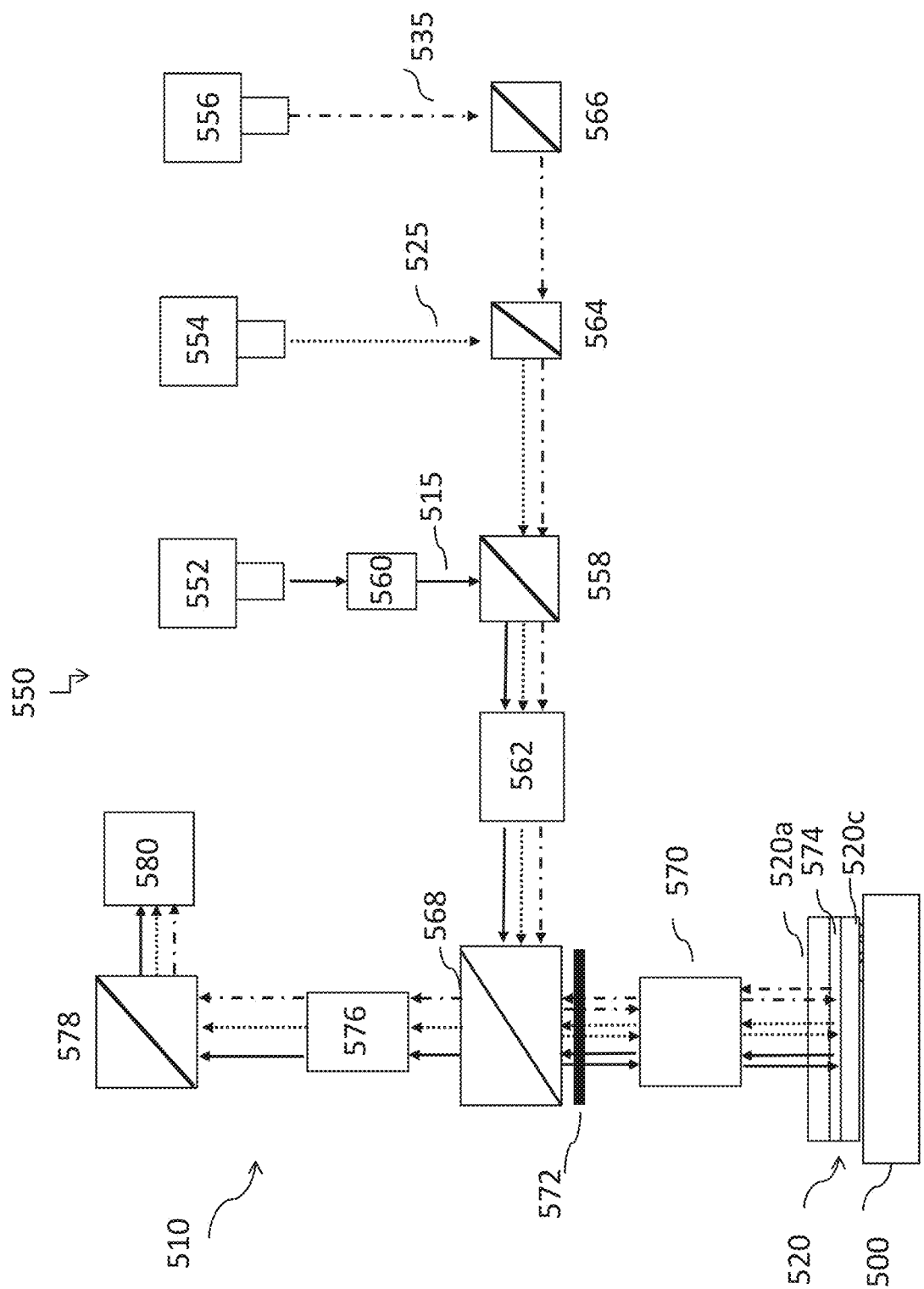
FIG. 5B illustrates an imaging device according to some embodiments of the disclosure.

Optical sub-system. FIG. 5B is a schematic of an optical sub-system 550 having an optical apparatus 510 for imaging and manipulating micro-objects in a microfluidic device 520, which can be any microfluidic device described herein. The optical apparatus 510 can be configured to perform imaging, analysis and manipulation of one or more micro-objects within the enclosure of the microfluidic device 520.

The optical apparatus 510 may have a first light source 552, a second light source 554, and a third light source 556. The first light source 552 can transmit light to a structured light modulator 560, which can include a digital mirror device (DMD) or a microshutter array system (MSA), either of which can be configured to receive light from the first light source 552 and selectively transmit a subset of the received light into the optical apparatus 510. Alternatively, the structured light modulator 560 can include a device that produces its own light (and thus dispenses with the need for a light source 552), such as an organic light emitting diode display (OLED), a liquid crystal on silicon (LCOS) device, a ferroelectric liquid crystal on silicon device (FLCOS), or a transmissive liquid crystal display (LCD). The structured light modulator 560 can be, for example, a projector. Thus, the structured light modulator 560 can be capable of emitting both structured and unstructured light. In certain embodiments, an imaging module and/or motive module of the system can control the structured light modulator 560.

In embodiments when the structured light modulator 560 includes a mirror, the modulator can have a plurality of mirrors. Each mirror of the plurality of mirrors can have a size of about 5 microns×5 microns to about 10 microns×10 microns, or any values therebetween. The structured light modulator 560 can include an array of mirrors (or pixels) that is 2000×1000, 2580×1600, 3000×2000, or any values therebetween. In some embodiments, only a portion of an illumination area of the structured light modulator 560 is used. The structured light modulator 560 can transmit the selected subset of light to a first dichroic beam splitter 558, which can reflect this light to a first tube lens 562.

The first tube lens 562 can have a large clear aperture, for example, a diameter larger than about 40 mm to about 50 mm, or more, providing a large field of view. Thus, the first tube lens 5621 can have an aperture that is large enough to capture all (or substantially all) of the light beams emanating from the structured light modulator 560.

The structured light 515 having a wavelength of about 400 nm to about 710 nm, may alternatively or in addition, provide fluorescent excitation illumination to the microfluidic device.

The second light source 554 may provide unstructured brightfield illumination. The brightfield illumination light 525 may have any suitable wavelength, and in some embodiments, may have a wavelength of about 400 nm to about 760 nm. The second light source 554 can transmit light to a second dichroic beam splitter 564 (which also may receive light 535 from the third light source 556), and the second light, brightfield illumination 525, may be transmitted therefrom to the first dichroic beam splitter 558. The second light, brightfield illumination 525, may then be transmitted from the first beam splitter 558 to the first tube lens 562.

The third light source 556 can transmit light through a matched pair relay lens (not shown) to a mirror 566. The third light illumination 535 may therefrom be reflected to the second dichroic beam splitter 5338 and be transmitted therefrom to the first beam splitter 5338, and onward to the first tube lens 5381. The third illumination light 535 may be a laser and may have any suitable wavelength. In some embodiments, the laser illumination 535 may have a wavelength of about 350 nm to about 900 nm. The laser illumination 535 may be configured to heat portions of one or more sequestration pens within the microfluidic device. The laser illumination 535 may be configured to heat fluidic medium, a micro-object, a wall or a portion of a wall of a sequestration pen, a metal target disposed within a microfluidic channel or sequestration pen of the microfluidic channel, or a photoreversible physical barrier within the microfluidic device, and described in more detail in U. S. Application Publication Nos. 2017/0165667 (Beaumont, et al.) and 2018/0298318 (Kurz, et al.), each of which disclosure is herein incorporated by reference in its entirety. In other embodiments, the laser illumination 535 may be configured to initiate photocleavage of surface modifying moieties of a modified surface of the microfluidic device or photocleavage of moieties providing adherent functionalities for micro-objects within a sequestration pen within the microfluidic device. Further details of photocleavage using a laser may be found in International Application Publication No. WO2017/205830 (Lowe, Jr. et al.), which disclosure is herein incorporated by reference in its entirety.

The light from the first, second, and third light sources (552, 554, 5560) passes through the first tube lens 562 and is transmitted to a third dichroic beam splitter 568 and filter changer 572. The third dichroic beam splitter 568 can reflect a portion of the light and transmit the light through one or more filters in the filter changer 572 and to the objective 570, which may be an objective changer with a plurality of different objectives that can be switched on demand. Some of the light (515, 525, and/or 535) may pass through the third dichroic beam splitter 568 and be terminated or absorbed by a beam block (not shown). The light reflected from the third dichroic beam splitter 568 passes through the objective 570 to illuminate the sample plane 574, which can be a portion of a microfluidic device 520 such as the sequestration pens described herein.

The nest 500, as described in FIG. 5A, can be integrated with the optical apparatus 510 and be a part of the apparatus 510. The nest 500 can provide electrical connection to the enclosure and be further configured to provide fluidic connections to the enclosure. Users may load the microfluidic apparatus 520 into the nest 500. In some other embodiments, the nest 500 can be a separate component independent of the optical apparatus 510.

Light can be reflected off and/or emitted from the sample plane 574 to pass back through the objective 570, through the filter changer 572, and through the third dichroic beam splitter 568 to a second tube lens 576. The light can pass through the second tube lens 576 (or imaging tube lens 576) and be reflected from a mirror 578 to an imaging sensor 580. Stray light baffles (not shown) can be placed between the first tube lens 562 and the third dichroic beam splitter 568, between the third dichroic beam splitter 568 and the second tube lens 576, and between the second tube lens 576 and the imaging sensor 580.

Objective. The optical apparatus can comprise the objective lens 570 that is specifically designed and configured for viewing and manipulating of micro-objects in the microfluidic device 520. For example, conventional microscope objective lenses are designed to view micro-objects on a slide or through 5 mm of aqueous fluid, while micro-objects in the microfluidic device 520 are inside the plurality of sequestration pens within the viewing plane 574 which have a depth of 20, 30, 40, 50, 60 70, 80 microns or any values therebetween. In some embodiments, a transparent cover 520a, for example, glass or ITO cover with a thickness of about 750 microns, can be placed on top of the plurality of sequestration pens, which are disposed above a microfluidic substrate 520c. Thus, the images of the micro-objects obtained by using the conventional microscope objective lenses may have large aberrations such as spherical and chromatic aberrations, which can degrade the quality of the images. The objective lens 570 of the optical apparatus 510 can be configured to correct the spherical and chromatic aberrations in the optical apparatus 1350. The objective lens 570 can have one or more magnification levels available such as, 4×, 10×, 20×.

Modes of illumination. In some embodiments, the structured light modulator 560 can be configured to modulate light beams received from the first light source 552 and transmits a plurality of illumination light beams 515, which are structured light beams, into the enclosure of the microfluidic device, e.g., the region containing the sequestration pens. The structured light beams can comprise the plurality of illumination light beams. The plurality of illumination light beams can be selectively activated to generate a plurality of illuminations patterns. In some embodiments, the structured light modulator 560 can be configured to generate an illumination pattern, similarly as described for FIGS. 4A-4B, which can be moved and adjusted. The optical apparatus 560 can further comprise a control unit (not shown) which is configured to adjust the illumination pattern to selectively activate the one or more of the plurality of DEP electrodes of a substrate 520c and generate DEP forces to move the one or more micro-objects inside the plurality of sequestration pens within the microfluidic device 520. For example, the plurality of illuminations patterns can be adjusted over time in a controlled manner to manipulate the micro-objects in the microfluidic device 520. Each of the plurality of illumination patterns can be shifted to shift the location of the DEP force generated and to move the structured light for one position to another in order to move the micro-objects within the enclosure of the microfluidic apparatus 520.

In some embodiments, the optical apparatus 510 may be configured such that each of the plurality of sequestration pens in the sample plane 574 within the field of view is simultaneously in focus at the image sensor 580 and at the structured light modulator 560. In some embodiments, the structured light modulator 560 can be disposed at a conjugate plane of the image sensor 580. In various embodiments, the optical apparatus 510 can have a confocal configuration or confocal property. The optical apparatus 510 can be further configured such that only each interior area of the flow region and/or each of the plurality of sequestration pens in the sample plane 574 within the field of view is imaged onto the image sensor 580 in order to reduce overall noise to thereby increase the contrast and resolution of the image.

In some embodiments, the first tube lens 562 can be configured to generate collimated light beams and transmit the collimated light beams to the objective lens 570. The objective 570 can receive the collimated light beams from the first tube lens 562 and focus the collimated light beams into each interior area of the flow region and each of the plurality of sequestration pens in the sample plane 574 within the field of view of the image sensor 580 or the optical apparatus 510. In some embodiments, the first tube lens 562 can be configured to generate a plurality of collimated light beams and transmit the plurality of collimated light beams to the objective lens 570. The objective 570 can receive the plurality of collimated light beams from the first tube lens 562 and converge the plurality of collimated light beams into each of the plurality of sequestration pens in the sample plane 574 within the field of view of the image sensor 580 or the optical apparatus 510.

In some embodiments, the optical apparatus 510 can be configured to illuminate the at least a portion of sequestration pens with a plurality of illumination spots. The objective 570 can receive the plurality of collimated light beams from the first tube lens 562 and project the plurality of illumination spots, which may form an illumination pattern, into each of the plurality of sequestration pens in the sample plane 574 within the field of view. For example, each of the plurality of illumination spots can have a size of about 5 microns×5 microns; 10 microns×10 microns; 10 microns× 30 microns, 30 microns×60 microns, 40 microns×40 microns, 40 microns×60 microns, 60 microns×120 microns, 80 microns×100 microns, 100 microns×140 microns and any values there between. The illumination spots may individually have a shape that is circular, square, or rectangular. Alternatively, the illumination spots may be grouped within a plurality of illumination spots (e.g., an illumination pattern) to form a larger polygonal shape such as a rectangle, square, or wedge shape. The illumination pattern may enclose (e.g., surround) an unilluminated space that may be square, rectangular or polygonal. For example, each of the plurality of illumination spots can have an area of about 150 to about 3000, about 4000 to about 10000, or 5000 to about 15000 square microns. An illumination pattern may have an area of about 1000 to about 8000, about 4000 to about 10000, 7000 to about 20000, 8000 to about 22000, 10000 to about 25000 square microns and any values there between.

The optical system 510 may be used to determine how to reposition micro-objects and into and out of the sequestration pens of the microfluidic device, as well as to count the number of micro-objects present within the microfluidic circuit of the device. Further details of repositioning and counting micro-objects are found in U. S. Application Publication No. 2016/0160259 (Du); U.S. Pat. No. 9,996,920 (Du et al.); and International Application Publication No. WO2017/102748 (Kim, et al). The optical system 510 may also be employed in assay methods to determine concentrations of reagents/assay products, and further details are found in U.S. Pat. No. 8,921,055 (Chapman), 10,010,882 (White et al.), and 9,889,445 (Chapman et al.); International Application Publication No. WO2017/181,135 (Lionberger, et al.); and International Application Serial No. PCT/US2018/055918 (Lionberger, et al). Further details of the features of optical apparatuses suitable for use within a system for observing and manipulating micro-objects within a microfluidic device, as described herein, may be found in WO2018/102747 (Lundquist, et al), the disclosure of which is herein incorporated by reference in its entirety.

Additional system components for maintenance of viability of cells within the sequestration pens of the microfluidic device. In order to promote growth and/or expansion of cell populations, environmental conditions conducive to maintaining functional cells may be provided by additional components of the system. For example, such additional components can provide nutrients, cell growth signaling species, pH modulation, gas exchange, temperature control, and removal of waste products from cells.

EXAMPLES

System and Microfluidic device: OPTOSELECT™ chip, a nanofluidic device manufactured by Berkeley Lights, Inc. and controlled by an optical instrument which was also manufactured by Berkeley Lights, Inc. The instrument included: a mounting stage for the chip coupled to a temperature controller; a pump and fluid medium conditioning component; and an optical train including a camera and a structured light source suitable for activating phototransistors within the chip. The OPTOSELECT™ chip included a substrate configured with OptoElectroPositioning (OEP™) technology, which provides a phototransistor-activated OET force. The chip also included a plurality of microfluidic channels, each having a plurality of NANOPEN™ chambers (or sequestration pens) fluidically connected thereto. The volume of each sequestration pen was around $0.5 \times 10^6$-$2 \times 10^6$ cubic microns.

Priming solution: Complete growth medium containing 0.1% Pluronic® F127 ((Life Technologies® Cat #P6866).

Preparation for culturing: The microfluidic device having a modified surface was loaded onto the system and purged with 100% carbon dioxide at 15 psi for 5 min. Immediately following the carbon dioxide purge, the priming solution was perfused through the microfluidic device at 5 microliters/sec for 8 min. Culture medium was then flowed through the microfluidic device at 5 microliters/sec for 5 min.

Priming regime: 250 microliters of 100% carbon dioxide was flowed in at a rate of 12 microliters/sec. This was followed by 250 microliters of PBS containing 0.1% Pluronic® F27 (Life Technologies® Cat #P6866), flowed in at 12 microliters/sec. The final step of priming included 250 microliters of PBS, flowed in at 12 microliters/sec. Introduction of the culture medium follows.

Perfusion regime. The perfusion method was either of the following two methods:

1. Perfuse at 0.01 microliters/sec for 2 h; perfuse at 2 microliters/sec for 64 sec; and repeat.
2. Perfuse at 0.02 microliters/sec for 100 sec; stop flow 500 sec; perfuse at 2 microliters/sec for 64 sec; and repeat.

Example 1

Preparation of a Microfluidic Device Having Modified Interior Surfaces of Formula III.

An OPTOSELECT' device having a first silicon electrode activation substrate and a second ITO substrate on the opposite wall, and photopatterned silicone microfluidic circuit material separating the two substrates, was treated in an oxygen plasma cleaner (Nordson Asymtek) for 1 min, using 100 W power, 240 mTorr pressure and 440 sccm oxygen flow rate. The plasma treated microfluidic device was treated in a vacuum reactor with 3-azidoundecyl) trimethoxysilane (Compound 5, 300 microliters) in a foil boat in the bottom of the vacuum reactor in the presence of magnesium sulfate heptahydrate (0.5 g, Acros), as a water reactant source in a separate foil boat in the bottom of the vacuum reactor. The chamber was then pumped to 750 mTorr using a vacuum pump and then sealed. The vacuum reactor was placed within an oven heated at 110° C. for 24-48 h. This introduced a functionalized surface to all of the inner facing surfaces of the microfluidic device, where the functionalized surface had a structure of Formula III:

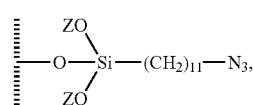

Formula III where Z is a bond to an adjacent silicon atom bound to the surface or is a bond to the surface and is the surface. After cooling to room temperature and introducing argon to the evacuated chamber, the microfluidic device was removed from the reactor. The microfluidic device having the functionalized surface was then treated with an alkynyl species to introduce the desired modified surface as described below and elsewhere herein.

Example 2

Introduction of a Covalently Modified Surface of Photocleavable Biotin Functionalized PEG Surface (Formula IV) to a Microfluidic Device.

The product microfluidic device from Example 1, having a surface of Formula III, as described above, was reacted with biotin functionalized photocleavable alkyne PEG3 (Compound 10, BROADPHARM®, Cat. #BP-22677, which contains the photocleavable nitro substituted phenyl group as part of the linker L), flowing at least 250 microliters of an aqueous solution containing 1.33 millimolar Compound 10, 500 micromolar copper sulfate, 550 micromolar THPTA ligand and 5 millimolar sodium ascorbate through the microfluidic devices having the 11-azidoundecylsiloxy surface modifying ligand. The reaction was allowed to proceed at room temperature for at least 1 hour. The microfluidic device having a biotinylated PEG modified surface of Formula XX1:

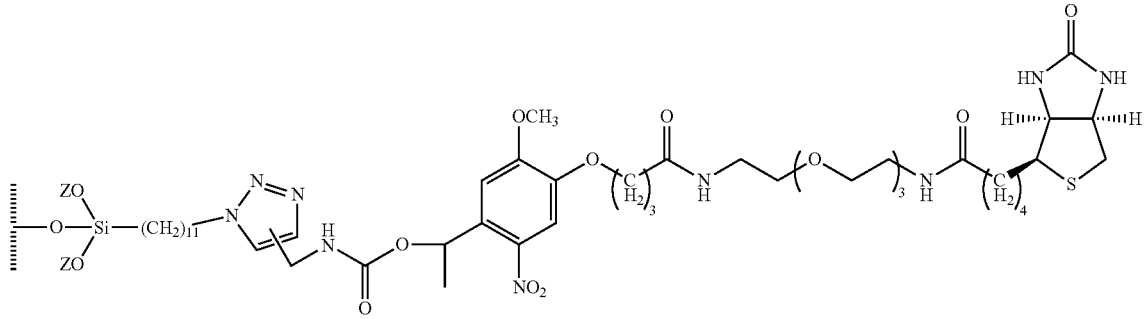

Formula IV was then rinsed by flowing at least 250 microliters of deionized water through the devices. After completion of the cyclization reaction that introduces the modified surface, the thickness of the layer increased from 1.4 nm (functionalized surface thickness) to approx. 5 nm in thickness. Additionally, the sessile drop water contact angle decreased from approximately 80 degrees (functionalized surface of Formula III) to 42 degrees (surface of Formula IV).

Example 3

Introduction of Regioselective Surface Modifications of PEG5k in a First Region of the Microfluidic Device and Poly-L-Lysine within Sequestration Pens A previously prepared, dry and unprimed (e.g., not flushed with carbon dioxide gas) microfluidic device having a surface of Formula III was treated with a 1.0 to 3.3 millimolar aqueous solution of dibenzylcyclooctynyl (DBCO) modified-PEG, weight averaged molecular weight 5000 Da (Compound 8, BROADPHARM®, Cat. #BP-22461) by aspirating the solution through the microfluidic channel of the device at slightly lower than atmospheric pressure. The channel was resultingly filled with the reagent solution. However, due to the low pressure of the fluidic introduction and the unprimed nature of the surfaces within the microfluidic device, the DBCO modified PEG5 kDa solution does not enter the sequestration pens opening off of the microfluidic channel. After incubation for 30 min at room temperature, 80 microliters of water was aspirated at reduced pressure through the channel, washing any remaining reagent out of the microfluidic device. The solution was still controlled to flow only through the microfluidic channel. Additional flushing with water at 1 microliter/sec at low pressure was continued for about 5 min. The surface modified microfluidic channel was flushed with carbon dioxide gas repeatedly, while heating the device to 90° C.

The dried microfluidic device having a first surface modification of PEG5K was then primed with carbon dioxide as described above. The sequestration pens opening off of the microfluidic channel then were modified regioselectively by flowing through a 1.33 micromolar solution including a 1:1 stoichiometric mixture of alkyne-poly-L-lysine HBr salt (100 mer unit, Alamanda Polymers) and alkyne-modified PEG (j=MW ~5000 Da, Compound 6, JenKem Technologies) along with copper sulfate (in excess), THPTA ligand, and sodium ascorbate. The excess copper sulfate prevents disulfide cleavage by ascorbate during the reaction, which was performed at 40° C. for about 15 min (and may alternatively be performed for about 1 hr at room temperature). After the incubation period was complete, the excess reagent and byproducts were removed by flushing with water. The interior of the microfluidic device was dried by flushing with carbon dioxide gas while heating the microfluidic device to 40° C., providing a microfluidic device with a regioselective introduction of a first surface modification, having only PEG5K, within the microfluidic channel and a second regioselective surface modification including poly-L-lysine, which provides positive charge for enhancing adherence of biological cells, only in the sequestration pens. Of note is the ability to modulate the ratios of the reagents used to modify the surface of the sequestration pens. The ratio of PEG-5K:poly-L-lysine was varied from 0:100 to 99.9999:0.0001% and adherence of HeLa cells was observed within the sequestration pens, while migration of the motile HeLa cells was inhibited by the presence of the merely hydrophilic surfaces within the channel.

A microfluidic device having inner surfaces modified with a first surface modification of PEG 5 kDa and a second surface modification of poly-L-lysine having a percentage of poly-L-lysine surface modifications of about 0.00001% or 0.000001% is expected to permit adhesion of adherent cells (such as HeLa cells) while still permitting export of cultured cells using dielectrophoretic forces, without laser initiation of displacement.

Further generalization. Any type of surface modifying reagent may be used in introduction of the second surface modification within the sequestration pen, and is not limited to a poly-L-lysine.

Secondary passivation of the microfluidic channel with a second surface modification only in the channel region. After the initial surface modification of the microfluidic channel as described above, there can be unreacted reactive moieties (e.g., azide) still present in the channel. Without wishing to be bound by theory, this may occur if the modifying reagent is bulky. Secondary passivation with a less sterically demanding surface modifying reagent may be able to access remaining reactive moieties to add a second surface modification to the modified surfaces of the channel without modifying the surfaces in the sequestration pen.

The microfluidic device, having a PEG5 kDa surface modification introduced only to the microfluidic channel, was only rinsed with water after the surface introduction. A second treatment with DBCO-PEG4-OH (Aldrich Catalog #761982 at a concentration of 1.3 micromolar in an aqueous solution was performed similarly to the first treatment as described above. Since the microfluidic device was not primed, none of the second surface modifying reagent entered the sequestration pens and accordingly only the channel was further modified. After washing, drying and heating, followed by carbon dioxide priming, regioselective modification of the sequestration pens is then performed as above.

Experiment 4. Photo-Initiated Surface Introduction.

4. A Photo-initiated cleavage. A microfluidic device having modified interior surfaces of Formula III was prepared as in Experiment 1. The clean and dry azido surface-modified microfluidic device (FIG. 6A) is primed with carbon dioxide gas and reacted with a surface modifying reagent having a hydrophobic surface modifying moiety such as a fluorinated or perfluorinated alkyl moiety linked via a photocleavable nitro substituted phenyl containing linker, such as a PEG linker, to a DBCO Click reactive moiety. The reagent is flowed into the microfluidic channel and displace the carbon dioxide gaseous environment within the channel and sequestration pens, and allowed to react over 30 minutes. Deionized water is flushed through the microfluidic channel for 30 to 40 minutes to flush any remaining unreacted reagent out of the microfluidic device. A hydrophobic modified surface 610 is introduced as shown in FIG. 6B, distributed throughout the inner surfaces of the channel 618 and the sequestration pens 622, 623, 624, 625, 626, 627, which may be like any sequestration pens as described herein. Photo-initiated photocleavage may be performed manually by directing laser illumination at selected portions of the microfluidic channel and/or sequestration pens to selectively cleave the fluorinated or perfluorinated alkyl moiety from the covalently bound surface modifying ligand, leaving a less hydrophobic (e.g., more hydrophilic) PEG "scar" ligand 615 (as shown in FIG. 6D) at the illuminated regions, which provides a less hydrophobic surface 620. Thus, a hydrophobic region may be selectively introduced within the microfluidic channel that may be less than about 50% of the surface areas of the channel (or more than about 50% of the surface areas of the channel) disposed adjacent or proximal to the openings of the sequestration pens to the microfluidic channel, and nowhere else, as shown in FIG. 6C. The hydrophobic surface may be removed by photo-initiated photocleavage from the isolation region of the sequestration pen, from a portion of the connection region of the sequestration pen or entirely from the sequestration pen. The region of hydrophobicity left in place can assist in retaining the encapsulation layer and, in particular, may assist in defining the distance that the encapsulation layer extends from a contact with the aqueous medium within the rest of the sequestration pen out to the opening of the sequestration pen at the channel. For example, the encapsulation layer may extend from about 5 microns to about 50 microns from the contact point with the aqueous medium within the sequestration pen. A schematic representation of the ligands in each area is shown in FIG. 6D, where the hydrophobic ligands 605 are the modified surface left in place in the surface 610 near the openings of the sequestration pen and in the portion of the connection region near the opening to the channel. The cleaved ligands 625 left as the "scar" form the less hydrophobic (or more hydrophilic surface 620 within the channel distal from the sequestration pen openings and the surface 620 within the connection region distal from the opening and within the isolation region of the sequestration pen.

B. Photo-initiated ligation. A microfluidic device having modified interior surfaces presenting alkynyl reactive moieties is prepared, using eight arm PEG alkyne (BROADPHARM® Cat. No. PSB-866) similarly as described for a four arm PEG alkyne in PCT/US2017/034832, filed on May 26, 2017, titled "Covalently Modified Surfaces, Kits, and Methods of Preparation and Use", its disclosure incorporated herein by reference in its entirety. The microfluidic device has a covalently bonded hydrophobic surface upon the interior surfaces as shown schematically in FIG. 6B having a surface 610.

Lipoamido-PEG4-COOH (Iris Biotech GMBH Cat. No. PEG3500) is dissolved to 100 mM in DMSO. Lithium phenyl-2,4,6-trimethyl-benzoylphosphinate (LAP) photoinitiator is dissolved to 5 mM in PBS pH 7.4. TCEP is dissolved to 40 mM in PBS, and reduces the disulfide of lipoamide to provide the thiyl radical for photo-ligation. 20 (a surfactant) is dissolved to 10% w/v in water. The reaction mixture for importation into the microfluidic device provides: lipoamido surface modifying reagent solution (10 mM final); LAP solution (1 mM final); TCEP solution (20 mM final) and solution (2% final).

The microfluidic device is prepared for the photoligation reaction by flushing with a solution of 2% 20 in PBS. The photo-ligation reaction solution is imported by aspiration through the export line. A 100 µL aliquot is imported and is allowed to equilibrate for about 10 minutes.

The microfluidic device is cooled to 15° C. The chambers (e.g., sequestration pens) are illuminated with light from the DAPI cube for about 1 to 10 seconds. To remove residual initiator products, the microfluidic device is flushed with 2% PBS solution at 15° C., then 2% at 55° C. The chip is finally flushed with 0.05 Tween/PBS solution.

This provides a microfluidic device 600 having a hydrophobic surface 610, presenting alkynyl moieties 605, in the channel 618 which supports the encapsulation layer and hydrophilic surfaces 674 within the sequestration pens which provide a compatible surface for culturing and expanding biological cells. The hydrophilic surface ligands of surface 674 has hydrophilic surface contact moieties 628, e.g., PEG4-COOH, and the surface modifying ligand includes a coupling group (CG) 629, an olefinic thio moiety, resulting from the coupling of the thiyl radical and the alkyne (hydrophobic surface contact moiety 605).

Experiment 5. Regioselective surface modification using temperature control. A microfluidic device having modified interior surfaces of Formula III was prepared as in Experiment 1. The clean and dry azido surface-modified microfluidic device is flushed with ambient air, and not primed with 100% carbon dioxide gas, and is maintained at 18 degrees C.

A 1.0 to 3.3 millimolar solution of a first (hydrophobic) surface modifying reagent, dibenzylcyclooctanol (DBCO)-PEG4-alkyne (Conju-Probe Catalog No. CP-2039) in 1-5% DMSO in deionized water is prepared and is chilled to the same lowered temperature (18 degrees C.) as the microfluidic device. The reagent solution is saturated with carbon at normal pressure. A deionized water solution saturated with carbon dioxide is also prepared and chilled to 18 degrees C. The carbon dioxide saturated deionized water solution is introduced into the channel of the microfluidic device by aspirating the solution through the channel of the device at slightly lower than atmospheric pressure. The channel is filled with the deionized water solution, however, due to the low pressure of the fluidic introduction and the unprimed nature of the surfaces within the microfluidic device, the deionized water solution does not enter the sequestration pens opening off of the microfluidic channel. After introduction of the deionized water solution, the microfluidic device is warmed to 36 degrees C. Upon warming, the trapped air in each sequestration pen expands and gas solubility in the aqueous phase reduces releasing gas into the pens causing the gas volume in pens to grow outward from the sequestration pen, forming a bubble extending into the microfluidic channel. The chilled DBCO-PEG4 alkyne reagent is slowly aspirated through the channel at a rate of 0.01 ul/min for a period of 30 min, flowing around the bubbles extending from the sequestration pens, and reacting only with surfaces in the channel where the bubbles do not extend, forming a hydrophobic surface 650, presenting hydrophobic ligands 635 as shown in FIG. 6H. The extent of bubble extension out from the sequestration pen is controlled by the temperature at which the microfluidic device is maintained while the chilled first surface modifying reagent is slowly aspirated through the channel. In some variations, the bubble may extend beyond the opening of the sequestration pen to occupy about 60%, about 50%, about 40% about 30%, about 20%, about 10%, or about 5% of the area of the channel. Accordingly, the surface within the sequestration pens and within the region of the bubbles extending out into the channel is an unmodified surface 602 (e.g., azide moieties still present).

After completion of the 30 minute reaction period, 80 microliters of the chilled, carbon dioxide saturated deionized water is aspirated slowly through the microfluidic channel, e.g. at about 0.01 ul/s to flush any remaining DBCO-PEG4-alkyne reagent from the channel and device. Additional flushing with water at 1 microliter/sec is continued for about 5 min. The surface modified microfluidic channel is dried by flushing with carbon dioxide gas while heating the microfluidic device to 40° C., thus priming the interior of the microfluidic device for regioselective surface modification with a second surface modification reagent in the remainder of the microfluidic channel and within the sequestration pens (e.g., where surface 602 as in FIG. 6H is present). The microfluidic device is then maintained at about 36 degrees C., and the second surface modification is performed regioselectively by flowing a second surface modifying reagent, a 1.33 micromolar solution of DBCO-PEG4-OH (Aldrich Catalog #761982, equilibrated at normal atmosphere pressure air and 36 degrees C., through the microfluidic device. This second modification reagent, which is hydrophilic, is now able to enter the sequestration pens and to react with the remaining nucleophilic moieties still present in the channel (where the bubbles had prevented previous reaction) and in the sequestration pens, forming surface 670, composed of hydrophilic ligands 625 upon the modified surface, as shown in FIG. 6H. Thus, a hydrophobic surface 650 is introduced to less than 50% of the surface area of the channel and a hydrophilic surface 670 is introduced within the sequestration pen and in the proximity of the opening of the sequestration pen, extending into the channel.

In another variation, a combination of two ligands 635 and 645 may be introduced as described where surface contact moiety 635 provides a hydrophobic surface contact moiety and surface contract moiety 645 may be a different hydrophobic surface contact moiety, a hydrophilic surface contact moiety or a surface contact moiety providing a different surface chemistry, which may be used in any ratio, thus fine tuning the hydrophobic surface 660 as needed for specific applications.

Experiment 6. Regioselective surface modification using temperature control. A microfluidic device having modified interior surfaces of Formula III was prepared as in Experiment 1. The clean and dry azido surface-modified microfluidic device was flushed with ambient air, and not primed with 100% carbon dioxide gas, and was maintained at 30 degrees C.

A 1.0 to 3.3 millimolar solution of a first surface modifying reagent (which is hydrophilic), DBCO-terminated methoxy PEG Mw=5K in deionized water was prepared and was equilibrated to the same temperature (30 degrees C.) as the microfluidic device. The reagent solution was saturated with air at normal pressure. The first surface modifying reagent solution was introduced into the channel of the microfluidic device by aspirating the solution through the channel of the device at slightly lower than atmospheric pressure at 30 degrees C. Due to the low pressure of the fluidic introduction and the unprimed nature of the surfaces within the microfluidic device, the first surface modifying reagent solution did not enter the sequestration pens opening of the microfluidic channel 718. Once the channels in the device were full, the microfluidic device was warmed to 36 degrees C., expanding air bubbles 704 from the pens, just slightly out into the channel, preventing the first surface modifying reagent from entering the sequestration pens, as shown in FIG. 7A, and the channel outside of the regions broached by the bubbles 704 was modified with the hydrophilic methoxy PEG surface modifying reagent with surface 770, which may be similar to surfaces 670 of FIGS. 6F-6L. The surface 702 within the sequestration pens remained unreacted and bubble artifacts 706 are shown in FIG. 7A. Air was flushed through the microfluidic channel to expel the first surface modifying reagent, and the device was then flushed with 1000 microliters of deionized water at 1 microliter/sec. The device was then extensively flushed with 5% carbon dioxide. The second surface modifying reagent, hydrophobic reagent DBCO-PEG4-alkyne was flowed in (60 microliters at 1 microliters/sec). The temperature was then adjusted from 36 degrees to 18 degrees C. The bubbles from each sequestration pen shrank back into the sequestration pen, and permitted entry of the hydrophobic reagent into a portion of the connection region of the sequestration pen. The reagent was allowed to react for another 30 minutes, thereby forming a hydrophobic surface 750 adjacent to the pen openings (where the bubbles extended in FIG. 7A) and into the portion of the connection region exposed by the shrinkage of the bubbles, as shown in FIG. 7B. The hydrophobic surface 750 may be like hydrophobic surface 650 or like mixed hydrophobic surface 660 of FIGS. 6F-6L. The reagent was then flushed from the microfluidic channel and connection regions of the sequestration pens of the microfluidic device.

In some variations, the isolation region and the portion of the connection region of the sequestration pens distal from the opening of the sequestration pen to the channel may still retain the unmodified azide surface, which may be modified as suitable for the particular experiment. This subsequent surface modification may be performed just after completion of the modification of the channel and proximal portion of the connection regions, or may be performed at a later date.

Example 7

Generating and Selectively Removing Encapsulation Layers for Single Cell Analysis.

FIGS. 8A-8B illustrates the encapsulation of individual cells in corresponding individual chambers, with an encapsulation layer formed by water immiscible fluid media, e.g., an oil, filling the microfluidic channel, visible at the distinct boundary 812 at the opening of each individual chamber (e.g., sequestration pen) in the brightfield image 8B. In this illustration, a single secreting cell has been disposed into each of the chambers, e.g., sequestration pens, and cultured. The cultured cell has divided over time into a population of secreting cells. The cells in this assay secrete a fluorescent small molecule that can be imaged to determine information about the cells. Information can include, but is not limited to, correlations between characteristics of the individual cell or cell populations encapsulated in each chamber and the amount of florescent small molecules or the amount of emission (e.g., fluorescence) measured in each chamber.

FIG. 8A shows a fluorescent image of a set of chamber, e.g., sequestration pens, and FIG. 8B, is a brightfield image of the same set of chambers. The brightfield image depicts the density of cells in the chamber as well as the shape of the chamber and the encapsulation layer at the connection region of the chamber. FIG. 8A illustrates that, in this instance, the chamber with the highest apparent density of cells under brightfield imaging also exhibits higher fluorescence than the chambers that have lower apparent density of cells according to the brightfield image. Quantification can be performed on these images to determine the volume of cells, the density of cells, the amount of emission (e.g., fluorescence), the concentration of secreted small molecules, and other metrics that may be relevant to the secretion of cells, cell health, and/or to distinguish one subpopulation of cells from another subpopulation of cells. Quantification can be performed at a single fixed time point or at discrete time points over a fixed period of time, and ratios, relationships, and/or other mathematical manipulations can be performed on the quantified information to make deductions about the cells in each of the chambers, over a population of similar cells encapsulated in discrete chambers across the micro-fluidic chip, or over populations of functionally different cells encapsulated in discrete chambers across the micro-fluidic chip. The duration of the accumulation of signal under the oil seal can be varied from 24 hrs to just a few minutes. In this instance, the oil seal during a culturing period over about 24 h, permitting expansion to larger colony size.

The encapsulation layer prevents the secreted small molecules within sequestration pen 802 from diffusing out of the sequestration pen. Thus the observed fluorescence in each of the pens shown is due only to the secretions of the cells resident in each one. There is no contribution to the fluorescence in pens other than 802, from the fluorescent molecules secreted within pen 802, and correspondingly, the amount of fluorescence observed in pen 802 is not diminished by secreted small molecule diffusion out of the pen 802.

FIGS. 9A-9C illustrate methods for generating and optionally removing a water immiscible fluid encapsulation layer. Different cells (e.g., different cells from the same population, genotypically/phenotypically distinguishable cells, cells secreting different types of molecules, etc.) were loaded into chambers in an OptoSelect™ chip (Berkeley Lights, Inc., Emeryville, Calif.). which include at least one channel and a plurality of sequestration pens opening into the channel. Cells suspended in an aqueous medium were flowed into the channel of the micro-fluidic chip. Flowing can comprise pulling solution through and out of the microfluidic channel (e.g., aspirating) or pushing fluid into and through a microfluidic channel (e.g. perfusing). Individual cells were loaded into separate chambers or sequestration pens, for example, using optically actuated DEP force.

In each of FIGS. 9A-9C, each sequestration pen was encapsulated with a layer of a water immiscible fluidic medium and cultured and/or monitored for a period of time before removal of the encapsulation layer of a selected chamber. The encapsulation layer was removed by application of a laser pulse to the aqueous medium within the chamber, proximal to the encapsulation layer. Laser illumination generated a bubble, which pushed the water immiscible fluid of the encapsulation layer out into the microfluidic channel and away from the opening to the chamber. Laser illumination was selected to generate a bubble directed towards the thin encapsulation layer, pushing the water immiscible fluid of the encapsulation layer out into the microfluidic channel and away from the opening to the chamber. The power (the effective power exiting the optical system may be about 10-100 mW) and wavelength (which may be from about 450 nm to about 1000 nm, and may be about 800 nm) of the laser can be selected to nucleate bubbles in the medium that generate mechanical perturbations and shear forces sufficient to break the encapsulation layer. While laser illumination may require selection of a programmed ramp/delivery over a period of about 50 ms to deliver the threshold amount of energy to nucleate a bubble, the actual period of energy delivery is much shorter, e.g. on the order of a few microseconds, e.g., about 3 ms, about 5 ms, about 6 ms, or the like. Use of longer illumination periods are not necessary, as once the initiation/nucleation energy input has been exceeded, the ability of the nucleated bubble to break through the encapsulation layer does not significantly change. Once the bubble is nucleated, the bubble itself slows down further rate of increase of the size of the bubble.

In each of the microfluidic devices of FIGS. 9A-9C, interior surfaces were modified with PEG4-alkyne moieties in order to support the encapsulating layer, having regioselective hydrophobic and hydrophilic regions of the channel and/or sequestration pens, as mentioned below for each figure.

In FIG. 9A, the microfluidic device included a hydrophobic surface throughout the entire channel and a non-hydrophobic surface within the chambers (e.g., sequestration pens) which was introduced using a variation of the methods described in Experiments 5 and/or 6, where the entire channel surface was modified, using temperature control to keep the gaseous bubbles just to the opening of the sequestration pens. After introducing the hydrophobic surface in the channel, the interior surfaces of the chambers (e.g., sequestration pens) were modified with a more hydrophilic surface which permits disposition and exportation of biological cells using DEP forces only.

Once the cells were introduced and disposed within the chamber, a water immiscible fluid 914 was flowed into the channel, as shown in FIG. 9A. In FIG. 9A, aqueous media containing cells were encapsulated in the chambers, while a water immiscible oil 916 filled the microfluidic channel, having a contact boundary 912. The water immiscible oil was oxygenated, or saturated with a gas or a mixture of gasses, to provide appropriate boundary conditions for culturing the cells of interest. For example, 5% $CO_2$ saturation may be used for most mammalian cells or 20% oxygen gas saturation for microbial systems. In some variations, the water immiscible oil may be perfused during the period of culturing to increase the exchange of gas. The water immiscible oil was paired with the composition of the hydrophobic or hydrophilic coating, in this case PEG4-alkyne moieties, such that the pairing facilitated thermodynamically favorable formation of an encapsulation layer in the connection region of the chamber or sequestration pen, e.g., at a portion of the connection region proximal to the microfluidic channel.

In FIG. 9B, a microfluidic device having a hydrophobic surface within the channel 918 and hydrophilic surfaces within the chambers (e.g., sequestration pens) like that described for the microfluidic device of FIG. 9A, was filled with a first aqueous medium which distributed into the sequestration pens and throughout the channel. A water immiscible oil was then introduced into the channel, displacing the first aqueous medium in the channel, but not disturbing the first aqueous medium 916 in the sequestration pens. A second aqueous solution 922 was introduced (e.g., aspirated) into the microfluidic channel, pulling the water immiscible fluidic medium out of the channel and leaving a thin encapsulation layer 914, capping the aqueous medium retained within the sequestration pens, and disposing a second aqueous medium 922, which may have the same or different composition as the first aqueous medium 914, in the remainder of the channel. The second aqueous solution can be introduced at a rate that facilitated the formation of encapsulation layers, e.g., including at a rate from about 0.01 ul/sec to about 2.0 ul/sec. The encapsulation layers generated in the disclosed methods had a "thickness" of about 1 micron to about 100 microns, that is, the encapsulation layer extends from the contact boundary 912 with the aqueous medium 916 in the sequestration pen out towards the channel to a contact boundary 932 with the second aqueous medium in the channel. In some instances, the "thickness" may be less than about 1 micron while still retaining encapsulation. The "thickness" depended on a number of variables including but not limited to the rate at which the water immiscible fluidic medium was flowed (e.g., aspirated) from the microfluidic channel, the composition of the water immiscible fluidic medium, the composition and distribution of the hydrophobic and/or hydrophilic coatings, and the length of the connection region Lcon. As shown in FIG. 9C, the encapsulation layer was removed at a single selected sequestration pen 924, by directing laser illumination at the contact boundary 912 between the aqueous medium within the sequestration pen and the encapsulation layer 914, with a raster directed towards the direction of the channel 918, to dislodge the immiscible medium of the encapsulation layer into the channel and away from any micro-objects, including cells and/or capture beads disposed within the isolation region of the sequestration pen. Selective de-encapsulation is desirable for removal of selected micro-objects from the sequestration pen to the channel (and in some instances, followed by export out of the microfluidic device). Amongst other non-limiting uses, a sequestration pen containing a selected micro-object (cell or capture object) may be de-encapsulated in order to deliver or remove a reagent or capture object into/out of the selected sequestration pen.

FIGS. 10A-10E are photographs of the same set of sequestration taken at successive timepoints, and illustrate an exemplary method for bulk removal of the encapsulation layer(s). In the microfluidic device shown in FIGS. 10A-10E, a hydrophobic surface was introduced throughout the entire channel 1018, e.g., a surface having PEG4-alkyne ligands, while a hydrophilic surface, e.g., a surface having PEG4-OH ligands was introduced within the sequestration pen. Methods for bulk removal of encapsulation layers can comprise flowing a medium comprising surfactant through the channel. The types of surfactants and the rate of perfusion can be configured to remove encapsulation layers at a particular rate. In FIG. 10A, channel 1018 is filled with a water immiscible fluid, e.g., oil, HFE-7500™ Novec™ Engineered fluid (2-(Trifluoromethyl)-3-ethoxydodecafluorohexane, 3M). The contact boundary 1012 between the oil and the aqueous medium encapsulated in each sequestration pen is visible in FIG. 10A with each sequestration pen completely encapsulated. A surfactant solution including DI water with 0.1% CAPSTONE™ FS-30 fluorosurfactant (SynQuest Laboratories, Cat. No. 2108-3-38) was used for bulk removal of the encapsulating layer. The surfactant solution was flowed through the channel 1018, starting at the timepoint visible in FIG. 10B over the course of 10 minutes at any flow rate between 0.2 and 5 ul/s. A change in contact angle between FIG. 10B and FIG. 10C is easily observable in the figures indicating a transition from an hydrophobic to an hydrophilic medium meeting at contact boundary 1012, which permitted continuing removal as the encapsulating layer material progresses to nearly removed at FIG. 10D, and completely removed at FIG. 10E.

Figure 11D:
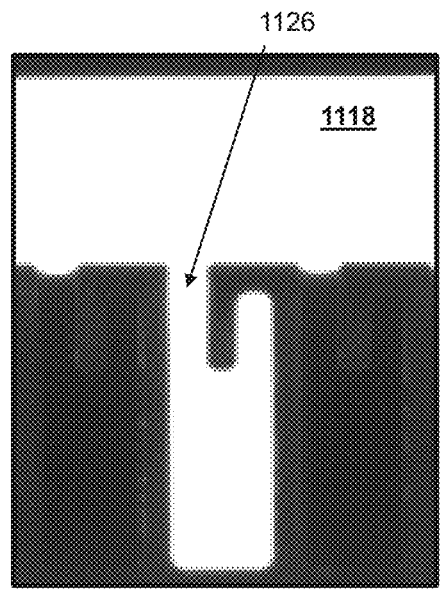

FIGS. 11A-11D illustrate an exemplary method for selectively ablating the encapsulation layer(s). Encapsulation layers can be formed using any single or combination of the methods disclosed herein. Removal of the encapsulation layers can comprise the application of targeted laser removal. In one exemplary method, a laser can be targeted proximal to the encapsulation layer, e.g., in the aqueous medium of the chamber or sequestration pen just internal to the encapsulation layer, with the laser configured such that the power and frequency of the laser can nucleate bubbles in the medium that generate mechanical perturbations and sheer forces sufficient to break the encapsulation layer. FIG. 11A illustrates a brightfield image comprising an array of encapsulated pens having an encapsulation layer 1112 at the opening of each pen, where the channel 1118 includes a fluorescent dye, which is visible in the corresponding fluorescent image FIG. 11B, of the same field of view taken at the same time point as that of FIG. 11A. Laser de-encapsulation of only a single selected sequestration pen was then performed. FIG. 11C is a brightfield image of the same field of view after selective removal of one encapsulation layers. FIG. 11D is a fluorescent image taken at the same time point as the brightfield image of FIG. 11C. FIG. 11D illustrates that the fluorescent dye in the microfluidic channel of the micro-fluidic device diffused into the chamber 1126 (e.g., sequestration pen) only where the encapsulation layer was removed. Further importation or export of micro-objects and/or importation of reagents may be subsequently effected.

Example 8

Culturing and Processing/Assaying Cells Using Encapsulation Methods.

FIGS. 12A-12C illustrate an exemplary method for culturing and selectively lysing cells. Cells were encapsulated in chambers or sequestration pens with encapsulation layers using any combination of the methods disclosed herein. In this method, cells suspended in an aqueous medium (e.g., culture media) are flowed into the channel of the microfluidic chip, where the surfaces of the channel 1218 have a hydrophobic surface and the surfaces of the chambers or sequestration pens (e.g., pen 1228) have hydrophilic surfaces, produced as described herein. The aqueous medium (e.g., in which the cells are suspended) diffused from the channel into the chambers or sequestration pens, and the cells in the channel were loaded from the channel into separate chambers or sequestration pens, for example using optically actuated DEP force.

In some variations of experiments using encapsulation layers to isolate sequestration pens from each other, reagents in aqueous media may also be introduced to the channel before, during or subsequent to loading of cells, thereby filling the channel and delivering in parallel to all the sequestration pens by exchanging by diffusion with the aqueous medium within the sequestration pen. Once the water immiscible phase is introduced into the main channel, the reagent-bearing aqueous medium is "pinched off" by the water immiscible medium, preventing any further exchange into/out of the sequestration pen. This can deliver reagents quickly to all the sequestration pens in the microfluidic device.

In the specific example shown in FIGS. 12A-12C, once the cells were penned, a water immiscible fluid was flowed into the channel (e.g., an oil). In methods for lysing cells, lysis buffer can be perfused into the channel, driving the water immiscible fluid out of the channel and leaving the conditions illustrated in FIG. 12A, where a thin encapsulating layer was formed at the opening of the sequestration pen/chamber to the channel 1218.

In FIG. 12A, the aqueous solution comprising cell(s) and culture media was retained within the sequestration pens, and each sequestration pen was encapsulated by a thin film coating of water immiscible fluidic medium. External to the thin film or encapsulation layer 1212, in the channel 1218, is cell lysis buffer. FIG. 12B is a brightfield image from the same field of view as FIGS. 12A and 12C, taken after the encapsulation layer of a single pen was selectively removed 1202 (e.g., by laser-induced formation of a bubble). In FIG. 12B, the lysis buffer has selectively perfused from the channel into the sequestration pen 1228. The contours of the cell 1203 in the de-encapsulated sequestration pen of the brightfield image of FIG. 12B appears to be more diffuse than the cells 1209 in adjacent, still encapsulated pens (which did not experience any lysis buffer), indicating that the cell membrane is breaking down. The lysing is confirmed in FIG. 12C, which is a fluorescence image of the same field of view as FIG. 12B after a Propidium Iodide stain has been perfused into the channel and diffused into the open pen. Emission 1207 (e.g., fluorescence) is generated confirming that the cell is successfully lysed. In some non-limiting embodiments, a capture bead (e.g., nucleic acid capture bead, protein purification bead) may also be loaded into the channel. The capture bead (e.g., nucleic acid capture bead) can be loaded with the cell from a medium comprising cells and capture beads (e.g., nucleic acid capture beads), prior to loading the cell from a medium comprising only capture beads (e.g., nucleic acid capture bead), or after loading the cell for example with the lysis buffer (e.g., using optically actuated DEP force), permitting capture of the released nucleic acids to the capture bead.

The forgoing example can be varied, for example, by introducing one or more assay capture beads (other than a nucleic acid capture bead) into the chambers (or sequestration pens) along with the cells and incubating the assay capture beads and cells in the chambers for a first period of time. The assay capture beads can bind to biological materials, such as small molecules, carbohydrates, peptides, proteins, or the like, either specifically or non-specifically. During the first incubation period, the assay capture beads can optionally be monitored for binding to biological materials (e.g., using a labeled reporter molecule, as described elsewhere herein). Following the first incubation period, the cells can be selectively or non-selectively de-encapsulated, and one or more assay capture beads can be unpenned and exported for off-chip analysis (e.g., mass spectrometry, ELISA, enzymatic assays, or the like). After exporting the assay capture beads, one or more new assay capture beads can be loaded into the chambers and the process can be repeated (i.e., addition of new assay capture beads, encapsulation, incubation, selective or non-selective de-encapsulation, unpenning and export of capture beads for subsequent analysis) one or more times (e.g., 1, 2, 3, 4, 5, or more times). Alternatively, if multiple assay capture beads are introduced into the chambers along with the cells, the process can be repeated without having to introduce new assay capture beads at each repetition. Finally, once the assay capture beads have been exported and no further rounds of assay capture bead incubation and export are planned, the cells can optionally be lysed (as described above) and the nucleic acids released from the cells can be captured and processed for sequencing. By associating data produced during the various steps of the process to the pen from which the assay capture beads and nucleic acid capture beads originate, the assay data can be linked to the genomic data of a single cell population (e.g., clonal cell population).

Example 9

Detection of Different Levels of Secretion of a Small Molecule by Yeast.

Different strains of yeast, each secreting different levels of a small molecule, were loaded into an OPTOSELECT™ chip (Berkeley Lights, Inc., Emeryville, Calif.), encapsulated, and assayed for secretion of the small molecule. The OPTOSELECT™ chip comprised a channel and a plurality of sequestration pens, and individual yeast cells were loaded into separate pens using optically actuated DEP force. The surfaces of the channel featured a hydrophobic coating, while the surfaces of the sequestration pens featured a hydrophilic coating. Once the cells were penned, oil was flowed into the channel, thereby encapsulating the cells in their respective sequestration pens. Cells were monitored over a period of 24 hours using brightfield microscopy and emission (e.g., fluorescence) light emitted from the small molecule secreted by the yeast strains.

Figure 13A:
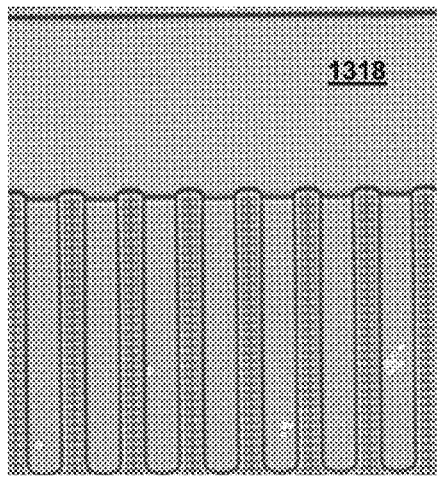
FIGS. 13A to 13D illustrate an exemplary embodiment in which yeast cells have been encapsulated in sequestration pens and an assay is in progress.
Figure 13B:
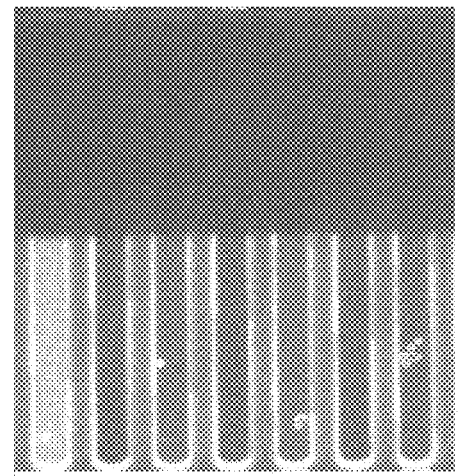

FIGS. 13A-13B illustrate the cells at 30 minutes after the assay start. Cells from different strains of the same type of yeast, differing in their level of secretion of the small molecule, were selectively placed in individual sequestration pens so as to allow for the pens containing cells to alternate with empty pens. Such alternate loading is not required but was performed in this manner in this particular experimental run for imaging purposes only. The individual sequestration pen number are shown on the bottom of the image, and pens with cells are numbered 276, 274, 272, and 270. The cells in each pen are identified and outlined, as illustrated.

FIG. 13A is a brightfield image of the cells in aqueous media within a pen, with the pen encapsulated by oil so as to separate the solution in each pen from the solution in the other pens. In FIG. 13A, the channel 1318 was filled with oil, however alternative embodiments or steps of a process may comprise removing oil from the majority of the channel and flowing one or more of air or aqueous medium, which can contain reagents, solubilized gasses, etc., while leaving an encapsulation layer of defined thickness (e.g., 5-50 microns) capping the aqueous medium in the sequestration pens. In other variations of this method, the oil is not removed from the channel during the experiment, but the oil is perfused and may contain oil soluble reagents, nutrients, and optionally saturated with appropriate gases as mentioned elsewhere herein. FIG. 13B is a fluorescent image of the same pens, with a fluorescent readout indicating the concentration of the small molecule secreted by the cells within each sequestration pen. The oil acted as a barrier preventing diffusion of the small molecule outside of the sequestration pen. As shown in FIG. 13B, the single cell in sequestration pen 276 appears to have the greatest expression of fluorescence, indicating the greatest expression of the small molecule. Note that the boundaries (walls) of the sequestration pen can contribute some autofluorescence to the image. However, such autofluorescence can be subtracted out during image processing to ensure accurate quantification of the concentration of the small molecule secreted by the cells within each sequestration pen.

Figure 13C:
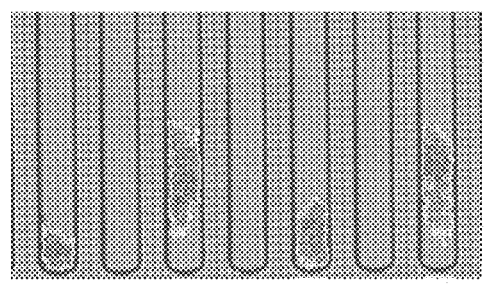
Figure 13D:
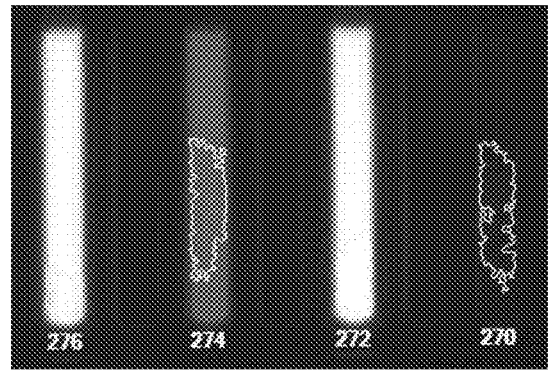

FIGS. 13C and 13D illustrate the same set of pens 16 hours after the assay start. The fluorescent signal may be integrated over time and may provide metrics such as yield (e.g., yield of product, cell yield, yield that corresponds to a quantifiable component based on a correlation between the fluorescence signal produced and the component in which the fluorescence is associated). FIG. 13C is a brightfield image illustrating that the yeast cells have divided, with an outline of the growing mass of cells providing a visual indication of growth. FIG. 13D is a corresponding fluorescent image. The four different yeast strains are labeled in FIG. 13D. The cells in sequestration pen 276 (4) and 272 (2) were high expression yeast strains. The emission (e.g., fluorescence) intensity from these two pens was high, consistent with the known behavior of the strains. The cells in sequestration pen 274 (3) were from a low expression yeast strain. As expected, sequestration pen 274 exhibits low fluorescent intensity. A negative control strain (1) located in sequestration pen 270 also illustrates low fluorescent intensity.

Figure 14A:
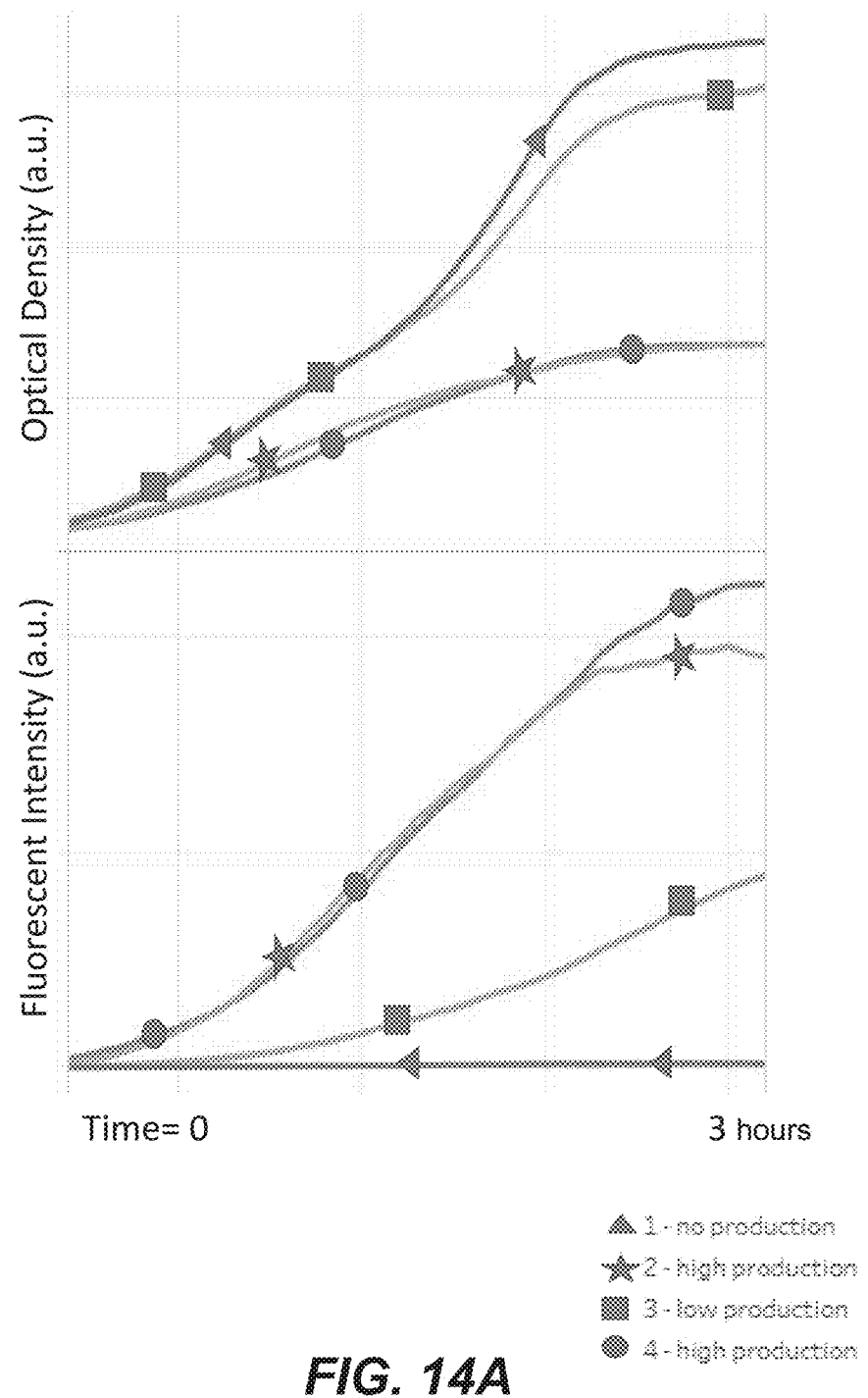
FIGS. 14A to 14B illustrates exemplary time course plots of average density, the derivative of average density, average intensity of emission (e.g., fluorescence), and the derivative of intensity for the yeast strains of FIGS. 13A to 13D.
Figure 14B:
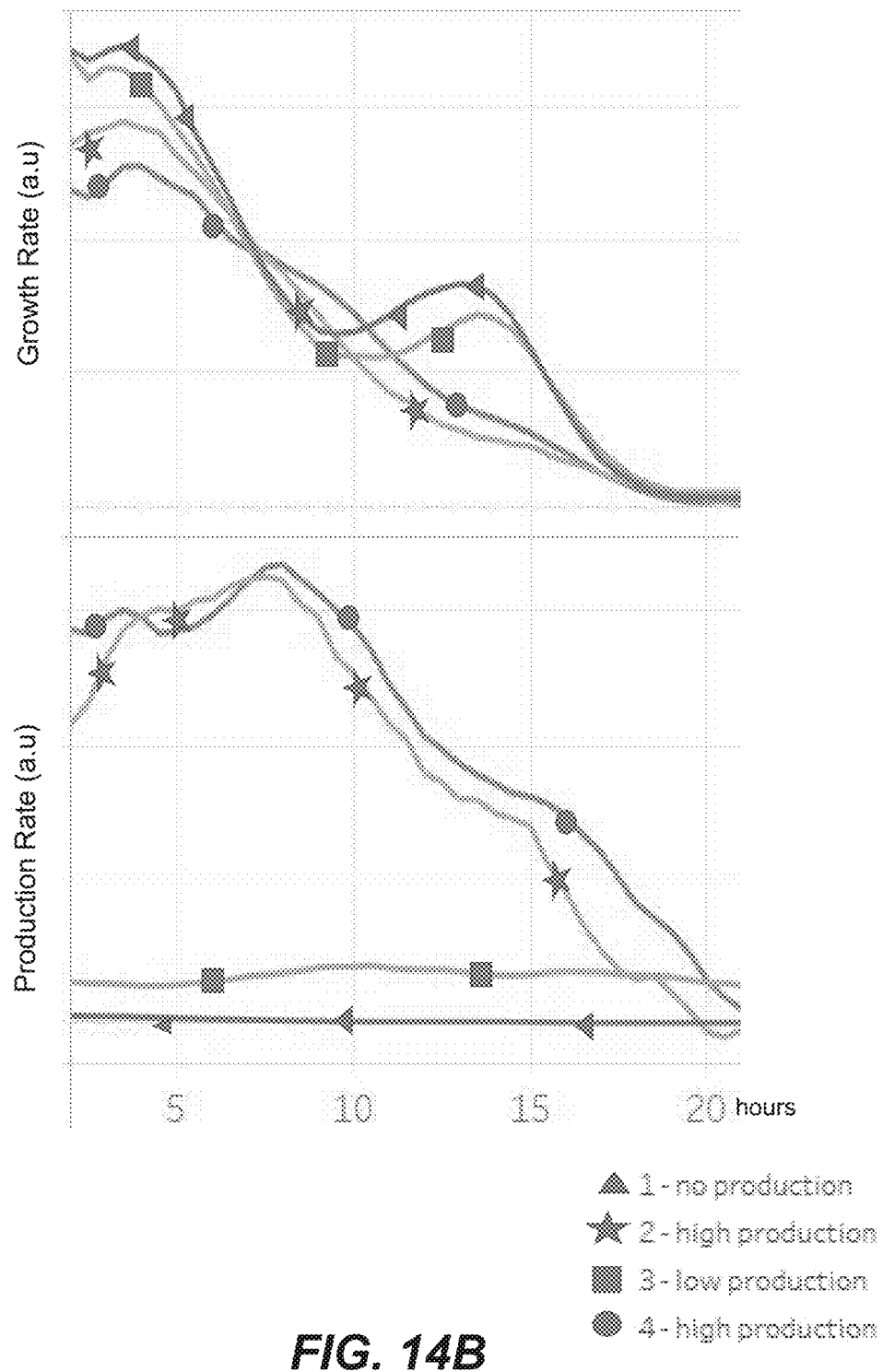

FIGS. 14A and 14B illustrate time course plots of optical density, fluorescent intensity, growth rate, and production rate for each of the yeast strains: negative control strain (1); strain (2), high expression; strain (3), low expression; and strain (4), high expression. Optical Density is the reduction in intensity in an brightfield image of a nanopen, e.g., sequestration pen, due to the presence of cells compared to an empty pen. It is proportional to the total biomass within a nanopen at a given time within the used boundaries/parameters. Fluorescent intensity is the average intensity of a pen image recorded in the green fluorescent channel (e.g., adjusted as needed to subtract out pen wall autofluorescence or the like). Growth Rate is the change of the optical density over time normalized by the current optical density. It describes the rate by which a colony within a nanopen expands (independent of its current biomass). Production Rate is the change in fluorescent intensity over time normalized by its current optical density. It describes the specific productivity per biomass at a given time.

The optical density and fluorescent intensity over a 3 hour window, as shown in FIG. 14A illustrates that the low expression strain (3) and negative control strain (1) increased in cell density over time, suggesting that resources are diverted to growth and division instead of producing the small molecule. The high expression strains (2) and (4) divide at a much slower rate as shown by the low optical density change in the top panel of FIG. 14A corresponding growth rate and production rate data are illustrated in the top and bottom panels of FIG. 14B, over a 20 hour period, respectively. The production rate measurement of the small molecule secreted by the yeast strains, is higher throughout most of the 20 hr period for the high expression yeast strains (2) and (4). In contrast, the low expression strain (3) shows slow sustained secretion of the small molecule over time. The larger drop in productivity in the high secreting strains can be attributed to a depletion of resources within the pen while the low secreting strain does not deplete nutrients required for production over the course of the experiment. The negative control strain (1) shows a production rate of 0 indicating that the yeast strain is not expressing any of the fluorescent small molecule. The modulation in the growth rate of the high secreting strains suggests a transition within the various metabolic processes (e.g., aerobic to anaerobic metabolism).

Figure 15:
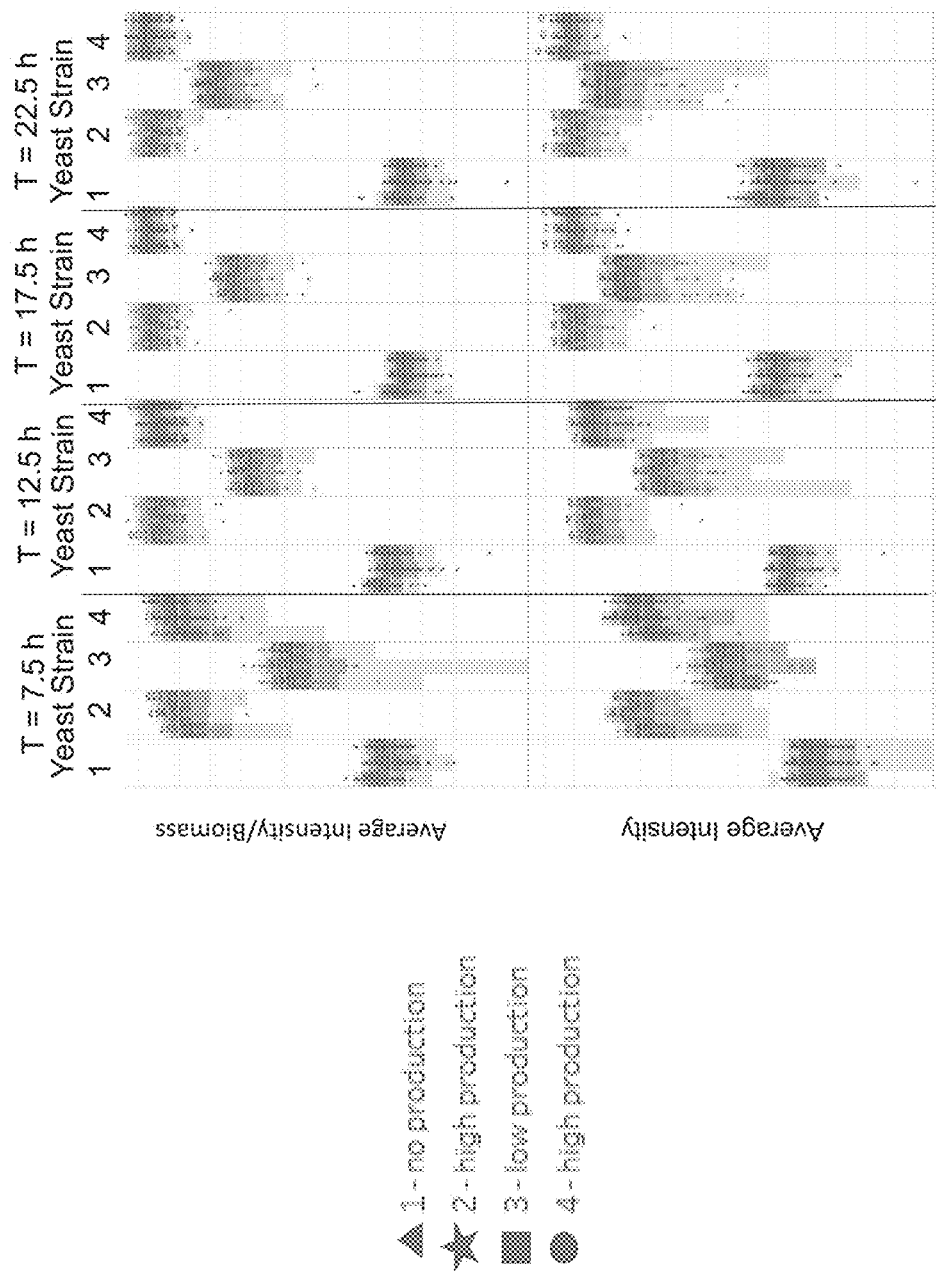
FIG. 15 illustrates the cumulative data collected from the yeast strains of FIGS. 13A to 13D, including average expression level (with first, second and third standard deviations indicated by dark grey to light grey shading) for each of the four strains, on each of three different OptoSelect chips, at four different time points.

FIG. 15 illustrates the cumulative data, including average expression level, with first, second and third standard deviations indicated by dark grey to light grey shading, for each of the four strains on each of three different OPTOSE-LECT™ chips, at four different time points (7.5, 12.5, 17.5, and 22.5 hours). FIG. 15 shows how to select the best time point for ranking strains by their specific productivity (intensity/biomass). Specifically, the coefficient of variation (CV) is the smallest at 17.5 hours. (light gray: +−3 StDev, medium gray: +−2 StDev, dark gray +−1 StDev). The data reveals that the different strains can be readily differentiated using this assay.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the FIGS. is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. It should also be noted, that while the term step is used herein, that term may be used to simply draw attention to different portions of the described methods and is not meant to delineate a starting point or a stopping point for any portion of the methods, or to be limiting in any other way. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

RECITATION OF SOME EMBODIMENTS OF THE DISCLOSURE

1. A process for encapsulating cells in a microfluidic device having an enclosure including a channel and a plurality of chambers, each chamber of the plurality having an opening (e.g., a single opening) fluidically connecting the chamber to the channel, where at least a portion of surfaces forming the channel proximal to the opening to each chamber of the plurality and/or at least a portion of surfaces forming each chamber of the plurality proximal to the channel includes a hydrophobic coating, said process including: filling the channel and the plurality of chambers in the enclosure of the microfluidic device with a first aqueous medium; disposing a first cell in a first chamber of the plurality of chambers; disposing a second cell in a second chamber of the plurality of chambers; and flowing a water immiscible fluidic medium into the channel, displacing substantially all of the first aqueous medium in the channel without substantially displacing the first aqueous medium in the chambers of the plurality of chambers, thereby reversibly encapsulating the first and second cells in their respective chambers.

2. The process of embodiment 1, where all of the channel surfaces proximal to and surrounding the opening to each chamber of the plurality of chambers may include the hydrophobic coating.

3. The process of embodiment 1 or 2, where all of the channel surfaces within 10 microns of the opening to each chamber of the plurality of chambers may include the hydrophobic coating.

4. The process of any one of embodiments 1 to 3, where the hydrophobic coating may have a contact angle from about 45 degrees to about 100 degrees.

5. The process of any one of embodiments 1 to 4, where the hydrophobic coating may be covalently bonded to the at least a portion of the surfaces forming the channel proximal to the opening to each chamber of the plurality of chambers.

6. The process of any one of embodiments 1 to 5, where the water immiscible fluidic medium may include an alkane, a fluoroalkane, an oil, a hydrophobic polymer, or any combination thereof.

7. The process of any one of embodiments 1 to 6, further including aspirating the water immiscible fluidic medium out of the channel.

8. The process of embodiment 7, where the rate of aspiration of the water immiscible fluidic medium out of the channel may be at or between 0.01 µl/sec and 1.0 µl/sec.

9. The process of embodiment 7 or 8, where aspirating the water immiscible fluidic medium further may include subsequently aspirating a second aqueous medium into the channel.

10. The process of embodiment 9, where the second aqueous medium may include a surfactant.

11. The process of any one of embodiments 7 to 10, where at least a portion of the surfaces forming each chamber of the plurality may include a hydrophobic coating, and where the at least a portion of the chamber surfaces having a hydrophobic coating may be located proximal to the opening to the channel, where the process may further include: generating an encapsulation layer of water immiscible fluidic media in each chamber of the plurality of chambers, where the encapsulation layer of each chamber of the plurality is located immediately adjacent to the channel and shares an interface with the first aqueous medium in the chamber so as to separate (e.g., isolate) the first aqueous medium in the chamber from a medium present in the channel (e.g., second aqueous medium, air, $CO_2$, another gas, or a different water immiscible fluidic medium).

12. The process of embodiment 11, where all of the chamber surfaces proximal to and surrounding the opening of each chamber of the plurality of chambers may include the hydrophobic coating.

13. The process of embodiment 11 or 12, where all of the chamber surfaces within 10 microns of the opening of each chamber of the plurality of chambers may include the hydrophobic coating.

14. The process of any one of embodiments 11 to 13, where the hydrophobic coating of the channel surfaces may be the same as the hydrophobic coating of the chamber surfaces.

15. The process of any one of embodiments 11 to 14, where the encapsulation layer of each chamber of the plurality of chambers may have an average thickness of about 5 µm to about 50 µm.

16. The process of any one of embodiments 11 to 15, where the process may further include: selecting one (or more) of the first and second chambers having a cell disposed therein; and removing the encapsulation layer formed by the water immiscible fluidic medium at the opening to the channel of the selected chamber(s), thereby generating a de-encapsulated chamber.

17. The process of embodiment 16, where selectively removing the encapsulation layer may include generating a bubble within the chamber (e.g., generating a bubble proximal to the encapsulation layer).

18. The process of embodiment 17, where generating the bubble may include directing a laser at a location on an inner surface of a base of the chamber proximal to the interface between the first aqueous medium and the water immiscible fluid medium.

19. The process of any one of embodiments 16 to 18, wherein the process may further include flowing a third aqueous medium into the channel.

20. The process of embodiment 19, where the third aqueous medium may include a reagent, such as an assay reagent or a lytic reagent (e.g., the third aqueous medium can be a lysis buffer), or an export buffer.

21. The process of any one of embodiments 1 to 20, wherein the process may further include disposing a capture bead (e.g., a bead that binds biological material, such as a non-specific capture bead, an antigen-specific capture bead, an enzyme capture bead, or a nucleic acid capture bead) into one or both of the first and second chambers.

22. The process of embodiment 21, wherein the process may further include unpenning the capture bead from the de-encapsulated chamber (e.g., and further analyzing material bound to the capture bead); and, optionally, exporting the capture bead from the microfluidic device (e.g., and further analyzing material bound to the capture bead).

23. The process of any one of embodiments 1 to 22, where disposing the first and second cells in the first and second chambers may include: flowing in a cell-containing aqueous medium including a plurality of cells into the channel of the microfluidic device; and selecting the first and second cells from the plurality of cells in the cell-containing aqueous medium in the channel of the microfluidic device for disposition in each of the first and second chambers, respectively.

24. The process of embodiment 23, where the selected first and second cells may be individually moved from the channel to the first and second chambers, respectively, using DEP force (e.g., light-actuated DEP force).

25. The process of any one of embodiments 1 to 24, where each chamber of the plurality of chambers may be a sequestration pen having a single opening to the channel and may including an isolation region (e.g., having a single opening) and a connection region fluidically connecting the isolation region to the channel.

26. The process of embodiment 25, where the connection region of each sequestration pen may include a proximal opening to the channel and a distal opening to the isolation region, the proximal opening of the connection region having a width $W_{con}$ ranging from about 20 microns to about 100 microns, and where a length $L_{con}$ of the connection region from the proximal opening to the distal opening may be as least 1.0 times the width $W_{con}$ of the proximal opening of the connection region.

27. The process of embodiment 26, where the width $W_{con}$ at the proximal opening of each sequestration pen may be about 20 microns to about 60 microns or about 30 microns to about 90 microns.

28. The process of embodiment 26 or 27, where the length $L_{con}$ of the connection region may be at least 1.5 times the width $W_{con}$.

29. The process of embodiment 26 or 27, where the length $L_{con}$ of the connection region may be at least 2.0 times the width $W_{con}$.

30. The process of any one of embodiments 26 to 29, where the length $L_{con}$ of the connection region may be between about 20 microns and about 500 microns.

31. The process of any one of embodiments 25 to 30, where a ratio of a width $W_{ch}$ of the channel (e.g., a channel having a substantially uniform width) to a width $W_{op}$ of the opening of each chamber of the plurality of chambers (or a width $W_{con}$ of the proximal opening of the connection region of each sequestration pen) may be about 1.25 or greater (e.g., about 1.5 or greater, about 2.0 or greater, about 2.5 or greater, or about 3.0 or greater).

32. The process of any one of embodiments 1 to 30, where a width $W_{ch}$ of the channel (e.g., a channel having a substantially uniform width) at the opening of each chamber of the plurality (e.g., at a proximal opening to a connection region of a sequestration pen) may have a size between about 50 microns and about 500 microns.

33. The process of any one of embodiments 1 to 30, where a width $W_{ch}$ of the channel (e.g., a channel having a substantially uniform width) at the opening of each chamber of the plurality (e.g., a proximal opening to a connection region of a sequestration pen) may have a size of about 70 microns to about 250 microns (e.g., about 80 microns to about 200 microns, about 90 microns to about 150 microns, or about 200 microns to about 250 microns).

34. The process of any one of embodiments 1 to 33, where a height of the channel at the opening of each chamber of the plurality of chambers (or at the proximal opening of the connection region of each sequestration pen) may be between about 20 microns and about 100 microns (e.g., about 30 microns to about 50 microns, about 50 microns to about 70 microns, about 70 microns to about 90 microns, about 35 microns to about 45 microns, about 45 microns to about 55 microns, about 55 microns to about 65 microns, about 65 microns to about 75 microns, or about 75 microns to about 85 microns).

35. The process of any one of embodiments 1 to 34, where a volume of each chamber of the plurality (or each sequestration pen) may range from about $2 \times 10^5$ to about $2 \times 10^6$ cubic microns.

36. The process of any one of embodiments 1 to 35, where less than or equal to 50% of a total surface area of the surfaces forming the channel may include the hydrophobic coating.

37. The process of any one of embodiments 1 to 35, where greater than or equal to 50% of a total surface area of the surfaces forming the channel may include the hydrophobic coating.

38. The process of any one of embodiments 1 to 37, where each chamber of the plurality of chambers may include a plurality of surfaces forming the chamber, where at least one chamber surface of the plurality may include a hydrophilic coating.

39. The process of embodiment 38, where the plurality of chambers may include a plurality of sequestration pens, each sequestration pen having a single opening to the channel and may include an isolation region (e.g., having a single opening) and a connection region fluidically connecting the isolation region to the channel, and where at least one surface (e.g., all surfaces) forming the isolation region of each sequestration pen may include the hydrophilic coating.

40. The process of embodiment 39, where at least one surface (e.g., all surfaces) forming the connection region of each sequestration pen may include the hydrophilic coating.

41. The process of embodiment 40, where each of the at least one surface (e.g., all surfaces) forming the connection region may include a portion proximal to the isolation region having the hydrophilic coating and a portion proximal to the channel having the hydrophobic coating, and, optionally, when all surfaces forming the connection region may include a portion proximal to the channel having the hydrophobic coating, providing a hydrophobic coating that encircles a portion of the connection region immediately adjacent to the channel.

42. The process of any one of embodiments 1 to 41, where the hydrophobic coating may include a first covalently bound surface modification may including: a first linking group, and a first moiety, where the first moiety is nonpolar (e.g., an oleic acid moiety, alkynyl moiety, alkynyl-terminated PEG moiety, or fluorinated moiety).

43. The process of embodiment 42, where the hydrophilic coating may include a plurality of second covalently bound surface modifications, each including a second linking group, and a second moiety, where the second moiety is polar (e.g., a methoxy terminated PEG moiety, a carboxylic acid, a carboxylic acid terminated PEG moiety, an alcohol moiety or an alcohol terminated PEG moiety).

44. The process of embodiment 42 or 43, where the hydrophobic coating may be formed by: contacting the at least a portion of surfaces forming the channel with a first modifying reagent; and reacting the first modifying reagent with a plurality of first reactive moieties on the at least a portion of surfaces forming the channel.

45. The process of embodiment 43 or 44, where the hydrophilic coating may be formed by: contacting the at least one surface of the chamber (e.g., sequestration pen) with a hydrophilic modifying reagent; and reacting the second modifying reagent with a plurality of second reactive moieties on the at least one surface of the chamber.

46. A process of assaying encapsulated cells in a microfluidic device having an enclosure including a channel and a plurality of chambers, each chamber of the plurality having an opening (e.g., a single opening) fluidically connecting the chamber to the channel, where at least a portion of surfaces forming the channel proximal to each chamber of the plurality and/or at least a portion of surfaces forming each chamber of the plurality proximal to the channel includes a hydrophobic coating, where the process includes: filling the channel and the plurality of chambers in the enclosure of the microfluidic device with a first aqueous medium; disposing a first cell in a first chamber of the plurality of chambers; disposing a second cell in a second chamber of the plurality of chambers; flowing a water immiscible fluidic medium into the channel, displacing substantially all of the first aqueous medium in the channel without substantially displacing the first aqueous medium in any of the plurality of chambers, thereby reversibly encapsulating the first and second cells in their respective chambers; and monitoring an activity of the cell(s) encapsulated in the first and second chambers.

47. The process of embodiment 46, where all of the channel surfaces proximal to and surrounding the opening to each chamber of the plurality of chambers may include the hydrophobic coating.

48. The process of embodiment 46 or 47, where all of the channel surfaces within 10 microns of the opening to each chamber of the plurality of chambers may include the hydrophobic coating.

49. The process of any one of embodiments 46 to 48, where the hydrophobic coating may have a contact angle from about 45 degrees to about 100 degrees.

50. The process of any one of embodiments 46 to 49, where the hydrophobic coating may be covalently bonded to the portion of the surfaces forming the channel proximal to each chamber of the plurality of chambers.

51. The process of any one of embodiments 46 to 50, where the water immiscible fluidic medium may include an alkane, a fluoroalkane, an oil, a hydrophobic polymer, or any combination thereof.

52. The process of any one of embodiments 46 to 51, further including aspirating the water immiscible fluidic medium out of the channel.

53. The process of embodiment 52, where the rate of aspiration of the water immiscible fluidic medium out of the channel may be at or between 0.01 µl/sec and 1.0 µl/sec.

54. The process of embodiment 52 or 53, where aspirating the water immiscible fluidic medium further may include subsequently aspirating a second aqueous medium into the channel.

55. The process of embodiment 54, where the second aqueous medium may include a surfactant.

56. The process of any one of embodiments 52 to 55, where at least a portion of the surfaces forming each chamber of the plurality may include a hydrophobic coating, and where the at least a portion of the chamber surfaces having a hydrophobic coating is located proximal to the opening to the channel, where the process may further include: generating an encapsulation layer of water immiscible fluidic media in each chamber of the plurality of chamber, where the encapsulation layer of each chamber of the plurality may be located immediately adjacent to the channel and may share an interface with the first aqueous medium in the chamber so as to separate (e.g., isolate) the first aqueous medium in the chamber from a medium present in the channel (e.g., second aqueous medium, air, $CO_2$, another gas, or a different water immiscible fluidic medium).

57. The process of embodiment 56, where all of the chamber surfaces proximal to and surrounding the opening of each chamber of the plurality of chambers may include the hydrophobic coating.

58. The process of embodiment 56 or 57, where all of the chamber surfaces within 10 microns of the opening of each chamber of the plurality of chambers may include the hydrophobic coating.

59. The process of any one of embodiments 56 to 58, where the hydrophobic coating of the channel surfaces may be the same as the hydrophobic coating of the chamber surfaces.

60. The process of any one of embodiments 56 to 59, where the encapsulation layer of each chamber of the plurality of chambers may have an average thickness of about 5 microns to about 50 microns.

61. The process of any one of embodiments 56 to 60, further including: selecting one (or more) of the at least two chambers having a cell disposed therein; and removing the encapsulation layer formed by the immiscible fluidic medium at the opening to the channel of the selected chamber(s), thereby generating a de-encapsulated chamber.

62. The process of embodiment 61, where selectively removing the encapsulation layer may include generating a bubble within the chamber (e.g., generating a bubble proximal to the encapsulation layer).

63. The process of embodiment 62, where generating the bubble may include directing a laser at a location on an inner surface of a base of the chamber proximal to the interface between the first aqueous medium and the water immiscible fluidic medium.

64. The process of any one of embodiments 61 to 63, further including flowing a third aqueous medium into the channel.

65. The process of embodiment 64, where the third aqueous medium may include a reagent, such as an assay reagent or a lytic reagent (e.g., the third aqueous medium can be a lysis buffer), or an export buffer.

66. The process of any one of embodiments 46 to 65, further including disposing a capture bead (e.g., a bead that binds biological material, such as a non-specific capture bead, an antigen capture bead, an enzyme capture bead, or a nucleic acid capture bead) into one or both of the first and second chambers.

67. The process of embodiment 66, further including unpenning the capture bead from the de-encapsulated chamber (e.g., a further analyzing material bound to the capture bead); and, optionally, exporting the capture bead from the microfluidic device (e.g., and further analyzing material bound to the capture bead).

68. The process of any one of embodiments 46 to 67, where disposing the first and second cells in the first and second chambers may include: flowing an aqueous medium including a plurality of cells into the channel of the microfluidic device; and selecting the first and second cells from the cell-containing aqueous medium in the channel of the microfluidic device for disposition in the first and second chambers, respectively.

69. The process of embodiment 68, where the selected first and second cells may be individually moved from the channel to the first and second chambers, respectively, using DEP force (e.g., light-actuated DEP force).

70. The process of any one of embodiments 46 to 69, where each chamber of the plurality of chambers may be a sequestration pen having a single opening to the channel and may include an isolation region (e.g., having a single opening) and a connection region fluidically connecting the isolation region to the channel.

71. The process of embodiment 70, where the connection region of each sequestration pen may include a proximal opening to the channel and a distal opening to the isolation region, the proximal opening of the connection region having a width $W_{con}$ ranging from about 20 microns to about 100 microns, and where a length $L_{con}$ of the connection region from the proximal opening to the distal opening may be as least 1.0 times the width $W_{con}$ of the proximal opening of the connection region.

72. The process of embodiment 71, where the width $W_{con}$ at the proximal opening of each sequestration pen may be about 20 microns to about 60 microns or about 30 microns to about 90 microns.

73. The process of embodiment 71 or 72, where the length $L_{con}$ of the connection region may be at least 1.5 times the width $W_{con}$.

74. The process of embodiment 71 or 72, where the length $L_{con}$ of the connection region may be at least 2.0 times the width $W_{con}$.

75. The process of any one of embodiments 71 to 74, where the length $L_{con}$ of the connection region may be between about 20 microns and about 500 microns.

76. The process of any one of embodiments 46 to 75, where a ratio of a width $W_{ch}$ of the channel (e.g., a channel having substantially uniform width) to a width $W_{op}$ of the opening of each chamber of the plurality of chambers (or a width $W_{con}$ of the proximal opening of the connection region of each sequestration pen) to the channel may be about 1.25 or greater (e.g., about 1.5 or greater, about 2.0 or greater, about 2.5 or greater, or about 3.0 or greater).

77. The process of any one of embodiments 46 to 76, where a width $W_{ch}$ of the channel (e.g., a channel having substantially uniform width) at the opening of each chamber of the plurality of chambers (or at the proximal opening of the connection region of each sequestration pen) may be between about 50 microns and about 500 microns.

78. The process of any one of embodiments 46 to 76, where a width $W_{ch}$ of the channel (e.g., a channel having substantially uniform width) at the opening of each chamber of the plurality of chambers (or at the proximal opening of the connection region of each sequestration pen) may be about 70 microns to about 250 microns, about 80 microns to about 200 microns, or about 90 microns to about 150 microns.

79. The process of any one of embodiments 46 to 78, where a height of the channel at the opening of each chamber of the plurality of chambers (or at the proximal opening of the connection region of each sequestration pen) may be between about 20 microns and about 100 microns (e.g., about 30 microns to about 50 microns, about 50 microns to about 70 microns, about 70 microns to about 90 microns, about 35 microns to about 45 microns, about 45 microns to about 55 microns, about 55 microns to about 65 microns, about 65 microns to about 75 microns, or about 75 microns to about 85 microns).

80. The process of any one of embodiments 46 to 79, where a volume of each chamber of the plurality of chambers (or each sequestration pen) may range from about $2 \times 10^5$ to about $2 \times 10^6$ cubic microns.

81. The process of any one of embodiments 46 to 80, where less than or equal to 50% of a total surface area of the surfaces forming the channel may include the hydrophobic coating.

82. The process of any one of embodiments 46 to 80, where greater than or equal to 50% of a total surface area of the surfaces forming the channel may include the hydrophobic coating.

83. The process of any one of embodiments 46 to 82, where each chamber of the plurality of chambers may include a plurality of surfaces forming the chamber, where at least one chamber surface of the plurality may include a hydrophilic coating.

84. The process of embodiment 83, where the plurality of chambers may include a plurality of sequestration pens, each sequestration pen having a single opening to the channel and may including an isolation region (e.g., having a single opening) and a connection region fluidically connecting the isolation region to the channel, and where at least one surface (e.g., all surfaces) forming the isolation region of each sequestration pen of the plurality may include the hydrophilic coating.

85. The process of embodiment 84, where at least one surface (e.g., all surfaces) forming the connection region of each sequestration pen of the plurality may include the hydrophilic coating.

86. The process of embodiment 85, where each of the at least one surface (e.g., all surfaces) forming the connection region may include a portion proximal to the isolation region having the hydrophilic coating and a portion proximal to the channel having the hydrophobic coating, and, optionally when all surfaces forming the connection region may include a portion proximal to the channel having the hydrophobic coating, they provide a hydrophobic coating that encircles a portion of the connection region immediately adjacent to the channel.

87. The process of any one of embodiments 46 to 86, where the hydrophobic coating may include a first covalently bound surface modification including: a first linking group, and a first moiety, where the first moiety is nonpolar (e.g., an oleic acid moiety, alkynyl moiety, alkynyl-terminated PEG moiety, or fluorinated moiety).

88. The process of embodiment 87, where the hydrophilic coating may include a plurality of second covalently bound surface modifications, each including a second linking group, and a second moiety, where the second moiety may be polar (e.g., a methoxy terminated PEG moiety, a carboxylic acid, a carboxylic acid terminated PEG moiety, an alcohol moiety or an alcohol terminated PEG moiety).

89. The process of any one of embodiments 46 to 88, further including incubating the first and second cells encapsulated in the first and second chambers for a first period of time before monitoring the activity of the first and second cells.

90. The process of any one of embodiments 46 to 88, further including incubating the first and second cells encapsulated in each of the first and second chambers for a first period of time and monitoring the activity of the first and second cells at a plurality of time points during the first period of time.

91. The process of embodiment 90, further including monitoring the activity of the incubating first and second cells substantially continuously during the first period of time.

92. The process of any one of embodiments 89 to 91, where the first period of time may be at least 30 minutes.

93. The process of any one of embodiments 89 to 92, where the first period of time may be between 4 hours and 24 hours (e.g., between 8 hours and 12 hours, between 12 hours and 16 hours, between 16 hours and 20 hours).

94. The process of any one of embodiments 46 to 93, further including incubating the cells at a temperature between 18° C. and 50° C. (e.g., between 25° C. and 37° C.).

95. The process of any one of embodiments 46 to 94, where the first and second cells may express variable amounts of a molecule of interest or a reporter molecule.

96. The process of embodiment 95, where the molecule of interest may be a small molecule.

97. The process of embodiment 95, where the molecule of interest may be a protein.

98. The process of embodiment 95, where the molecule of interest may be a nucleic acid.

99. The process of any one of embodiments 95 to 98, where the molecule of interest may be secreted.

100. The process of any one of embodiments 95 to 99, where monitoring the activity of the first and second cells encapsulated in the first and second chambers, respectively, may include detecting the molecule of interest or reporter molecule present in each of the first and section chambers.

101. The process of embodiment 100, where detecting the molecule of interest or reporter molecule may include detecting a fluorescent signal associated with or produced by the molecule of interest or reporter molecule.

102. The process of embodiment 100 or 101, where detecting the molecule of interest or reporter molecule may include detecting binding of the molecule of interest or reporter molecule to a solid substrate, where the solid substrate (e.g., a bead) may include a receptor for the molecule of interest.

103. The process of any one of embodiments 46 to 102, where monitoring the activity of the first and second cells may include imaging the first and second chambers, respectively.

104. The process of embodiment 103, where the first and second cells may be imaged to monitor one or more phenotypic parameters of the cells.

105. The process of embodiment 103 or 104, where monitoring the activity of the first and second cells may include monitoring cell growth.

106. The process of any one of embodiments 46 to 105, where the water immiscible fluidic medium flowed/flowing through the channel may include soluble oxygen.

107. The process of any one of embodiments 46 to 106, where the first aqueous medium may include a carbon/energy source and, optionally, other minerals and nutrients.

108. The process of any one of embodiments 46 to 107 further including selecting cells of interest from the first and second cells for additional assays based upon a detected activity of the cell. e.g., based on predetermined criteria or relative to the detected activity of cells in other chambers of the microfluidic device).

109. The process of embodiment 108, where the selection may be based upon an amount of expression of the molecule of interest, an amount of cell growth, or a combination thereof.

110. The process of any one of embodiments 46 to 109, further including disposing a micro-object into each of the first and second chambers of the plurality of chambers, where the micro-object may include a molecule configured to affect or test a biological activity of the first and second cells disposed therein.

111. The process of embodiment 110, where the molecule may be associated with the micro-object non-covalently.

112. The process of embodiment 110 or 111, where disposing the micro-object into each of the first and second chambers may be performed prior to encapsulating the first and second cells within their respective chambers.

113. The process of any one of embodiments 110 to 112, further including introducing a release reagent into each of the first and second chambers subsequent to introducing the micro-objects therein, where the release reagent is configured to trigger release of the molecule from the micro-objects.

114. The process of embodiment 113, where introducing the release reagent into each of the first and second chambers may be performed prior to encapsulating the first and second cells within their respective chambers.

115. The process of embodiment 113 or 114, further including triggering release of the molecule from the micro-object.

116. The process of embodiment 115, where triggering release of the molecule from the micro-objects may include increasing a temperature of each of the first and second chambers of the microfluidic device.

117. The process of any one of embodiments 113 to 116, where triggering release may include directing laser illumination at the micro-object in each of the first and second chambers.

118. The process of any one of embodiments 113 to 117, further including assessing whether the molecule may include by the micro-objects changes the expression of the molecule of interest (or the reporter molecule) by the first or second cells.

119. The process of embodiment 118, further including quantifying the change in expression of the molecule of interest (or the reporter molecule) of the first and second cells (e.g., quantifying the change in the first cell relative to the second cell, or vice versa, or relative to one more cells disposed in chambers of the plurality of chambers other than the first and second chambers).

120. The process of any one of embodiments 113 to 119, where the micro-object may further include an identifier configured to permit tracking of the identity of the molecule.

121. The process of any one of embodiments 1 to 120, where each chamber of the plurality of chambers opens laterally from the channel.

122. The process of any one of embodiments 1 to 121, where the enclosure of the microfluidic device may further include: a base; a microfluidic circuit structure disposed on an inner surface of the base; and a cover disposed over the microfluidic circuit structure, where the base, the microfluidic circuit structure, and the cover together define the channel and the plurality of chambers.

123. The process of embodiment 122, where the inner surface of the base and/or an inner surface of the cover may include a metal, metal oxide, glass, polymer, or any combination thereof.

124. The process of embodiment 122 or 123, where the cover or the base of the microfluidic device may include a DEP configuration.

125. The process of embodiment 124, where the DEP configuration may be optically actuated.

126. The process of any one of embodiments 1 to 125, where the first and second cells may be yeast cells.

127. The process of any one of embodiments 1 to 125, where the first and second cells may be spores derived from filamentous fungus.

128. The process of any one of embodiments 1 to 125, where the first and second cells may be mammalian cells.

129. The process of any one of embodiments 1 to 125, where the first and second cells may be immune cells.

130. The process of any one of embodiments 1 to 125, where the first and second cells may be T cells.

131. The process of any one of embodiments 1 to 125, where the first and second cells may be B cells.

132. The process of any one of embodiments 1 to 125, where the first and second cells are bacterial cells.

133. The process of any one of embodiments 1 to 125, where the first and second cells may be plant cells.

134. The process of any one of embodiments 1 to 125, where the first and second cells may be fetal cells.

135. The process of any one of embodiments 1 to 125, where the first and second cells may be stem cells or progenitor cells.

136. A microfluidic device having an enclosure including a channel and a plurality of chambers, each chamber of the plurality of chambers having an opening (e.g., a single opening) fluidically connecting the chamber to the channel, where each chamber of the plurality of chambers is formed by a plurality of surfaces having a total surface area, with a first portion of the total surface of each chamber including a hydrophobic coating and a second portion of the total surface area of each chamber including a hydrophilic coating, and where the first portion of the total surface area of each chamber may be located proximal to a boundary between the chamber opening and the channel.

137. The microfluidic device of embodiment 136, where the first portion of the total surface area of each chamber of the plurality of chambers is proximal to and surrounding the opening of the chamber to the channel (e.g., each surface forming the opening of the chamber may include the hydrophobic coating at a location proximal to the boundary between the chamber opening and the channel).

138. The microfluidic device of embodiment 136 or 137, where all of the total surface area of each chamber of the plurality of chambers located within about 10 microns (e.g., within about 20 microns, about 25 microns, about 30 microns, about 35 microns, about 40 microns, about 45 microns, about 50 microns, about 55 microns, about 60 microns, or more) of the boundary between the chamber opening and the channel may include the hydrophobic coating.

139. The microfluidic device of any one of embodiments 136 to 138, where the channel may be formed by a plurality of surfaces having a total surface area, with one or more portions of the total surface area of the channel including a hydrophobic coating (e.g., the same hydrophobic coating as the plurality of chambers).

140. The microfluidic device of embodiment 139, where each of the one or more portions of the total surface area of the channel including the hydrophobic coating may be located proximal to the boundary between the channel and a corresponding chamber of the plurality of chambers.

141. The microfluidic device of embodiment 139 or 140, where all of the total surface area of the channel located within about 10 microns (e.g., within about 20 microns, about 25 microns, about 30 microns, about 35 microns, about 40 microns, about 45 microns, about 50 microns, about 55 microns, about 60 microns, or more) of the boundaries between the channel and the openings of the plurality of chambers may include the hydrophobic coating.

142. The microfluidic device of embodiment 141, where substantially all (e.g., at least 80%, 85%, 90%, 95%, 98%, 99%, or more) of the total surface area of the channel may include the hydrophobic coating.

143. The microfluidic device of any one of embodiments 136 to 142, where the hydrophobic coating of the plurality of chambers may have a contact angle from about 45 degrees to about 100 degree.

144. The microfluidic device of any one of embodiments 136 to 143, where each chamber of the plurality of chambers may be a sequestration pen including an isolation region and a connection region fluidically connecting the isolation region to the channel.

145. The microfluidic device of embodiment 144, where the hydrophobic coating of each sequestration pen may be present in the connection region and substantially absent from the isolation region (e.g., a total surface area of chamber surfaces forming the isolation region may include less than 5%, 4%, 3%, 2%, 1.5%, 1%, 0.5% of the hydrophobic coating).

146. The microfluidic device of embodiment 145, where less than or equal to 50% of a total surface area of chamber surfaces forming the connection region of each sequestration pen may include the hydrophobic coating.

147. The microfluidic device of embodiment 145, where greater than or equal to 50% of a total surface area of chamber surfaces forming the connection region of each sequestration pen may include the hydrophobic coating.

148. The microfluidic device of embodiment 145, where chamber surfaces forming the connection region of each sequestration pen and including the hydrophobic coating may form a ring surrounding a proximal end of the connection region (e.g., starting at the boundary between the channel and the proximal opening of the connection region and extending into the connection region).

149. The microfluidic device of any one of embodiments 144 to 148, where greater than or equal to 50% of a total surface area of chamber surfaces forming the isolation region of each sequestration pen may include the hydrophilic coating.

150. The microfluidic device of any one of embodiments 144 to 148, where substantially all of a total surface area of chamber surfaces forming the isolation region of each sequestration pen may include the hydrophilic coating (e.g., at least 80%, 85%, 90%, 95%, 98%, 99%, or more).

151. The microfluidic device of any one of embodiments 144 to 150, where the connection region of each sequestration pen may include a proximal opening to the channel and a distal opening to the isolation region, the proximal opening of the connection region having a width $W_{con}$ ranging from about 20 microns to about 100 microns (e.g., about 20 microns to about 60 microns, or about 30 microns to about 90 microns), and where a length $L_{con}$ of the connection region from the proximal opening to the distal opening is as least 1.0 times the width $W_{con}$ of the proximal opening of the connection region.

152. The microfluidic device of embodiment 151, where the length $L_{con}$ of the connection region may be at least 1.5 times the width $W_{con}$.

153. The microfluidic device of embodiment 151, where the length $L_{con}$ of the connection region may be at least 2.0 times the width $W_{con}$.

154. The microfluidic device of embodiment 151, where the length $L_{con}$ of the connection region may be between about 20 microns and about 500 microns.

155. The microfluidic device of any one of embodiments 136 to 154, where a ratio of a width $W_{ch}$ of the channel (e.g., a channel having substantially uniform width) to a width $W_{op}$ of the opening of each chamber of the plurality of chambers (or a width $W_{con}$ of a proximal opening of the connection region of each sequestration pen) to the channel may be about 1.25 or greater (e.g., about 1.5 or greater, about 2.0 or greater, or about 3.0 or greater).

156. The microfluidic device of any one of embodiments 136 to 155, where a width $W_{ch}$ of the channel (e.g., a channel having substantially uniform width) at the opening of each chamber of the plurality of chambers (or at a proximal opening of the connection region of each sequestration pen) may be between about 50 microns and about 500 microns.

157. The microfluidic device of any one of embodiments 136 to 156, where a width $W_{ch}$ of the channel (e.g., a channel having substantially uniform width) at the opening of each chamber of the plurality of chambers (or at a proximal opening of the connection region of each sequestration pen) may be about 70 microns to about 250 microns (e.g., about 80 microns to about 200 microns, or about 90 microns to about 150 microns).

158. The microfluidic device of any one of embodiments 136 to 157, where a height of the channel at the opening of each chamber of the plurality of chambers (or at a proximal opening of the connection region of each sequestration pen) may be between about 20 microns and about 100 microns (e.g., about 30 microns to about 50 microns).

159. The microfluidic device of any one of embodiments 136 to 157, where a volume of each chamber of the plurality of chambers (or each sequestration pen) may range from about $2 \times 10^5$ to about $2 \times 10^6$ cubic microns.

160. The microfluidic device of any one of embodiments 136 to 159, where the enclosure of the microfluidic device may further include: a base; a microfluidic circuit structure disposed on an inner surface of the base; and a cover disposed over the microfluidic circuit structure, where the base, the microfluidic circuit structure, and the cover together define the channel and the plurality of chambers.

161. The microfluidic device of any one of embodiments 136 to 160, where the hydrophobic coating may include a first covalently bound surface modification may including: a first linking group, and a first moiety, where the first moiety is nonpolar (e.g., an oleic acid moiety, alkynyl moiety, PEG-linked alkynyl, or fluorinated moiety).

162. The microfluidic device of embodiment 161, where the hydrophilic coating may include a plurality of second covalently bound surface modifications, each including a second linking group, and a second moiety, where the second moiety is polar (e.g., a methoxy terminated PEG moiety, a carboxylic acid, a carboxylic acid terminated PEG moiety, an alcohol moiety or an alcohol terminated PEG moiety).

163. A kit for encapsulating cells, including: a microfluidic device having an enclosure including a channel and a plurality of chambers, each chamber of the plurality having an opening (e.g., a single opening) fluidically connecting the chamber to the channel, where at least a portion of inner surfaces forming the channel and each chamber may include a plurality of reactive moieties; a first surface modifying reagent may including a first linking group configured to covalently bind with the reactive moieties, and a first surface contact moiety, where the first surface contact moiety may be nonpolar (e.g., an oleic acid moiety, alkynyl moiety, PEG-linked alkynyl, or fluorinated moiety); and a second surface modifying reagent including a second linking group configured to covalently bind with the reactive moieties, and a second surface contact moiety, where the second surface contact moiety is polar (e.g., a methoxy terminated PEG moiety, a carboxylic acid, a carboxylic acid terminated PEG moiety, an alcohol moiety or an alcohol terminated PEG moiety)), where the kit can be used to generate the microfluidic device of any one of embodiments 135 to 161.

164. The kit of embodiment 163, where the plurality of reactive moieties may include azido moieties or alkynyl moieties.

165. The kit of embodiment 163 or 164, further including a plurality of capture beads (e.g., a bead that binds biological material, such as a non-specific capture bead, an antigen capture bead, an enzyme capture bead, or a nucleic acid capture bead).

166. The kit of any one of embodiments 163 to 165, further including one or more of an aqueous medium, a water immiscible fluidic medium (e.g., an alkane, a fluoroalkane, an oil, a hydrophobic polymer, or any combination thereof), an assay reagent (e.g., a lytic reagent, such as a lysis buffer), or an export buffer.

What is claimed:

1. A process for encapsulating cells in a microfluidic device having an enclosure comprising a channel and a plurality of chambers, each chamber of the plurality of chambers having an opening fluidically connecting the chamber to the channel, wherein at least a portion of surfaces forming the channel proximal to the opening to each chamber of the plurality of chambers and/or at least a portion of surfaces forming each chamber of the plurality of chambers proximal to the channel comprises a hydrophobic coating, said process comprising:

filling the channel and the plurality of chambers in the enclosure of the microfluidic device with a first aqueous medium;

disposing a first cell in a first chamber of the plurality of chambers;

disposing a second cell in a second chamber of the plurality of chambers; and flowing a water immiscible fluidic medium into the channel, displacing substantially all of the first aqueous medium in the channel without substantially displacing the first aqueous medium in the chambers of the plurality of chambers, thereby reversibly encapsulating the first and second cells in their respective chambers.

2. The process of claim 1, wherein all surfaces of the channel proximal to and surrounding the opening to each chamber of the plurality of chambers comprises the hydrophobic coating.

3. The process of claim 2, wherein all surfaces of the channel within 10 microns of the opening to each chamber of the plurality of chambers comprises the hydrophobic coating.

4. The process of claim 3, wherein the hydrophobic coating has a contact angle from about 45 degrees to about 100 degrees.

5. The process of claim 1, further comprising aspirating the water immiscible fluidic medium out of the channel.

6. The process of claim 5, wherein aspirating the water immiscible fluidic medium further comprises subsequently aspirating a second aqueous medium into the channel.

7. The process of claim 5, wherein all surfaces of each chamber proximal to and surrounding the opening of each chamber of the plurality of chambers comprise the hydrophobic coating, the process further comprising:
    generating an encapsulation layer of water immiscible fluidic media in each chamber of the plurality of chambers, wherein the encapsulation layer of each chamber of the plurality of chambers is located immediately adjacent to the channel and shares an interface with the first aqueous medium in the chamber so as to separate the first aqueous medium in the chamber from a medium present in the channel.

8. The process of claim 7, further comprising:
    selecting one of the first and second chambers having the respective first or second cell disposed therein; and
    removing the encapsulation layer formed by the water immiscible fluidic medium at the opening to the channel of the selected one of the first and second chambers, thereby generating a de-encapsulated chamber.

9. The process of claim 8, wherein selectively removing the encapsulation layer comprises generating a bubble within the chamber.

10. The process of claim 8, further comprising flowing a third aqueous medium into the channel, and wherein the third aqueous medium comprises a reagent, wherein the reagent is an assay reagent, a lytic reagent, or an export buffer.

11. The process of claim 1, further comprising disposing a capture bead into one or both of the first and second chambers.

12. The process of claim 1, wherein each chamber of the plurality of chambers comprises a plurality of surfaces forming the chamber, wherein at least one chamber surface of the plurality comprises a hydrophilic coating.

13. The process of claim 1, wherein the water immiscible fluidic medium includes an alkane, a fluoroalkane, an oil, a hydrophobic polymer, or any combination thereof.

14. A process of assaying encapsulated cells in a microfluidic device having an enclosure comprising a channel and a plurality of chambers, each chamber of the plurality of chambers having an opening fluidically connecting the chamber to the channel, wherein at least a portion of surfaces forming the channel proximal to each chambers of the plurality of chambers and/or at least a portion of surfaces forming each chamber of the plurality of chambers proximal to the channel comprises a hydrophobic coating, wherein the process comprises:
    filling the channel and the plurality of chambers in the enclosure of the microfluidic device with a first aqueous medium;
    disposing a first cell in a first chamber of the plurality of chambers;
    disposing a second cell in a second chamber of the plurality of chambers;
    flowing a water immiscible fluidic medium into the channel, displacing substantially all of the first aqueous medium in the channel without substantially displacing the first aqueous medium in any of the plurality of chambers, thereby reversibly encapsulating the first and second cells in their respective chambers; and
    monitoring an activity of the first and second cells encapsulated in the respective first and second chambers.

15. The process of claim 14, wherein all surfaces of the channel proximal to and surrounding the opening to each chamber of the plurality of chambers comprises the hydrophobic coating.

16. The process of claim 15, wherein all surfaces of the channel within 10 microns of the opening to each chamber of the plurality of chambers comprises the hydrophobic coating.

17. The process of claim 14, wherein the hydrophobic coating has a contact angle from about 45 degrees to about 100 degrees.

18. The process of claim 14, further comprising aspirating the water immiscible fluidic medium out of the channel.

19. The process of claim 18, wherein aspirating the water immiscible fluidic medium further comprises subsequently aspirating a second aqueous medium into the channel.

20. The process of claim 14, wherein all surfaces of each chamber proximal to and surrounding the opening of each chamber of the plurality of chambers comprise the hydrophobic coating, the process further comprising:
    generating an encapsulation layer of water immiscible fluidic media in each chamber of the plurality of chambers, wherein the encapsulation layer of each chamber of the plurality of chambers is located immediately adjacent to the channel and shares an interface with the first aqueous medium in the chamber so as to separate the first aqueous medium in the chamber from a medium present in the channel.

21. The process of claim 20, further comprising:
    selecting one or more of the plurality of chambers having a cell disposed therein; and
    removing the encapsulation layer formed by the water immiscible fluidic media at the opening to the channel of the selected one or more of the plurality of chambers, thereby generating a de-encapsulated chamber.

22. The process of claim 21, wherein selectively removing the encapsulation layer comprises generating a bubble within the chamber.

23. The process of claim 21, further comprising flowing a third aqueous medium into the channel, and wherein the third aqueous medium comprises a reagent, wherein the reagent is an assay reagent, a lytic reagent, or an export buffer.

24. The process of claim 14, further comprising disposing a capture bead into one or both of the first and second chambers.

25. The process of claim 14, wherein each chamber of the plurality of chambers comprises a plurality of surfaces forming the chamber, wherein at least one chamber surface of the plurality comprises a hydrophilic coating.

26. The process of claim 14, wherein the water immiscible fluidic medium includes an alkane, a fluoroalkane, an oil, a hydrophobic polymer, or any combination thereof.

27. The process of claim 14, further comprising incubating the first and second cells encapsulated in the first and second chambers for a first period of time before monitoring the activity of the first and second cells.

28. The process of claim 14, wherein the first and second cells express variable amounts of a molecule of interest or a reporter molecule.

29. The process of claim 28, wherein monitoring the activity of the first and second cells encapsulated in the first and second chambers, respectively, comprises detecting the molecule of interest or the reporter molecule present in each of the first and second chambers.

30. The process of claim 14, further comprising disposing a micro-object into each of the first and second chambers of the plurality of chambers, wherein the micro-object comprises a molecule configured to affect or test a biological activity of the first and second cells disposed therein.

31. The process of claim 30, further comprising:
triggering release of the molecule from the micro-object; and/or
introducing a release reagent into each of the first and second chambers subsequent to introducing the micro-object therein, wherein the release reagent is configured to trigger release of the molecule from the micro-object.

32. The process of claim 30, further comprising assessing whether the molecule comprised by the micro-object changes an expression of the molecule of interest or a reporter molecule by the first or second cells.

* * * * *